(12) United States Patent
Ryan et al.

(10) Patent No.: US 12,227,475 B2
(45) Date of Patent: Feb. 18, 2025

(54) AZA-HETEROCYCLYL CARBOXAMIDE AND RELATED COMPOUNDS AND THEIR USE IN TREATING MEDICAL CONDITIONS

(71) Applicant: X-Biotix Therapeutics, Inc., Waltham, MA (US)

(72) Inventors: Michael Dominic Ryan, Littleton, MA (US); Thomas David Pallin, Essex (GB); Toby Jonathan Blench, Essex (GB); Toby Matthew Grover Mullins, Essex (GB); David Edward Clark, Essex (GB); Emanuela Gancia, Essex (GB); Nadia Mamoona Ahmad, Essex (GB)

( * ) Notice: Subject to any disclaimer, the term of this patent is extended or adjusted under 35 U.S.C. 154(b) by 0 days.

(21) Appl. No.: 17/730,565

(22) Filed: Apr. 27, 2022

(65) Prior Publication Data

US 2023/0139502 A1    May 4, 2023

Related U.S. Application Data

(60) Provisional application No. 63/180,197, filed on Apr. 27, 2021.

(51) Int. Cl.
| | |
|---|---|
| *C07D 207/16* | (2006.01) |
| *A61P 31/04* | (2006.01) |
| *C07D 207/14* | (2006.01) |
| *C07D 207/48* | (2006.01) |
| *C07D 401/14* | (2006.01) |
| *C07D 403/14* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 498/08* | (2006.01) |
| *C07F 9/6558* | (2006.01) |

(52) U.S. Cl.
CPC ............ *C07D 207/16* (2013.01); *A61P 31/04* (2018.01); *C07D 207/14* (2013.01); *C07D 207/48* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 498/08* (2013.01); *C07F 9/65583* (2013.01)

(58) Field of Classification Search
CPC .. C07D 207/16; C07D 207/14; C07D 207/48; C07D 401/14; C07D 403/14; C07D 405/14; C07D 409/14; C07D 413/14; C07D 417/14; C07D 498/08; A61P 31/04
See application file for complete search history.

(56) References Cited

U.S. PATENT DOCUMENTS

| | | |
|---|---|---|
| 8,835,476 B2 | 9/2014 | Wu et al. |
| 2017/0088532 A1 | 3/2017 | Cohen et al. |

FOREIGN PATENT DOCUMENTS

| | | | |
|---|---|---|---|
| WO | WO-2006092059 A1 | 9/2006 | |
| WO | WO-2006099379 A2 * | 9/2006 | ......... A61K 31/4725 |
| WO | WO-2015085238 A1 | 6/2015 | |
| WO | WO-2017083431 A2 | 5/2017 | |
| WO | WO-2017083434 A1 | 5/2017 | |
| WO | WO-2018208985 A2 | 11/2018 | |
| WO | WO-2018208987 A2 | 11/2018 | |
| WO | WO-2018216822 A1 | 11/2018 | |
| WO | WO-2018216823 A1 | 11/2018 | |

OTHER PUBLICATIONS

Patani, G. A.; LaVoie, E. J. "Bioisosterism: A Rational Approach in Drug Design" Chem. Rev. 1996, 96, 3147-3176. (Year: 1996).*
Cas Registry, Cas Registry No. 1136364-89-0, Entered Database Apr. 19, 2009 (Year: 2009).*
Käck, H. et al., "DPP1 Inhibitors: Exploring the Role of Water in the S2 Pocket of DPP1 with Substituted Pyrrolidines," *ACS Med. Chem. Lett.* 2019, 10, pp. 1222-1227.

* cited by examiner

*Primary Examiner* — Andrew D Kosar
*Assistant Examiner* — John D McAnany
(74) *Attorney, Agent, or Firm* — Dechert LLP

(57) ABSTRACT

The invention provides aza-heterocyclyl carboxamide and related compounds, pharmaceutical compositions, and their use in the treatment of medical conditions, such as bacterial infections, and in inhibiting LpxC activity.

21 Claims, No Drawings

AZA-HETEROCYCLYL CARBOXAMIDE AND RELATED COMPOUNDS AND THEIR USE IN TREATING MEDICAL CONDITIONS

CROSS REFERENCE TO RELATED APPLICATIONS

This application claims the benefit of and priority to U.S. Provisional Patent Application Ser. No. 63/180,197, filed Apr. 27, 2021, the contents of which are hereby incorporated by reference.

FIELD OF THE INVENTION

The invention provides aza-heterocyclyl carboxamide and related compounds, pharmaceutical compositions, and their use in the treatment of medical conditions, such as bacterial infections, and in inhibiting LpxC activity.

BACKGROUND

Bacterial infection continues to be a serious health problem despite the substantial research efforts and scientific advances reported in the literature. Difficulties in treating bacterial infections are exacerbated by the development of bacteria with resistance to one or more antibiotics, particularly those that are used routinely.

Without effective treatment, bacterial infections can cause significant health problems and even result in death. For example, *Escherichia coli* can infect the urinary tract, lungs, and gastrointestinal system. Severe and bloody diarrhea from gastrointestinal *E. coli* infection can lead to serious complications. Hemolytic uremic syndrome, which can induce life-threatening kidney failure, can also be caused by *E. coli* infection.

A frequent hospital-acquired infection is *Pseudomonas aeruginosa*, which can be particularly dangerous to immunocompromised patients or patients recovering from major surgery. According to the United States Centers for Disease Control and Prevention, in the United States each year, more than 50,000 healthcare-associated *P. aeruginosa* infections are estimated to occur, with over 6,000 cases being multi-drug-resistant, and approximately 400 deaths being attributed to *P. aeruginosa* infections.

Accordingly, a need exists for improved treatments for bacterial infections. The present invention addresses this need and provides other related advantages.

SUMMARY

The invention provides aza-heterocyclyl carboxamide and related compounds, pharmaceutical compositions, and their use in the treatment of medical conditions, such as bacterial infections, and in inhibiting LpxC activity. In particular, one aspect of the invention provides a collection of aza-heterocyclyl carboxamide and related compounds, such as a compound represented by Formula I:

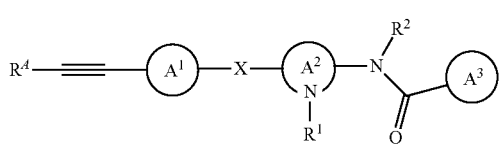

or a pharmaceutically acceptable salt thereof; wherein the variables are as defined in the detailed description. Further description of additional collections of aza-heterocyclyl carboxamide and related compounds are described in the detailed description. The compounds may be part of a pharmaceutical composition comprising a pharmaceutically acceptable carrier.

Another aspect of the invention provides a collection of aza-heterocyclyl carboxamide and related compounds, such as a compound represented by Formula II:

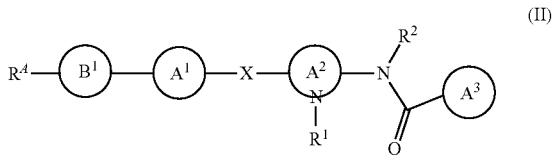

or a pharmaceutically acceptable salt thereof; wherein the variables are as defined in the detailed description. Further description of additional collections of aza-heterocyclyl carboxamide and related compounds are described in the detailed description. The compounds may be part of a pharmaceutical composition comprising a pharmaceutically acceptable carrier.

Another aspect of the invention provides a method of treating a bacterial infection in a patient. The method comprises administering to the patient a therapeutically effective amount of one or more aza-heterocyclyl carboxamide or related compounds described herein, e.g., a compound of Formula I, I-A, II, or II-A, to treat the bacterial infection. In certain embodiments, the bacterial infection is an infection by *Escherichia coli*, *Pseudomonas aeruginosa*, or a combination thereof. The compound may be used as monotherapy, or as part of a combination therapy, to treat the bacterial infection. In certain embodiments, the compound is a compound of Formula I or I-A.

Another aspect of the invention provides a method of inducing death of a bacterial cell. The method comprises exposing the bacterial cell to an effective amount of one or more aza-heterocyclyl carboxamide or related compounds described herein, e.g., a compound of Formula I, I-A, II, or II-A, to induce death of the bacterial cell. In certain embodiments, the bacterial cell is an *Escherichia coli* or *Pseudomonas aeruginosa* bacterium. In certain embodiments, the compound is a compound of Formula I or I-A.

Another aspect of the invention provides a method of inhibiting the activity of LpxC. The method comprises exposing a LpxC to an effective amount of one or more aza-heterocyclyl carboxamide or related compounds described herein, e.g., a compound of Formula I, I-A, II, or II-A, or a pharmaceutical composition described herein. In certain embodiments, the compound is a compound of Formula I or I-A.

DETAILED DESCRIPTION

The invention provides aza-heterocyclyl carboxamide and related compounds, pharmaceutical compositions, and their use in the treatment of medical conditions, such as bacterial infections, and in inhibiting LpxC activity. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —CH$_2$—, —CH$_2$CH$_2$—, and —CH$_2$C(H)(CH$_3$)CH$_2$—. The term "—(C$_0$ alkylene)-" refers to a bond. Accordingly, the term "—(C$_{0-3}$ alkylene)-" encompasses a bond (i.e., C$_0$) and a —(C$_{1-3}$ alkylene) group.

The term "heteroalkyl" refers to an alkyl group in which one or more carbon atoms has been replaced by a heteroatom (e.g., N, O, or S). Exemplary heteroalkyl groups include —CH$_2$O—, —CH$_2$OCH$_2$—, and —CH$_2$CH$_2$O—. The heteroalkyl group may contain, for example, from 2-4, 2-6, or 2-8 atoms selected from the group consisting of carbon and a heteroatom (e.g., N, O, or S). The term "hydroxy-heteroalkyl" refers to a heteroalkyl group that is substituted with at least one hydroxyl. Exemplary hydroxyl-heteroalkyl groups include —C(OCH$_3$)(H)CH$_2$OH, —CH$_2$C(OCH$_3$)(H) CH$_2$OH, and the like.

The term "cycloalkyl" refers to a monovalent saturated cyclic, bicyclic, bridged cyclic (e.g., adamantyl), or spirocyclic hydrocarbon group of 3-12, 3-8, 4-8, or 4-6 carbons, referred to herein, e.g., as "C$_3$-C$_6$ cycloalkyl," derived from a cycloalkane. Exemplary cycloalkyl groups include cyclohexyl, cyclopentyl, cyclobutyl, and cyclopropyl.

The term "cycloalkylene" refers to a diradical of a cycloalkyl group. Exemplary cycloalkylene groups include

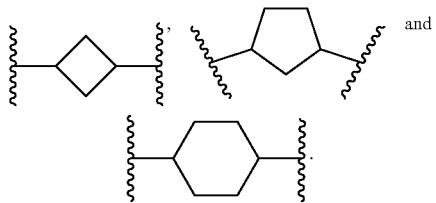

The term "haloalkyl" refers to an alkyl group that is substituted with at least one halogen. Exemplary haloalkyl groups include —CH$_2$F, —CHF$_2$, —CF$_3$, —CH$_2$CF$_3$, —CF$_2$CF$_3$, and the like.

The term "hydroxyalkyl" refers to an alkyl group that is substituted with at least one hydroxyl. Exemplary hydroxyalkyl groups include —CH$_2$CH$_2$OH, —C(H)(OH)CH$_3$, —CH$_2$C(H)(OH)CH$_2$CH$_2$OH, and the like.

The term "aralkyl" refers to an alkyl group substituted with an aryl group. Exemplary aralkyl groups include

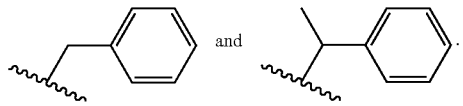

The term "heteroaralkyl" refers to an alkyl group substituted with a heteroaryl group.

The terms "alkenyl" and "alkynyl" refer to unsaturated aliphatic groups analogous in length and possible substitution to the alkyls described above, but that contain at least one double or triple bond respectively.

The term "carbocyclyl" refers to a mono-radical of a saturated, partially unsaturated, or aromatic carbocyclic ring (e.g., a monocyclic, bicyclic, bridged (e.g., adamantyl), or spirocyclic ring). In certain embodiments, the carbocyclyl contains 3-10, 4-8, or 5-6 carbons, referred to herein, e.g., as "C$_5$-C$_6$ carbocyclyl". Unless specified otherwise, the carbocyclic ring may be substituted at one or more ring positions with, for example, halogen, azide, alkyl, aralkyl, alkenyl, alkynyl, cycloalkyl, hydroxyl, alkoxyl, hydroxyalkyl, alkoxyalkyl, oxo, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the carbocyclyl is substituted at one or more ring positions. In certain embodiments, the carbocyclyl is not substituted.

The term "aryl" refers to a carbocyclic aromatic group and includes polycyclic aromatic ring systems having two or more carbocyclic rings in which two or more carbons are common to two adjoining rings (the rings are "fused rings") wherein all of the fused rings are aromatic rings, e.g., in a naphthyl group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, hydroxyalkyl, alkoxyalkyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aryl is a 6-10 membered ring. In certain embodiments, the aryl is a 6 membered ring. In certain embodiments, the aryl is substituted with 1, 2, or 3 substituents. In certain embodiments, the aryl is not substituted.

The term "arylene" refers to a multivalent radical (e.g., a divalent or trivalent radical) of a carbocyclic aromatic group. The term "phenylene" refers to a multivalent radical (e.g., a divalent or trivalent radical) of benzene. To illustrate, a divalent radical of benzene is illustrated by the formula

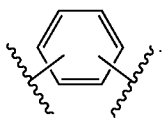

The terms "heterocyclic" and "heterocyclyl" refer to a saturated, partially unsaturated, or aromatic ring (e.g., a monocyclic, bicyclic ring, bridged, or spirocyclic ring) containing one or more heteroatoms (e.g., 1, 2, 3, or 4 heteroatoms, such as where the heteroatom is selected from oxygen, nitrogen, and sulfur). The heteroatoms can be the same or different from each other. Examples of heteroatoms include, but are not limited to nitrogen, oxygen and sulfur. Aromatic and nonaromatic heterocyclic rings are well-known in the art. Some non-limiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. Unless specified otherwise, the "heterocyclic" and "heterocyclyl" ring is optionally substituted at one or more ring positions with, for example, halogen, azide, alkyl, aralkyl, alkenyl, alkynyl, cycloalkyl, hydroxyl, alkoxyl, hydroxyalkyl, alkoxyalkyl, oxo, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-10 membered ring that, unless specified otherwise, is substituted or unsubstituted. In certain embodiments, the heterocyclyl group is a 3-7 membered ring that, unless specified otherwise, is substituted or unsubstituted. In certain embodiments, the heterocyclyl group is a 5-6 membered ring that, unless specified otherwise, is substituted or unsubstituted.

The term "aza-heterocyclyl" refers to a heterocyclyl containing at least one ring nitrogen atom.

The term "heterocyclylene" refers to a multivalent radical (e.g., a divalent or trivalent radical) of a saturated, partially unsaturated, or aromatic ring (e.g., a monocyclic, bicyclic ring, bridged, or spirocyclic ring) containing one or more heteroatoms (e.g., 1, 2, 3, or 4 heteroatoms, such as where the heteroatom is selected from oxygen, nitrogen, and sulfur). The heteroatoms can be the same or different from each other. Examples of heteroatoms include, but are not limited to nitrogen, oxygen and sulfur. Unless specified otherwise, the "heterocyclylene" is optionally substituted at one or more ring positions with, for example, halogen, azide, alkyl, aralkyl, alkenyl, alkynyl, cycloalkyl, hydroxyl, alkoxyl, hydroxyalkyl, alkoxyalkyl, oxo, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclylene is a 3-7 membered ring that, unless specified otherwise, is substituted or unsubstituted. In certain embodiments, the heterocyclylene is a 5-6 membered ring that, unless specified otherwise, is substituted or unsubstituted.

The term "heterocycloalkyl" refers to a saturated heterocyclyl group having, for example, 3-7 ring atoms selected from carbon and heteroatoms (e.g., O, N, or S).

The term "heterocycloalkylene" refers to a multi-valent (e.g., di-valent or trivalent) saturated heterocyclyl group having, for example, 3-7 ring atoms. An exemplary "heterocycloalkylene" is piperidinylene, which is a multi-valent radical of piperidine. In certain embodiments, the "heterocycloalkylene" is a divalant, 5-6 membered saturated heterocyclyl containing 1 or 2 ring heteroatoms (e.g., O, N, or S). Pyrrolidinylene is a multi-valent radical of pyrrolidine.

The term "heteroaryl" refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, hydroxyalkyl, alkoxyalkyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocylic ring or a 9-10 membered bicyclic ring.

The term "heteroarylene" refers to a multi-valent (e.g., di-valent or trivalent) aromatic group that comprises at least one ring heteroatom. An exemplary "heteroarylene" is pyridinylene, which is a multi-valent radical of pyridine. For example, a divalent radical of pyridine is illustrated by the formula

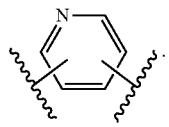

In certain embodiments, the "heteroarylene" is a divalent, 5-6 membered heteroaromatic group containing 1, 2, or 3 ring heteroatoms (e.g., O, N, or S).

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

The terms "amine" and "amino" are art-recognized and refer to both unsubstituted and substituted amines, e.g., a moiety that may be represented by the general formulas:

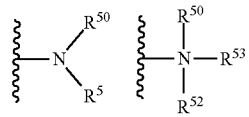

wherein $R^{50}$, $R^{51}$, $R^{52}$ and $R^{53}$ each independently represent a hydrogen, an alkyl, an alkenyl, —$(CH_2)_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O— alkenyl, —O-alkynyl, and —O—$(CH_2)_m$—$R^{61}$, where m and $R^{61}$ are described above.

The term "oxo" is art-recognized and refers to a "=O" substituent. For example, a cyclopentane substituted with an oxo group is cyclopentanone.

The symbol " " indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound" or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required to achieve 50% of the maximum possible activation of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_3$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

As a general matter, compositions specifying a percentage are by weight unless otherwise specific.

I. Aza-Heterocyclyl Carboxamide and Related Compounds

The invention provides aza-heterocyclyl carboxamide and related compounds. Exemplary compounds are described in the following sections. Additional exemplary compounds and synthetic procedures are described in the Examples.

One aspect of the invention provides a compound represented by Formula I:

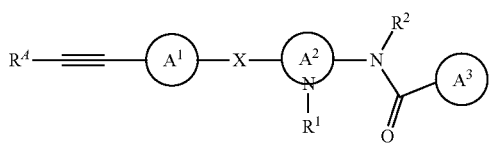

or a pharmaceutically acceptable salt thereof; wherein:
$A^1$ is 6-10 membered arylene or 5-10 membered heterocyclylene;
$A^2$ is a 4-10 membered aza-heterocyclylene;
$A^3$ is one of the following:
  a 4-10 membered aza-heterocyclyl optionally substituted with 1, 2, or 3 occurrences of $R^7$; or
  a 3-10 membered cycloalkyl substituted by (i) —N($R^3$)($R^4$) and (ii) 0, 1, 2, or 3 occurrences of $R^7$;
X is —C(O)N($R^3$)—($C_{0-6}$ alkylene)-ψ or —($C_{0-6}$ alkylene)-N($R^3$)C(O)-ψ; wherein ψ is a bond to $A^2$;
$R^A$ is one of the following:
  3-6 membered carbocyclyl or 3-6 membered heterocyclyl, each of which is substituted with (i) 0, 1, or 2 occurrences of $R^6$ and (ii) 1 occurrence of $Y^1$; or

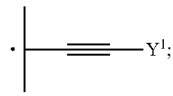

$Y^1$ is —($C_{0-6}$ alkylene)-(3-10 membered heterocyclyl), —($C_{0-6}$ alkylene)-(3-10 membered carbocyclyl), —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, —($C_{1-6}$ alkylene)-N($R^3$)($R^4$), 3-7 membered heteroalkyl, —O—($C_{1-6}$ alkylene)-$CO_2R^3$, or hydrogen;
$R^1$ is —C(O)—$R^5$, —$CO_2$—$R^5$, —S(O)$_2$—$R^5$, —C(O)N($R^3$)($R^4$), $R^5$, or hydrogen;
$R^2$ is hydrogen, $C_{1-6}$ alkyl, —($C_{0-6}$ alkylene)-($C_{3-6}$ cycloalkyl), —($C_{1-6}$ alkylene)-($C_{1-6}$ alkoxyl), or —($C_{1-6}$ alkylene)-$CO_2R^3$;

$R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl); or an occurrence of $R^3$ and $R^4$ attached to the same nitrogen atom are taken together with the nitrogen atom to which they are attached to form a heterocyclic ring;
$R^5$ is —$C_{1-6}$ alkyl, —$C_{1-6}$ haloalkyl, —$C_{1-6}$ hydroxyalkyl, —($C_{0-6}$ alkylene)-(3-7 membered heterocyclyl), —($C_{0-6}$ alkylene)-(3-7 membered saturated carbocyclyl), —($C_{1-6}$ alkylene)-N($R^3$)($R^4$), —($C_{1-6}$ alkylene)-($C_{1-6}$ alkoxyl), —($C_{1-6}$ alkylene)-$CO_2R^3$, —($C_{1-6}$ alkylene)-$SO_2R^3$, or —($C_{1-6}$ alkylene)-O—P(O)(OH)($R^3$);
$R^6$ represents independently for each occurrence halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or cyano; and
$R^7$ represents independently for each occurrence halogen, hydroxyl, cyano, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), —($C_{0-6}$ alkylene)-N($R^3$)($R^4$), —($C_{0-6}$ alkylene)-($C_{3-7}$ cycloalkyl), or —($C_{0-6}$ alkylene)-(4-10 membered heterocycloalkyl).

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is represented by Formula I.

In certain embodiments, $A^1$ is 6-10 membered arylene. In certain embodiments, $A^1$ is 6-membered arylene. In certain embodiments, $A^1$ is phenylene. In certain embodiments, $A^1$ is 5-10 membered heterocyclylene. In certain embodiments, $A^1$ is 5-6 membered heteroarylene.

In certain embodiments, $A^2$ is a 4-10 membered saturated aza-heterocyclylene. In certain embodiments, $A^2$ is a 4-6 membered saturated aza-heterocyclylene. In certain embodiments, $A^2$ is a 5-membered saturated aza-heterocyclylene. In certain embodiments, $A^2$ is pyrrolidinylene. In certain embodiments, $A^2$ is

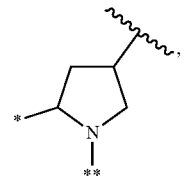

wherein * is a bond to X and ** is a bond to $R^1$. In certain embodiments, $A^2$ is

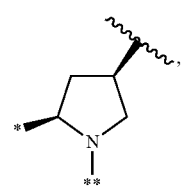

wherein * is a bond to X and ** is a bond to $R^1$.

In certain embodiments, $A^3$ is a 4-10 membered aza-heterocyclyl optionally substituted with 1, 2, or 3 occurrences of $R^7$. In certain embodiments, $A^3$ is a 4-10 membered saturated aza-heterocyclyl optionally substituted with 1, 2, or 3 occurrences of $R^7$. In certain embodiments, $A^3$ is a 4-6 membered saturated aza-heterocyclyl optionally substituted with 1, 2, or 3 occurrences of $R^7$. In certain embodiments, $A^3$ is a 5-membered saturated aza-heterocyclyl optionally substituted with 1, 2, or 3 occurrences of $R^7$. In certain embodiments, $A^3$ is pyrrolidinyl optionally substituted with 1, 2, or 3 occurrences of $R^7$. In certain embodiments, $A^3$ is

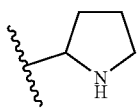 [SMILES: *C1CCCN1]

optionally substituted with 1, 2, or 3 occurrences of $R^7$. In certain embodiments, $A^3$ is

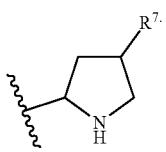

In certain embodiments, $A^3$ is

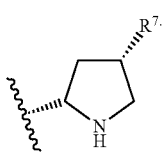

In certain embodiments, $A^3$ is a 3-10 membered cycloalkyl substituted by (i) $-N(R^3)(R^4)$ and (ii) 0, 1, 2, or 3 occurrences of $R^7$.

In certain embodiments, X is $-C(O)N(R^3)-(C_{0-6}$ alkylene)-$\psi$. In certain embodiments, X is $-C(O)N(R^3)-$ $(C_{1-3}$ alkylene)-$\psi$. In certain embodiments, X is $-C(O)N$ $(R^3)-(CH_2)-\psi$. In certain embodiments, X is $-(C_{0-6}$ alkylene)-$N(R^3)C(O)-\psi$. In certain embodiments, X is $-(C_{1-3}$ alkylene)-$N(R^3)C(O)-\psi$. In certain embodiments, X is $-(CH_2)-N(R^3)C(O)-\psi$.

In certain embodiments, $R^A$ is 3-6 membered carbocyclyl or 3-6 membered heterocyclyl, each of which is substituted with (i) 0, 1, or 2 occurrences of $R^6$ and (ii) 1 occurrence of $Y^1$. In certain embodiments, $R^A$ is phenyl or 5-6 membered heteroaryl substituted with (i) 0, 1, or 2 occurrences of $R^6$ and (ii) 1 occurrence of $Y^1$.

In certain embodiments, $R^A$ is 3-6 membered carbocyclyl substituted with (i) 0, 1, or 2 occurrences of $R^6$ and (ii) 1 occurrence of $Y^1$. In certain embodiments, $R^A$ is phenyl substituted with (i) 0, 1, or 2 occurrences of $R^6$ and (ii) 1 occurrence of $Y^1$. In certain embodiments, $R^A$ is phenyl substituted with 1 occurrence of $Y^1$.

In certain embodiments, $R^A$ is 3-6 membered heterocyclyl substituted with (i) 0, 1, or 2 occurrences of $R^6$ and (ii) 1 occurrence of $Y^1$. In certain embodiments, $R^A$ is 5-6 membered heteroaryl substituted with (i) 0, 1, or 2 occurrences of $R^6$ and (ii) 1 occurrence of $Y^1$. In certain embodiments, $R^A$ is 5-6 membered heteroaryl substituted with 1 occurrence of $Y^1$.

In certain embodiments, $R^A$ is

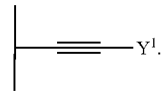

In certain embodiments, $Y^1$ is $-(C_{0-6}$ alkylene)-(3-10 membered heterocyclyl) or $-(C_{0-6}$ alkylene)-(3-10 membered carbocyclyl). In certain embodiments, $Y^1$ is $-(C_{1-3}$ alkylene)-(3-10 membered saturated heterocyclyl). In certain embodiments, $Y^1$ is $-(C_{1-3}$ alkylene)-(5-6 membered saturated heterocyclyl). In certain embodiments, $Y^1$ is $-(C_{1-3}$ alkylene)-(5-6 membered saturated heterocyclyl selected from the group consisting of morpholinyl, piperidinyl, piperazinyl, tetrahydropyranyl, pyrrolidinyl, oxazolidinyl, and imidazolidinyl, each of which is optionally substituted with 1, 2, or 3 substituents independently selected from the group consisting of halogen, hydroxyl, $C_{1-6}$ alkyl, $C_{1-6}$ haloalkyl, $C_{1-6}$ hydroxyalkyl, $C_{1-6}$ alkoxyl, $-(C_{1-6}$ alkylene)-$(C_{1-6}$ alkoxyl), and cyano). In certain embodiments, $Y^1$ is $-(C_{1-3}$ alkylene)-(morpholinyl optionally substituted with 1 or 2 substituents independently selected from the group consisting of halogen, hydroxyl, $C_{1-6}$ alkyl, $C_{1-6}$ haloalkyl, $C_{1-6}$ hydroxyalkyl, and $C_{1-6}$ alkoxyl). In certain embodiments, $Y^1$ is $-(C_{1-3}$ alkylene)-(morpholinyl).

In certain embodiments, $Y^1$ is $-(C_{0-6}$ alkylene)-$CO_2R^3$, $-(C_{0-6}$ alkylene)-$C(O)N(R^3)(R^4)$, $-(C_{0-6}$ alkylene)-$N(R^3)C(O)R^4$, $-(C_{0-6}$ alkylene)-$N(R^3)C(O)N(R^3)(R^4)$, $-(C_{0-6}$ alkylene)-$N(R^3)S(O)_2R^4$, $-(C_{0-6}$ alkylene)-$S(O)_2N(R^3)R^4$, $C_{1-6}$ hydroxyalkyl, $-(C_{1-6}$ alkylene)-$N(R^3)(R^4)$, 3-7 membered heteroalkyl, or hydrogen. In certain embodiments, $Y^1$ is $-(C_{0-6}$ alkylene)-$CO_2R^3$, $-(C_{0-6}$ alkylene)-$C(O)N(R^3)$ $(R^4)$, $-(C_{0-6}$ alkylene)-$N(R^3)C(O)R^4$, $-(C_{0-6}$ alkylene)-$N(R^3)C(O)N(R^3)(R^4)$, $-(C_{0-6}$ alkylene)-$N(R^3)S(O)_2R^4$, $-(C_{0-6}$ alkylene)-$S(O)_2N(R^3)R^4$, $C_{1-6}$ hydroxyalkyl, or $-(C_{1-6}$ alkylene)-$N(R^3)(R^4)$. In certain embodiments, $Y^1$ is $-(C_{0-6}$ alkylene)-$CO_2R^3$. In certain embodiments, $Y^1$ is $-(C_{0-6}$ alkylene)-$C(O)N(R^3)(R^4)$. In certain embodiments, $Y^1$ is $-(C_{0-6}$ alkylene)-$N(R^3)C(O)R^4$. In certain embodiments, $Y^1$ is $-(C_{0-6}$ alkylene)-$N(R^3)C(O)N(R^3)(R^4)$. In certain embodiments, $Y^1$ is $-(C_{0-6}$ alkylene)-$N(R^3)S(O)_2R^4$. In certain embodiments, $Y^1$ is $-(C_{0-6}$ alkylene)-$S(O)_2N(R^3)$ $R^4$. In certain embodiments, $Y^1$ is $C_{1-6}$ hydroxyalkyl. In certain embodiments, $Y^1$ is $-(C_{1-6}$ alkylene)-$N(R^3)(R^4)$. In certain embodiments, $Y^1$ is 3-7 membered heteroalkyl In certain embodiments, $Y^1$ is hydrogen.

In certain embodiments, $Y^1$ is $-(C_{0-6}$ alkylene)-(3-10 membered carbocyclyl). In certain embodiments, $Y^1$ is $-(C_{0-6}$ alkylene)-(3-6 membered saturated carbocyclyl). In certain embodiments, $Y^1$ is cyclopropyl.

In certain embodiments, $R^1$ is $-C(O)-R^5$. In certain embodiments, $R^1$ is $-CO_2-R^5$ or $-S(O)_2-R^5$. In certain embodiments, $R^1$ is $-CO_2-R^5$. In certain embodiments, $R^1$ is $-S(O)_2-R^5$. In certain embodiments, $R^1$ is $-C(O)$ $N(R^3)(R^4)$. In certain embodiments, $R^1$ is $R^5$.

In certain embodiments, $R^2$ is hydrogen. In certain embodiments, $R^2$ is $C_{1-6}$ alkyl. In certain embodiments, $R^2$ is $-(C_{0-6}$ alkylene)-$(C_{3-6}$ cycloalkyl).

In certain embodiments, $R^3$ and $R^4$ each represent independently for each occurrence hydrogen, $C_{1-6}$ alkyl, $C_{1-6}$ haloalkyl, or $-(C_{0-6}$ alkylene)-$(C_{3-6}$ cycloalkyl). In certain embodiments, $R^3$ and $R^4$ each represent independently for each occurrence hydrogen, $C_{1-6}$ alkyl, or $C_{1-6}$ haloalkyl. In certain embodiments, an occurrence of $R^3$ and $R^4$ attached to the same nitrogen atom are taken together with the nitrogen atom to which they are attached to form a heterocyclic ring.

In certain embodiments, $R^5$ is —$C_{1-6}$ alkyl or —($C_{0-6}$ alkylene)-(3-7 membered cycloalkyl). In certain embodiments, $R^5$ is —$C_{1-6}$ alkyl or -(3-7 membered cycloalkyl). In certain embodiments, $R^5$ is —$C_{1-6}$ alkyl. In certain embodiments, $R^5$ is —$C_{1-6}$ haloalkyl. In certain embodiments, $R^5$ is —($C_{0-6}$ alkylene)-(3-7 membered heterocyclyl). In certain embodiments, $R^5$ is —($C_{0-6}$ alkylene)-(3-7 membered saturated carbocyclyl). In certain embodiments, $R^5$ is -(3-7 membered cycloalkyl). In certain embodiments, $R^5$ is —($C_{1-6}$ alkylene)-N($R^3$)($R^4$). In certain embodiments, $R^5$ is —($C_{1-6}$ alkylene)-O—P(O)(OH)($R^3$). In certain embodiments, $R^5$ is -(3-7 membered cycloalkylene)-O—P(O)(OH)($R^3$).

In certain embodiments, $R^6$ represents independently for each occurrence halogen or $C_{1-6}$ alkyl.

In certain embodiments, $R^7$ represents independently for each occurrence halogen, hydroxyl, cyano, $C_{1-6}$ alkyl, or $C_{1-6}$ haloalkyl. In certain embodiments, $R^7$ represents independently for each occurrence halogen, hydroxyl, or cyano. In certain embodiments, $R^7$ represents independently for each occurrence halogen or cyano. In certain embodiments, $R^7$ is halogen. In certain embodiments, $R^7$ is fluoro. In certain embodiments, $R^7$ represents independently for each occurrence fluoro or cyano. In certain embodiments, $R^7$ is cyano.

The description above describes multiple embodiments relating to compounds of Formula I. The patent application specifically contemplates all combinations of the embodiments.

Another aspect of the invention provides a compound represented by Formula I-A:

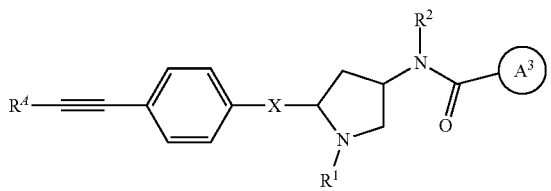

(I-A)

or a pharmaceutically acceptable salt thereof; wherein:
$A^3$ is 4-7 membered aza-heterocyclyl optionally substituted with 1, 2, or 3 occurrences of $R^7$;
X is —C(O)N($R^3$)—($C_{1-3}$ alkylene)-ψ or —($C_{1-3}$ alkylene)-N($R^3$)C(O)-ψ; wherein ψ is a bond to the pyrrolidinyl group;
$R^4$ is one of the following:
phenyl or 5-6 membered heteroaryl substituted with (i) 0, 1, or 2 occurrences of $R^6$ and (ii) 1 occurrence of $Y^1$; or

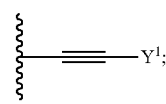

$Y^1$ is —($C_{0-6}$ alkylene)-(3-10 membered heterocyclyl), —($C_{0-6}$ alkylene)-(3-10 membered carbocyclyl), —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, or —($C_{1-6}$ alkylene)-N($R^3$)($R^4$);

$R^1$ is —C(O)—$R^5$, —$CO_2$—$R^5$, or —S(O)$_2$—$R^5$;

$R^2$ is hydrogen, $C_{1-6}$ alkyl, or —($C_{0-6}$ alkylene)-($C_{3-6}$ cycloalkyl);

$R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl); or an occurrence of $R^3$ and $R^4$ attached to the same nitrogen atom are taken together with the nitrogen atom to which they are attached to form a heterocyclic ring;

$R^5$ is —$C_{1-6}$ alkyl, —$C_{1-6}$ haloalkyl, —($C_{0-6}$ alkylene)-(3-7 membered heterocyclyl), —($C_{0-6}$ alkylene)-(3-7 membered saturated carbocyclyl), or —($C_{1-6}$ alkylene)-N($R^3$)($R^4$);

$R^6$ represents independently for each occurrence halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or cyano; and $R^7$ represents independently for each occurrence halogen, hydroxyl, cyano, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or —($C_{0-6}$ alkylene)-N($R^3$)($R^4$).

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is represented by Formula I-A.

In certain embodiments, $A^3$ is a 5-membered saturated aza-heterocyclyl optionally substituted with 1, 2, or 3 occurrences of $R^7$. In certain embodiments, $A^3$ is pyrrolidinyl optionally substituted with 1, 2, or 3 occurrences of $R^7$. In certain embodiments, $A^3$ is

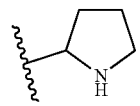 [SMILES: *C1CCCN1]

optionally substituted with 1, 2, or 3 occurrences of $R^7$. In certain embodiments, $A^3$ is

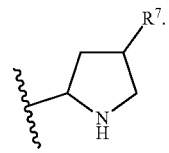

In certain embodiments, $A^3$ is

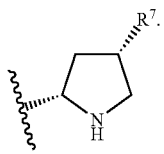

In certain embodiments, X is —C(O)N($R^3$)—($C_{1-3}$ alkylene)-ψ. In certain embodiments, X is —C(O)N($R^3$)—(CH$_2$)-ψ. In certain embodiments, X is —($C_{1-3}$ alkylene)-N($R^3$)C(O)-ψ. In certain embodiments, X is —(CH$_2$)—N($R^3$)C(O)-ψ.

In certain embodiments, $R^1$ is —C(O)—$R^5$. In certain embodiments, $R^1$ is —CO$_2$—$R^5$ or —S(O)$_2$—$R^5$. In certain embodiments, $R^1$ is —CO$_2$—$R^5$. In certain embodiments, $R^1$ is —S(O)$_2$—$R^5$.

In certain embodiments, $R^A$ is phenyl or 5-6 membered heteroaryl substituted with (i) 0, 1, or 2 occurrences of $R^6$ and (ii) 1 occurrence of $Y^1$. In certain embodiments, $R^A$ is phenyl substituted with (i) 0, 1, or 2 occurrences of $R^6$ and (ii) 1 occurrence of $Y^1$. In certain embodiments, $R^A$ is phenyl substituted with 1 occurrence of $Y^1$. In certain embodiments, $R^A$ is 5-6 membered heteroaryl substituted with (i) 0, 1, or 2 occurrences of $R^6$ and (ii) 1 occurrence of $Y^1$. In certain embodiments, $R^A$ is 5-6 membered heteroaryl substituted with 1 occurrence of $Y^1$. In certain embodiments, $R^A$ is

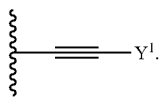

In certain embodiments, $Y^1$ is —($C_{0-6}$ alkylene)-(3-10 membered heterocyclyl) or —($C_{0-6}$ alkylene)-(3-10 membered carbocyclyl). In certain embodiments, $Y^1$ is —($C_{1-3}$ alkylene)-(3-10 membered saturated heterocyclyl). In certain embodiments, $Y^1$ is —($C_{1-3}$ alkylene)-(5-6 membered saturated heterocyclyl). In certain embodiments, $Y^1$ is —($C_{1-3}$ alkylene)-(5-6 membered saturated heterocyclyl selected from the group consisting of morpholinyl, piperidinyl, piperazinyl, tetrahydropyranyl, pyrrolidinyl, oxazolidinyl, and imidazolidinyl, each of which is optionally substituted with 1, 2, or 3 substituents independently selected from the group consisting of halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), and cyano). In certain embodiments, $Y^1$ is —($C_{1-3}$ alkylene)-(morpholinyl optionally substituted with 1 or 2 substituents independently selected from the group consisting of halogen, hydroxyl, $C_{1-6}$ alkyl, $C_{1-6}$ haloalkyl, $C_{1-6}$ hydroxyalkyl, and $C_{1-6}$ alkoxyl). In certain embodiments, $Y^1$ is —($C_{1-3}$ alkylene)-(morpholinyl).

In certain embodiments, $Y^1$ is —($C_{0-6}$ alkylene)-CO$_2$$R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2$$R^4$, —($C_{0-6}$ alkylene)-S(O)$_2$N($R^3$)$R^4$, $C_{1-6}$ hydroxyalkyl, or —($C_{1-6}$ alkylene)-N($R^3$)($R^4$). In certain embodiments, $Y^1$ is —($C_{0-6}$ alkylene)-CO$_2$$R^3$. In certain embodiments, $Y^1$ is —($C_{0-6}$ alkylene)-C(O)N($R^3$)($R^4$). In certain embodiments, $Y^1$ is —($C_{0-6}$ alkylene)-N($R^3$)C(O)$R^4$. In certain embodiments, $Y^1$ is —($C_{0-6}$ alkylene)-N($R^3$)C(O)N($R^3$)($R^4$). In certain embodiments, $Y^1$ is —($C_{0-6}$ alkylene)-N($R^3$)S(O)$_2$$R^4$. In certain embodiments, $Y^1$ is —($C_{0-6}$ alkylene)-S(O)$_2$N($R^3$)$R^4$. In certain embodiments, $Y^1$ is $C_{1-6}$ hydroxyalkyl. In certain embodiments, $Y^1$ is —($C_{1-6}$ alkylene)-N($R^3$)($R^4$).

In certain embodiments, $Y^1$ is —($C_{0-6}$ alkylene)-(3-10 membered carbocyclyl). In certain embodiments, $Y^1$ is —($C_{0-6}$ alkylene)-(3-6 membered saturated carbocyclyl). In certain embodiments, $Y^1$ is cyclopropyl.

In certain embodiments, $R^2$ is hydrogen. In certain embodiments, $R^2$ is $C_{1-6}$ alkyl. In certain embodiments, $R^2$ is —($C_{0-6}$ alkylene)-($C_{3-6}$ cycloalkyl).

In certain embodiments, $R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl). In certain embodiments, $R^3$ and $R^4$ each represent independently for each occurrence hydrogen, $C_{1-6}$ alkyl, or $C_{1-6}$ haloalkyl. In certain embodiments, an occurrence of $R^3$ and $R^4$ attached to the same nitrogen atom are taken together with the nitrogen atom to which they are attached to form a heterocyclic ring.

In certain embodiments, $R^5$ is —$C_{1-6}$ alkyl or —($C_{0-6}$ alkylene)-(3-7 membered cycloalkyl). In certain embodiments, $R^5$ is —$C_{1-6}$ alkyl or -(3-7 membered cycloalkyl). In certain embodiments, $R^5$ is —$C_{1-6}$ alkyl. In certain embodiments, $R^5$ is —$C_{1-6}$ haloalkyl. In certain embodiments, $R^5$ is —($C_{0-6}$ alkylene)-(3-7 membered heterocyclyl). In certain embodiments, $R^5$ is —($C_{0-6}$ alkylene)-(3-7 membered saturated carbocyclyl). In certain embodiments, $R^5$ is —($C_{1-6}$ alkylene)-N($R^3$)($R^4$).

In certain embodiments, $R^6$ represents independently for each occurrence halogen or $C_{1-6}$ alkyl.

In certain embodiments, $R^7$ represents independently for each occurrence halogen, hydroxyl, cyano, $C_{1-6}$ alkyl, or $C_{1-6}$ haloalkyl. In certain embodiments, $R^7$ represents independently for each occurrence halogen, hydroxyl, or cyano. In certain embodiments, $R^7$ represents independently for each occurrence halogen or cyano. In certain embodiments, $R^7$ is halogen. In certain embodiments, $R^7$ is fluoro. In certain embodiments, $R^7$ represents independently for each occurrence fluoro or cyano. In certain embodiments, $R^7$ is cyano.

The description above describes multiple embodiments relating to compounds of Formula I-A. The patent application specifically contemplates all combinations of the embodiments.

Another aspect of the invention provides a compound represented by Formula I-B:

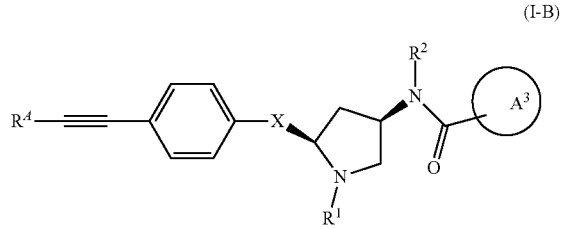

(I-B)

or a pharmaceutically acceptable salt thereof; wherein:
$A^3$ is 4-7 membered aza-heterocyclyl optionally substituted with 1, 2, or 3 occurrences of $R^7$;
X is —C(O)N($R^3$)—($C_{1-3}$ alkylene)-ψ or —($C_{1-3}$ alkylene)-N($R^3$)C(O)-ψ; wherein ψ is a bond to the pyrrolidinyl group;
$R^A$ is one of the following:
phenyl or 5-6 membered heteroaryl substituted with (i) 0, 1, or 2 occurrences of $R^6$ and (ii) 1 occurrence of $Y^1$; or

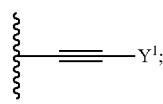

$Y^1$ is —($C_{0-6}$ alkylene)-(3-10 membered heterocyclyl), —($C_{0-6}$ alkylene)-(3-10 membered carbocyclyl), —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, or —($C_{1-6}$ alkylene)-N($R^3$)($R^4$);

$R^1$ is —C(O)—$R^5$, —$CO_2$—$R^5$, or —S(O)$_2$—$R^5$;

$R^2$ is hydrogen, $C_{1-6}$ alkyl, or —($C_{0-6}$ alkylene)-($C_{3-6}$ cycloalkyl);

$R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl); or an occurrence of $R^3$ and $R^4$ attached to the same nitrogen atom are taken together with the nitrogen atom to which they are attached to form a heterocyclic ring;

$R^5$ is —$C_{1-6}$ alkyl, —$C_{1-6}$ haloalkyl, —($C_{0-6}$ alkylene)-(3-7 membered heterocyclyl), —($C_{0-6}$ alkylene)-(3-7 membered saturated carbocyclyl), or —($C_{1-6}$ alkylene)-N($R^3$)($R^4$);

$R^6$ represents independently for each occurrence halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or cyano; and $R^7$ represents independently for each occurrence halogen, hydroxyl, cyano, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or —($C_{0-6}$ alkylene)-N($R^3$)($R^4$).

The definitions of variables in Formula I-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is represented by Formula I-B.

In certain embodiments, $A^3$ is a 5-membered saturated aza-heterocyclyl optionally substituted with 1, 2, or 3 occurrences of $R^7$. In certain embodiments, $A^3$ is pyrrolidinyl optionally substituted with 1, 2, or 3 occurrences of $R^7$. In certain embodiments, $A^3$ is

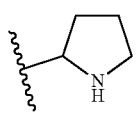 [SMILES: *C1CCCN1]

optionally substituted with 1, 2, or 3 occurrences of $R^7$. In certain embodiments, $A^3$ is

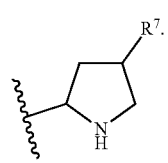

In certain embodiments, $A^3$ is

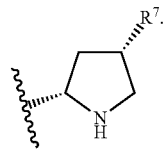

In certain embodiments, X is —C(O)N($R^3$)—($C_{1-3}$ alkylene)-ψ. In certain embodiments, X is —C(O)N($R^3$)—(CH$_2$)-ψ. In certain embodiments, X is —($C_{1-3}$ alkylene)-N($R^3$)C(O)-ψ. In certain embodiments, X is —(CH$_2$)—N($R^3$)C(O)-ψ.

In certain embodiments, $R^1$ is —C(O)—$R^5$. In certain embodiments, $R^1$ is —$CO_2$—$R^5$ or —S(O)$_2$—$R^5$. In certain embodiments, $R^1$ is —$CO_2$—$R^5$. In certain embodiments, $R^1$ is —S(O)$_2$—$R^5$.

In certain embodiments, $R^A$ is phenyl or 5-6 membered heteroaryl substituted with (i) 0, 1, or 2 occurrences of $R^6$ and (ii) 1 occurrence of $Y^1$. In certain embodiments, $R^A$ is phenyl substituted with (i) 0, 1, or 2 occurrences of $R^6$ and (ii) 1 occurrence of $Y^1$. In certain embodiments, $R^A$ is phenyl substituted with 1 occurrence of $Y^1$. In certain embodiments, $R^A$ is 5-6 membered heteroaryl substituted with (i) 0, 1, or 2 occurrences of $R^6$ and (ii) 1 occurrence of $Y^1$. In certain embodiments, $R^A$ is 5-6 membered heteroaryl substituted with 1 occurrence of $Y^1$. In certain embodiments, $R^A$ is

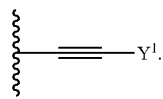

In certain embodiments, $Y^1$ is —($C_{0-6}$ alkylene)-(3-10 membered heterocyclyl) or —($C_{0-6}$ alkylene)-(3-10 membered carbocyclyl). In certain embodiments, $Y^1$ is —($C_{1-3}$ alkylene)-(3-10 membered saturated heterocyclyl). In certain embodiments, $Y^1$ is —($C_{1-3}$ alkylene)-(5-6 membered saturated heterocyclyl). In certain embodiments, $Y^1$ is —($C_{1-3}$ alkylene)-(5-6 membered saturated heterocyclyl selected from the group consisting of morpholinyl, piperidinyl, piperazinyl, tetrahydropyranyl, pyrrolidinyl, oxazolidinyl, and imidazolidinyl, each of which is optionally substituted with 1, 2, or 3 substituents independently selected from the group consisting of halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), and cyano). In certain embodiments, $Y^1$ is —($C_{1-3}$ alkylene)-(morpholinyl optionally substituted with 1 or 2 substituents independently selected from the group consisting of halogen, hydroxyl, $C_{1-6}$ alkyl, $C_{1-6}$ haloalkyl, $C_{1-6}$ hydroxyalkyl, and $C_{1-6}$ alkoxyl). In certain embodiments, $Y^1$ is —($C_{1-3}$ alkylene)-(morpholinyl).

In certain embodiments, $Y^1$ is —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N(R³)S(O)₂R⁴, —(C₀₋₆ alkylene)-S(O)₂N(R³)R⁴, C₁₋₆ hydroxyalkyl, or —(C₁₋₆ alkylene)-N(R³)(R⁴). In certain embodiments, Y¹ is —(C₀₋₆ alkylene)-CO₂R³. In certain embodiments, Y¹ is —(C₀₋₆ alkylene)-C(O)N(R³)(R⁴). In certain embodiments, Y¹ is —(C₀₋₆ alkylene)-N(R³)C(O)R⁴. In certain embodiments, Y¹ is —(C₀₋₆ alkylene)-N(R³)C(O)N(R³)(R⁴). In certain embodiments, Y¹ is —(C₀₋₆ alkylene)-N(R³)S(O)₂R⁴. In certain embodiments, Y¹ is —(C₀₋₆ alkylene)-S(O)₂N(R³)R⁴. In certain embodiments, Y¹ is C₁₋₆ hydroxyalkyl. In certain embodiments, Y¹ is —(C₁₋₆ alkylene)-N(R³)(R⁴).

In certain embodiments, Y¹ is —(C₀₋₆ alkylene)-(3-10 membered carbocyclyl). In certain embodiments, Y¹ is —(C₀₋₆ alkylene)-(3-6 membered saturated carbocyclyl). In certain embodiments, Y¹ is cyclopropyl.

In certain embodiments, R² is hydrogen. In certain embodiments, R² is C₁₋₆ alkyl. In certain embodiments, R² is —(C₀₋₆ alkylene)-(C₃₋₆ cycloalkyl).

In certain embodiments, R³ and R⁴ each represent independently for each occurrence hydrogen, C₁₋₆ alkyl, C₁₋₆ haloalkyl, or —(C₀₋₆ alkylene)-(C₃₋₆ cycloalkyl). In certain embodiments, R³ and R⁴ each represent independently for each occurrence hydrogen, C₁₋₆ alkyl, or C₁₋₆ haloalkyl. In certain embodiments, an occurrence of R³ and R⁴ attached to the same nitrogen atom are taken together with the nitrogen atom to which they are attached to form a heterocyclic ring.

In certain embodiments, R⁵ is —C₁₋₆ alkyl or —(C₀₋₆ alkylene)-(3-7 membered cycloalkyl). In certain embodiments, R⁵ is —C₁₋₆ alkyl or -(3-7 membered cycloalkyl). In certain embodiments, R⁵ is —C₁₋₆ alkyl. In certain embodiments, R⁵ is —C₁₋₆ haloalkyl. In certain embodiments, R⁵ is —(C₀₋₆ alkylene)-(3-7 membered heterocyclyl). In certain embodiments, R⁵ is —(C₀₋₆ alkylene)-(3-7 membered saturated carbocyclyl). In certain embodiments, R⁵ is —(C₁₋₆ alkylene)-N(R³)(R⁴).

In certain embodiments, R⁶ represents independently for each occurrence halogen or C₁₋₆ alkyl.

In certain embodiments, R⁷ represents independently for each occurrence halogen, hydroxyl, cyano, C₁₋₆ alkyl, or C₁₋₆ haloalkyl. In certain embodiments, R⁷ represents independently for each occurrence halogen, hydroxyl, or cyano. In certain embodiments, R⁷ represents independently for each occurrence halogen or cyano. In certain embodiments, R⁷ is halogen. In certain embodiments, R⁷ is fluoro. In certain embodiments, R⁷ represents independently for each occurrence fluoro or cyano. In certain embodiments, R⁷ is cyano.

The description above describes multiple embodiments relating to compounds of Formula I-B. The patent application specifically contemplates all combinations of the embodiments.

In certain other embodiments, the compound is one of the compounds listed in Tables 1-4 below, or a pharmaceutically acceptable salt thereof. In certain embodiments, the compound is one of the compounds listed in Tables 1-4 below. In certain other embodiments, the compound is one of the compounds listed in Tables 2-4 below, or a pharmaceutically acceptable salt thereof. In certain embodiments, the compound is one of the compounds listed in Tables 2-4 below.

TABLE 1

| Compound No. | Chemical Structure |
|---|---|
| I-1 | 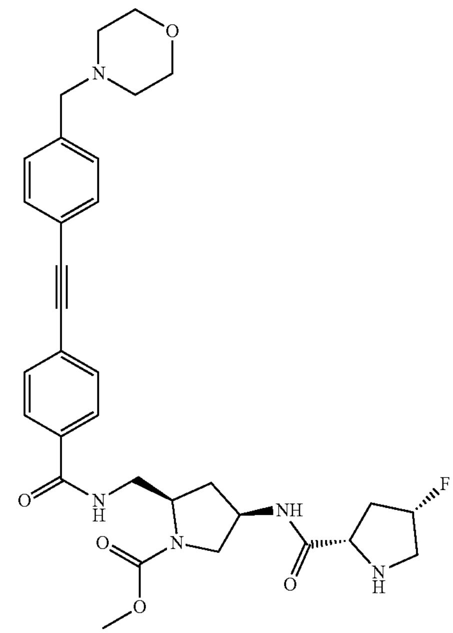 [SMILES: COC(=O)N1C[C@H](NC(=O)[C@@H]2C[C@H](F)CN2)C[C@@H]1CNC(=O)c1ccc(C#Cc2ccc(CN3CCOCC3)cc2)cc1] |
| I-2 | 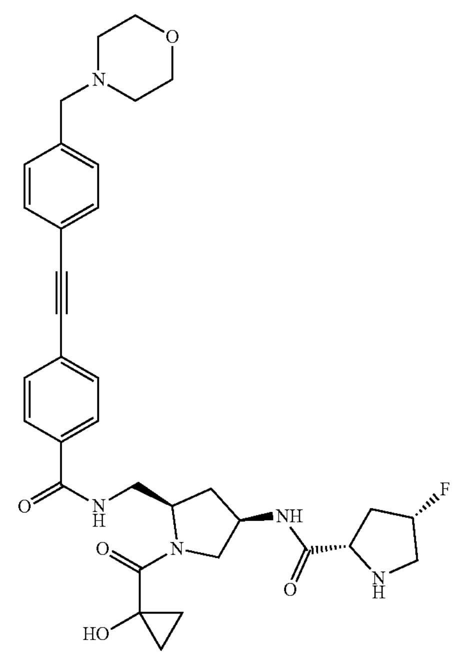 [SMILES: O=C(NC[C@H]1C[C@@H](NC(=O)[C@@H]2C[C@H](F)CN2)CN1C(=O)C1(O)CC1)c1ccc(C#Cc2ccc(CN3CCOCC3)cc2)cc1] |

TABLE 1-continued
| Compound No. | Chemical Structure |
| --- | --- |
| I-3 | 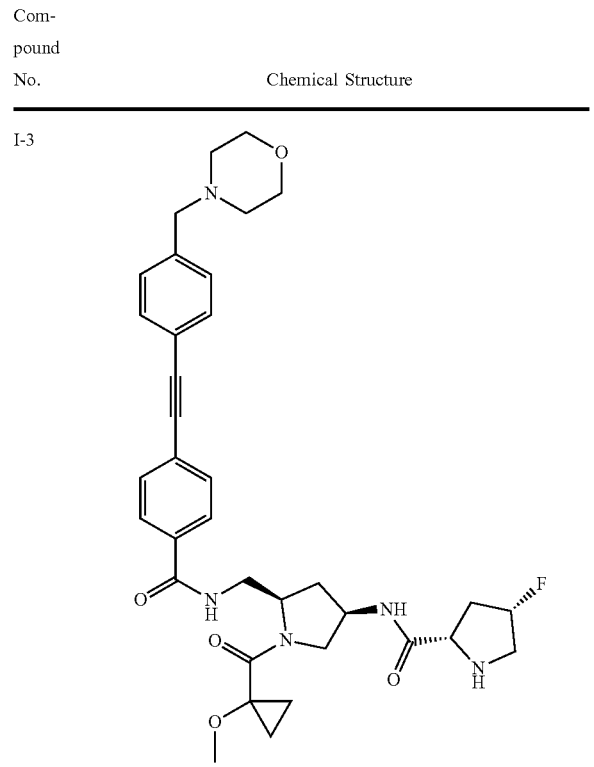 |
| I-4 | 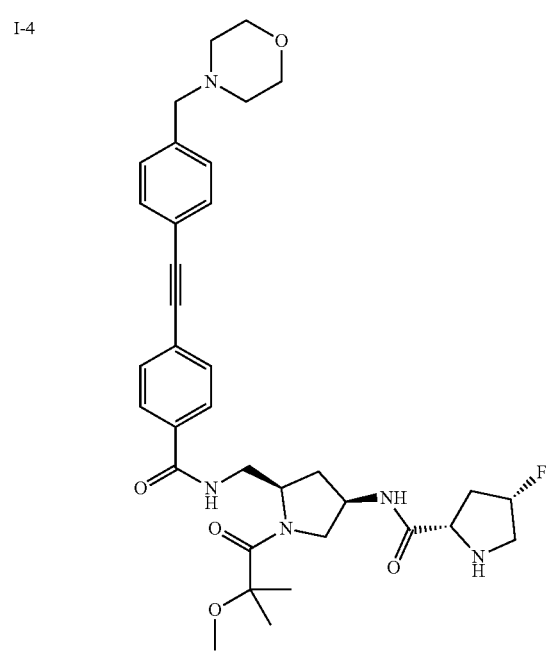 |
| I-5 | 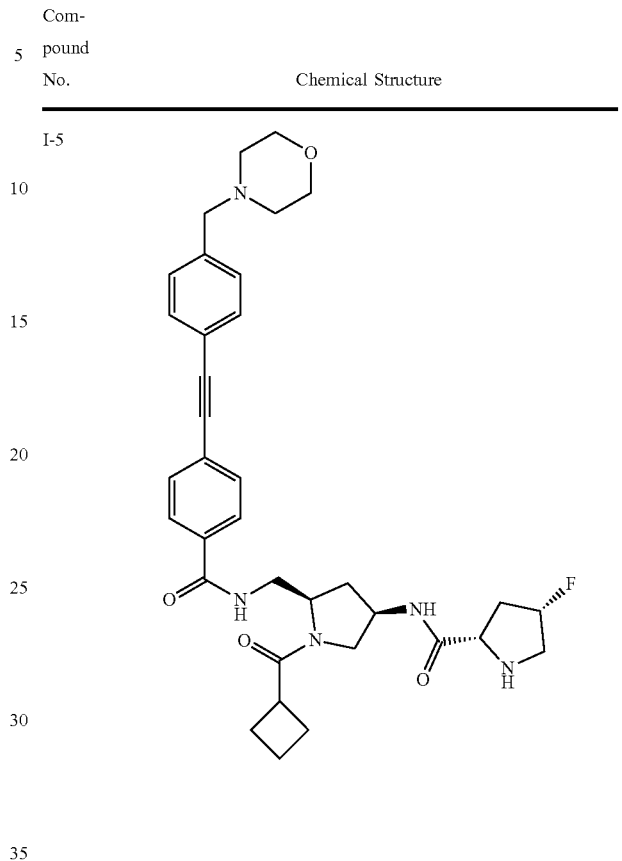 |
| I-6 | 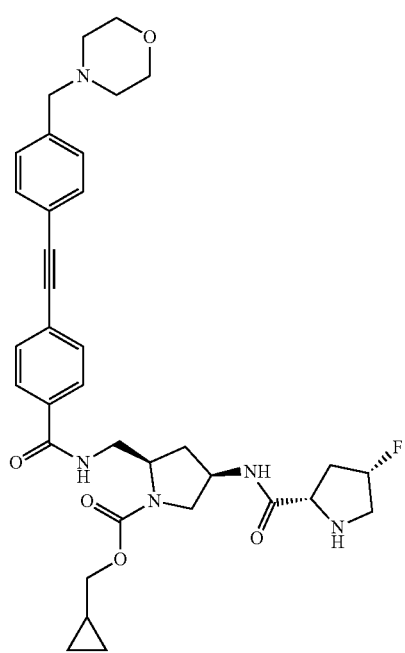 [SMILES: O=C(NC[C@H]1C[C@@H](NC(=O)[C@@H]2C[C@H](F)CN2)CN1C(=O)OCC1CC1)c1ccc(C#Cc2ccc(CN3CCOCC3)cc2)cc1] |

TABLE 1-continued
| Compound No. | Chemical Structure |
|---|---|
| I-7 | 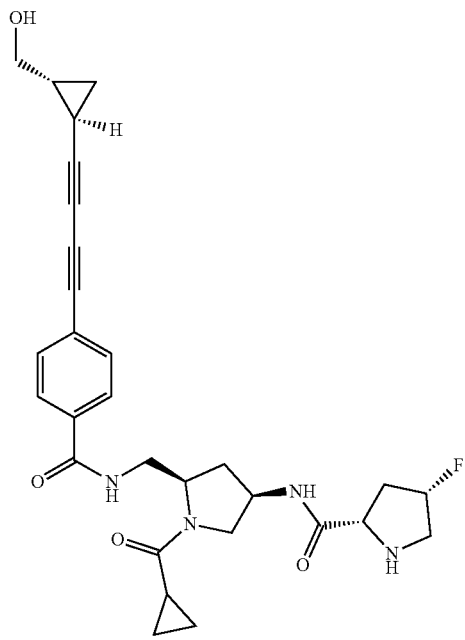 [SMILES: O=C(NC[C@H]1C[C@@H](NC(=O)[C@@H]2C[C@H](F)CN2)CN1C(=O)C1CC1)c1ccc(C#CC#C[C@@H]2C[C@H]2CO)cc1] |
| I-8 | 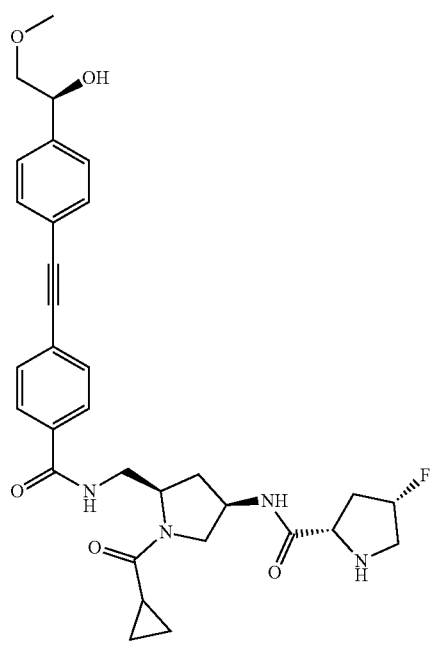 [SMILES: COC[C@@H](O)c1ccc(C#Cc2ccc(C(=O)NC[C@H]3C[C@@H](NC(=O)[C@@H]4C[C@H](F)CN4)CN3C(=O)C3CC3)cc2)cc1] |
| I-9 | 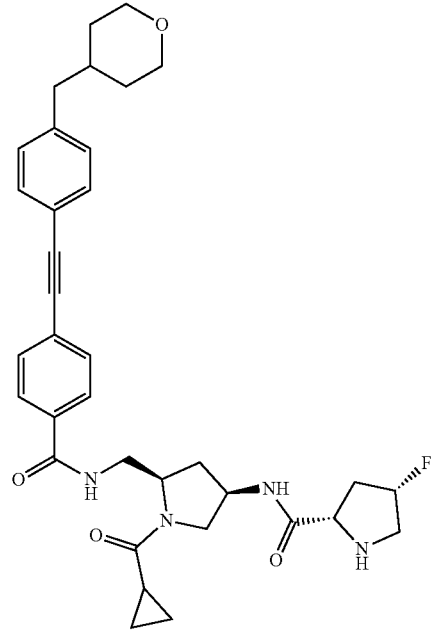 [SMILES: O=C(NC[C@H]1C[C@@H](NC(=O)[C@@H]2C[C@H](F)CN2)CN1C(=O)C1CC1)c1ccc(C#Cc2ccc(CC3CCOCC3)cc2)cc1] |
| I-10 | 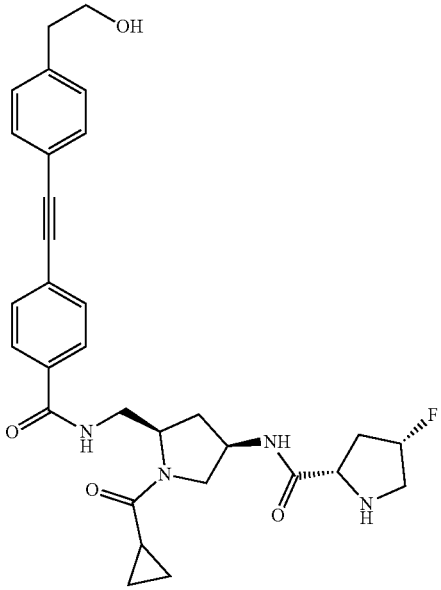 [SMILES: O=C(NC[C@H]1C[C@@H](NC(=O)[C@@H]2C[C@H](F)CN2)CN1C(=O)C1CC1)c1ccc(C#Cc2ccc(CCO)cc2)cc1] |

TABLE 1-continued
| Compound No. | Chemical Structure |
|---|---|
| I-11 | 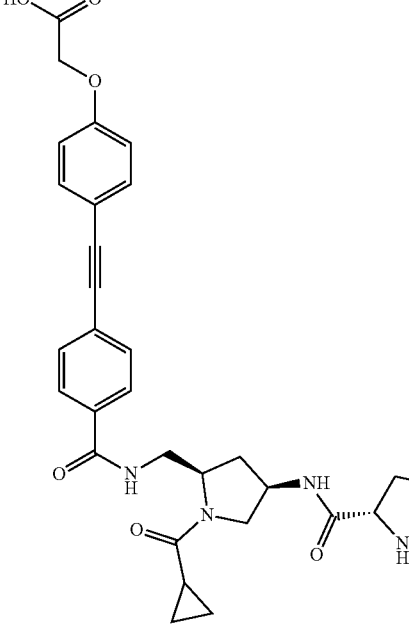 |
| I-12 | 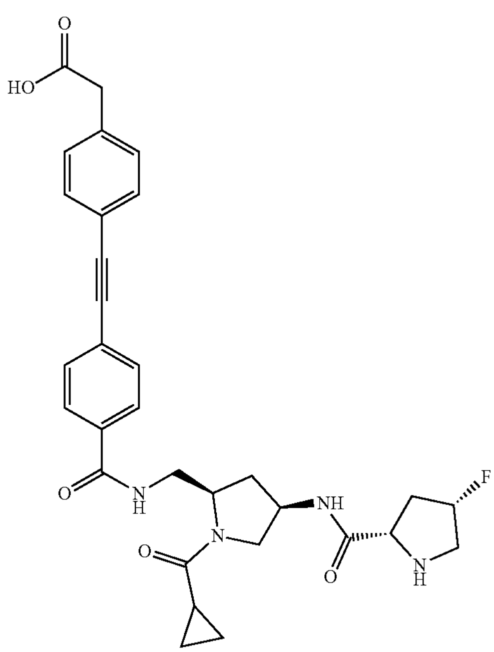 [SMILES: O=C(O)Cc1ccc(C#Cc2ccc(C(=O)NC[C@H]3C[C@@H](NC(=O)[C@@H]4C[C@H](F)CN4)CN3C(=O)C3CC3)cc2)cc1] |
TABLE 1-continued
| Compound No. | Chemical Structure |
|---|---|
| I-13 | 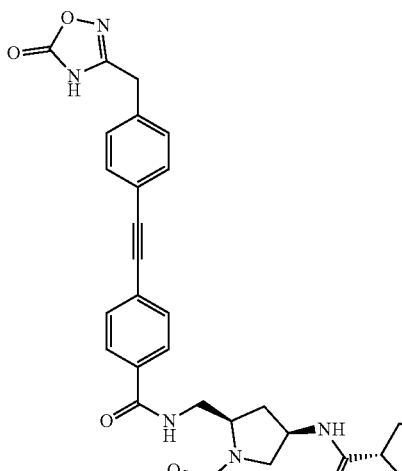 |
| I-14 | 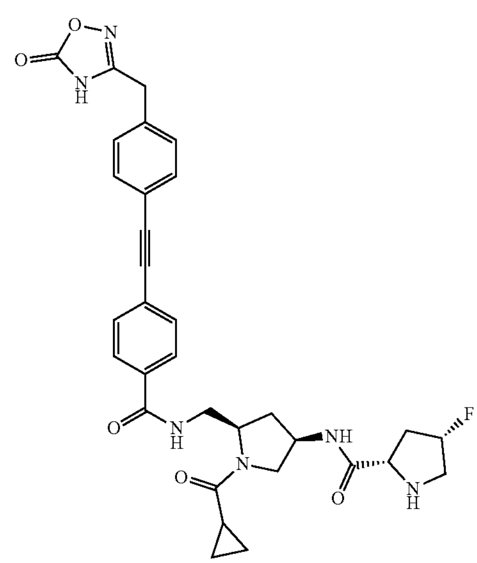 [SMILES: O=C(NC[C@H]1C[C@@H](NC(=O)[C@@H]2C[C@H](F)CN2)CN1C(=O)C1CC1)c1ccc(C#Cc2ccc(Cc3noc(=O)[nH]3)cc2)cc1] |

TABLE 1-continued
| Compound No. | Chemical Structure |
|---|---|
| I-15 | 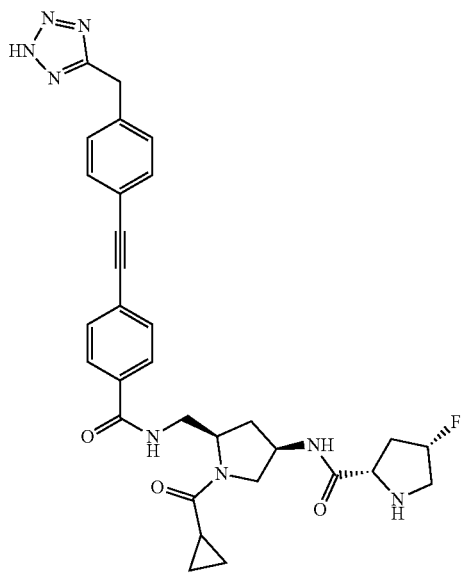 [SMILES: O=C(NC[C@H]1C[C@@H](NC(=O)[C@@H]2C[C@H](F)CN2)CN1C(=O)C1CC1)c1ccc(C#Cc2ccc(Cc3nn[nH]n3)cc2)cc1] |
| I-16 | 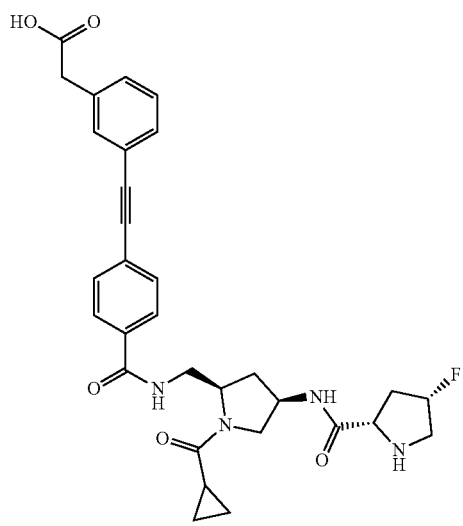 [SMILES: O=C(O)Cc1cccc(C#Cc2ccc(C(=O)NC[C@H]3C[C@@H](NC(=O)[C@@H]4C[C@H](F)CN4)CN3C(=O)C3CC3)cc2)c1] |
| I-17 | 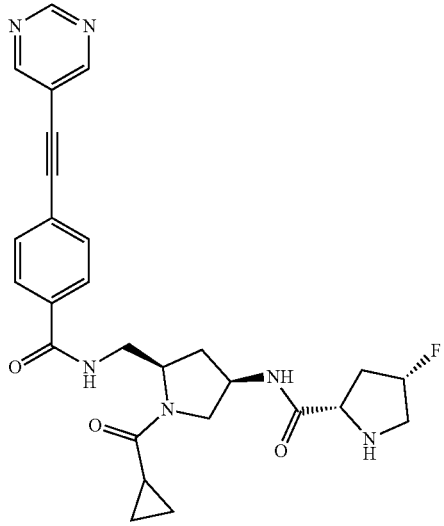 [SMILES: O=C(NC[C@H]1C[C@@H](NC(=O)[C@@H]2C[C@H](F)CN2)CN1C(=O)C1CC1)c1ccc(C#Cc2cncnc2)cc1] |
| I-18 | 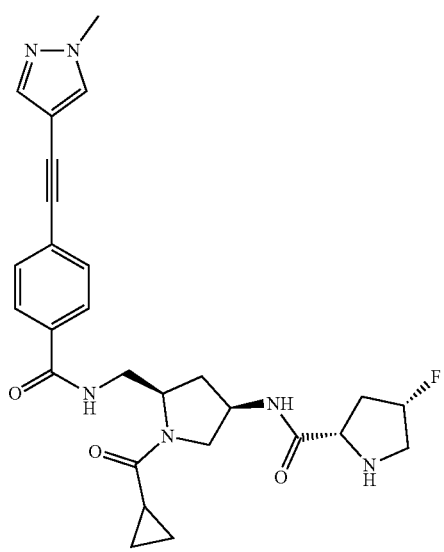 [SMILES: Cn1cc(C#Cc2ccc(C(=O)NC[C@H]3C[C@@H](NC(=O)[C@@H]4C[C@H](F)CN4)CN3C(=O)C3CC3)cc2)cn1] |

TABLE 1-continued
| Compound No. | Chemical Structure |
|---|---|
| I-19 | 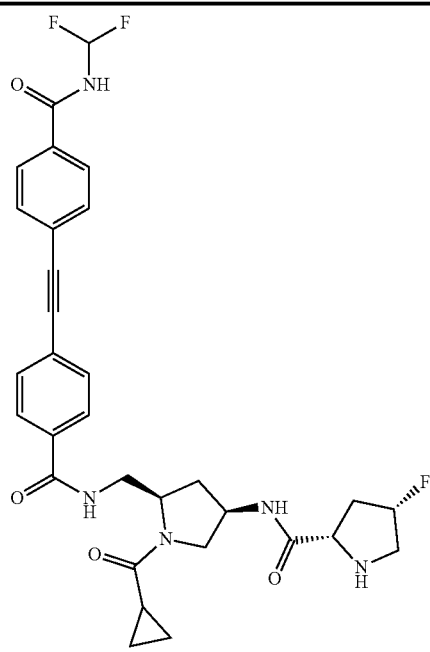 |
| I-20 | 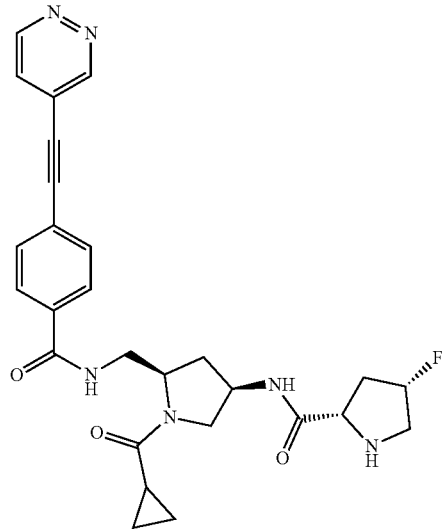 [SMILES: O=C(NC[C@H]1C[C@@H](NC(=O)[C@@H]2C[C@H](F)CN2)CN1C(=O)C1CC1)c1ccc(C#Cc2ccnnc2)cc1] |
| I-21 | 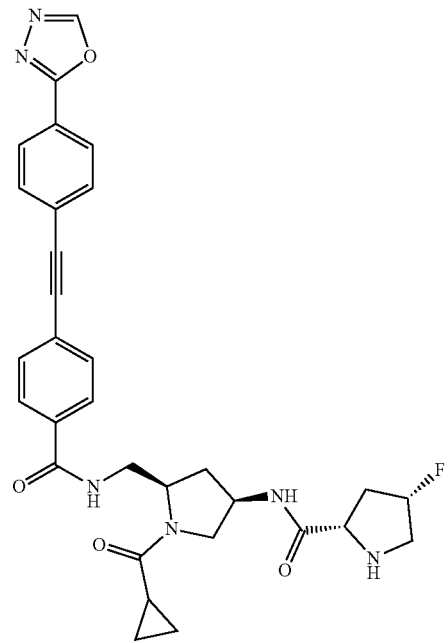 [SMILES: O=C(NC[C@H]1C[C@@H](NC(=O)[C@@H]2C[C@H](F)CN2)CN1C(=O)C1CC1)c1ccc(C#Cc2ccc(-c3nnco3)cc2)cc1] |
| I-22 | 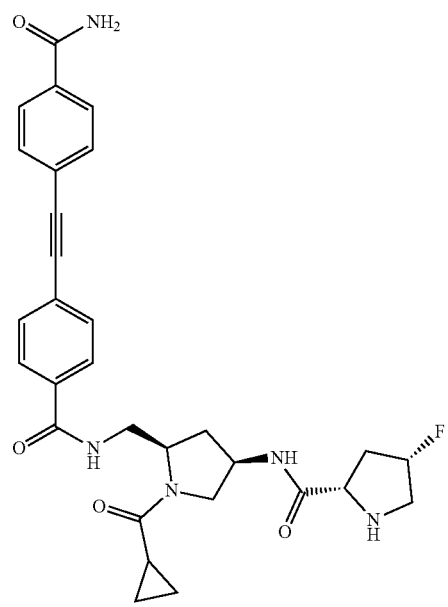 [SMILES: NC(=O)c1ccc(C#Cc2ccc(C(=O)NC[C@H]3C[C@@H](NC(=O)[C@@H]4C[C@H](F)CN4)CN3C(=O)C3CC3)cc2)cc1] |

TABLE 1-continued
| Compound No. | Chemical Structure |
|---|---|
| I-23 | 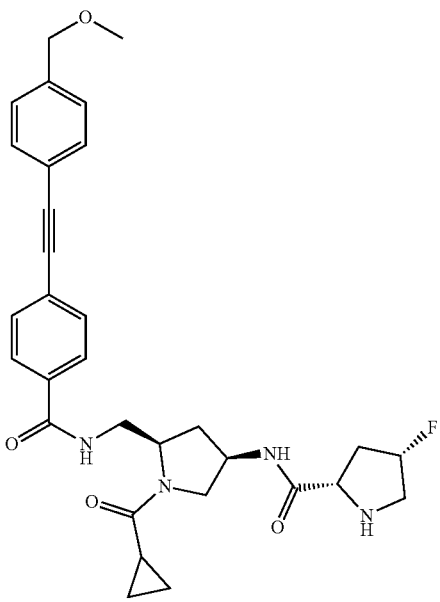 [SMILES: COCc1ccc(C#Cc2ccc(C(=O)NC[C@H]3C[C@@H](NC(=O)[C@@H]4C[C@H](F)CN4)CN3C(=O)C3CC3)cc2)cc1] |
| I-24 | 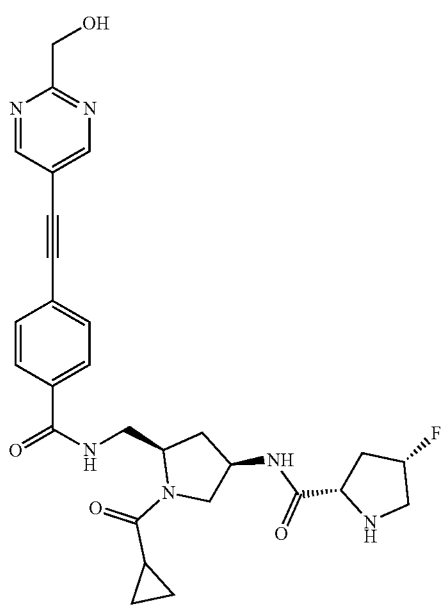 [SMILES: O=C(NC[C@H]1C[C@@H](NC(=O)[C@@H]2C[C@H](F)CN2)CN1C(=O)C1CC1)c1ccc(C#Cc2cnc(CO)nc2)cc1] |
| I-25 | |
| I-26 | |

TABLE 1-continued
| Compound No. | Chemical Structure |
|---|---|
| I-27 | 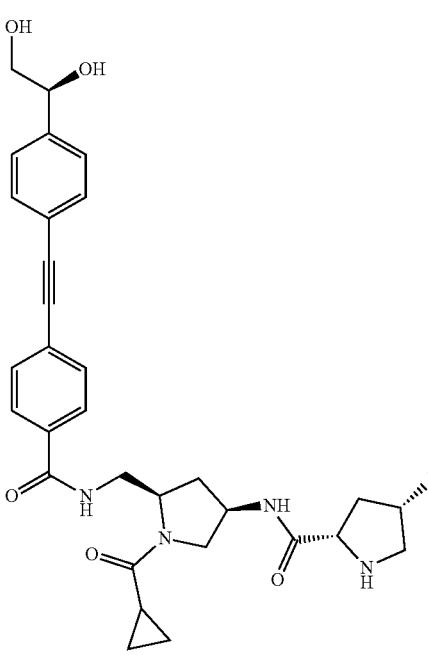 |
| I-28 | 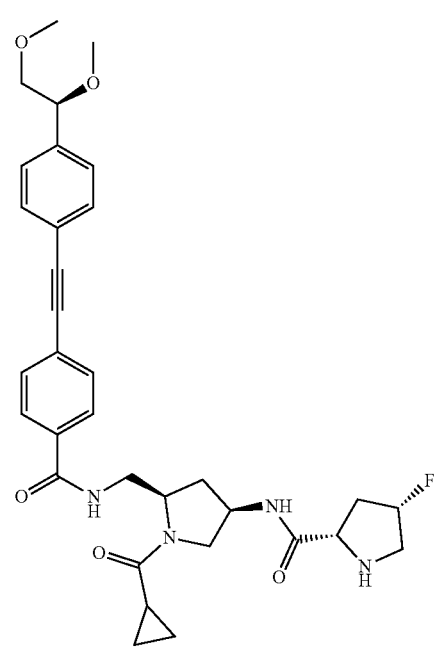 [SMILES: COC[C@@H](OC)c1ccc(C#Cc2ccc(C(=O)NC[C@H]3C[C@@H](NC(=O)[C@@H]4C[C@H](F)CN4)CN3C(=O)C3CC3)cc2)cc1] |
| I-29 | 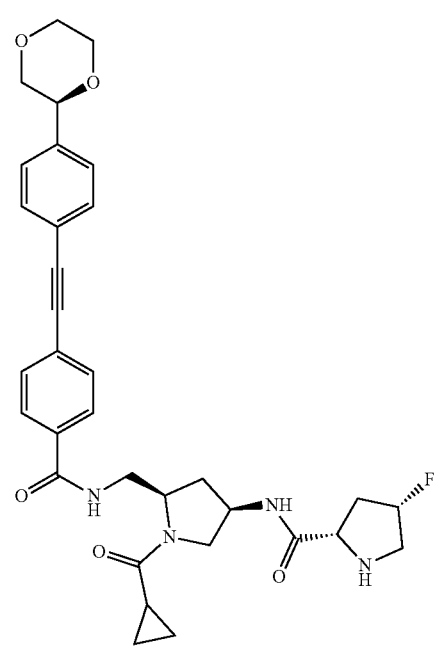 [SMILES: O=C(NC[C@H]1C[C@@H](NC(=O)[C@@H]2C[C@H](F)CN2)CN1C(=O)C1CC1)c1ccc(C#Cc2ccc([C@H]3COCCO3)cc2)cc1] |
| I-30 | 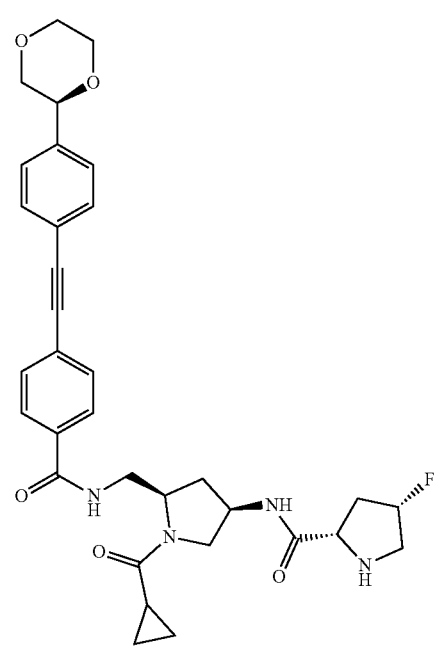 [SMILES: O=C(NC[C@H]1C[C@@H](NC(=O)[C@@H]2C[C@H](F)CN2)CN1C(=O)C1CC1)c1ccc(C#Cc2ccc([C@H]3COCCO3)cc2)cc1] |

TABLE 1-continued
| Compound No. | Chemical Structure |
|---|---|
| I-31 | 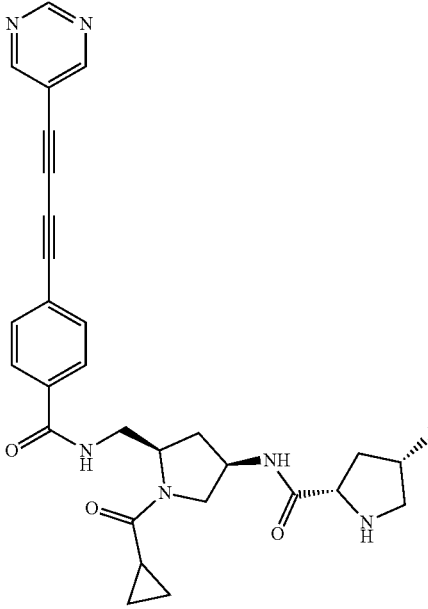 |
| I-32 | 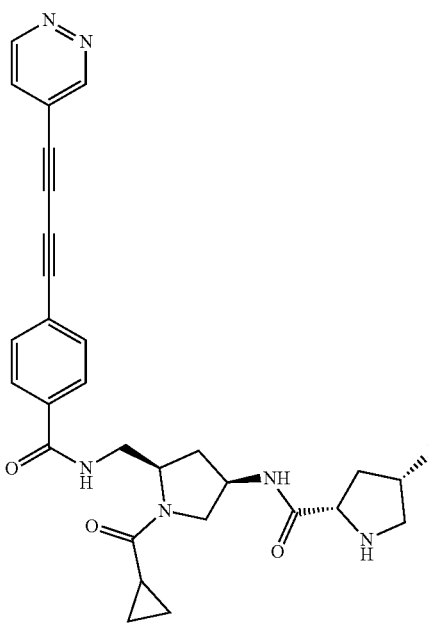 |
| I-33 | 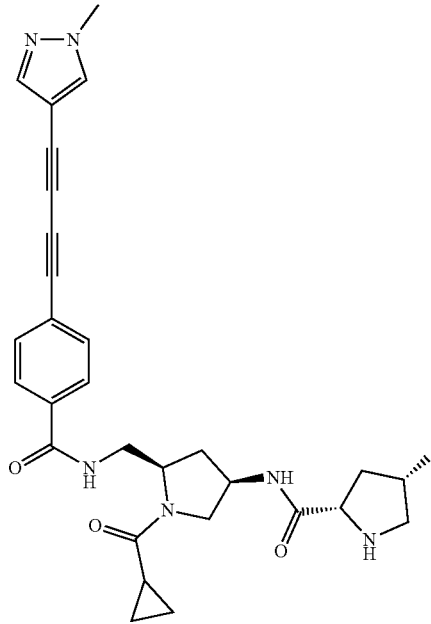 |
| I-34 | 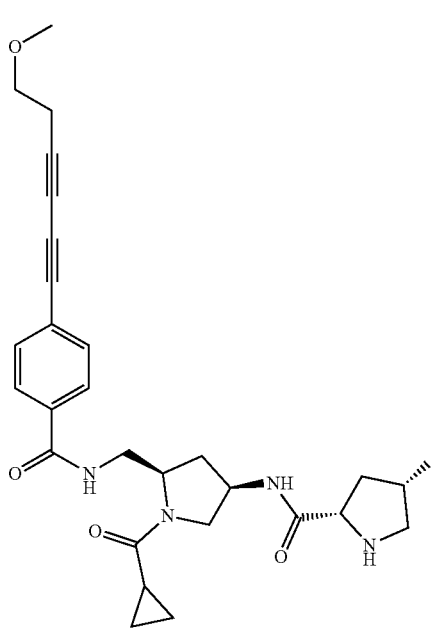 |

TABLE 1-continued
| Compound No. | Chemical Structure |
|---|---|
| I-35 | 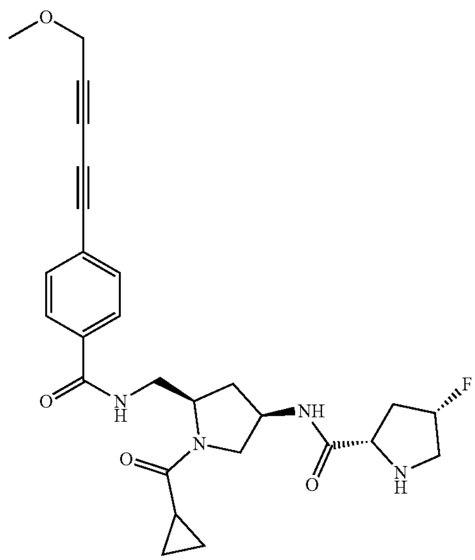 [SMILES: COCC#CC#Cc1ccc(C(=O)NC[C@H]2C[C@@H](NC(=O)[C@@H]3C[C@H](F)CN3)CN2C(=O)C2CC2)cc1] |
| I-36 | 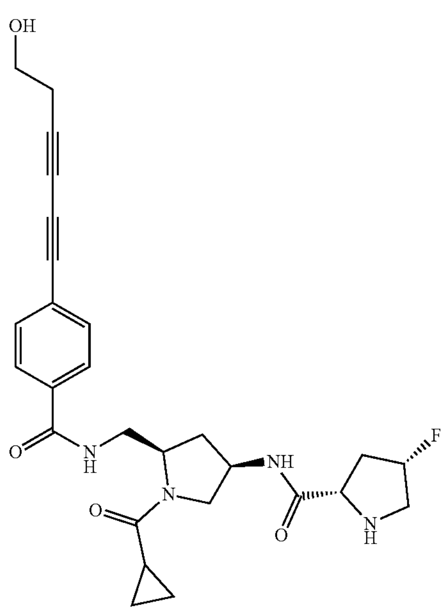 [SMILES: O=C(NC[C@H]1C[C@@H](NC(=O)[C@@H]2C[C@H](F)CN2)CN1C(=O)C1CC1)c1ccc(C#CC#CCCO)cc1] |
| I-37 | |
| I-38 | |
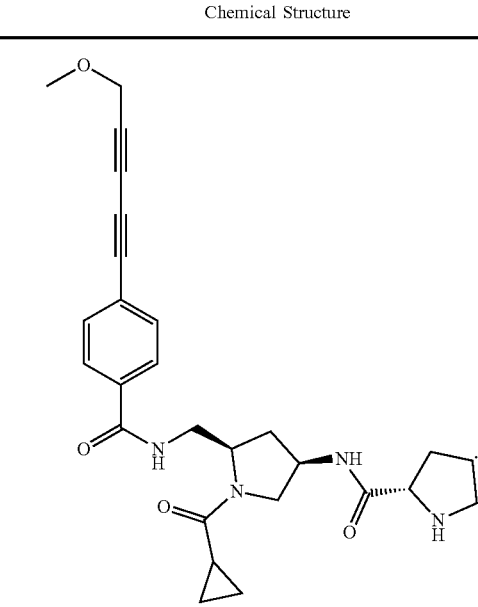

TABLE 1-continued
| Compound No. | Chemical Structure |
|---|---|
| I-39 | 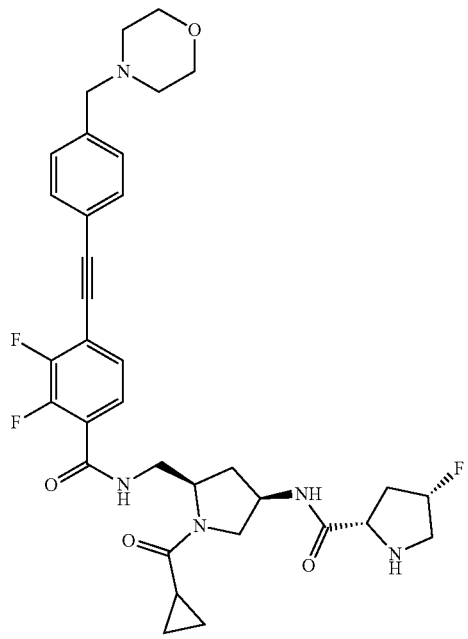 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)c(F)c1F] |
| I-40 | 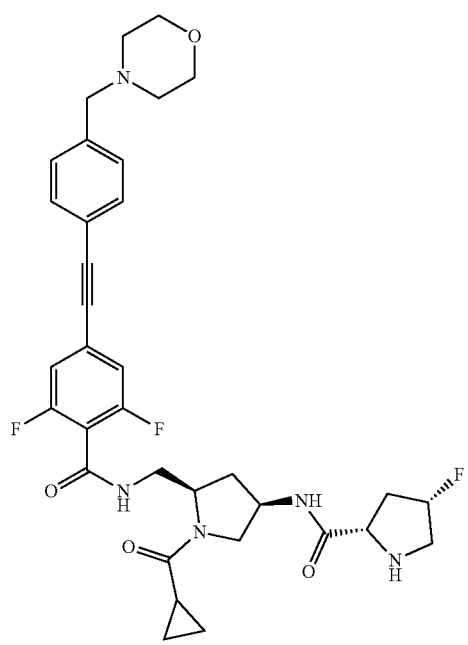 [SMILES: O=C(NC[C@H]1C[C@@H](NC(=O)[C@@H]2C[C@H](F)CN2)CN1C(=O)C1CC1)c1c(F)cc(C#Cc2ccc(CN3CCOCC3)cc2)cc1F] |
| I-41 | 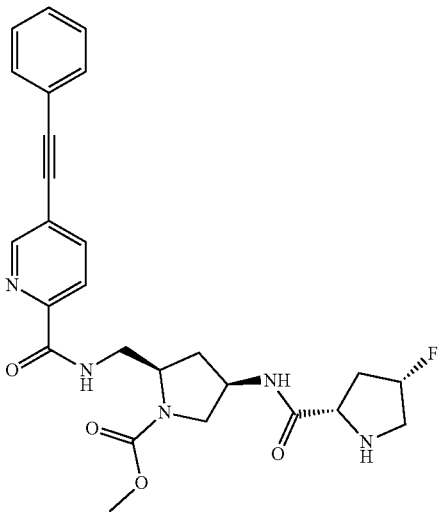 [SMILES: COC(=O)N1C[C@H](NC(=O)[C@@H]2C[C@H](F)CN2)C[C@@H]1CNC(=O)c1ccc(C#Cc2ccccc2)cn1] |
| I-42 | 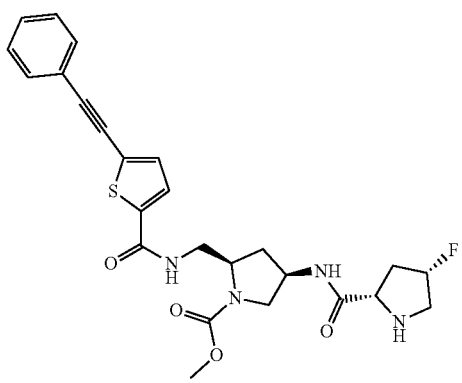 |
| I-43 | 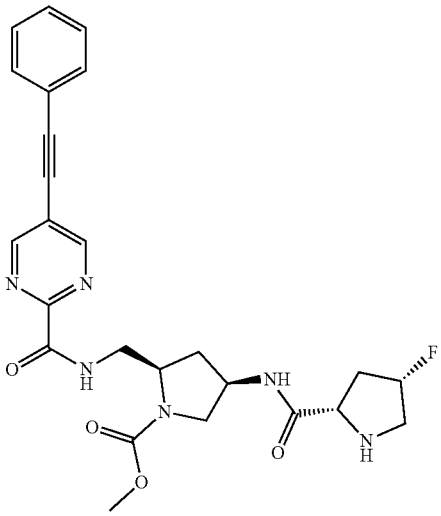 [SMILES: COC(=O)N1C[C@H](NC(=O)[C@@H]2C[C@H](F)CN2)C[C@@H]1CNC(=O)c1ncc(C#Cc2ccccc2)cn1] |

TABLE 1-continued

| Compound No. | Chemical Structure |
|---|---|
| I-44 | (structure) |
| I-45 | (structure) |
| I-46 | (structure) |
| I-47 | (structure) |
| I-48 | (structure) |

TABLE 1-continued
| Compound No. | Chemical Structure |
|---|---|
| I-49 | 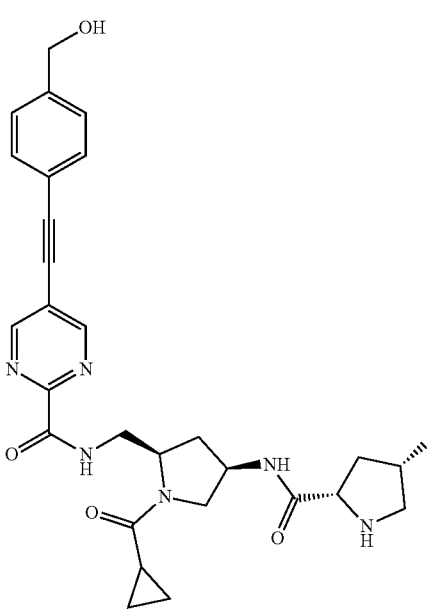 |
| I-50 | 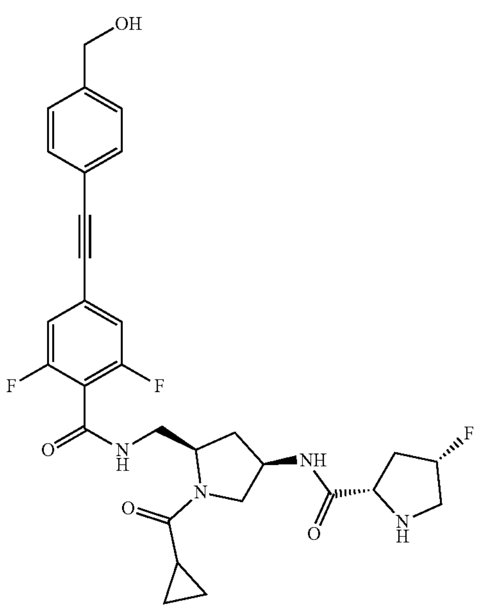 [SMILES: O=C(NC[C@H]1C[C@@H](NC(=O)[C@@H]2C[C@H](F)CN2)CN1C(=O)C1CC1)c1c(F)cc(C#Cc2ccc(CO)cc2)cc1F] |
| I-51 | |
| I-52 | |

TABLE 1-continued
| Compound No. | Chemical Structure |
|---|---|
| I-53 | 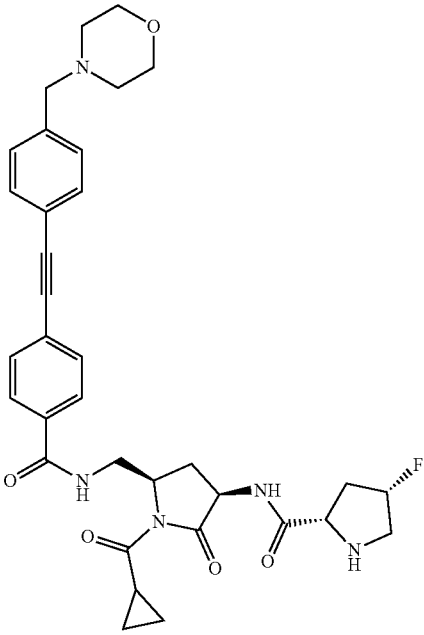 [SMILES: O=C(NC[C@H]1C[C@@H](NC(=O)[C@@H]2C[C@H](F)CN2)C(=O)N1C(=O)C1CC1)c1ccc(C#Cc2ccc(CN3CCOCC3)cc2)cc1] |
| I-54 | 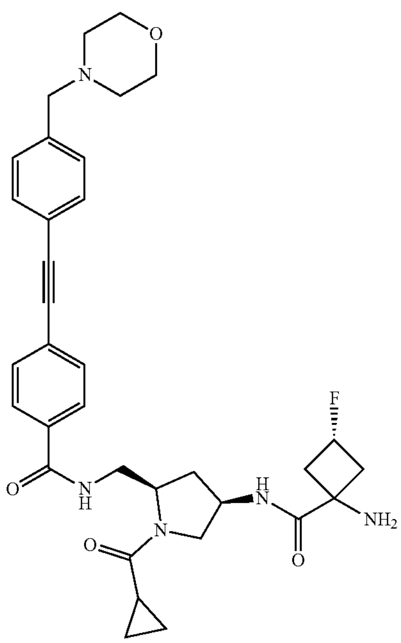 |
| I-55 | |
| I-56 | |

TABLE 1-continued

| Compound No. | Chemical Structure |
|---|---|
| I-57 | 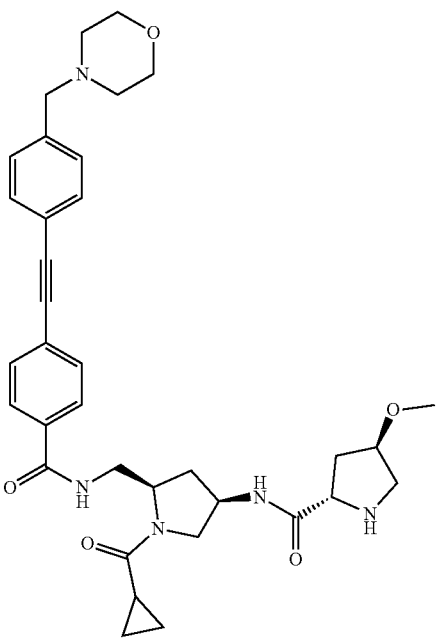 [SMILES: CO[C@H]1CN[C@H](C(=O)N[C@@H]2C[C@H](CNC(=O)c3ccc(C#Cc4ccc(CN5CCOCC5)cc4)cc3)N(C(=O)C3CC3)C2)C1] |
| I-58 | 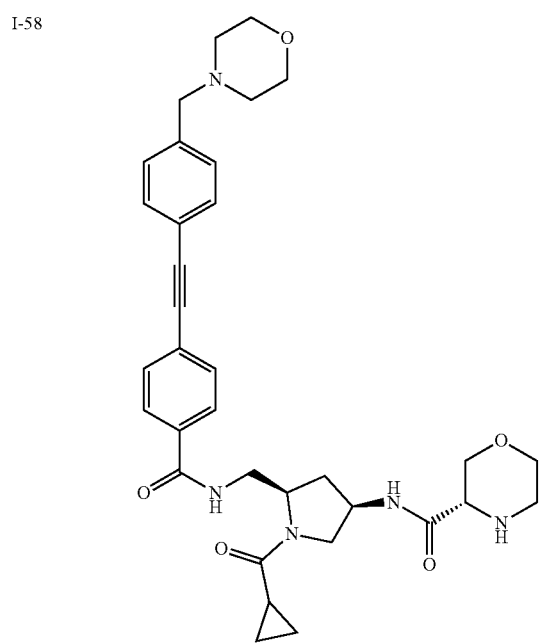 |
| I-59 | 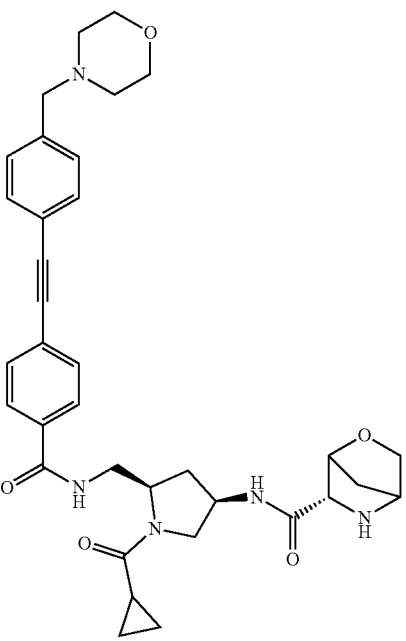 [SMILES: O=C(NC[C@H]1C[C@@H](NC(=O)[C@H]2NC3COC2C3)CN1C(=O)C1CC1)c1ccc(C#Cc2ccc(CN3CCOCC3)cc2)cc1] |

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

Scheme 1 illustrates a general method for preparing compounds of the type 11. Amine 1A is described in the literature. Acids 1B are described in the literature and/or are commercially available. Acyl chlorides, carboxylic acids, alkyl halides, chloroformates, carbamyl chlorides or sulfonyl chlorides 1E are described in the literature and/or are commercially available. Amines 1H are described in the literature and/or are commercially available or prepared under standard conditions. Reaction between amine 1A and acid 1B using amide coupling conditions (e.g., HATU or T₃P®) affords amide 1C. The Cbz protecting group in 1C can then be removed under hydrogenolysis conditions to afford amine 1D. Reaction between 1D and 1E under a variety of standard acylation, alkylation or sulfonylation conditions (including the use of coupling agents such as HATU and T₃P) provides 1F. The ester protecting group in 1F can then be removed under basic hydrolysis conditions to yield 1G. Amide coupling between amine 1H and acid 1G under amide coupling conditions (e.g., HATU or T₃P®) affords amide 11.

SCHEME 1.

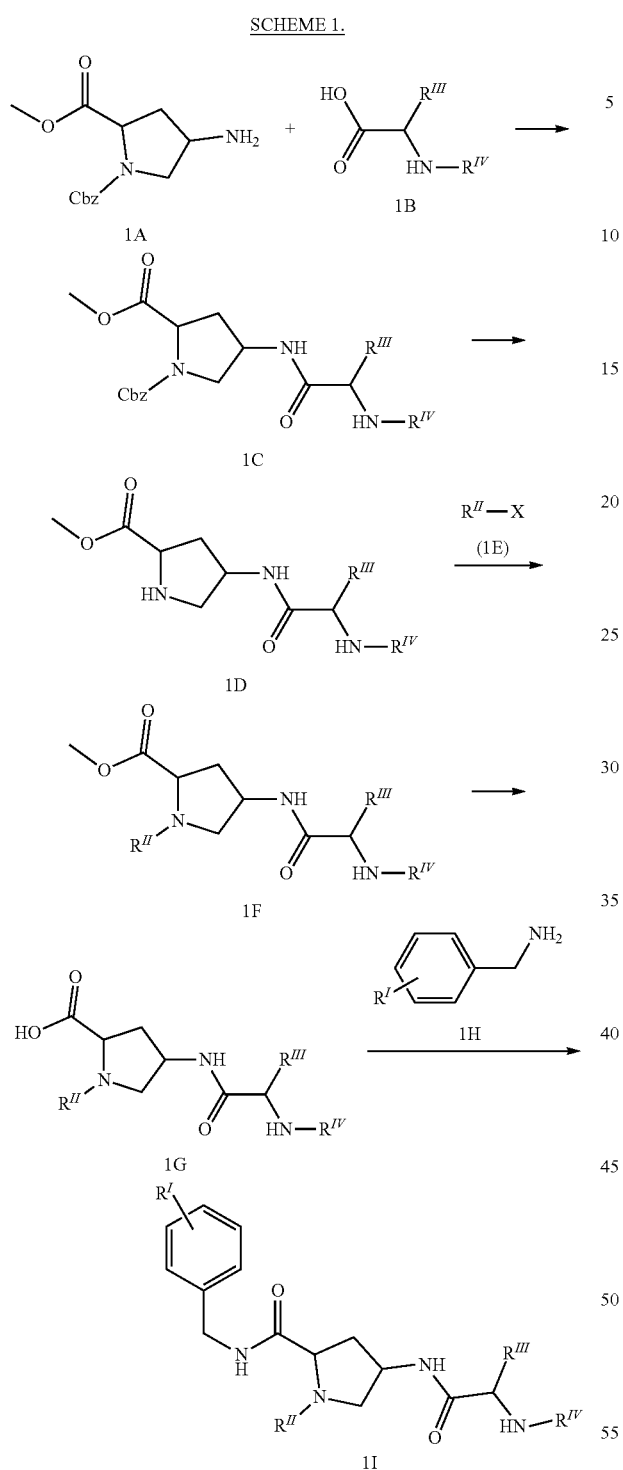

SCHEME 2.

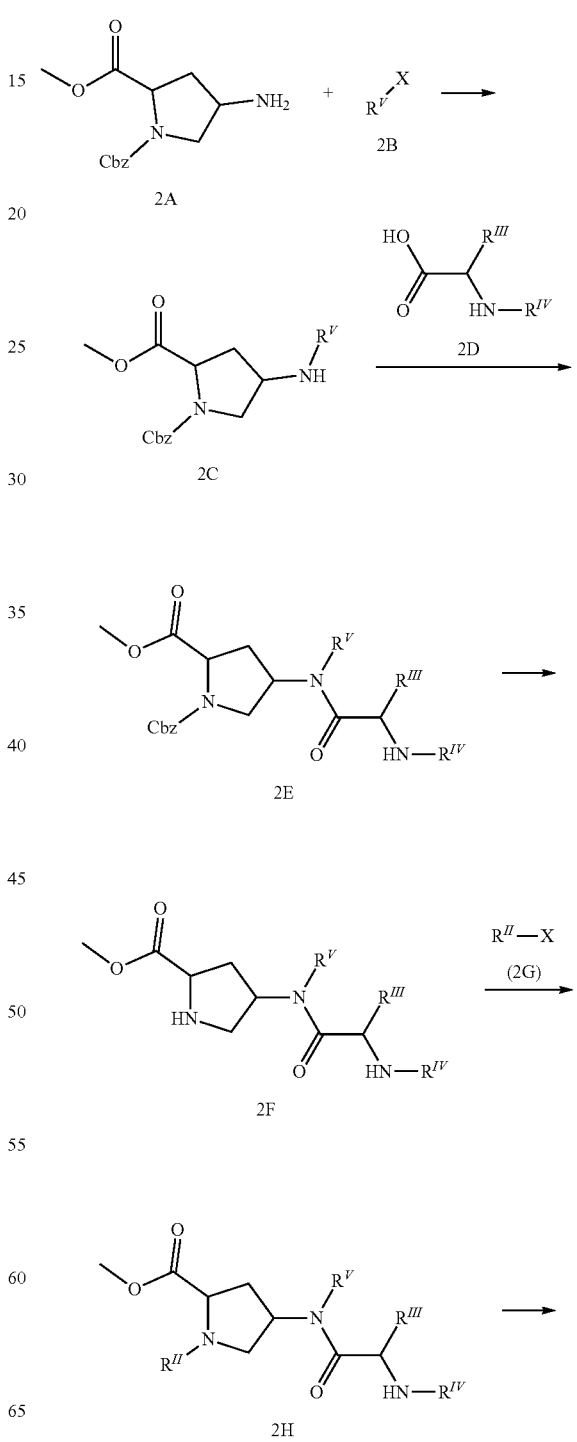

available or prepared under standard conditions. Reaction between primary amine 2A and alkyl halide 2B under standard alkylation conditions provides secondary amine 2C. Amide coupling between amine 2C and acid 2D under amide coupling conditions (e.g., HATU or T$_3$P®) affords amide 2E. The ester and carbamate groups in 2E can be converted to additional functional groups via the methodologies described above in connection with Scheme 1.

Scheme 2 illustrates a general method for preparing compounds of the type 2K. Amine 2A is described in the literature. Alkyl halides 2B are described in the literature and/or are commercially available. Acids 2D are described in the literature and/or are commercially available. Acyl chlorides, carboxylic acids, alkyl halides, chloroformates, carbamyl chlorides or sulfonyl chlorides 2G are described in the literature and/or are commercially available. Amines 2J are described in the literature and/or are commercially

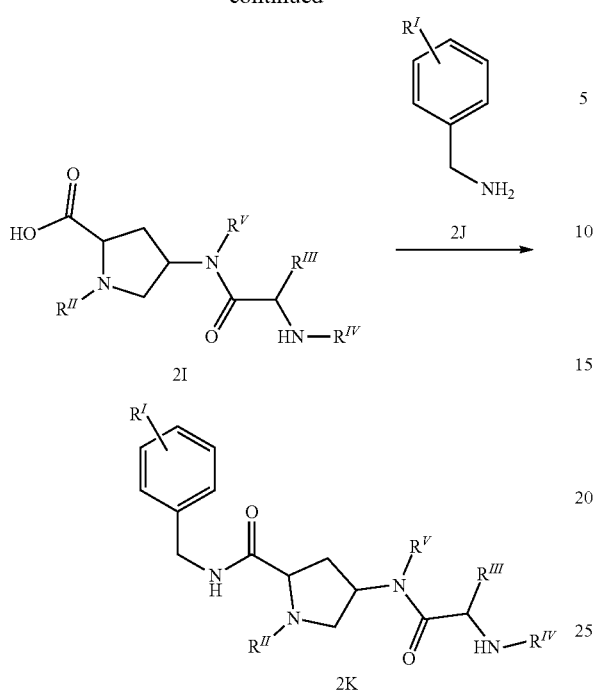

2I

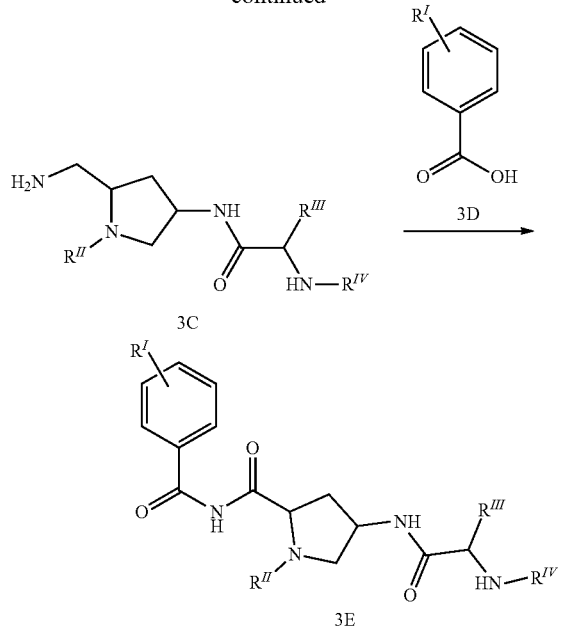

3C

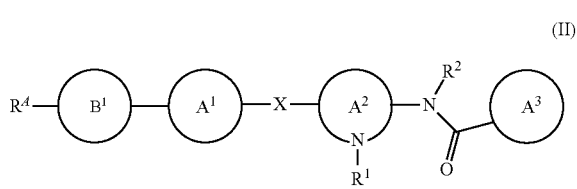

3E

2K

Scheme 3 illustrates a general method for preparing compounds of the type 3E. A general procedure for the preparation of esters 3A is given in Scheme 1. Acids 3D are described in the literature and/or are commercially available or prepared under standard conditions. Reduction of the ester moiety in 3A with lithium borohydride affords alcohol 3B. Alcohol 3B can be converted to amine 3C by either reaction with phthalimide under Mitsunobu conditions and subsequent deprotection; or by mesylation, displacement with azide and reduction. Amide coupling between acid 3D and amine 3C under amide coupling conditions (e.g., HATU or T₃P®) affords amide 3E.

SCHEME 3.

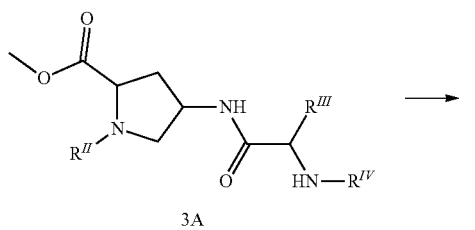

3A

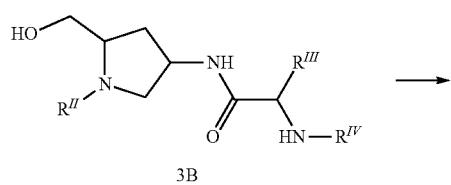

3B

If a functional group is not amenable to a reaction condition, it is envisioned that the functional group can first be protected under standard conditions and then the protecting group removed after completing the transformation.

Another aspect of the invention provides a compound represented by Formula II:

(II)

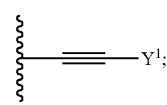

or a pharmaceutically acceptable salt thereof; wherein:
$A^1$ is 6-10 membered arylene or 5-10 membered heterocyclylene;
$A^2$ is a 4-10 membered aza-heterocyclylene;
$A^3$ is one of the following:
  a 4-10 membered aza-heterocyclyl optionally substituted with 1, 2, or 3 occurrences of $R^7$; or
  a 3-10 membered cycloalkyl substituted by (i) —N($R^3$)($R^4$) and (ii) 0, 1, 2, or 3 occurrences of $R^7$;
$B^1$ is a 3-10 membered cycloalkylene or 3-10 membered heterocyclylene;
X is —C(O)N($R^3$)—($C_{0-6}$ alkylene)-ψ or —($C_{0-6}$ alkylene)-N($R^3$)C(O)-ψ; wherein ψ is a bond to $A^2$;
$R^4$ is one of the following:
  3-6 membered carbocyclyl or 3-6 membered heterocyclyl, each of which is substituted with (i) 0, 1, or 2 occurrences of $R^6$ and (ii) 1 occurrence of $Y^1$; or

≡—$Y^1$;

Y¹ is —(C$_{0-6}$ alkylene)-(3-10 membered heterocyclyl), —(C$_{0-6}$ alkylene)-(3-10 membered carbocyclyl), —(C$_{0-6}$ alkylene)-CO$_2$R³, —(C$_{0-6}$ alkylene)-C(O)N(R³)(R⁴), —(C$_{0-6}$ alkylene)-N(R³)C(O)R⁴, —(C$_{0-6}$ alkylene)-N(R³)C(O)N(R³)(R⁴), —(C$_{0-6}$ alkylene)-N(R³)S(O)$_2$R⁴, —(C$_{0-6}$ alkylene)-S(O)$_2$N(R³)R⁴, C$_{1-6}$ hydroxyalkyl, —(C$_{1-6}$ alkylene)-N(R³)(R⁴), 3-7 membered heteroalkyl, 3-7 membered hydroxyl-heteroalkyl, —O—(C$_{1-6}$ alkylene)-CO$_2$R³, or hydrogen;

R¹ is —C(O)—R⁵, —CO$_2$—R⁵, —S(O)$_2$—R⁵, —C(O)N(R³)(R⁴), R⁵, or hydrogen;

R² is hydrogen, C$_{1-6}$ alkyl, —(C$_{0-6}$ alkylene)-(C$_{3-6}$ cycloalkyl), —(C$_{1-6}$ alkylene)-(C$_{1-6}$ alkoxyl), or —(C$_{1-6}$ alkylene)-CO$_2$R³;

R³ and R⁴ each represent independently for each occurrence hydrogen, C$_{1-6}$ alkyl, C$_{1-6}$ haloalkyl, or —(C$_{0-6}$ alkylene)-(C$_{3-6}$ cycloalkyl); or an occurrence of R³ and R⁴ attached to the same nitrogen atom are taken together with the nitrogen atom to which they are attached to form a heterocyclic ring;

R⁵ is —C$_{1-6}$ alkyl, —C$_{1-6}$ haloalkyl, —C$_{1-6}$ hydroxyalkyl, —(C$_{0-6}$ alkylene)-(3-7 membered heterocyclyl), —(C$_{0-6}$ alkylene)-(3-7 membered saturated carbocyclyl), —(C$_{1-6}$ alkylene)-N(R³)(R⁴%, —(C$_{1-6}$ alkylene)-(C$_{1-6}$ alkoxyl), —(C$_{1-6}$ alkylene)-CO$_2$R³, —(C$_{1-6}$ alkylene)-SO$_2$R³, or —(C$_{1-6}$ alkylene)-O—P(O)(OH)(R³);

R⁶ represents independently for each occurrence halogen, hydroxyl, C$_{1-6}$ alkyl, C$_{1-6}$ haloalkyl, C$_{1-6}$ hydroxyalkyl, C$_{1-6}$ alkoxyl, —(C$_{1-6}$ alkylene)-(C$_{1-6}$ alkoxyl), or cyano; and R⁷ represents independently for each occurrence halogen, hydroxyl, cyano, C$_{1-6}$ alkyl, C$_{1-6}$ haloalkyl, C$_{1-6}$ hydroxyalkyl, C$_{1-6}$ alkoxyl, —(C$_{1-6}$ alkylene)-(C$_{1-6}$ alkoxyl), —(C$_{0-6}$ alkylene)-N(R³)(R⁴), —(C$_{0-6}$ alkylene)-(C$_{3-7}$ cycloalkyl), or —(C$_{0-6}$ alkylene)-(4-10 membered heterocycloalkyl).

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is represented by Formula II.

In certain embodiments, A¹ is 6-10 membered arylene. In certain embodiments, A¹ is 6-membered arylene. In certain embodiments, A¹ is phenylene. In certain embodiments, A¹ is 5-10 membered heterocyclylene. In certain embodiments, A¹ is 5-6 membered heteroarylene.

In certain embodiments, A² is a 4-10 membered saturated aza-heterocyclylene. In certain embodiments, A² is a 4-6 membered saturated aza-heterocyclylene. In certain embodiments, A² is a 5-membered saturated aza-heterocyclylene. In certain embodiments, A² is pyrrolidinylene. In certain embodiments, A² is

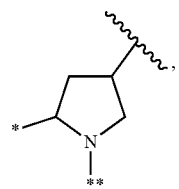

wherein * is a bond to X and ** is a bond to R¹. In certain embodiments, A² is

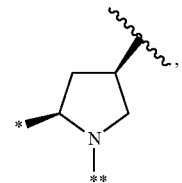

wherein * is a bond to X and ** is a bond to R¹.

In certain embodiments, A³ is a 4-10 membered aza-heterocyclyl optionally substituted with 1, 2, or 3 occurrences of R⁷. In certain embodiments, A³ is a 4-10 membered saturated aza-heterocyclyl optionally substituted with 1, 2, or 3 occurrences of R⁷. In certain embodiments, A³ is a 4-6 membered saturated aza-heterocyclyl optionally substituted with 1, 2, or 3 occurrences of R⁷. In certain embodiments, A³ is a 5-membered saturated aza-heterocyclyl optionally substituted with 1, 2, or 3 occurrences of R⁷. In certain embodiments, A³ is pyrrolidinyl optionally substituted with 1, 2, or 3 occurrences of R⁷. In certain embodiments, A³ is

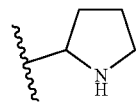

optionally substituted with 1, 2, or 3 occurrences of R⁷. In certain embodiments, A³ is

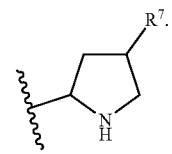

In certain embodiments, A³ is

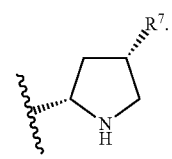

In certain embodiments, A³ is a 3-10 membered cycloalkyl substituted by (i) —N(R³)(R⁴) and (ii) 0, 1, 2, or 3 occurrences of R⁷.

In certain embodiments, B¹ is a 3-10 membered cycloalkylene. In certain embodiments, B¹ is a 4-6 membered cycloalkylene. In certain embodiments, B¹ is cyclobutylene. In certain embodiments, B¹ is a 3-10 membered heterocyclylene. In certain embodiments, B¹ is a 5-6 membered heteroarylene. In certain embodiments, B¹ is thiazolylene, thiophenylene, imidazolylene, pyrrolylene, or furanylene. In certain embodiments, B¹ is thiazolylene.

In certain embodiments, X is —C(O)N(R³)—(C$_{0-6}$ alkylene)-ψ. In certain embodiments, X is —C(O)N(R³)—

($C_{1-3}$ alkylene)-ψ. In certain embodiments, X is —C(O)N($R^3$)—($CH_2$)-ψ. In certain embodiments, X is —($C_{0-6}$ alkylene)-N($R^3$)C(O)-ψ. In certain embodiments, X is —($C_{1-3}$ alkylene)-N($R^3$)C(O)-ψ. In certain embodiments, X is —($CH_2$)—N($R^3$)C(O)-ψ.

In certain embodiments, $R^4$ is 3-6 membered carbocyclyl or 3-6 membered heterocyclyl, each of which is substituted with (i) 0, 1, or 2 occurrences of $R^6$ and (ii) 1 occurrence of $Y^1$. In certain embodiments, $R^4$ is phenyl or 5-6 membered heteroaryl substituted with (i) 0, 1, or 2 occurrences of $R^6$ and (ii) 1 occurrence of $Y^1$.

In certain embodiments, $R^4$ is 3-6 membered carbocyclyl substituted with (i) 0, 1, or 2 occurrences of $R^6$ and (ii) 1 occurrence of $Y^1$. In certain embodiments, $R^4$ is phenyl substituted with (i) 0, 1, or 2 occurrences of $R^6$ and (ii) 1 occurrence of $Y^1$. In certain embodiments, $R^4$ is phenyl substituted with 1 occurrence of $Y^1$.

In certain embodiments, $R^4$ is 3-6 membered heterocyclyl substituted with (i) 0, 1, or 2 occurrences of $R^6$ and (ii) 1 occurrence of $Y^1$. In certain embodiments, $R^4$ is 5-6 membered heteroaryl substituted with (i) 0, 1, or 2 occurrences of $R^6$ and (ii) 1 occurrence of $Y^1$. In certain embodiments, $R^4$ is 5-6 membered heteroaryl substituted with 1 occurrence of $Y^1$.

In certain embodiments, $R^4$ is

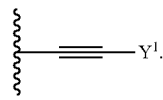

In certain embodiments, $Y^1$ is —($C_{0-6}$ alkylene)-(3-10 membered heterocyclyl) or —($C_{0-6}$ alkylene)-(3-10 membered carbocyclyl). In certain embodiments, $Y^1$ is —($C_{1-3}$ alkylene)-(3-10 membered saturated heterocyclyl). In certain embodiments, $Y^1$ is —($C_{1-3}$ alkylene)-(5-6 membered saturated heterocyclyl). In certain embodiments, $Y^1$ is —($C_{1-3}$ alkylene)-(5-6 membered saturated heterocyclyl selected from the group consisting of morpholinyl, piperidinyl, piperazinyl, tetrahydropyranyl, pyrrolidinyl, oxazolidinyl, and imidazolidinyl, each of which is optionally substituted with 1, 2, or 3 substituents independently selected from the group consisting of halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), and cyano). In certain embodiments, $Y^1$ is —($C_{1-3}$ alkylene)-(morpholinyl optionally substituted with 1 or 2 substituents independently selected from the group consisting of halogen, hydroxyl, $C_{1-6}$ alkyl, $C_{1-6}$ haloalkyl, $C_{1-6}$ hydroxyalkyl, and $C_{1-6}$ alkoxyl). In certain embodiments, $Y^1$ is —($C_{1-3}$ alkylene)-(morpholinyl).

In certain embodiments, $Y^1$ is —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, —($C_{1-6}$ alkylene)-N($R^3$)($R^4$), 3-7 membered heteroalkyl, or hydrogen. In certain embodiments, $Y^1$ is —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, or —($C_{1-6}$ alkylene)-N($R^3$)($R^4$). In certain embodiments, $Y^1$ is —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, —($C_{1-6}$ alkylene)-N($R^3$)($R^4$), or 3-7 membered hydroxylheteroalkyl. In certain embodiments, $Y^1$ is —($C_{0-6}$ alkylene)-$CO_2R^3$. In certain embodiments, $Y^1$ is —($C_{0-6}$ alkylene)-C(O)N($R^3$)($R^4$). In certain embodiments, $Y^1$ is —($C_{0-6}$ alkylene)-N($R^3$)C(O)$R^4$. In certain embodiments, $Y^1$ is —($C_{0-6}$ alkylene)-N($R^3$)C(O)N($R^3$)($R^4$). In certain embodiments, $Y^1$ is —($C_{0-6}$ alkylene)-N($R^3$)S(O)$_2R^4$. In certain embodiments, $Y^1$ is —($C_{0-6}$ alkylene)-S(O)$_2$N($R^3$)$R^4$. In certain embodiments, $Y^1$ is $C_{1-6}$ hydroxyalkyl. In certain embodiments, $Y^1$ is —($C_{1-6}$ alkylene)-N($R^3$)($R^4$). In certain embodiments, $Y^1$ is 3-7 membered heteroalkyl In certain embodiments, $Y^1$ is hydrogen.

In certain embodiments, $Y^1$ is —($C_{0-6}$ alkylene)-(3-10 membered carbocyclyl). In certain embodiments, $Y^1$ is —($C_{0-6}$ alkylene)-(3-6 membered saturated carbocyclyl). In certain embodiments, $Y^1$ is cyclopropyl.

In certain embodiments, $R^1$ is —C(O)—$R^5$. In certain embodiments, $R^1$ is —$CO_2$—$R^5$ or —S(O)$_2$—$R^5$. In certain embodiments, $R^1$ is —$CO_2$—$R^5$. In certain embodiments, $R^1$ is —S(O)$_2$—$R^5$. In certain embodiments, $R^1$ is —C(O)N($R^3$)($R^4$). In certain embodiments, $R^1$ is $R^5$.

In certain embodiments, $R^2$ is hydrogen. In certain embodiments, $R^2$ is $C_{1-6}$ alkyl. In certain embodiments, $R^2$ is —($C_{0-6}$ alkylene)-($C_{3-6}$ cycloalkyl).

In certain embodiments, $R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl). In certain embodiments, $R^3$ and $R^4$ each represent independently for each occurrence hydrogen, $C_{1-6}$ alkyl, or $C_{1-6}$ haloalkyl. In certain embodiments, an occurrence of $R^3$ and $R^4$ attached to the same nitrogen atom are taken together with the nitrogen atom to which they are attached to form a heterocyclic ring.

In certain embodiments, $R^5$ is —$C_{1-6}$ alkyl or —($C_{0-6}$ alkylene)-(3-7 membered cycloalkyl). In certain embodiments, $R^5$ is —$C_{1-6}$ alkyl or -(3-7 membered cycloalkyl). In certain embodiments, $R^5$ is —$C_{1-6}$ alkyl. In certain embodiments, $R^5$ is —$C_{1-6}$ haloalkyl. In certain embodiments, $R^5$ is —($C_{0-6}$ alkylene)-(3-7 membered heterocyclyl). In certain embodiments, $R^5$ is —($C_{0-6}$ alkylene)-(3-7 membered saturated carbocyclyl). In certain embodiments, $R^5$ is -(3-7 membered cycloalkyl). In certain embodiments, $R^5$ is —($C_{1-6}$ alkylene)-N($R^3$)($R^4$). In certain embodiments, $R^5$ is —($C_{1-6}$ alkylene)-O—P(O)(OH)($R^3$). In certain embodiments, $R^5$ is -(3-7 membered cycloalkylene)-O—P(O)(OH)($R^3$).

In certain embodiments, $R^6$ represents independently for each occurrence halogen or $C_{1-6}$ alkyl.

In certain embodiments, $R^7$ represents independently for each occurrence halogen, hydroxyl, cyano, $C_{1-6}$ alkyl, or $C_{1-6}$ haloalkyl. $R^7$ represents independently for each occurrence halogen, hydroxyl, or cyano. In certain embodiments, $R^7$ represents independently for each occurrence halogen or cyano. In certain embodiments, $R^7$ is halogen. In certain embodiments, $R^7$ is fluoro. In certain embodiments, $R^7$ represents independently for each occurrence fluoro or cyano. In certain embodiments, $R^7$ is cyano.

The description above describes multiple embodiments relating to compounds of Formula II. The patent application specifically contemplates all combinations of the embodiments.

Another aspect of the invention provides a compound represented by Formula II-A:

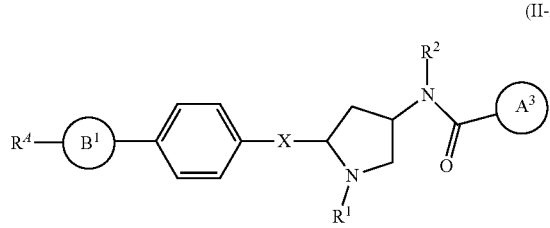

(II-A)

or a pharmaceutically acceptable salt thereof; wherein:
$A^3$ is 4-7 membered aza-heterocyclyl optionally substituted with 1, 2, or 3 occurrences of $R^7$;
$B^1$ is a 3-10 membered cycloalkylene or 3-10 membered heterocyclylene; X is $-C(O)N(R^3)-(C_{1-3}$ alkylene)-ψ or $-(C_{1-3}$ alkylene)-$N(R^3)C(O)$-ψ; wherein ψ is a bond to the pyrrolidinyl group;
$R^4$ is one of the following:
  phenyl or 5-6 membered heteroaryl substituted with (i) 0, 1, or 2 occurrences of $R^6$ and (ii) 1 occurrence of $Y^1$; or

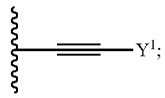

$Y^1$ is $-(C_{0-6}$ alkylene)-(3-10 membered heterocyclyl), $-(C_{0-6}$ alkylene)-(3-10 membered carbocyclyl), $-(C_{0-6}$ alkylene)-$CO_2R^3$, $-(C_{0-6}$ alkylene)-$C(O)N(R^3)(R^4)$, $-(C_{0-6}$ alkylene)-$N(R^3)C(O)R^4$, $-(C_{0-6}$ alkylene)-$N(R^3)C(O)N(R^3)(R^4)$, $-(C_{0-6}$ alkylene)-$N(R^3)S(O)_2R^4$, $-(C_{0-6}$ alkylene)-$S(O)_2N(R^3)R^4$, $C_{1-6}$ hydroxyalkyl, 3-7 membered hydroxyl-heteroalkyl, or $-(C_{1-6}$ alkylene)-$N(R^3)(R^4)$;
$R^1$ is $-C(O)-R^5$, $-CO_2-R^5$, or $-S(O)_2-R^5$;
$R^2$ is hydrogen, $C_{1-6}$ alkyl, or $-(C_{0-6}$ alkylene)-($C_{3-6}$ cycloalkyl);
$R^3$ and $R^4$ each represent independently for each occurrence hydrogen, $C_{1-6}$ alkyl, $C_{1-6}$ haloalkyl, or $-(C_{0-6}$ alkylene)-($C_{3-6}$ cycloalkyl); or an occurrence of $R^3$ and $R^4$ attached to the same nitrogen atom are taken together with the nitrogen atom to which they are attached to form a heterocyclic ring;
$R^5$ is $-C_{1-6}$ alkyl, $-C_{1-6}$ haloalkyl, $-(C_{0-6}$ alkylene)-(3-7 membered heterocyclyl), $-(C_{0-6}$ alkylene)-(3-7 membered saturated carbocyclyl), or $-(C_{1-6}$ alkylene)-$N(R^3)(R^4)$;
$R^6$ represents independently for each occurrence halogen, hydroxyl, $C_{1-6}$ alkyl, $C_{1-6}$ haloalkyl, $C_{1-6}$ hydroxyalkyl, $C_{1-6}$ alkoxyl, $-(C_{1-6}$ alkylene)-($C_{1-6}$ alkoxyl), or cyano; and
$R^7$ represents independently for each occurrence halogen, hydroxyl, cyano, $C_{1-6}$ alkyl, $C_{1-6}$ haloalkyl, $C_{1-6}$ hydroxyalkyl, $C_{1-6}$ alkoxyl, $-(C_{1-6}$ alkylene)-($C_{1-6}$ alkoxyl), or $-(C_{0-6}$ alkylene)-$N(R^3)(R^4)$.

The definitions of variables in Formula II-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is represented by Formula II-A.

In certain embodiments, $A^3$ is a 5-membered saturated aza-heterocyclyl optionally substituted with 1, 2, or 3 occurrences of $R^7$. In certain embodiments, $A^3$ is pyrrolidinyl optionally substituted with 1, 2, or 3 occurrences of $R^7$. In certain embodiments, $A^3$ is

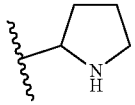

optionally substituted with 1, 2, or 3 occurrences of $R^7$. In certain embodiments, $A^3$ is

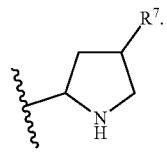

In certain embodiments, $A^3$ is

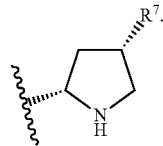

In certain embodiments, $B^1$ is a 3-10 membered cycloalkylene. In certain embodiments, $B^1$ is a 4-6 membered cycloalkylene. In certain embodiments, $B^1$ is cyclobutylene. In certain embodiments, $B^1$ is a 3-10 membered heterocyclylene. In certain embodiments, $B^1$ is a 5-6 membered heteroarylene. In certain embodiments, $B^1$ is thiazolylene, thiophenylene, imidazolylene, pyrrolylene, or furanylene. In certain embodiments, $B^1$ is thiazolylene.

In certain embodiments, X is $-C(O)N(R^3)-(C_{1-3}$ alkylene)-ψ. In certain embodiments, X is $-C(O)N(R^3)-(CH_2)$-ψ. In certain embodiments, X is $-(C_{1-3}$ alkylene)-$N(R^3)C(O)$-ψ. In certain embodiments, X is $-(CH_2)-N(R^3)C(O)$-ψ.

In certain embodiments, $R^1$ is $-C(O)-R^5$. In certain embodiments, $R^1$ is $-CO_2-R^5$ or $-S(O)_2-R^5$. In certain embodiments, $R^1$ is $-CO_2-R^5$. In certain embodiments, $R^1$ is $-S(O)_2-R^5$.

In certain embodiments, $R^4$ is phenyl or 5-6 membered heteroaryl substituted with (i) 0, 1, or 2 occurrences of $R^6$ and (ii) 1 occurrence of $Y^1$. In certain embodiments, $R^4$ is phenyl substituted with (i) 0, 1, or 2 occurrences of $R^6$ and (ii) 1 occurrence of $Y^1$. In certain embodiments, $R^4$ is phenyl substituted with 1 occurrence of $Y^1$. In certain embodiments, $R^4$ is 5-6 membered heteroaryl substituted with (i) 0, 1, or 2 occurrences of $R^6$ and (ii) 1 occurrence of $Y^1$. In certain embodiments, $R^4$ is 5-6 membered heteroaryl substituted with 1 occurrence of $Y^1$. In certain embodiments, $R^4$ is

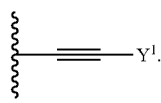

In certain embodiments, $Y^1$ is —($C_{0-6}$ alkylene)-(3-10 membered heterocyclyl) or —($C_{0-6}$ alkylene)-(3-10 membered carbocyclyl). In certain embodiments, $Y^1$ is —($C_{1-3}$ alkylene)-(3-10 membered saturated heterocyclyl). In certain embodiments, $Y^1$ is —($C_{1-3}$ alkylene)-(5-6 membered saturated heterocyclyl). In certain embodiments, $Y^1$ is —($C_{1-3}$ alkylene)-(5-6 membered saturated heterocyclyl selected from the group consisting of morpholinyl, piperidinyl, piperazinyl, tetrahydropyranyl, pyrrolidinyl, oxazolidinyl, and imidazolidinyl, each of which is optionally substituted with 1, 2, or 3 substituents independently selected from the group consisting of halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), and cyano). In certain embodiments, $Y^1$ is —($C_{1-3}$ alkylene)-(morpholinyl optionally substituted with 1 or 2 substituents independently selected from the group consisting of halogen, hydroxyl, $C_{1-6}$ alkyl, $C_{1-6}$ haloalkyl, $C_{1-6}$ hydroxyalkyl, and $C_{1-6}$ alkoxyl). In certain embodiments, $Y^1$ is —($C_{1-3}$ alkylene)-(morpholinyl).

In certain embodiments, $Y^1$ is —($C_{0-6}$ alkylene)-$CO_2R^3$, —($C_{0-6}$ alkylene)-$C(O)N(R^3)(R^4)$, —($C_{0-6}$ alkylene)-$N(R^3)C(O)R^4$, —($C_{0-6}$ alkylene)-$N(R^3)C(O)N(R^3)(R^4)$, —($C_{0-6}$ alkylene)-$N(R^3)S(O)_2R^4$, —($C_{0-6}$ alkylene)-$S(O)_2N(R^3)R^4$, $C_{1-6}$ hydroxyalkyl, or —($C_{0-6}$ alkylene)-$N(R^3)(R^4)$. In certain embodiments, $Y^1$ is —($C_{0-6}$ alkylene)-$CO_2R^3$. In certain embodiments, $Y^1$ is —($C_{0-6}$ alkylene)-$C(O)N(R^3)(R^4)$. In certain embodiments, $Y^1$ is —($C_{0-6}$ alkylene)-$N(R^3)C(O)R^4$. In certain embodiments, $Y^1$ is —($C_{0-6}$ alkylene)-$N(R^3)C(O)N(R^3)(R^4)$. In certain embodiments, $Y^1$ is —($C_{0-6}$ alkylene)-$N(R^3)S(O)_2R^4$. In certain embodiments, $Y^1$ is —($C_{0-6}$ alkylene)-$S(O)_2N(R^3)R^4$. In certain embodiments, $Y^1$ is $C_{1-6}$ hydroxyalkyl. In certain embodiments, $Y^1$ is —($C_{1-6}$ alkylene)-$N(R^3)(R^4)$. In certain embodiments, $Y^1$ is 3-7 membered hydroxyl-heteroalkyl.

In certain embodiments, $Y^1$ is —($C_{0-6}$ alkylene)-(3-10 membered carbocyclyl). In certain embodiments, $Y^1$ is —($C_{0-6}$ alkylene)-(3-6 membered saturated carbocyclyl). In certain embodiments, $Y^1$ is cyclopropyl.

In certain embodiments, $R^2$ is hydrogen. In certain embodiments, $R^2$ is $C_{1-6}$ alkyl. In certain embodiments, $R^2$ is —($C_{0-6}$ alkylene)-($C_{3-6}$ cycloalkyl).

In certain embodiments, $R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl). In certain embodiments, $R^3$ and $R^4$ each represent independently for each occurrence hydrogen, $C_{1-6}$ alkyl, or $C_{1-6}$ haloalkyl. In certain embodiments, an occurrence of $R^3$ and $R^4$ attached to the same nitrogen atom are taken together with the nitrogen atom to which they are attached to form a heterocyclic ring.

In certain embodiments, $R^5$ is —$C_{1-6}$ alkyl or —($C_{0-6}$ alkylene)-(3-7 membered cycloalkyl). In certain embodiments, $R^5$ is —$C_{1-6}$ alkyl or -(3-7 membered cycloalkyl). In certain embodiments, $R^5$ is —$C_{1-6}$ alkyl. In certain embodiments, $R^5$ is —$C_{1-6}$ haloalkyl. In certain embodiments, $R^5$ is —($C_{0-6}$ alkylene)-(3-7 membered heterocyclyl). In certain embodiments, $R^5$ is —($C_{0-6}$ alkylene)-(3-7 membered saturated carbocyclyl). In certain embodiments, $R^5$ is —($C_{1-6}$ alkylene)-$N(R^3)(R^4)$.

In certain embodiments, $R^6$ represents independently for each occurrence halogen or $C_{1-6}$ alkyl.

In certain embodiments, $R^7$ represents independently for each occurrence halogen, hydroxyl, cyano, $C_{1-6}$ alkyl, or $C_{1-6}$ haloalkyl. In certain embodiments, $R^7$ represents independently for each occurrence halogen, hydroxyl, or cyano. In certain embodiments, $R^7$ represents independently for each occurrence halogen or cyano. In certain embodiments, $R^7$ is halogen. In certain embodiments, $R^7$ is fluoro. In certain embodiments, $R^7$ represents independently for each occurrence fluoro or cyano. In certain embodiments, $R^7$ is cyano.

The description above describes multiple embodiments relating to compounds of Formula II-A. The patent application specifically contemplates all combinations of the embodiments.

Another aspect of the invention provides a compound represented by Formula II-B:

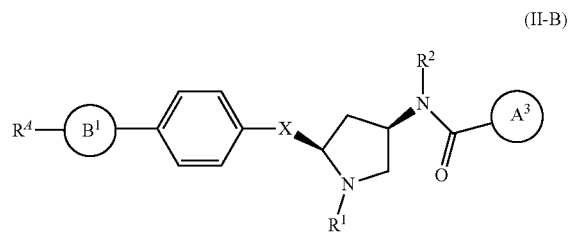

(II-B)

or a pharmaceutically acceptable salt thereof; wherein:
$A^3$ is 4-7 membered aza-heterocyclyl optionally substituted with 1, 2, or 3 occurrences of $R^7$;
$B^1$ is a 3-10 membered cycloalkylene or 3-10 membered heterocyclylene;
X is —$C(O)N(R^3)$—($C_{1-3}$ alkylene)-ψ or —($C_{1-3}$ alkylene)-$N(R^3)C(O)$-ψ; wherein ψ is a bond to the pyrrolidinyl group;
$R^4$ is one of the following:
  phenyl or 5-6 membered heteroaryl substituted with (i) 0, 1, or 2 occurrences of $R^6$ and (ii) 1 occurrence of $Y^1$; or

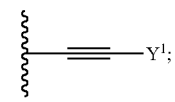

$Y^1$ is —($C_{0-6}$ alkylene)-(3-10 membered heterocyclyl), —($C_{0-6}$ alkylene)-(3-10 membered carbocyclyl), —($C_{0-6}$ alkylene)-$CO_2R^3$, —($C_{0-6}$ alkylene)-$C(O)N(R^3)(R^4)$, —($C_{0-6}$ alkylene)-$N(R^3)C(O)R^4$, —($C_{0-6}$ alkylene)-$N(R^3)C(O)N(R^3)(R^4)$, —($C_{0-6}$ alkylene)-$N(R^3)S(O)_2R^4$, —($C_{0-6}$ alkylene)-$S(O)_2N(R^3)R^4$, $C_{1-6}$ hydroxyalkyl, 3-7 membered hydroxyl-heteroalkyl, or —($C_{1-6}$ alkylene)-$N(R^3)(R^4)$;
$R^1$ is —$C(O)$—$R^5$, —$CO_2$—$R^5$, or —$S(O)_2$—$R^5$;
$R^2$ is hydrogen, $C_{1-6}$ alkyl, or —($C_{0-6}$ alkylene)-($C_{3-6}$ cycloalkyl);
$R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl); or an occurrence of $R^3$ and $R^4$ attached to the same nitrogen atom are taken together with the nitrogen atom to which they are attached to form a heterocyclic ring;
$R^5$ is —$C_{1-6}$ alkyl, —$C_{1-6}$ haloalkyl, —($C_{0-6}$ alkylene)-(3-7 membered heterocyclyl), —($C_{0-6}$ alkylene)-(3-7 membered saturated carbocyclyl), or —($C_{1-6}$ alkylene)-$N(R^3)(R^4)$;

$R^6$ represents independently for each occurrence halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or cyano; and $R^7$ represents independently for each occurrence halogen, hydroxyl, cyano, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or —($C_{0-6}$ alkylene)-N($R^3$)($R^4$).

The definitions of variables in Formula II-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is represented by Formula II-B.

In certain embodiments, $A^3$ is a 5-membered saturated aza-heterocyclyl optionally substituted with 1, 2, or 3 occurrences of $R^7$. In certain embodiments, $A^3$ is pyrrolidinyl optionally substituted with 1, 2, or 3 occurrences of $R^7$. In certain embodiments, $A^3$ is

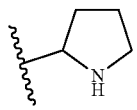

optionally substituted with 1, 2, or 3 occurrences of $R^7$. In certain embodiments, $A^3$ is

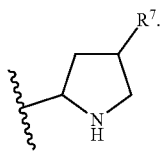

In certain embodiments, $A^3$ is

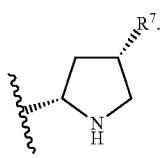

In certain embodiments, $B^1$ is a 3-10 membered cycloalkylene. In certain embodiments, $B^1$ is a 4-6 membered cycloalkylene. In certain embodiments, $B^1$ is cyclobutylene. In certain embodiments, $B^1$ is a 3-10 membered heterocyclylene. In certain embodiments, $B^1$ is a 5-6 membered heteroarylene. In certain embodiments, $B^1$ is thiazolylene, thiophenylene, imidazolylene, pyrrolylene, or furanylene. In certain embodiments, $B^1$ is thiazolylene.

In certain embodiments, X is —C(O)N($R^3$)—($C_{1-3}$ alkylene)-ψ. In certain embodiments, X is —C(O)N($R^3$)—(CH$_2$)-ψ. In certain embodiments, X is —($C_{1-3}$ alkylene)-N($R^3$)C(O)-ψ. In certain embodiments, X is —(CH$_2$)—N($R^3$)C(O)-ψ.

In certain embodiments, $R^1$ is —C(O)—$R^5$. In certain embodiments, $R^1$ is —CO$_2$—$R^5$ or —S(O)$_2$—$R^5$. In certain embodiments, $R^1$ is —CO$_2$—$R^5$. In certain embodiments, $R^1$ is —S(O)$_2$—$R^5$.

In certain embodiments, $R^4$ is phenyl or 5-6 membered heteroaryl substituted with (i) 0, 1, or 2 occurrences of $R^6$ and (ii) 1 occurrence of $Y^1$. In certain embodiments, $R^4$ is phenyl substituted with (i) 0, 1, or 2 occurrences of $R^6$ and (ii) 1 occurrence of $Y^1$. In certain embodiments, $R^4$ is phenyl substituted with 1 occurrence of $Y^1$. In certain embodiments, $R^4$ is 5-6 membered heteroaryl substituted with (i) 0, 1, or 2 occurrences of $R^6$ and (ii) 1 occurrence of $Y^1$. In certain embodiments, $R^4$ is 5-6 membered heteroaryl substituted with 1 occurrence of $Y^1$. In certain embodiments, $R^4$ is

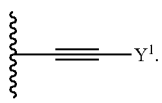

In certain embodiments, $Y^1$ is —($C_{0-6}$ alkylene)-(3-10 membered heterocyclyl) or —($C_{0-6}$ alkylene)-(3-10 membered carbocyclyl). In certain embodiments, $Y^1$ is —($C_{1-3}$ alkylene)-(3-10 membered saturated heterocyclyl). In certain embodiments, $Y^1$ is —($C_{1-3}$ alkylene)-(5-6 membered saturated heterocyclyl). In certain embodiments, $Y^1$ is —($C_{1-3}$ alkylene)-(5-6 membered saturated heterocyclyl selected from the group consisting of morpholinyl, piperidinyl, piperazinyl, tetrahydropyranyl, pyrrolidinyl, oxazolidinyl, and imidazolidinyl, each of which is optionally substituted with 1, 2, or 3 substituents independently selected from the group consisting of halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), and cyano). In certain embodiments, $Y^1$ is —($C_{1-3}$ alkylene)-(morpholinyl optionally substituted with 1 or 2 substituents independently selected from the group consisting of halogen, hydroxyl, $C_{1-6}$ alkyl, $C_{1-6}$ haloalkyl, $C_{1-6}$ hydroxyalkyl, and $C_{1-6}$ alkoxyl). In certain embodiments, $Y^1$ is —($C_{1-3}$ alkylene)-(morpholinyl).

In certain embodiments, $Y^1$ is —($C_{0-6}$ alkylene)-CO$_2$$R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2$$R^4$, —($C_{0-6}$ alkylene)-S(O)$_2$N($R^3$)$R^4$, $C_{1-6}$ hydroxyalkyl, or —($C_{1-6}$ alkylene)-N($R^3$)($R^4$). In certain embodiments, $Y^1$ is —($C_{0-6}$ alkylene)-CO$_2$$R^3$. In certain embodiments, $Y^1$ is —($C_{0-6}$ alkylene)-C(O)N($R^3$)($R^4$). In certain embodiments, $Y^1$ is —($C_{0-6}$ alkylene)-N($R^3$)C(O)$R^4$. In certain embodiments, $Y^1$ is —($C_{0-6}$ alkylene)-N($R^3$)C(O)N($R^3$)($R^4$). In certain embodiments, $Y^1$ is —($C_{0-6}$ alkylene)-N($R^3$)S(O)$_2$$R^4$. In certain embodiments, $Y^1$ is —($C_{0-6}$ alkylene)-S(O)$_2$N($R^3$)$R^4$. In certain embodiments, $Y^1$ is $C_{1-6}$ hydroxyalkyl. In certain embodiments, $Y^1$ is —($C_{1-6}$ alkylene)-N($R^3$)($R^4$). In certain embodiments, $Y^1$ is 3-7 membered hydroxyl-heteroalkyl.

In certain embodiments, $Y^1$ is —($C_{0-6}$ alkylene)-(3-10 membered carbocyclyl). In certain embodiments, $Y^1$ is —($C_{0-6}$ alkylene)-(3-6 membered saturated carbocyclyl). In certain embodiments, $Y^1$ is cyclopropyl.

In certain embodiments, $R^2$ is hydrogen. In certain embodiments, $R^2$ is $C_{1-6}$ alkyl. In certain embodiments, $R^2$ is —($C_{0-6}$ alkylene)-($C_{3-6}$ cycloalkyl).

In certain embodiments, $R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl). In certain embodiments, $R^3$ and $R^4$ each represent independently for each occurrence hydrogen, $C_{1-6}$ alkyl, or $C_{1-6}$ haloalkyl. In certain embodiments, an occurrence of $R^3$ and $R^4$ attached to the same nitrogen atom are taken together with the nitrogen atom to which they are attached to form a heterocyclic ring.

In certain embodiments, $R^5$ is —$C_{1-6}$ alkyl or —($C_{0-6}$ alkylene)-(3-7 membered cycloalkyl). In certain embodiments, $R^5$ is —$C_{1-6}$ alkyl or -(3-7 membered cycloalkyl). In certain embodiments, $R^5$ is —$C_{1-6}$ alkyl. In certain embodiments, $R^5$ is —$C_{1-6}$ haloalkyl. In certain embodiments, $R^5$ is —($C_{0-6}$ alkylene)-(3-7 membered heterocyclyl). In certain embodiments, $R^5$ is —($C_{0-6}$ alkylene)-(3-7 membered saturated carbocyclyl). In certain embodiments, $R^5$ is —($C_{1-6}$ alkylene)-N($R^3$)($R^{4o}$%.

In certain embodiments, $R^6$ represents independently for each occurrence halogen or $C_{1-6}$ alkyl.

In certain embodiments, $R^7$ represents independently for each occurrence halogen, hydroxyl, cyano, $C_{1-s}$ alkyl, or $C_{1-s}$ haloalkyl. In certain embodiments, $R^7$ represents independently for each occurrence halogen, hydroxyl, or cyano. In certain embodiments, $R^7$ represents independently for each occurrence halogen or cyano. In certain embodiments, $R^7$ is halogen. In certain embodiments, $R^7$ is fluoro. In certain embodiments, $R^7$ represents independently for each occurrence fluoro or cyano. In certain embodiments, $R^7$ is cyano.

The description above describes multiple embodiments relating to compounds of Formula II-B. The patent application specifically contemplates all combinations of the embodiments.

In certain other embodiments, the compound is one of the compounds listed in Table 5 below, or a pharmaceutically acceptable salt thereof. In certain embodiments, the compound is one of the compounds listed in Table 5 below.

TABLE 5

| Compound No. | Chemical Structure |
|---|---|
| V-1 | |
| V-2 | 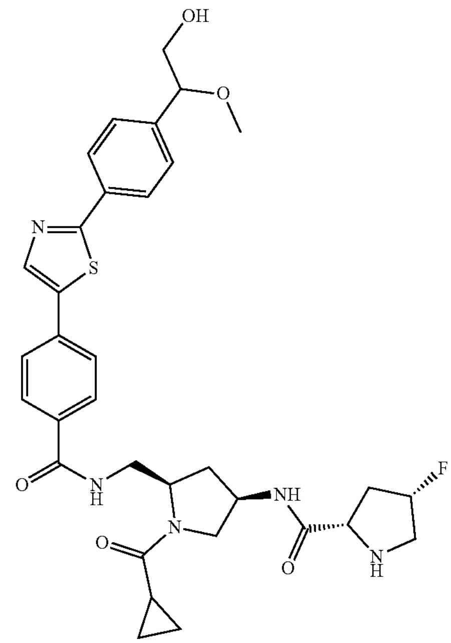 [SMILES: COC(CO)c1ccc(-c2ncc(-c3ccc(C(=O)NC[C@H]4C[C@@H](NC(=O)[C@@H]5C[C@H](F)CN5)CN4C(=O)C4CC4)cc3)s2)cc1] |
| V-3 | 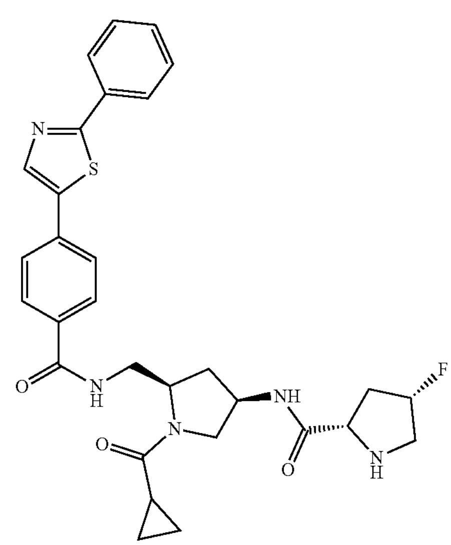 [SMILES: O=C(NC[C@H]1C[C@@H](NC(=O)[C@@H]2C[C@H](F)CN2)CN1C(=O)C1CC1)c1ccc(-c2cnc(-c3ccccc3)s2)cc1] |

TABLE 5-continued
| Compound No. | Chemical Structure |
|---|---|
| V-4 | 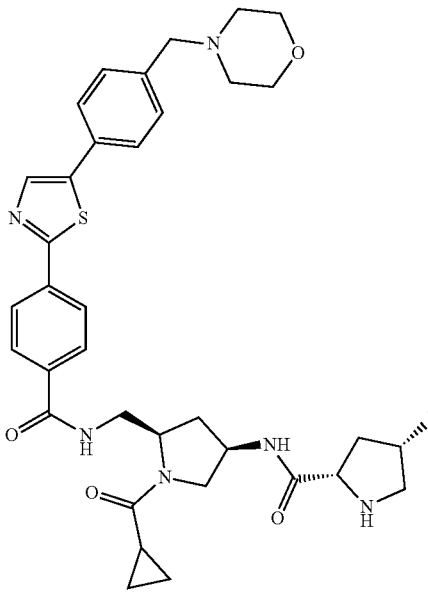 |
| V-5 | 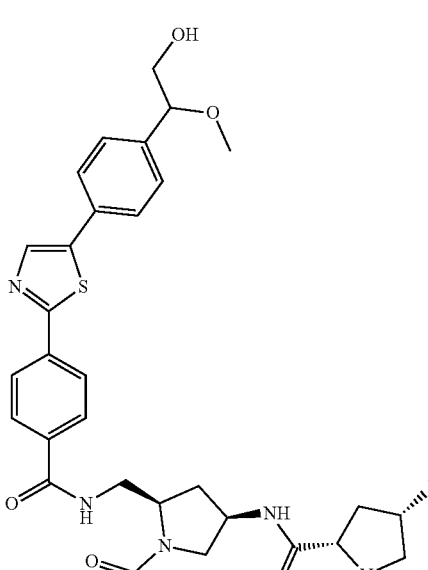 |
| V-6 | 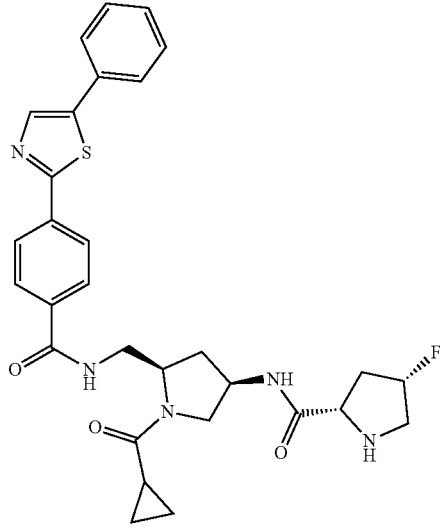 [SMILES: O=C(NC[C@H]1C[C@@H](NC(=O)[C@@H]2C[C@H](F)CN2)CN1C(=O)C1CC1)c1ccc(-c2ncc(-c3ccccc3)s2)cc1] |
| V-7 | 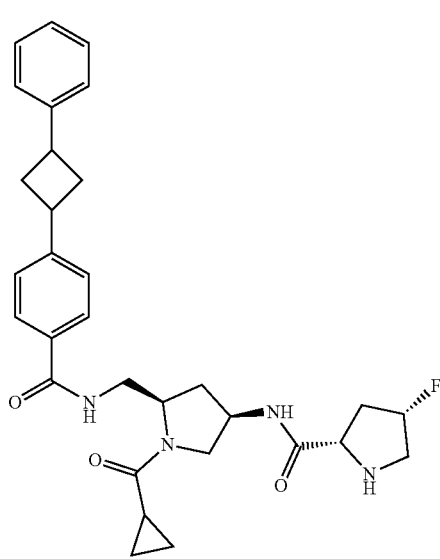 [SMILES: O=C(NC[C@H]1C[C@@H](NC(=O)[C@@H]2C[C@H](F)CN2)CN1C(=O)C1CC1)c1ccc(C2CC(c3ccccc3)C2)cc1] |

TABLE 5-continued

| Compound No. | Chemical Structure |
|---|---|
| V-8 | |
| V-9 | |
| V-10 | 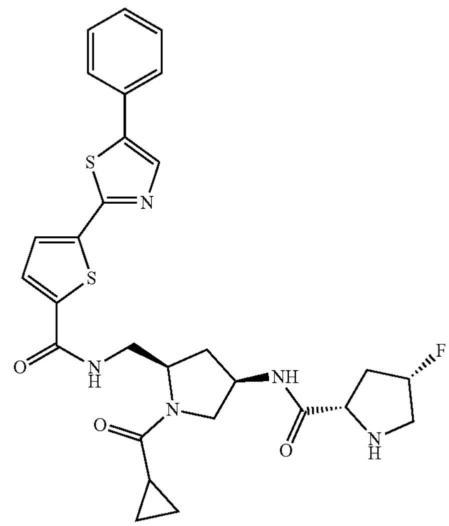 [SMILES: O=C(NC[C@H]1C[C@@H](NC(=O)[C@@H]2C[C@H](F)CN2)CN1C(=O)C1CC1)c1ccc(-c2ncc(-c3ccccc3)s2)s1] |
| V-11 | 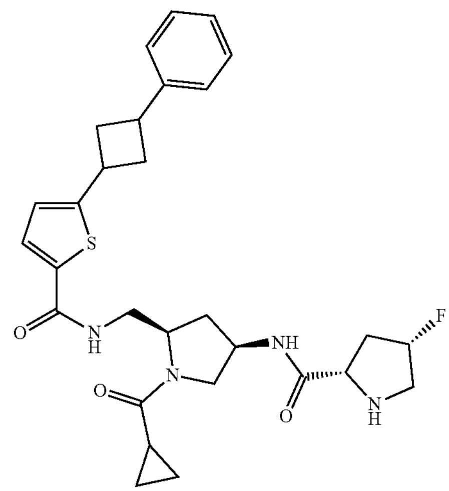 [SMILES: O=C(NC[C@H]1C[C@@H](NC(=O)[C@@H]2C[C@H](F)CN2)CN1C(=O)C1CC1)c1ccc(C2CC(c3ccccc3)C2)s1] |
| V-12 | 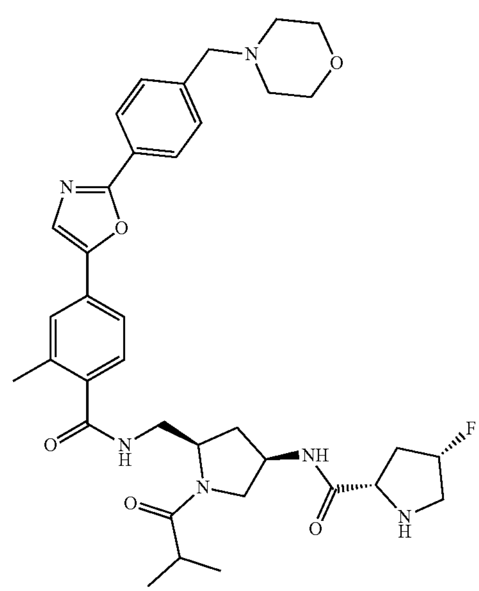 [SMILES: Cc1cc(-c2cnc(-c3ccc(CN4CCOCC4)cc3)o2)ccc1C(=O)NC[C@H]1C[C@@H](NC(=O)[C@@H]2C[C@H](F)CN2)CN1C(=O)C(C)C] |

TABLE 5-continued
| Compound No. | Chemical Structure |
|---|---|
| V-13 | 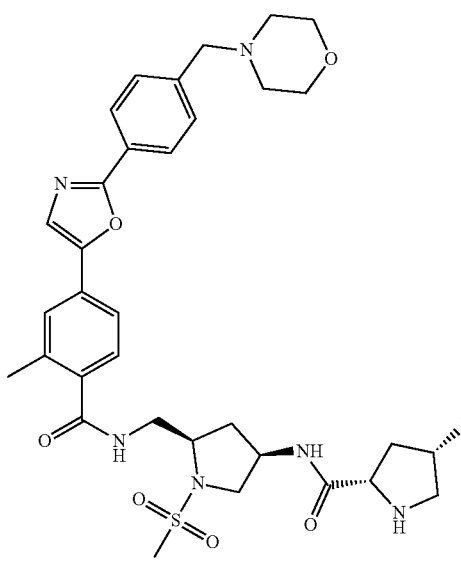 |
| V-14 | 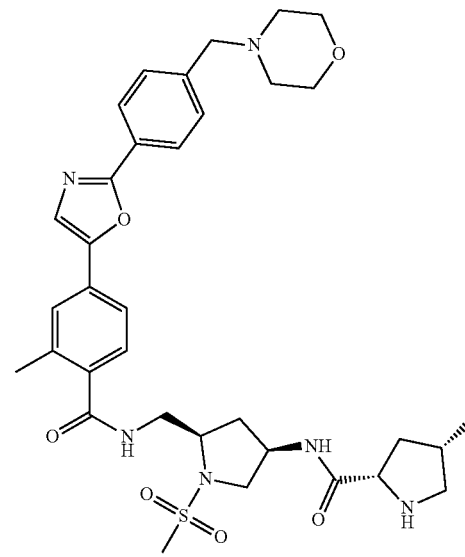 |
| V-15 | 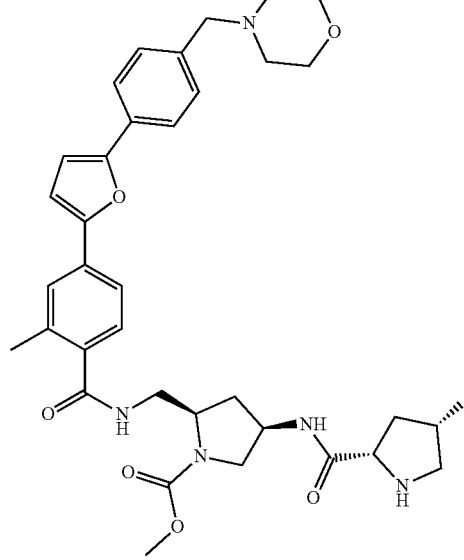 |
| V-16 | 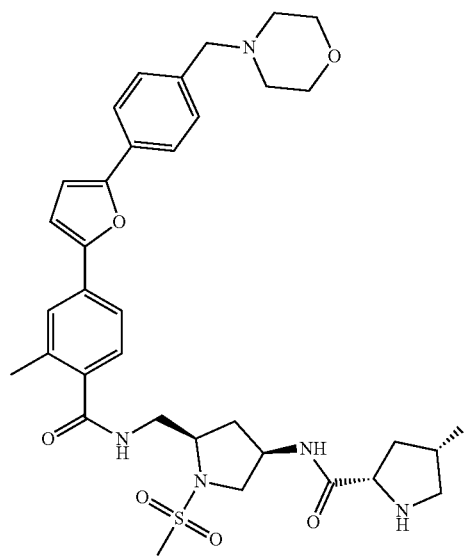 |

TABLE 5-continued

| Compound No. | Chemical Structure |
|---|---|
| V-17 | 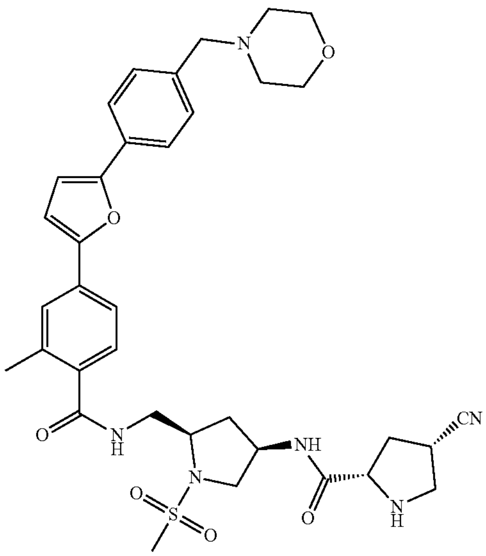 [SMILES: Cc1cc(-c2ccc(-c3ccc(CN4CCOCC4)cc3)o2)ccc1C(=O)NC[C@H]1C[C@@H](NC(=O)[C@@H]2C[C@H](C#N)CN2)CN1S(C)(=O)=O] |
| V-18 | 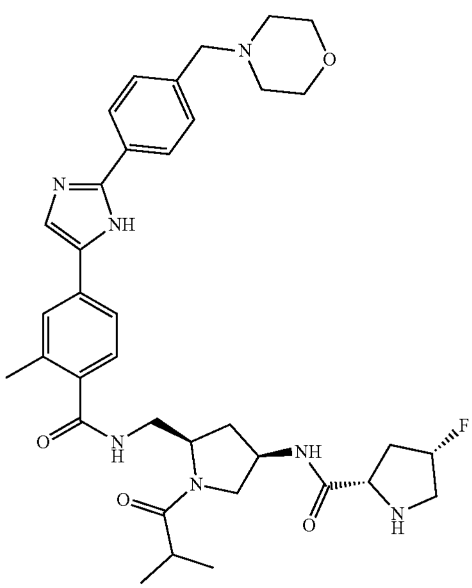 [SMILES: Cc1cc(-c2cnc(-c3ccc(CN4CCOCC4)cc3)[nH]2)ccc1C(=O)NC[C@H]1C[C@@H](NC(=O)[C@@H]2C[C@H](F)CN2)CN1C(=O)C(C)C] |
| V-19 | |
| V-20 | |

TABLE 5-continued
| Compound No. | Chemical Structure |
|---|---|
| V-21 | 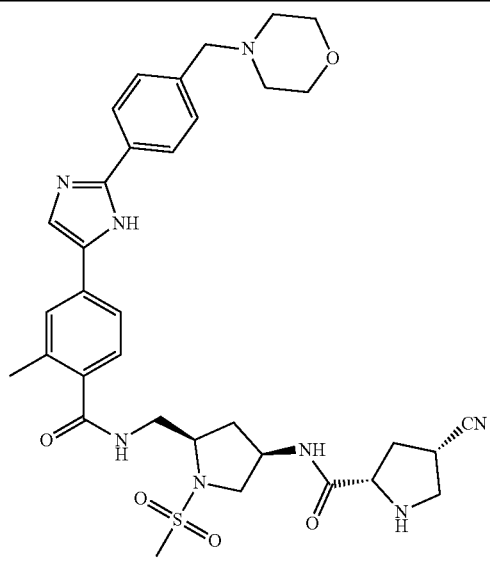 |
| V-22 | 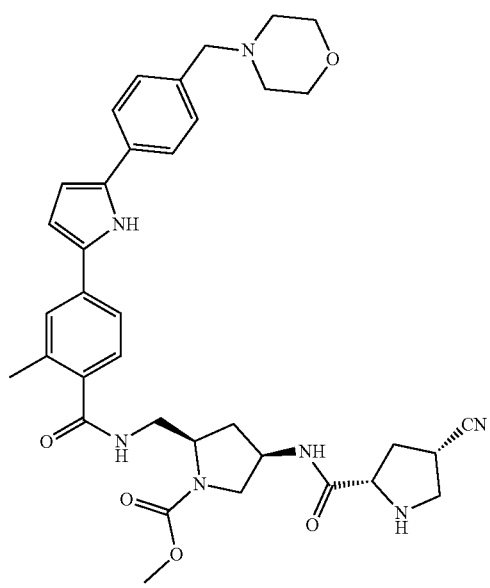 [SMILES: COC(=O)N1C[C@H](NC(=O)[C@@H]2C[C@H](C#N)CN2)C[C@@H]1CNC(=O)c1ccc(-c2ccc(-c3ccc(CN4CCOCC4)cc3)[nH]2)cc1C] |
| V-23 | 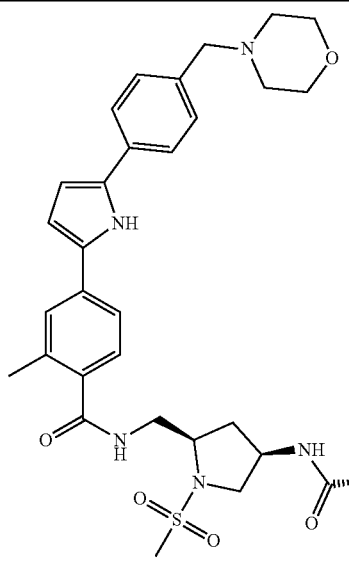 |
| V-24 | 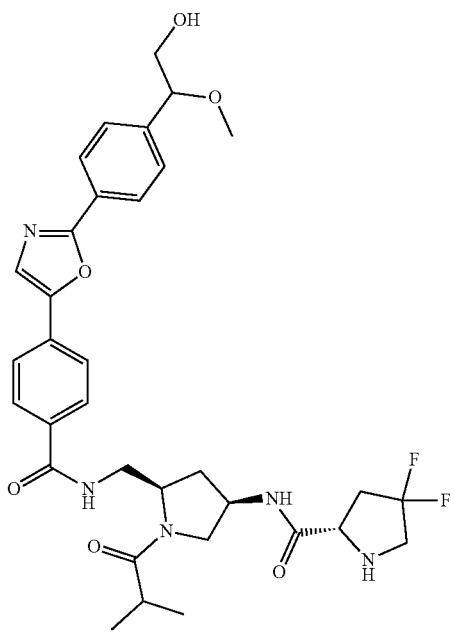 [SMILES: COC(CO)c1ccc(-c2ncc(-c3ccc(C(=O)NC[C@H]4C[C@@H](NC(=O)[C@@H]5CC(F)(F)CN5)CN4C(=O)C(C)C)cc3)o2)cc1] |

TABLE 5-continued
| Compound No. | Chemical Structure |
|---|---|
| V-25 | 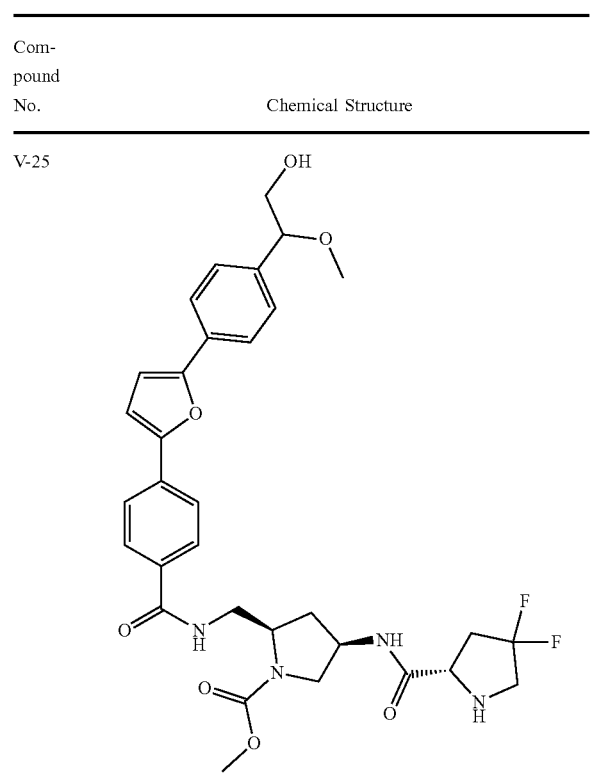 |
| V-26 | 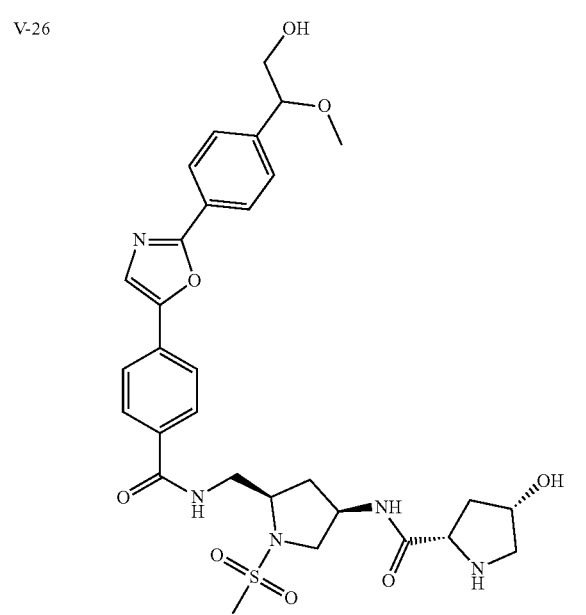 |
| V-27 | 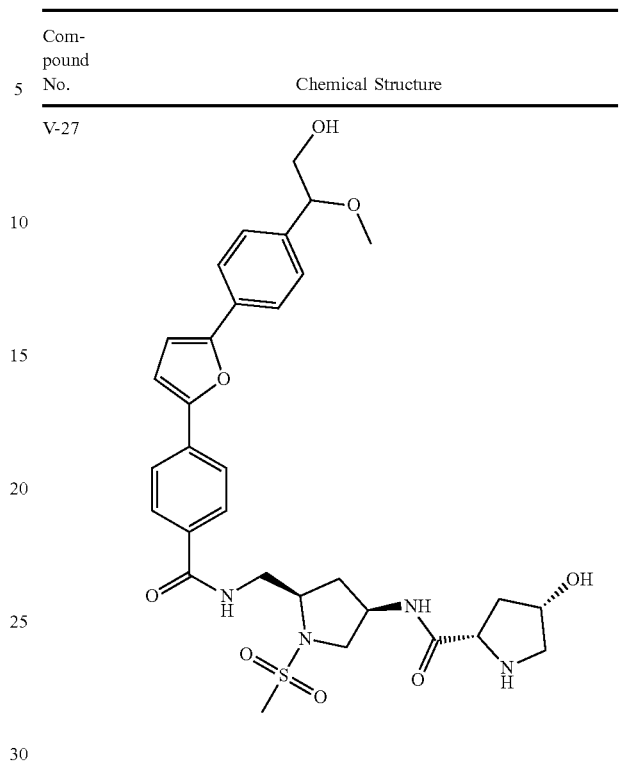 |
| V-28 | 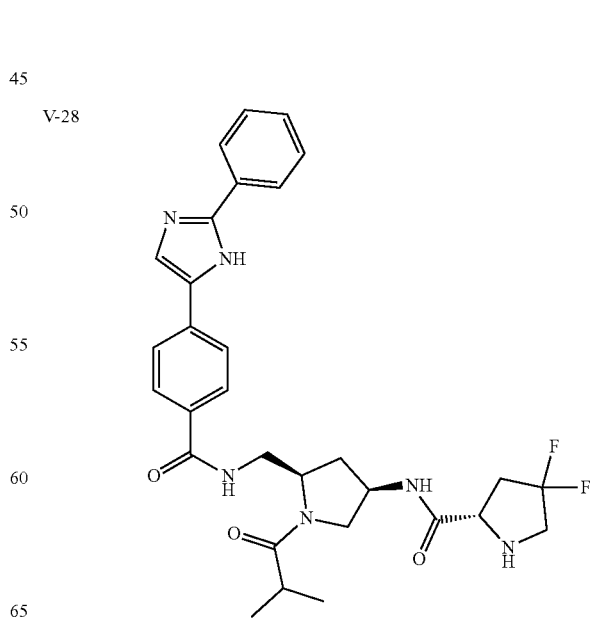 |

TABLE 5-continued
| Compound No. | Chemical Structure |
|---|---|
| V-29 | 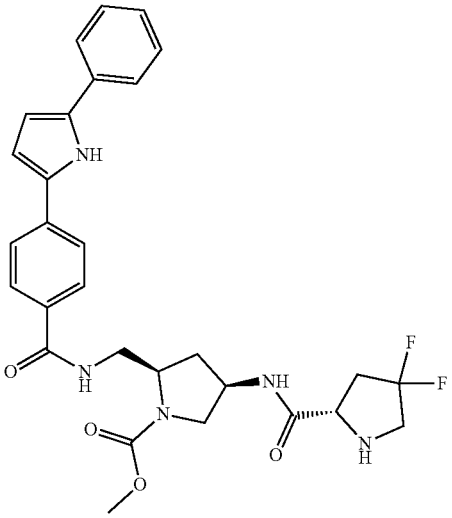 [SMILES: COC(=O)N1C[C@H](NC(=O)[C@@H]2CC(F)(F)CN2)C[C@@H]1CNC(=O)c1ccc(-c2ccc(-c3ccccc3)[nH]2)cc1] |
| V-30 | 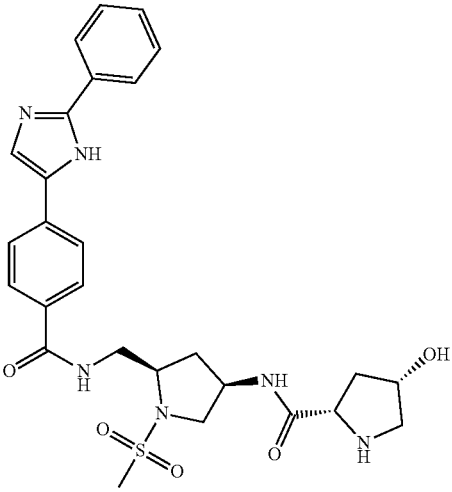 [SMILES: CS(=O)(=O)N1C[C@H](NC(=O)[C@@H]2C[C@H](O)CN2)C[C@@H]1CNC(=O)c1ccc(-c2cnc(-c3ccccc3)[nH]2)cc1] |
| V-31 | 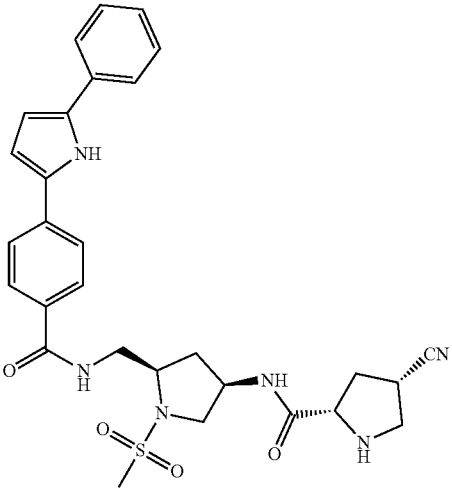 [SMILES: CS(=O)(=O)N1C[C@H](NC(=O)[C@@H]2C[C@H](C#N)CN2)C[C@@H]1CNC(=O)c1ccc(-c2ccc(-c3ccccc3)[nH]2)cc1] |
| V-32 | 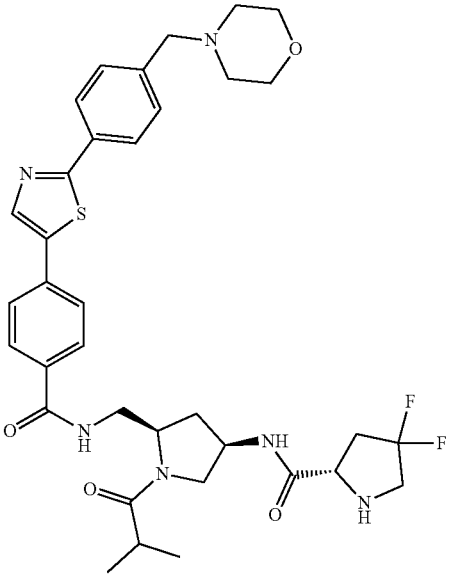 [SMILES: CC(C)C(=O)N1C[C@H](NC(=O)[C@@H]2CC(F)(F)CN2)C[C@@H]1CNC(=O)c1ccc(-c2cnc(-c3ccc(CN4CCOCC4)cc3)s2)cc1] |
| V-33 | 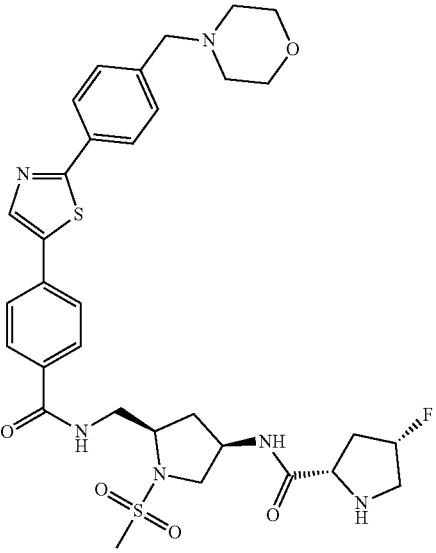 [SMILES: CS(=O)(=O)N1C[C@H](NC(=O)[C@@H]2C[C@H](F)CN2)C[C@@H]1CNC(=O)c1ccc(-c2cnc(-c3ccc(CN4CCOCC4)cc3)s2)cc1] |

TABLE 5-continued
| Compound No. | Chemical Structure |
|---|---|
| V-34 | 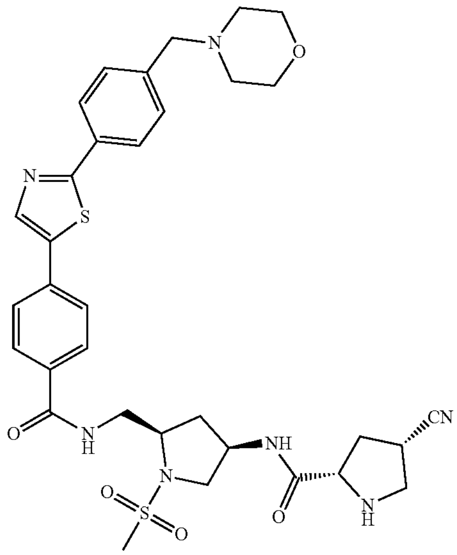 [SMILES: CS(=O)(=O)N1C[C@H](NC(=O)[C@@H]2C[C@H](C#N)CN2)C[C@@H]1CNC(=O)c1ccc(-c2cnc(-c3ccc(CN4CCOCC4)cc3)s2)cc1] |
| V-35 | 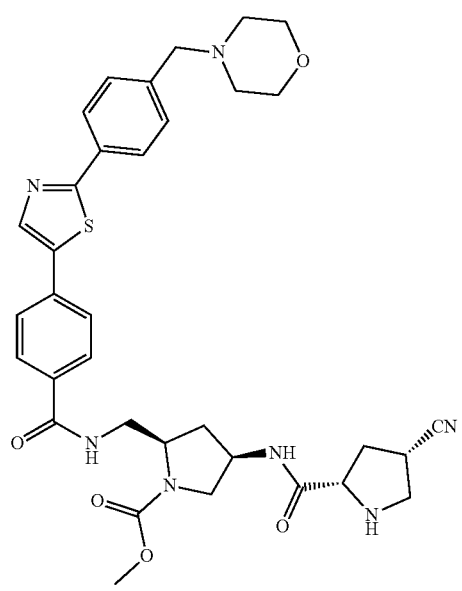 [SMILES: COC(=O)N1C[C@H](NC(=O)[C@@H]2C[C@H](C#N)CN2)C[C@@H]1CNC(=O)c1ccc(-c2cnc(-c3ccc(CN4CCOCC4)cc3)s2)cc1] |
| V-36 | |
| V-37 | 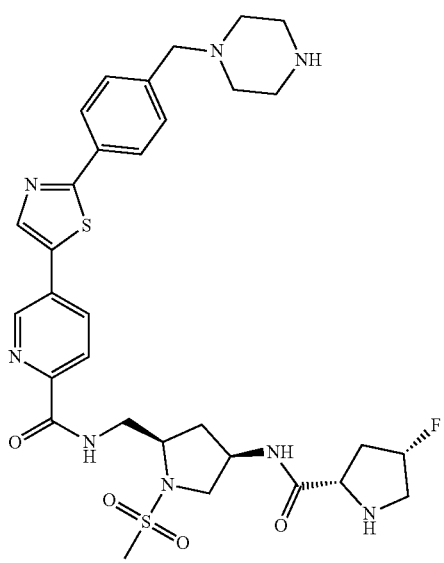 [SMILES: CS(=O)(=O)N1C[C@H](NC(=O)[C@@H]2C[C@H](F)CN2)C[C@@H]1CNC(=O)c1ccc(-c2cnc(-c3ccc(CN4CCNCC4)cc3)s2)cn1] |

TABLE 5-continued
| Compound No. | Chemical Structure |
| --- | --- |
| V-38 | 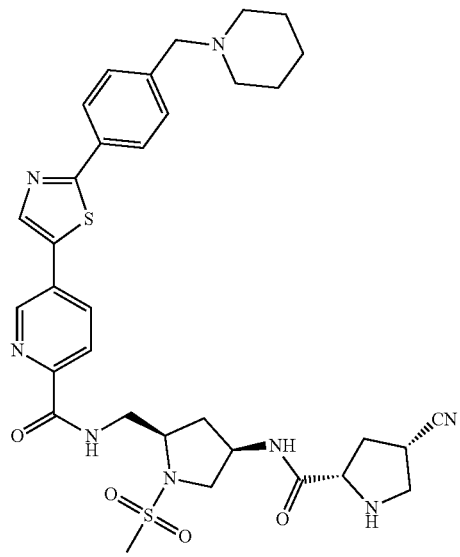 [SMILES: CS(=O)(=O)N1C[C@H](NC(=O)[C@@H]2C[C@H](C#N)CN2)C[C@@H]1CNC(=O)c1ccc(-c2cnc(-c3ccc(CN4CCCCC4)cc3)s2)cn1] |
| V-39 | 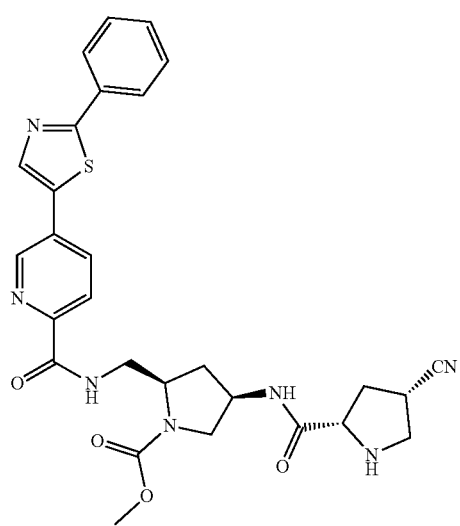 [SMILES: COC(=O)N1C[C@H](NC(=O)[C@@H]2C[C@H](C#N)CN2)C[C@@H]1CNC(=O)c1ccc(-c2cnc(-c3ccccc3)s2)cn1] |
| V-40 | 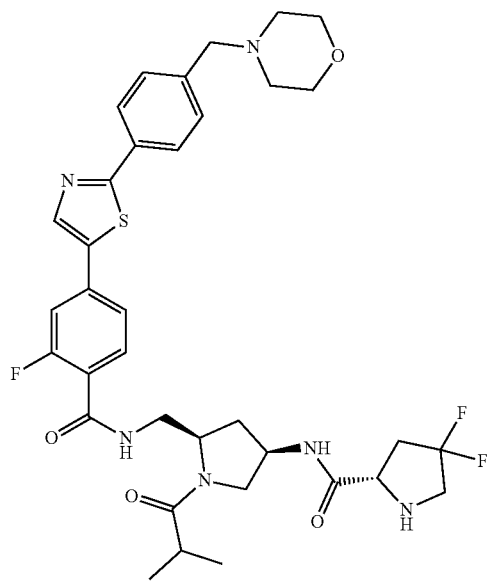 [SMILES: CC(C)C(=O)N1C[C@H](NC(=O)[C@@H]2CC(F)(F)CN2)C[C@@H]1CNC(=O)c1ccc(-c2cnc(-c3ccc(CN4CCOCC4)cc3)s2)cc1F] |
| V-41 | 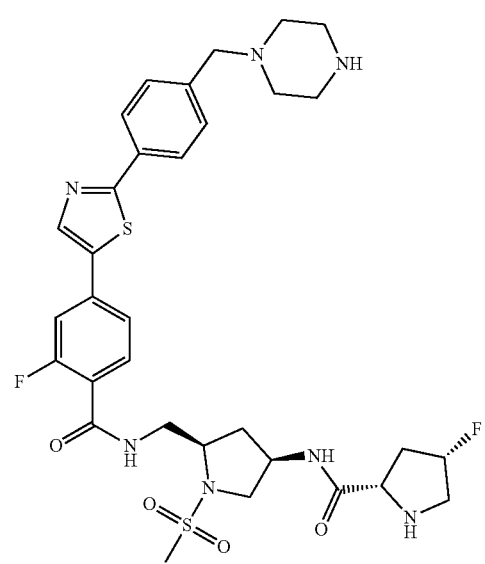 [SMILES: CS(=O)(=O)N1C[C@H](NC(=O)[C@@H]2C[C@H](F)CN2)C[C@@H]1CNC(=O)c1ccc(-c2cnc(-c3ccc(CN4CCNCC4)cc3)s2)cc1F] |

TABLE 5-continued

| Compound No. | Chemical Structure |
|---|---|
| V-42 | 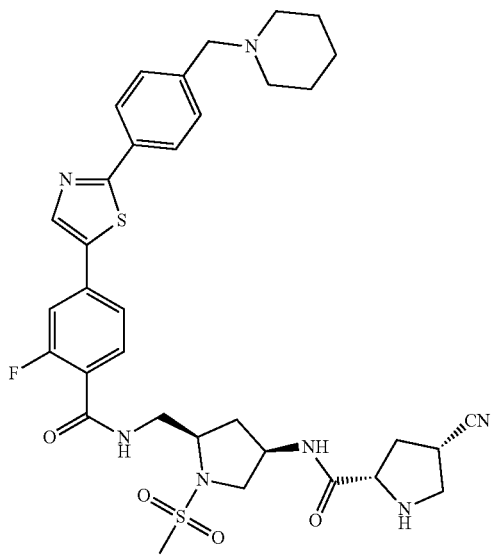 [SMILES: CS(=O)(=O)N1C[C@H](NC(=O)[C@@H]2C[C@H](C#N)CN2)C[C@@H]1CNC(=O)c1ccc(-c2cnc(-c3ccc(CN4CCCCC4)cc3)s2)cc1F] |
| V-43 | 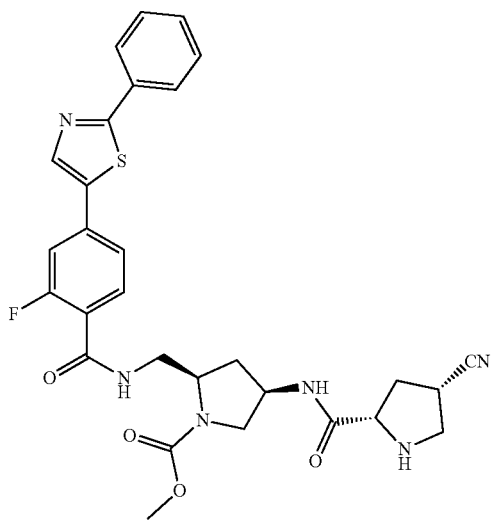 [SMILES: COC(=O)N1C[C@H](NC(=O)[C@@H]2C[C@H](C#N)CN2)C[C@@H]1CNC(=O)c1ccc(-c2cnc(-c3ccccc3)s2)cc1F] |
| V-44 | 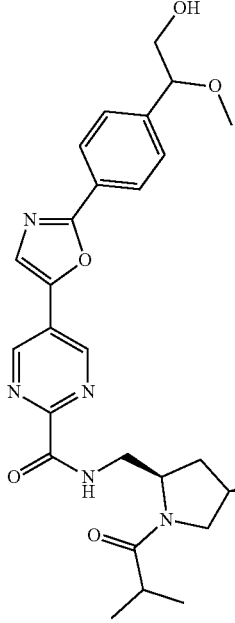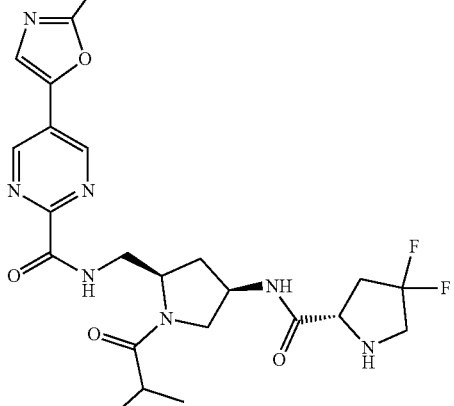 |
| V-45 | 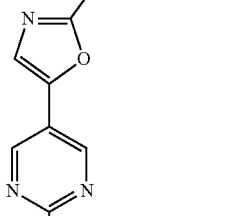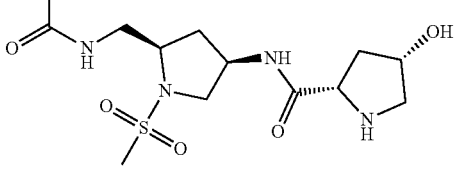 |

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

Scheme 4 (where Y is N, O, or S; X is halogen, and $R^{III}$ is a carbon substituent, such as alkyl) illustrates a general method for preparing compounds of the type 1F. Aryl halides 1A are known in the literature and/or are commercially available. Azoles 1B are commercially available. Aryl esters 1D are known in the literature and/or are commercially available. The C2 position of 1,3-azole 1B can be arylated by aryl halide 1A using palladium-catalysed conditions to give azole 1C. The C5 position of azole 1C can then be arylated using palladium-catalysed conditions to give ester 1E. Ester hydrolysis under standard hydrolytic conditions affords acid carboxylic acid 1F.

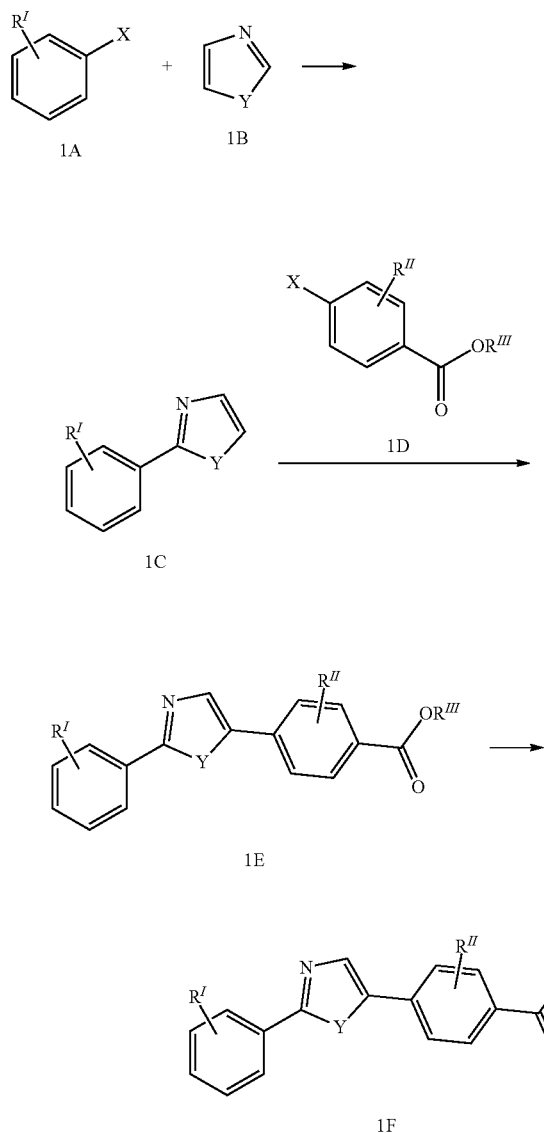

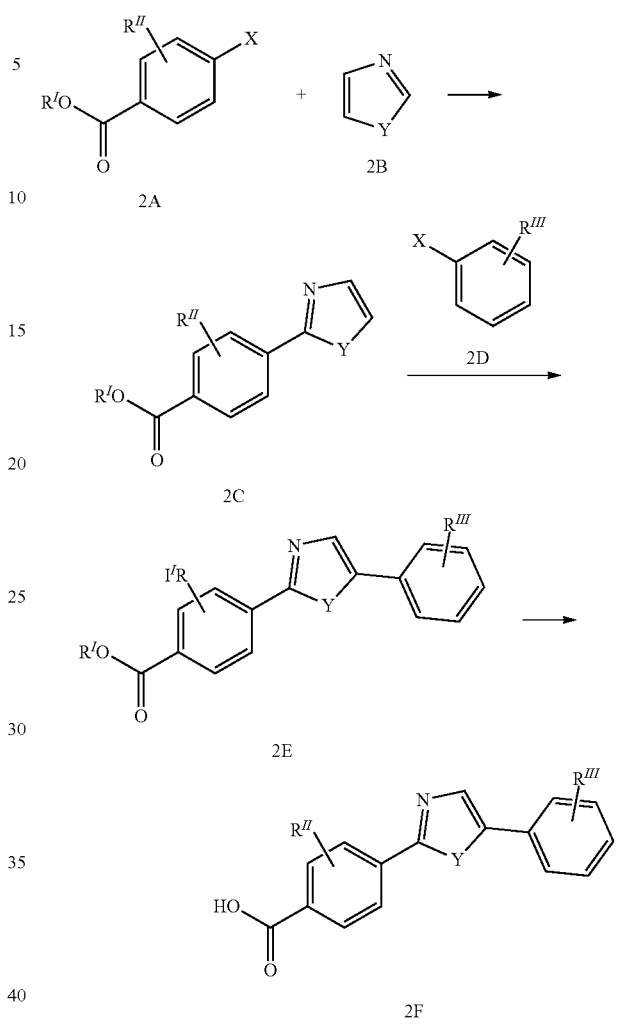

Scheme 5 (where Y is N, O, or S; X is halogen, and $R^{III}$ is a carbon substituent, such as alkyl) illustrates a general method for preparing compounds of the type 2F. Aryl esters 2A are known in the literature and/or are commercially available. Azoles 2B are commercially available. Aryl halides 2D are known in the literature and/or are commercially available. The C2 position of 1,3-azole 2B can be arylated by aryl ester 2A using palladium-catalysed conditions to give 2C. The C5 position of azole 2C can then be arylated using palladium-catalysed conditions to give 2E. Ester hydrolysis under standard hydrolytic conditions affords acid carboxylic acid 2F.

Scheme 6 (where $R^{III}$ is a carbon substituent, such as alkyl) illustrates a general method for preparing compounds of type 3E. Acids 3A are known in the literature and/or are commercially available. Aryl iodides 3C are known in the literature and/or are commercially available. Acid 3A can be converted to the symmetrical anhydride 3B by initial conversion to the corresponding acyl chloride under standard conditions followed by reaction with base and another equivalent of the starting acid. Anydride 3B can then undergo a decarboxylative alkylation with 3C to afford ester 3D. Ester hydrolysis under standard hydrolytic conditions yields carboxylic acid 3E.

SCHEME 6.

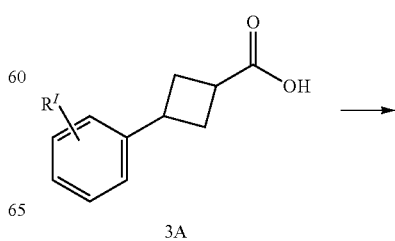

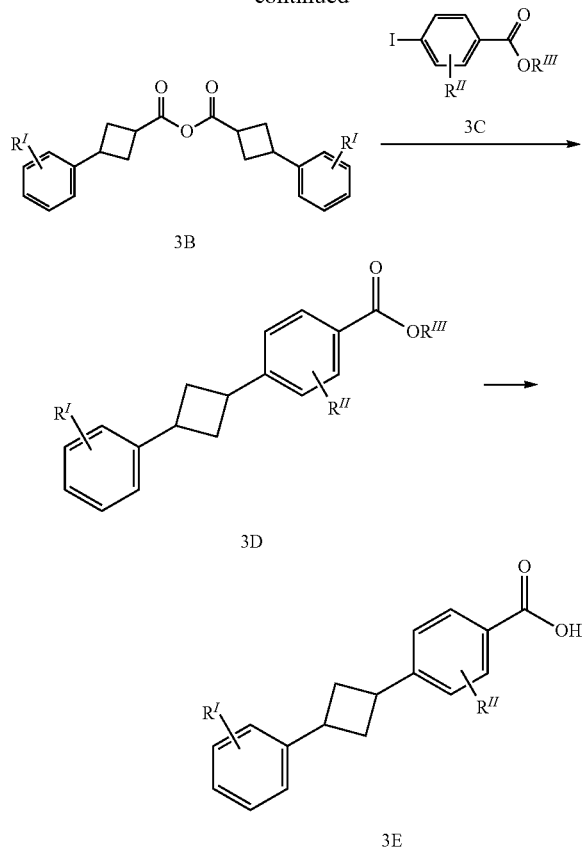

If a functional group is not amenable to a reaction condition, it is envisioned that the functional group can first be protected under standard conditions and then the protecting group removed after completing the transformation.

II. Therapeutic Applications of Aza-Heterocyclyl Carboxamide and Related Compounds The aza-heterocyclyl carboxamide and related compounds described herein, such as a compound of Formula I, I-A, II, II-A, or other compounds in Section I, provide therapeutic benefits to subjects suffering from a bacterial infection. Accordingly, one aspect of the invention provides a method of treating a bacterial infection in a patient. The method comprises administering a therapeutically effective amount of an aza-heterocyclyl carboxamide or related compound described herein, such as a compound of Formula I, I-A, II, II-A, or other compounds in Section I, to a patient in need thereof to treat the bacterial infection. In certain embodiments, the particular compound of Formula I, I-A, II, or II-A is a compound defined by one of the embodiments described above. In certain embodiments, the particular compound of Formula I or I-A is a compound defined by one of the embodiments described above.

In certain embodiments, the patient is a human.

In certain embodiments, the bacterial infection is an infection by a gram-negative bacteria. In certain embodiments, the bacterial infection is an infection by a gram-positive bacteria. In certain embodiments, the bacterial infection is an anaerobic bacterial infection. In certain other embodiments, the bacterial infection is an aerobic bacterial infection.

In certain embodiments, the bacterial infection is an infection by a *Staphylococcus, Streptococcus, Enterococcus, Pseudomonas, Escherichia, Fusobacterium, Klebsiella, Haemophilus, Bordetella, Serratia, Proteus, Enterobacter, Campylobacter, Citrobacter, Vibrio, Morganella, Salmonella, Shigella, Acinetobacter, Legionella, Bacteroides, Neisseria, Moraxella, Chlamydia, Helicobacter, Prevotella, Porphyromonas, Veillonella, Bilophila, Centipeda, Leptotrichia, Selenomonas*, or *Sutterella* bacterium, or a combination thereof. In certain embodiments, the bacterial infection is an infection by a *Staphylococcus, Streptococcus, Enterococcus, Pseudomonas, Escherichia, Fusobacterium, Klebsiella, Haemophilus, Bordetella, Serratia, Proteus, Enterobacter, Campylobacter, Citrobacter, Vibrio, Morganella, Salmonella, Shigella, Acinetobacter, Legionella, Bacteroides, Neisseria, Moraxella, Chlamydia*, or *Helicobacter* bacterium, or a combination thereof. In certain embodiments, the bacterial infection is an infection by a *Bacteroides, Prevotella, Fusobacterium, Porphyromonas, Veillonella, Bilophila, Centipeda, Leptotrichia, Selenomonas*, or *Sutterella* bacterium, or a combination thereof. In certain embodiments, the bacterial infection is an infection by a *Pseudomonas, Escherichia*, or *Fusobacterium* bacterium, or a combination thereof. In certain embodiments, the bacterial infection is an infection by a *Pseudomonas* or *Escherichia* bacterium, or a combination thereof.

In certain embodiments, the bacterial infection is an infection by *Staphylococcus aureus, Staphylococcus epidermidis, Streptococcus pyogenes, Streptococcus agalactiae, Streptococcus pneumoniae, Enterococcus faecalis, Enterococcus faecium, Pseudomonas aeruginosa, Escherichia coli, Fusobacterium nucleatum, Fusobacterium polymorphum, Fusobacterium vincentii, Fusobacterium aninalis, Fusobacterium fusiforme, Fusobacterium canifelium, Fusobacterium necrophorum, Fusobacterium funduliforme, Fusobacterium ulcerans, Fusobacterium gonidiaformans, Fusobacterium mortiferum, Fusobacterium naviforme, Fusobacterium necrogenes, Fusobacterium russii, Fusobacterium varium, Klebsiella pneumoniae, Klebsiella oxytoca, Haemophilus influenzae, Haemophilus parainfluenzae, Bordetella pertussis, Bordetella bronchiseptica, Serratia marcescens, Proteus mirabilis, Enterobacter cloacae, Campylobacter jejuni, Vibrio parahemolyticus, Vibrio cholerae, Morganella morganii, Salmonella typhi, Salmonella paratyphi, Shigella dysenteriae, Acinetobacter baumannii, Acinetobacter calcoaceticus, Legionella pneumophila, Bacteroides fragilis, Bacteroides thetaiotaomicron, Bacteroides vulgatus, Bacteroides distasonis, Bacteroides ovasus, Bacteroides unjormis, Bacteroides caceae, Neisseria gonorrhoeae, Neisseria meningitides, Moraxella catarrhalis, Chlamydia trachomatis, Chlamydia psittaci, Helicobacter pylori, Prevotella intermedia, Prevotella meloninogenica, Prevotella bivia, Prevotella nigrescens, Prevotella disiens, Porphyromonas gingivalis, Veillonella atypica, Veillonella caviae, Veillonella criceti, Veillonella denticariosi, Veillonella dispar, Veillonella magna, Veillonella montpellierensis, Veillonella parvula, Veillonella ratti, Veillonella rodentium, Veillonella rogosae, Veillonella seminalis, Veillonella tobetsuensis Bilophila wadsworthia, Centipeda periodontii, Leptotrichia buccalis, Leptotrichia goodfellowii, Leptotrichia hofstadii, Leptotrichia honkongensis, Leptotrichia shahii, Leptotrichia trevisanii, Leptotrichia wadei, Selenomonas sputigena, Sutterella wadsworthensis, Sutterella parvirubra, Sutterella stercoricanis*, or a combination thereof. In certain embodiments, the bacterial infection is an infection by *Staphylococcus aureus, Staphylococcus epidermidis, Streptococcus pyogenes, Streptococcus agalactiae,*

*Streptococcus pneumoniae, Enterococcus faecalis, Enterococcus faecium, Pseudomonas aeruginosa, Escherichia coli, Fusobacterium nucleatum, Klebsiella pneumoniae, Klebsiella oxytoca, Haemophilus influenzae, Haemophilus parainfluenzae, Bordetella pertussis, Bordetella bronchiseptica, Serratia marcescens, Proteus mirabilis, Enterobacter cloacae, Campylobacter jejuni, Vibrio parahemolyticus, Vibrio cholerae, Morganella morganii, Salmonella typhi, Salmonella paratyphi, Shigella dysenteriae, Acinetobacter baumannii, Acinetobacter calcoaceticus, Legionella pneumophila, Bacteroides fragilis, Neisseria gonorrhoeae, Neisseria meningitides, Moraxella catarrhalis, Chlamydia trachomatis, Chlamydia psittaci, Helicobacter pylori*, or a combination thereof. In certain embodiments, the bacterial infection is an infection by *Pseudomonas aeruginosa, Escherichia coli, Fusobacterium nucleatum*, or a combination thereof. In certain embodiments, the bacterial infection is an infection by *Pseudomonas aeruginosa, Escherichia coli*, or a combination thereof.

In certain embodiments, the bacterial infection is an infection of a bacteria selected from the group consisting of Enterobacteriaceae, *Acinetobacter, Stenotrophomonas, Burkholderia, Pseudomonas, Alcaligenes, Haemophilus, Franciscellaceae* and *Neisseria* species. In certain embodiments, the bacteria is Enterobacteriaceae or *Acinetobacter*. In certain embodiments, the Enterobacteriaceae is selected from the group consisting of *Serratia, Proteus, Klebsiella, Enterobacter, Citrobacter, Salmonella, Providencia, Yersinia, Morganella, Cedecea, Edwardsiella* species, and *Escherichia coli*. In certain embodiments, the *Burkholderia* is *Burkholderia cepacia, Burkholderia pseudomallei* or *Burkholderia mallei*. In certain embodiments, the *Burkholderia* is *Burkholderia pseudomallei, Burkholderia mallei*, or *Burkholderia cepacia*. In some embodiments, the *Pseudomonas* is *Pseudomonas aeruginosa*. In another embodiment, the *Stenotrophomonas* is *Stenotrophomonas maltophila*. In yet another embodiment, the *Alcaligenes* is *Alcaligenes xylosoxidans*.

In certain embodiments, the *Acinetobacter* is selected from the group consisting of *Acinetobacter baumannii, Acinetobacter lwoffi, Acinetobacter albensis, Acinetobacter apis, Acinetobacter beijerinckii, Acinetobacter bereziniae, Acinetobacter bohemicus, Acinetobacter boissieri, Acinetobacter bouvetii, Acinetobacter brisouii, Acinetobacter calcoaceticus, Acinetobacter courvalinii, Acinetobacter dispersus, Acinetobacter equi, Acinetobacter gandensis, Acinetobacter gerneri, Acinetobacter guangdongensis, Acinetobacter guillouiae, Acinetobacter gyllenbergii, Acinetobacter haemolyticus, Acinetobacter harbinensis, Acinetobacter indicus, Acinetobacter junii, Acinetobacter kookii, Acinetobacter modestus, Acinetobacter nectaris, Acinetobacter nosocomialis, Acinetobacter parvus, Acinetobacter pakistanensis, Acinetobacter populi, Acinetobacter proteolyticus, Acinetobacter pittii, Acinetobacter puyangensis, Acinetobacter qingfengensis, Acinetobacter radioresistens, Acinetobacter rudis, Acinetobacter schindleri, Acinetobacter seifertii, Acinetobacter soli, Acinetobacter tandoii, Acinetobacter tjernbergiae, Acinetobacter towneri, Acinetobacter ursingii, Acinetobacter variabilis, Acinetobacter venetianus*, and *Acinetobacter vivianii*.

In certain embodiments, the subject is a human.

Another aspect of the invention provides for the use of a compound described herein (such as a compound of Formula I, I-A, II, II-A, or other compounds in Section I) in the manufacture of a medicament. In certain embodiments, the medicament is for treating a bacterial infection described herein. In certain embodiments, the compound is a compound of Formula I or I-A.

Another aspect of the invention provides for the use of a compound described herein (such as a compound of Formula I, I-A, II, II-A, or other compounds in Section I) for treating a bacterial infection described herein. In certain embodiments, the compound is a compound of Formula I or I-A.

Further, the aza-heterocyclyl carboxamide and related compounds described herein, such as a compound of Formula I, I-A, II, II-A, or other compounds in Section I, can induce death of a bacterial cell. Accordingly, one aspect of the invention provides a method of inducing death of a bacterial cell. The method comprises exposing a bacterial cell to an effective amount of an aza-heterocyclyl carboxamide or related compound described herein, such as a compound of Formula I, I-A, II, II-A, or other compounds in Section I, to induce death of the bacterial cell. In certain embodiments, the particular compound of Formula I, I-A, II, or II-A is a compound defined by one of the embodiments described above. In certain embodiments, the compound is a compound of Formula I or I-A.

In certain embodiments, the bacterial cell is one of those described above as being the bacterial species causing a bacterial infection. For example, in certain embodiments, the bacterial cell is a gram-negative bacteria. In certain embodiments, the bacterial cell is a gram-positive bacteria. In certain embodiments, the bacterial cell is an anaerobic bacteria. In certain other embodiments, the bacterial cell is an aerobic bacteria.

In certain embodiments, the bacterial cell is a *Staphylococcus, Streptococcus, Enterococcus, Pseudomonas, Escherichia, Fusobacterium, Klebsiella, Haemophilus, Bordetella, Serratia, Proteus, Enterobacter, Campylobacter, Citrobacter, Vibrio, Morganella, Salmonella, Shigella, Acinetobacter, Legionella, Bacteroides, Neisseria, Moraxella, Chlamydia, Helicobacter, Prevotella, Porphyromonas, Veillonella, Bilophila, Centipeda, Leptotrichia, Selenomonas*, or *Sutterella* bacterium, or a combination thereof. In certain embodiments, the bacterial cell is a *Staphylococcus, Streptococcus, Enterococcus, Pseudomonas, Escherichia, Fusobacterium, Klebsiella, Haemophilus, Bordetella, Serratia, Proteus, Enterobacter, Campylobacter, Citrobacter, Vibrio, Morganella, Salmonella, Shigella, Acinetobacter, Legionella, Bacteroides, Neisseria, Moraxella, Chlamydia*, or *Helicobacter* bacterium. In certain embodiments, the bacterial cell is a *Bacteroides, Prevotella, Fusobacterium, Porphyromonas, Veillonella, Bilophila, Centipeda, Leptotrichia, Selenomonas*, or *Sutterella* bacterium, or a combination thereof. In certain embodiments, the bacterial cell is a *Pseudomonas, Escherichia*, or *Fusobacterium* bacterium. In certain embodiments, the bacterial cell is a *Pseudomonas* or *Escherichia* bacterium.

In certain embodiments, the bacterial cell is a *Staphylococcus aureus, Staphylococcus epidermidis, Streptococcus pyogenes, Streptococcus agalactiae, Streptococcus pneumoniae, Enterococcus faecalis, Enterococcus faecium, Pseudomonas aeruginosa, Escherichia coli, Fusobacterium nucleatum, Fusobacterium polynorphum, Fusobacterium vincentii, Fusobacterium animalis, Fusobacterium fusiforne, Fusobacterium canifelium, Fusobacterium necrophorum, Fusobacterium funduliforme, Fusobacterium ulcerans, Fusobacteriunm gonidiaformans, Fusobacterium nortiferum, Fusobacterium naviforne, Fusobacterium necrogenes, Fusobacterium russii, Fusobacterium varium, Klebsiella pneumoniae, Klebsiella oxytoca, Haemophilus* influenzae, Haemophilus parainfluenzae, Bordetella pertussis, Bordetella bronchiseptica, Serratia marcescens, Proteus mirabilis, Enterobacter cloacae, Campylobacter jejuni, Vibrio parahemolyticus, Vibrio cholerae, Morganella morganii, Salmonella typhi, Salmonella paratyphi, Shigella dysenteriae, Acinetobacter baumannii, Acinetobacter calcoaceticus, Legionella pneumophila, Bacteroides fragilis, Bacteroides hetaiotawmicron, Bacteroides vulgatus, Bacteroides distasonis, Bacteroides ovatus, Bacteroides uniformis, Bacieroides caccae, Neisseria gonorrhoeae, Neisseria meningitides, Moraxella catarrhalis, Chlamydia trachomatis, Chlamydia psittaci, Helicobacter pylori, Prevotella intermedia, Prevotella melaninogenica, Prevotella bivia, Prevotella nigrescens, Prevotella disiens, Porphyromonas gingivalis, Veillonella atypica, Veillonella caviae, Veillonella criceti, Veillonella denticariosi, Veillonella dispar, Veillonella magna, Veillonella montpellierensis, Veillonella parvula, Veillonella ratti, Veillonella rodentium, Veillonella rogosae, Veillonella seminalis, Veillonella tobetsuensis Bilophila wadsworthia, Centipeda periodontii, Leptotrichia buccalis, Leptotrichia goodfellowii, Leptoirichia hofstadii, Leptotrichia honkongensis, Leptotrichia shahii, Leptotrichia trevisanii, Leplotrichia wadei, Selenomonas sputigena, Sutterella wadsworthensis, Sutterella parvirubra, Sutterella stercoricanis, or a combination thereof. In certain embodiments, the bacterial cell is a Staphylococcus aureus, Staphylococcus epidermidis, Streptococcus pyogenes, Streptococcus agalactiae, Streptococcus pneumoniae, Enterococcus faecalis, Enterococcus faecium, Pseudomonas aeruginosa, Escherichia coli, Fusobacterium nucleatum, Klebsiella pneumoniae, Klebsiella oxytoca, Haemophilus influenzae, Haemophilus parainfluenzae, Bordetella pertussis, Bordetella bronchiseptica, Serratia marcescens, Proteus mirabilis, Enterobacter cloacae, Campylobacter jejuni, Vibrio parahemolyticus, Vibrio cholerae, Morganella morganii, Salmonella typhi, Salmonella paratyphi, Shigella dysenteriae, Acinetobacter baumannii, Acinetobacter calcoaceticus, Legionella pneumophila, Bacteroides fragilis, Neisseria gonorrhoeae, Neisseria meningitides, Moraxella catarrhalis, Chlamydia trachomatis, Chlamydia psittaci, Helicobacter pylori bacterium. In certain embodiments, the bacterial cell is a Pseudomonas aeruginosa, Escherichia coli, or Fusobacterium nucleatum bacterium. In certain embodiments, the bacterial cell is a Pseudomonas aeruginosa or Escherichia coli bacterium.

In certain embodiments, the bacterial cell is a bacteria selected from the group consisting of Enterobacteriaceae, Acinetobacter, Stenotrophomonas, Burkholderia, Pseudomonas, Alcaligenes, Haemophilus, Franciscellaceae and Neisseria species. In certain embodiments, the bacteria is Enterobacteriaceae or Acinetobacter. In certain embodiments, the Enterobacteriaceae is selected from the group consisting of Serratia, Proteus, Klebsiella, Enterobacter, Citrobacter, Salmonella, Providencia, Yersinia, Morganella, Cedecea, Edwardsiella species, and Escherichia coli. In certain embodiments, the Burkholderia is Burkholderia cepacia, Burkholderia pseudomallei or Burkholderia mallei. In certain embodiments, the Bulkholderia is Burkholderia pseudomallei, Burkholderia mallei, or Burkholderia cepacia. In some embodiments, the Pseudomonas is Pseudomonas aeruginosa. In another embodiment, the Stenotrophomonas is Stenotrophomonas maltophila. In yet another embodiment, the Alcaligenes is Alcaligenes xylosoxidans.

In certain embodiments, the Acinetobacter is selected from the group consisting of Acinetobacter baumannii, Acinetobacter lwoffi, Acinetobacter albensis, Acinetobacter apis, Acinetobacter beijerinckii, Acinetobacter bereziniae, Acinetobacter bohemicus, Acinetobacter boissieri, Acinetobacter bouvetii, Acinetobacter brisouii, Acinetobacter calcoaceticus, Acinetobacter courvalinii, Acinetobacter dispersus, Acinetobacter equi, Acinetobacter gandensis, Acinetobacter gerneri, Acinetobacter guangdongensis, Acinetobacter guillouiae, Acinetobacter gyllenbergii, Acinetobacter haemolyticus, Acinetobacter harbinensis, Acinetobacter indicus, Acinetobacter junii, Acinetobacter kookii, Acinetobacter modestus, Acinetobacter nectaris, Acinetobacter nosocomialis, Acinetobacter parvus, Acinetobacter pakistanensis, Acinetobacter populi, Acinetobacter proteolyticus, Acinetobacter pittii, Acinetobacter puyangensis, Acinetobacter qingfengensis, Acinetobacter radioresistens, Acinetobacter rudis, Acinetobacter schindleri, Acinetobacter seifertii, Acinetobacter soli, Acinetobacter tandoii, Acinetobacter tjernbergiae, Acinetobacter towneri, Acinetobacter ursingii, Acinetobacter variabilis, Acinetobacter venetianus, and Acinetobacter vivianii.

Further, the aza-heterocyclyl carboxamide and related compounds described herein, such as a compound of Formula I, I-A, II, II-A, or other compounds in Section I, can kill a bacterial cell. Accordingly, one aspect of the invention provides a method of killing a bacterial cell. The method comprises exposing a bacterial cell to an effective amount of an aza-heterocyclyl carboxamide or related compound described herein, such as a compound of Formula I, I-A, II, II-A, or other compounds in Section I, to kill the bacterial cell. In certain embodiments, the particular compound of Formula I, I-A, II, or II-A is a compound defined by one of the embodiments described above. In certain embodiments, the compound is a compound of Formula I or I-A.

In certain embodiments, the bacterial cell is one of those described above as being the bacterial species causing a bacterial infection. For example, in certain embodiments, the bacterial cell is a gram-negative bacteria. In certain embodiments, the bacterial cell is a gram-positive bacteria. In certain embodiments, the bacterial cell is an anaerobic bacteria. In certain other embodiments, the bacterial cell is an aerobic bacteria In certain embodiments, the bacterial cell is a Staphylococcus, Streptococcus, Enterococcus, Pseudomonas, Escherichia, Fusobacterium, Klebsiella, Haemophilus, Bordetella, Serratia, Proteus, Enterobacter, Campylobacter, Citrobacter, Vibrio, Morganella, Salmonella, Shigella, Acinetobacter, Legionella, Bacteroides, Neisseria, Moraxella, Chlamydia, Helicobacter, Prevotella, Porphyromonas, Veillonella, Bilophila, Centipeda, Leptotrichia, Selenomonas, or Sutterella bacterium, or a combination thereof. In certain embodiments, the bacterial cell is a Staphylococcus, Streptococcus, Enterococcus, Pseudomonas, Escherichia, Fusobacterium, Klebsiella, Haemophilus, Bordetella, Serratia, Proteus, Enterobacter, Campylobacter, Citrobacter, Vibrio, Morganella, Salmonella, Shigella, Acinetobacter, Legionella, Bacteroides, Neisseria, Moraxella, Chlamydia, or Helicobacter bacterium. In certain embodiments, the bacterial cell is a Pseudomonas, Escherichia, or Fusobacterium bacterium. In certain embodiments, the bacterial cell is a Pseudomonas or Escherichia bacterium.

In certain embodiments, the bacterial cell is a Staphylococcus aureus, Staphylococcus epidermidis, Streptococcus pyogenes, Streptococcus agalactiae, Streptococcus pneumoniae, Enterococcus faecalis, Enterococcus faecium, Pseudomonas aeruginosa, Escherichia coli, Fusobacterium nucleatum, Fusobacterium polynorphunm, Fusobacterium vincentii, Fusobacterium animalis, Fusobacterium fusiforme, Fusobacterium canifelium, Fusobacterium necrophorum, Fusobacterium funduliforme, Fusobacterium

*ulcerans, Fusobacterium gonidiaformans, Fusobacterium mortiferum, Fusobacterium naviforme, Fusobacterium necrogenes, Fusobacterium russii, Fusobacterium varium, Klebsiella pneumoniae, Klebsiella oxytoca, Haemophilus influenzae, Haemophilus parainfluenzae, Bordetella pertussis, Bordetella bronchiseptica, Serratia marcescens, Proteus mirabilis, Enterobacter cloacae, Campylobacter jejuni, Vibrio parahemolyticus, Vibrio cholerae, Morganella morganii, Salmonella typhi, Salmonella paratyphi, Shigella dysenteriae, Acinetobacter baumannii, Acinetobacter calcoaceticus, Legionella pneumophila, Bacteroides fragilis, Bacteroides thetaiotaomicron. Bacteroides vulgatus, Bacteroides distasonis, Bacteroides ovatus, Bacteroides uniformis, Bacteroides caccae, Neisseria gonorrhoeae, Neisseria meningitides, Moraxella catarrhalis, Chlamydia trachomatis, Chlamydia psittaci, Helicobacter pylori, Prevotella intermedia, Prevotella melaninogenica, Prevotella bivia, Prevotella nigrescens, Prevotella disiens, Porphyromonas gingivalis, Veillonella atypica, Veillonella caviae, Veillonella criceti, Veillonella denticariosi, Veillonella dispar, Veillonella magna, Veillonella montpellierensis, Veillonella parvula, Veillonella ratti, Veillonella rodentium, Veillonella rogosae, Veillonella seminalis, Veillonella tobetsuensis Bilophila wadsworthia, Centipeda periodontii, Leptotrichia* buccalis, *Leptotrichia goodfellowii, Leptotrichia hofstadii, Leptotrichia honkongensis, Leptotrichia shahii, Leptotrichia trevisanii, Leptotrichia wadei, Selenomonas sputigena, Sutterella wadsworthensis, Sutterella parvirubra, Sutterella stercoricanis*, or a combination thereof. In certain embodiments, the bacterial cell is a *Staphylococcus aureus, Staphylococcus epidermidis, Streptococcus pyogenes, Streptococcus agalactiae, Streptococcus pneumoniae, Enterococcus faecalis, Enterococcus faecium, Pseudomonas aeruginosa, Escherichia coli, Fusobacterium nucleatum, Klebsiella pneumoniae, Klebsiella oxytoca, Haemophilus influenzae, Haemophilus parainfluenzae, Bordetella pertussis, Bordetella bronchiseptica, Serratia marcescens, Proteus mirabilis, Enterobacter cloacae, Campylobacter jejuni, Vibrio parahemolyticus, Vibrio cholerae, Morganella morganii, Salmonella typhi, Salmonella paratyphi, Shigella dysenteriae, Acinetobacter baumannii, Acinetobacter calcoaceticus, Legionella pneumophila, Bacteroides fragilis, Neisseria gonorrhoeae, Neisseria meningitides, Moraxella catarrhalis, Chlamydia trachomatis, Chlamydia psittaci, Helicobacter pylori* bacterium. In certain embodiments, the bacterial cell is a *Pseudomonas aeruginosa, Escherichia coli*, or *Fusobacterium nucleatum* bacterium. In certain embodiments, the bacterial cell is a *Pseudomonas aeruginosa* or *Escherichia coli* bacterium.

In certain embodiments, the bacterial cell is a bacteria selected from the group consisting of Enterobacteriaceae, *Acinetobacter, Stenotrophomonas, Burkholderia, Pseudomonas, Alcaligenes, Haemophilus, Franciscellaceae* and *Neisseria* species. In certain embodiments, the bacteria is Enterobacteriaceae or *Acinetobacter*. In certain embodiments, the Enterobacteriaceae is selected from the group consisting of *Serratia, Proteus, Klebsiella, Enterobacter, Citrobacter, Salmonella, Providencia, Yersinia, Morganella, Cedecea, Edwardsiella* species, and *Escherichia coli*. In certain embodiments, the *Burkholderia* is *Burkholderia cepacia, Burkholderia pseudomallei* or *Burkholderia mallei*. In certain embodiments, the *Bulkholderia* is *Burkholderia pseudomallei, Burkholderia mallei*, or *Burkholderia cepacia*. In some embodiments, the *Pseudomonas* is *Pseudomonas aeruginosa*. In another embodiment, the *Stenotrophomonas* is *Stenotrophomonas maltophila*. In yet another embodiment, the *Alcaligenes* is *Alcaligenes xylosoxidans*.

In certain embodiments, the *Acinetobacter* is selected from the group consisting of *Acinetobacter baumannii, Acinetobacter lwoffi, Acinetobacter albensis, Acinetobacter apis, Acinetobacter beijerinckii, Acinetobacter bereziniae, Acinetobacter bohemicus, Acinetobacter boissieri, Acinetobacter bouvetii, Acinetobacter brisouii, Acinetobacter calcoaceticus, Acinetobacter courvalinii, Acinetobacter dispersus, Acinetobacter equi, Acinetobacter gandensis, Acinetobacter gerneri, Acinetobacter guangdongensis, Acinetobacter guillouiae, Acinetobacter gyllenbergii, Acinetobacter haemolyticus, Acinetobacter harbinensis, Acinetobacter indicus, Acinetobacter junii, Acinetobacter kookii, Acinetobacter modestus, Acinetobacter nectaris, Acinetobacter nosocomialis, Acinetobacter parvus, Acinetobacter pakistanensis, Acinetobacter populi, Acinetobacter proteolyticus, Acinetobacter pittii, Acinetobacter puyangensis, Acinetobacter qingfengensis, Acinetobacter radioresistens, Acinetobacter rudis, Acinetobacter schindleri, Acinetobacter seifertii, Acinetobacter soli, Acinetobacter tandoii, Acinetobacter tjernbergiae, Acinetobacter towneri, Acinetobacter ursingii, Acinetobacter variabilis, Acinetobacter venetianus*, and *Acinetobacter vivianii*.

Further, the aza-heterocyclyl carboxamide and related compounds described herein, such as a compound of Formula I, I-A, II, II-A, or other compounds in Section I, inhibit the activity of LpxC. Accordingly, one aspect of the invention provides a method of inhibiting the activity of LpxC. The method comprises exposing an LpxC to an effective amount of an aza-heterocyclyl carboxamide or related compound described herein, such as a compound of Formula I, I-A, II, II-A, or other compounds in Section I, to inhibit the activity of LpxC. In certain embodiments, the particular compound of Formula I, I-A, II, or II-A is a compound defined by one of the embodiments described above. In certain embodiments, the compound is a compound of Formula I or I-A.

III. Combination Therapy

Another aspect of the invention provides for combination therapy. Aza-heterocyclyl carboxamide and related compounds (e.g., a compound of Formula I, I-A, II, II-A, or other compounds in Section I) or their pharmaceutically acceptable salts may be used in combination with additional therapeutic agents to treat a bacterial infection. In certain embodiments, the compound is a compound of Formula I or I-A.

The amount of aza-heterocyclyl carboxamide or related compound (e.g., a compound of Formula I, I-A, II, II-A, or other compounds in Section I) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, an aza-heterocyclyl carboxamide or related compound (e.g., a compound of any one of Formula I, I-A, II, II-A, or other compounds in Section I) may be administered during a time when the additional therapeutic agent(s) exerts its prophylactic or therapeutic effect, or vice versa. In certain embodiments, the compound is a compound of Formula I or I-A.

The doses and dosage regimen of the active ingredients used in the combination therapy may be determined by an attending clinician. In certain embodiments, the aza-heterocyclyl carboxamide or related compound (e.g., a compound of any one of Formula I, I-A, II, II-A, or other compounds in Section I) and the additional therapeutic agent(s) are administered in doses commonly employed when such agents are used as monotherapy for treating the bacterial infection. In other embodiments, the aza-heterocyclyl carboxamide or related compound (e.g., a compound of any one of Formula I, I-A, II, II-A, or other compounds in Section I) and the additional therapeutic agent(s) are administered in doses lower than the doses commonly employed when such agents are used as monotherapy for treating the bacterial infection. In certain embodiments, the aza-heterocyclyl carboxamide or related compound (e.g., a compound of any one of Formula I, I-A, II, II-A, or other compounds in Section I) and the additional therapeutic agent(s) are present in the same composition, which is suitable for oral administration. In certain embodiments, the compound is a compound of Formula I or I-A.

In certain embodiments, the aza-heterocyclyl carboxamide or related compound (e.g., a compound of any one of Formula I, I-A, II, II-A, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy. In certain embodiments, the compound is a compound of Formula I or I-A.

In certain embodiments, the additional therapeutic agent is selected from the group consisting of amikacin, arbekacin, dibekacin, gentamicin, isepamicin, kanamycin a, neomycin, netilmicin, paromomycin, sisomicin, streptomycin, tobramycin, chloramphenicol, loracarbef, ertapenem, imipenem, meropenem, R-115685, ceflaclor, cefadroxil, cefamandole, cefazolin, cefdinir, cefditoren, cefepime, cefetamet, cefixime, cefmetazole, cefotaxime, cefoxitin, ceftibuten, cefoperazone, cefotetan, cefpirome, cefpodoxime, cefprozil, ceftazidime, ceftizoxime, ceftobiprole, ceftriaxone, cefuroxime, cephalexin, cephalothin, cephradine, T-91825, iclaprim, trimethoprim, ciprofloxacin, ABT-492, clinafloxacin, danofloxacin, difloxacin, DX-619, enoxacin, fleroxacin, garenoxacin, gatifloxacin, gemifloxacin, grepafloxacin, levofloxacin, lomefloxacin, moxifloxacin, nadifloxacin, nalidixic acid, norfloxacin, pefloxacin, rufloxacin, sitafloxacin, sparfloxacin, temafloxacin, trovafloxacin, dalbavancin, oritavancin, teicoplanin, telavancin, vancomycin, chlorobiocin, novobiocin, pseudomonic acid A, clindamycin, lincomycin, daptomycin, azithromycin, cethromycin, clarithromycin, dirithromycin, EP-13420, erythromycin, roxithromycin, telithromycin, aztreonam, fosfomycin, linezolid, ranbezolid, doripenem, faropenem, amoxicillin, ampicillin, azlocillin, carenicllin, cloxacillin, dicloxacillin, methicillin, mezlocillin, nafcillin, oxacillin, penicillin G, penicillin V, piperacillin, ticarcillin, rifalazil, rifampin, dalfopristin, quinupristin, sulfabenzamide, sulfacetamide, sulfachlorpyridazine, sulfadiazine, sulfadimethoxine, sulfaguanidine, sulfamerazine, sulfameter, sulfamethazine, sulfamethizole, sulfamethoxazole, sulfamethoxypyridazine, sulfamonomethoxine, sulfanitran, sulfaphenazole, sulfapyridine, sulfaquinoxaline, sulfathiazole, sulfisoxazole, gramicidin, polymyxin B1, triclosan, chlortetracycline, demeclocycline, doxycycline, meclocycline, methacycline, minocycline, oxytetracycline, PTK-0796, tetracycline, tigecycline, fusidic acid, and combinations thereof.

Another aspect of this invention is a kit comprising a therapeutically effective amount of the aza-heterocyclyl carboxamide or related compound (e.g., a compound of any one of Formula I, I-A, II, II-A, or other compounds in Section I), a pharmaceutically acceptable carrier, vehicle or diluent, and optionally at least one additional therapeutic agent listed above. In certain embodiments, the compound is a compound of Formula I or I-A.

IV. Pharmaceutical Compositions and Dosing Considerations

As indicated above, the invention provides pharmaceutical compositions. In one embodiment, the pharmaceutical composition comprises a compound described herein and a pharmaceutically acceptable carrier. In a more specific embodiment, the pharmaceutical composition comprises a therapeutically-effective amount of a compound described above, formulated together with a pharmaceutically acceptable carrier. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising an aza-heterocyclyl carboxamide or related compound described herein in a therapeutically effective amount for the treatment of a bacterial infection described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

General Experimental Details

Abbreviations used include: aq.=aqueous; DCE=dichloroethane; DCM=dichloromethane; DIAD=Diisopropyl azodicarboxylate; DIPEA=diisopropylethylamine; DMF=N,N-dimethylformamide; DMSO=dimethyl sulfoxide; EtOAc=ethyl acetate; FCC=flash column chromatography; h=hour; HATU=N-[(Dimethylamino)-1H-1,2,3-triazolo-[4,5-b]pyridin-1-ylmethylene]-N-methylmethanaminium hexafluorophosphate N-oxide; HPLC=high performance liquid chromatography; IMS=industrial methylated spirit; LCMS=liquid chromatography mass spectrometry; MDAP=mass-directed auto-purification; min=minutes; NMR=nuclear magnetic resonance; RT=room temperature; Rt=retention time; sat.=saturated; SCX-2=strong cation exchange chromatography; TBAF=tetrabutylammonium fluoride; TFA=trifluoroacetic acid; TFAA=Trifluoroacetic anhydride; THF=Tetrahydrofuran; T3P=propylphosphonic anhydride.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz throughout. NMR spectra were assigned using DataChord Spectrum Analyst Version 4.0.b21 or SpinWorks version 3.

Where products were purified by chromatography, silica refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d. Genesis column with 7 μm particle size), or a Phenyl-Hexyl column (250×21.2 mm i.d. Gemini column with 5 μm particle size), UV detection between 220-254 nm, flow 5-20 mL/min), eluting with gradients from 100-0 to 0-100% water/acetonitrile (containing 0.1% TFA or 0.1% formic acid) or a C18-reverse-phase column (19×250 mm, XBridge OBD, with 5 μm particle size), eluting with gradients from 100-0 to 0-100% water/acetonitrile (containing 0.1% NH$_4$OH); or a ChiralPak IC column (10×250 mm i.d., with 5 μm particle size), unless otherwise indicated. Fractions containing the required product (identified by LCMS analysis) were pooled, the organic solvent removed by evaporation, and the remaining aqueous residue lyophilised, to give the final product. Products purified by preparative HPLC were isolated as free base, formate or TFA salts, unless otherwise stated.

The Liquid Chromatography Mass Spectroscopy (LCMS) systems used are described below.

Method 1

Acquity H-Class UPLC with DAD detector and QDa

A: 0.1% Formic acid in water B: 0.1% formic acid in acetonitrile

Waters Acquity CSH UPLC column—2.1×50 mm, 1.7 um at 40° C.

2 μL injection, 1 mL/min flow rate

Mass ranges: 60-600 Low mass, 100-800 standard, 300-1200 high mass

Four gradients:

1. 2 min gradient, all three mass ranges:

| Time (mins) | % A | % B |
|---|---|---|
| 0.0 | 97 | 03 |
| 1.5 | 01 | 99 |
| 1.9 | 01 | 99 |

-continued

| Time (mins) | % A | % B |
|---|---|---|
| 2.0 | 97 | 03 |
| 2.5 | 97 | 03 |

2. 5 min gradient, standard mass range:

| Time (mins) | % A | % B |
|---|---|---|
| 0.0 | 97 | 03 |
| 4 | 01 | 99 |
| 4.4 | 01 | 99 |
| 4.5 | 97 | 03 |
| 5 | 97 | 03 |

3. Early-eluting (shallow) gradient, standard mass range:

| Time (mins) | % A | % B |
|---|---|---|
| 0.0 | 97 | 03 |
| 1.5 | 50 | 50 |
| 1.9 | 50 | 50 |
| 2.0 | 97 | 03 |
| 2.5 | 97 | 03 |

4. Late-eluting (fast) gradient, standard mass range:

| Time (mins) | % A | % B |
|---|---|---|
| 0.0 | 97 | 03 |
| 1.0 | 01 | 99 |
| 1.4 | 01 | 99 |
| 2.0 | 97 | 03 |
| 2.5 | 97 | 03 |

Method 2

Acquity UPLC, 996 DAD detector and Quattro Micro MSA: 0.1% Formic acid in water B: 0.1% formic acid in acetonitrile Waters Acquity CSH UPLC column—2.1×50 mm, 1.7 um at 40° C.

1 µL injection, 1 mL/min flow rate

Mass ranges: 60-800 Low mass, 160-1000 standard, 160-1500 high mass

Four gradients:

1. 2 min gradient, all three mass ranges:

| Time (mins) | % A | % B |
|---|---|---|
| 0.0 | 97 | 3 |
| 0.1 | 97 | 3 |
| 0.15 | 97 | 3 |
| 2.3 | 1 | 99 |
| 2.4 | 1 | 99 |
| 2.5 | 97 | 3 |

2. 5 min gradient, standard and high mass ranges:

| Time (mins) | % A | % B |
|---|---|---|
| 0.0 | 97 | 3 |
| 0.1 | 97 | 3 |
| 0.15 | 97 | 3 |
| 4.8 | 1 | 99 |
| 4.9 | 1 | 99 |
| 5 | 97 | 3 |

3. Early-eluting (shallow) gradient, standard mass range:

| Time (mins) | % A | % B |
|---|---|---|
| 0.0 | 97 | 3 |
| 0.1 | 97 | 3 |
| 0.15 | 97 | 3 |
| 2.3 | 50 | 50 |
| 2.4 | 50 | 50 |
| 2.5 | 97 | 3 |

4. Late-eluting (fast) gradient, standard mass range:

| Time (mins) | % A | % B |
|---|---|---|
| 0.0 | 97 | 3 |
| 0.1 | 97 | 3 |
| 0.15 | 97 | 3 |
| 1.8 | 1 | 99 |
| 2.4 | 1 | 99 |
| 2.5 | 97 | 3 |

Method 3

Acquity H-Class UPLC with DAD detector and QDa

A: 7.66 mM ammonia in water B: 7.66 mM ammonia in acetonitrile

Waters Acquity BEH UPLC column—2.1×50 mm, 1.7 um at 40° C.

1 µL injection, 0.8 mL/min flow rate

Mass ranges: 60-600 Low mass, 100-800 standard, 300-1200 high mass

Four gradients:

1. 2 min gradient, all three mass ranges:

| Time (mins) | % A | % B |
|---|---|---|
| 0.0 | 97 | 03 |
| 1.5 | 3 | 97 |
| 1.9 | 3 | 97 |
| 2.0 | 97 | 3 |
| 2.5 | 97 | 3 |

2. 5 min gradient, all three mass ranges:

| Time (mins) | % A | % B |
|---|---|---|
| 0.0 | 97 | 03 |
| 4.0 | 3 | 97 |
| 4.4 | 3 | 97 |
| 4.5 | 97 | 3 |
| 5.0 | 97 | 3 |

3. Early-eluting (shallow) gradient:

| Time (mins) | % A | % B |
| --- | --- | --- |
| 0.0 | 97 | 03 |
| 1.5 | 50 | 50 |
| 2.0 | 50 | 50 |

4. Late-eluting (fast) gradient, standard mass range:

| Time (mins) | % A | % B |
| --- | --- | --- |
| 0.0 | 97 | 03 |
| 1.0 | 3 | 97 |
| 1.4 | 3 | 97 |
| 1.5 | 97 | 3 |
| 2.0 | 97 | 3 |

Method 4
HPLC 1100 system with DAD detector, CTC autosampler, and ZQ MS
A: 7.66 mM ammonia in water B: 7.66 mM ammonia in acetonitrile
Waters XBridge column—4.6×50 mm, 3.5 um at 40° C.
20 µL injection, 2 mL/min flow rate
Mass ranges: 100-1000
Gradient:

| Time (mins) | % A | % B |
| --- | --- | --- |
| 0.0 | 95 | 5 |
| 0.3 | 95 | 5 |
| 4.3 | 5 | 95 |
| 5.3 | 5 | 95 |
| 5.8 | 95 | 5 |
| 6.0 | 95 | 5 |

Method 5
Acquity UPLC with PDA detector and ZQ, mass range detection 100-800, diode array detection 200-400 nm
A: 0.1% formic acid in water B: 0.1% formic acid in acetonitrile
Waters Acquity BEH UPLC column—2.1×100 mm, 1.7 um at 40° C.
1 µL injection, 0.4 mL/min flow rate
Mass ranges: 1000-1000
Gradient: 0.4 min hold at 5% B, 5%-95% B in 5.6 min, hold at 95% B for 0.8 min, back to 5% B.

Example 1—Synthesis of tert-Butyl (2S,4S)-2-(((3R,5R)-5-(aminomethyl)-1-(cyclopropanecarbonyl)pyrrolidin-3-yl)carbamoyl)-4-fluoropyrrolidine-1-carboxylate (Intermediate 1

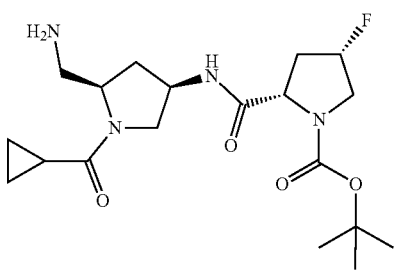 [SMILES: CC(C)(C)OC(=O)N1C[C@@H](F)C[C@H]1C(=O)N[C@@H]1C[C@H](CN)N(C(=O)C2CC2)C1]

Part I—Synthesis of 1-Benzyl 2-Methyl (2R,4R)-4-Aminopyrrolidine-1,2-dicarboxylate 1-Benzyl 2-methyl (2R,4R)-4-((tert-butoxycarbonyl)amino)pyrrolidine-1,2-dicarboxylate (2.3 g, 6.1 mmol) was dissolved in HCl in dioxane (4M, 30 mL) and stirred at room temperature for 4 hours. The solvent was removed to yield 1-benzyl 2-methyl (2R,4R)-4-aminopyrrolidine-1,2-dicarboxylate (1.9 g, 100%) as a white foam.

Part II—Synthesis of 1-Benzyl 2-Methyl (2R,4R)-4-((2S,4S)-1-(tert-Butoxycarbonyl)-4-fluoropyrrolidine-2-carboxamido)pyrrolidine-1,2-dicarboxylate To a suspension of 1-benzyl 2-methyl (2R,4R)-4-aminopyrrolidine-1,2-dicarboxylate (1.9 g, 6.1 mmol) and N-Boc-cis-4-fluoro-L-proline (1.55 g, 6.6 mmol) in 2-methyltetrahydrofuran (40 mL) was added triethylamine (3.5 mL, 25.4 mmol) followed by T3P (50% solution in ethyl acetate, 5.4 mL, 9.05 mmol) and the mixture stirred at room temperature for 4 hours. The mixture was partitioned between ethyl acetate and water and the phases separated. The organic layer was washed with brine, dried ($Na_2SO_4$), filtered and the solvent removed. The residue was purified by chromatography (80 g silica cartridge, 0-10% methanol/dichloromethane gradient) to yield 1-benzyl 2-methyl (2R,4R)-4-((2S,4S)-1-(tert-butoxycarbonyl)-4-fluoropyrrolidine-2-carboxamido)pyrrolidine-1,2-dicarboxylate (2.75 g, 92%) as a colourless oil.

Part III—Synthesis of tert-Butyl (2S,4S)-4-fluoro-2-(((3R,5R)-5-(methoxycarbonyl)pyrrolidin-3-yl)carbamoyl)pyrrolidine-1-carboxylate 1-Benzyl 2-methyl (2R,4R)-4-((2S,4S)-1-(tert-butoxycarbonyl)-4-fluoropyrrolidine-2-carboxamido)pyrrolidine-1,2-dicarboxylate (2.75 g, 5.57 mmol) and 10% palladium on carbon (140 mg) were suspended in ethanol (30 mL) under an atmosphere of nitrogen. The nitrogen was evacuated and replaced with hydrogen gas (1 atm). The mixture was stirred at room temperature for 18 hours. The hydrogen was evacuated, replaced with nitrogen and then the mixture was filtered through a celite pad eluting with ethyl acetate. The filtrate was collected and the solvent removed to yield tert-butyl (2S,4S)-4-fluoro-2-(((3R,5R)-5-(methoxycarbonyl)pyrrolidin-3-yl)carbamoyl)pyrrolidine-1-carboxylate (2.0 g, 100%) as a colourless oil.

Part IV—Synthesis of tert-Butyl (2S,4S)-2-(((3R,5R)-1-(cyclopropanecarbonyl)-5-(methoxycarbonyl)pyrrolidin-3-yl)carbamoyl)-4-fluoropyrrolidine-1-carboxylate To a solution of tert-butyl (2S,4S)-4-fluoro-2-(((3R,5R)-5-(methoxycarbonyl)pyrrolidin-3-yl)carbamoyl)pyrrolidine-1-carboxylate (2.0 g, 5.56 mmol) in dichloromethane (25 mL) at 0° C. under a nitrogen atmosphere was added triethylamine (1.16 mL, 8.35 mmol) then cyclopropanecarbonyl chloride (555 µL, 6.12 mmol) dropwise. The mixture was stirred at 0° C. for 3 hours, then partitioned between dichloromethane and brine. The phases were separated and the organic layer collected and the solvent removed in vacuo to yield tert-butyl (2S,4S)-2-(((3R,5R)-1-(cyclopropanecarbonyl)-5-(methoxycarbonyl)pyrrolidin-3-yl)carbamoyl)-4-fluoropyrrolidine-1-carboxylate (2.4 g, 100%) as a white foam.

Part V—Synthesis of tert-Butyl (2S,4S)-2-(((3R, 5R)-1-(cyclopropanecarbonyl)-5-(hydroxymethyl) pyrrolidin-3-yl)carbamoyl)-4-fluoropyrrolidine-1-carboxylate To a solution of tert-butyl (2S,4S)-2-(((3R,5R)-1-(cyclopropanecarbonyl)-5-(methoxycarbonyl)pyrrolidin-3-yl)carbamoyl)-4-fluoropyrrolidine-1-carboxylate (2.38 g, 5.56 mmol) in THF (15 mL) under a nitrogen atmosphere was added lithium chloride (0.71 g, 16.7 mmol) then sodium borohydride (0.63 g, 16.7 mmol) followed by ethanol (30 mL) in three portions. The mixture was stirred at room temperature for 18 hours, then further lithium chloride (0.23 g, 5.56 mmol) and sodium borohydride (0.21 g, 5.56 mmol) was added and stirring continued for a further 20 hours. The reaction was quenched by cautiously adding water (5 mL) and the solvent reduced to low volume in vacuo. The residue was partitioned between ethyl acetate and water and the phases separated. The organic layer was washed with brine, dried ($Na_2SO_4$), filtered and the solvent removed to yield tert-butyl (2S,4S)-2-(((3R,5R)-1-(cyclopropanecarbonyl)-5-(hydroxymethyl)pyrrolidin-3-yl)carbamoyl)-4-fluoropyrrolidine-1-carboxylate (2.2 g, 100%) as a white foam.

Part VI—Synthesis of tert-Butyl (2S,4S)-2-(((3R, 5R)-1-(cyclopropanecarbonyl)-5-((1,3-dioxoisoindolin-2-yl)methyl)pyrrolidin-3-yl)carbamoyl)-4-fluoropyrrolidine-1-carboxylate To a solution of tert-butyl (2S,4S)-2-(((3R,5R)-1-(cyclopropanecarbonyl)-5-(hydroxymethyl)pyrrolidin-3-yl)carbamoyl)-4-fluoropyrrolidine-1-carboxylate (2.2 g, 5.56 mmol), phthalimide (1.23 g, 8.34 mmol) and triphenylphosphine (2.19 g, 8.34 mmol) in THF at 0° C. under an atmosphere of nitrogen was added DIAD (1.64 mL, 8.34 mmol) dropwise over 5 minutes. The mixture was stirred at 0° C. for 1 hour and allowed to room temperature and stirred for a further 3 hours. The residue was partitioned between ethyl acetate and water and the phases separated. The organic layer was washed with brine, dried ($Na_2SO_4$), filtered and the solvent removed. The residue was purified by chromatography (120 g silica cartridge, 0-8% methanol/dichloromethane gradient) to yield tert-butyl (2S,4S)-2-(((3R,5R)-1-(cyclopropanecarbonyl)-5-((1,3-dioxoisoindolin-2-yl)methyl)pyrrolidin-3-yl)carbamoyl)-4-fluoropyrrolidine-1-carboxylate (3.2 g, >100% contains triphenylphosphine oxide) as a pale yellow foam.

Part VII—Synthesis of tert-Butyl (2S,4S)-2-(((3R, 5R)-5-(aminomethyl)-1-(cyclopropanecarbonyl)pyrrolidin-3-yl)carbamoyl)-4-fluoropyrrolidine-1-carboxylate To a solution of tert-butyl (2S,4S)-2-(((3R,5R)-1-(cyclopropanecarbonyl)-5-((1,3-dioxoisoindolin-2-yl)methyl)pyrrolidin-3-yl)carbamoyl)-4-fluoropyrrolidine-1-carboxylate (3.2 g, ~5.56 mmol) in ethanol (50 mL) was added hydrazine hydrate (0.64 mL, 11.3 mmol) and the mixture stirred at 70° C. for 4 hours. The mixture was allowed cool to room temperature and the solvent reduced to low volume in vacuo. The residue was partitioned between dichloromethane and water and the phases separated. The aqueous layer was saturated with solid $Na_2SO_4$ and further extracted with 10% methanol/dichloromethane. The organic layers were combined and washed with brine, dried ($Na_2SO_4$), filtered and the solvent removed. The residue was purified by chromatography (80 g silica cartridge, 0-10% 2M ammonia in methanol/dichloromethane gradient) to yield tert-butyl (2S, 4S)-2-(((3R,5R)-5-(aminomethyl)-1-(cyclopropanecarbonyl)pyrrolidin-3-yl)carbamoyl)-4-fluoropyrrolidine-1-carboxylate (900 mg, 40%) as a white foam. LCMS (Method 2, ESI): Rt=0.74 min, $[M+H]^+=399.1$.

Example 2—Synthesis of tert-Butyl (2S,4S)-2-(((3R,5R)-5-(Aminomethyl)-1-((2-(trimethylsilyl) ethoxy)carbonyl)pyrrolidin-3-yl)carbamoyl)-4-fluoropyrrolidine-1-carboxylate (Intermediate 2

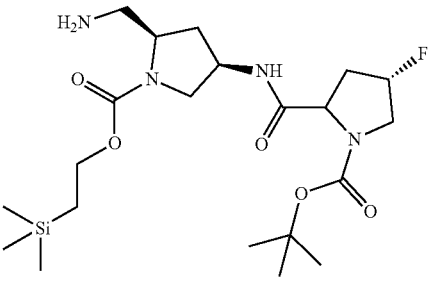 [SMILES: CC(C)(C)OC(=O)N1C[C@@H](F)CC1C(=O)N[C@@H]1C[C@H](CN)N(C(=O)OCC[Si](C)(C)C)C1]

Part I—Synthesis of 2-Methyl 1-(2-(Trimethylsilyl) ethyl) (2R,4R)-4-((2S,4S)-1-(tert-Butoxycarbonyl)-4-fluoropyrrolidine-2-carboxamido)pyrrolidine-1,2-dicarboxylate To a solution of tert-butyl (2S,4S)-4-fluoro-2-(((3R,5R)-5-(methoxycarbonyl)pyrrolidin-3-yl)carbamoyl)pyrrolidine-1-carboxylate (1.87 g, 5.20 mmol) in THF (26 mL) at 0° C. was added trimethylamine (1.60 mL, 11.45 mmol) followed by 1-[2-(trimethylsilyl)ethoxycarbonyloxy]pyrrolidin-2,5-dione (1.62 g, 6.24 mmol). The mixture was stirred at 0° C. for 10 mins then allowed to warm to room temperature and stirred for a further 3 hours. The mixture was concentrated in vacuo and the residue partitioned between ethyl acetate and water. The organic layer was washed with brine, dried ($Na_2SO_4$), filtered and the solvent removed. The residue was purified by chromatography (80 g silica cartridge, 30-100% ethyl acetate in cyclohexane gradient) to yield 2-methyl 1-(2-(trimethylsilyl)ethyl) (2R, 4R)-4-((2S,4S)-1-(tert-butoxycarbonyl)-4-fluoropyrrolidine-2-carboxamido)pyrrolidine-1,2-dicarboxylate as a white foam (1.75 g, 67%).

Part II—Synthesis of tert-Butyl (2S,4S)-4-Fluoro-2-(((3R,5R)-5-(hydroxymethyl)-1-((2-(trimethylsilyl) ethoxy)carbonyl)pyrrolidin-3-yl)carbamoyl)pyrrolidine-1-carboxylate To a solution of 2-methyl 1-(2-(trimethylsilyl)ethyl) (2R, 4R)-4-((2S,4S)-1-(tert-butoxycarbonyl)-4-fluoropyrrolidine-2-carboxamido)pyrrolidine-1,2-dicarboxylate (1.75 g, 3.47 mmol) in THF (12 mL) at RT under a nitrogen atmosphere was added lithium chloride (440 mg, 10.42 mmol) and sodium borohydride (390 gm, 10.42 mmol). Ethanol (24 mL) was then added and the reaction mixture was stirred at room temperature for 24 hours. The reaction was quenched by cautiously adding water and the solvent reduced to low volume in vacuo. The residue was partitioned between ethyl acetate and water and the phases separated. The organic layer was washed with brine, dried ($Na_2SO_4$), filtered and the solvent removed to yield tert-butyl (2S,4S)-

4-fluoro-2-(((3R,5R)-5-(hydroxymethyl)-1-((2-(trimethylsilyl)ethoxy)carbonyl)pyrrolidin-3-yl)carbamoyl)pyrrolidine-1-carboxylate as a white foam (1.64 g, 99%).

Part III—Synthesis of tert-Butyl (2S,4S)-2-(((3R,5R)-5-(((1,3-Dioxoisoindolin-2-yl)methyl)-1-((2-(trimethylsilyl)ethoxy)carbonyl)pyrrolidin-3-yl)carbamoyl)-4-fluoropyrrolidine-1-carboxylate To a solution of tert-butyl (2S,4S)-4-fluoro-2-(((3R,5R)-5-(hydroxymethyl)-1-((2-(trimethylsilyl)ethoxy)carbonyl)pyrrolidin-3-yl)carbamoyl)pyrrolidine-1-carboxylate (1.64 g, 3.45 mmol), phthalimide (760 mg, 5.17 mmol) and triphenylphosphine (1.36 g, 5.17 mmol) in THF at 0° C. under an atmosphere of nitrogen was added diisopropylazodicarboxylate (1.02 mL, 5.17 mmol) dropwise over 5 minutes. The mixture was stirred at 0° C. for 1 hour and allowed to room temperature and stirred for a further 4 hours. The mixture was concentrated in vacuo and the residue partitioned between ethyl acetate and water. The organic layer was washed with saturated NaHCO$_3$ (aq) and brine, dried (Na$_2$SO$_4$), filtered and the solvent removed. The residue was purified by chromatography (40 g silica cartridge, dry loaded, 0-100% ethyl acetate in cyclohexane gradient) to yield tert-butyl (2S,4S)-2-(((3R,5R)-5-((1,3-dioxoisoindolin-2-yl)methyl)-1-((2-(trimethylsilyl)ethoxy)carbonyl)pyrrolidin-3-yl)carbamoyl)-4-fluoropyrrolidine-1-carboxylate (3.63 g, >100% contains triphenylphosphine oxide) as a yellow oil that solidified on standing.

Part IV—Synthesis of tert-Butyl (2S,4S)-2-(((3R,5R)-5-(Aminomethyl)-1-((2-(trimethylsilyl)ethoxy)carbonyl)pyrrolidin-3-yl)carbamoyl)-4-fluoropyrrolidine-1-carboxylate To a solution of tert-butyl (2S,4S)-2-(((3R,5R)-5-((1,3-dioxoisoindolin-2-yl)methyl)-1-((2-(trimethylsilyl)ethoxy)carbonyl)pyrrolidin-3-yl)carbamoyl)-4-fluoropyrrolidine-1-carboxylate (3.63 g, ~3.45 mmol) in ethanol (35 mL) was added hydrazine hydrate (55%, 782 µL, 13.80 mmol) and the mixture stirred at 70° C. for 2.5 hours, during which a white precipitate formed. The mixture was allowed cool to room temperature, filtered and the filter cake washed with ethanol. The filtrate was concentrated in vacuo. The residue was purified by chromatography (80 g silica cartridge, dry loaded, 0-5% 2M ammonia in methanol/dichloromethane gradient) to yield tert-butyl (2S,4S)-2-(((3R,5R)-5-(aminomethyl)-1-((2-(trimethylsilyl)ethoxy)carbonyl)pyrrolidin-3-yl)carbamoyl)-4-fluoropyrrolidine-1-carboxylate as a yellow gum (931 mg, 57%).

Example 3—Synthesis of (2S,4S)—N-((3R,5R)-1-(cyclopropanecarbonyl)-5-((4-(phenylbuta-1,3-diyn-1-yl)benzamido)methyl)pyrrolidin-3-yl)-4-fluoropyrrolidine-2-carboxamide

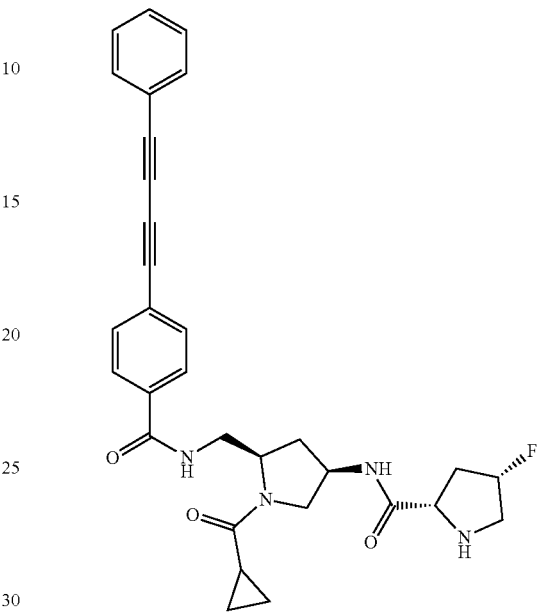

Part I—Synthesis of Methyl-4-(2,2-dibromovinyl)benzoate

Methyl 4-formylbenzoate (1.5 g, 9.14 mmol) and tetrabromomethane (3.18 g, 9.59 mmol) were stirred in dichloromethane (20 mL) at 0° C. for 10 minutes. Triphenylphosphine (5.03 g, 19.19 mmol) was added in four portions at three minute intervals. The reaction mixture was stirred at room temperature for two hours. Cyclohexane was added to the reaction mixture and the resulting slurry was filtered through silica (flash II column, 50 g) eluting with diethyl ether and cyclohexane (1:1). The eluent was collected and concentrated in vacuo. The residue was purified by chromatography (40 g silica cartridge, dichloromethane) to yield methyl-4-(2,2-dibromovinyl)benzoate as a colourless oil, which formed a white solid on standing (2.35 g, 81%).

Part II—Synthesis of Methyl 4-(Phenylbuta-1,3-diyn-1-yl)benzoate

Methyl 4-(2,2-dibromovinyl)benzoate (500 mg, 1.56 mmol), phenylacetylene (240 µL, 2.19 mmol), Pd$_2$(dba)$_3$ (14 mg, 0.0156 mmol) and tris(2,4,6-trimethoxyphenyl)phosphine (22 mg, 0.0625 mmol) were dissolved in DMF (6 mL). The reaction mixture was sparged with argon for 10 minutes at room temperature. Triethylamine (653 µL 4.69 mmol) was added and the mixture stirred at 85° C. for 4 hours. The reaction mixture was cooled to room temperature, and diluted with ethyl acetate and cyclohexane (1:1). The organic phase was washed with hydrochloric acid (1_M, 2×2 mL), aqueous sodium hydroxide (2M, 3×1 mL), water (3×5 mL) and brine (3×5 mL). The organic layer was dried (Na$_2$SO$_4$), filtered and the solvent removed. The residue was purified by chromatography (25 g silica cartridge, 0-10% ethyl acetate/cyclohexane gradient) to yield methyl 4-(phenylbuta-1,3-diyn-1-yl)benzoate as a yellow solid (320 mg, 79%).

Part III—Synthesis of 4-(Phenylbuta-1,3-diyn-1-yl)benzoic Acid

To a solution of methyl 4-(phenylbuta-1,3-diyn-1-yl)benzoate (318 mg, 1.22 mmol) in THF (5 mL) and methanol (1.4 mL) was added aqueous lithium hydroxide (2.0 M, 1.22 mL, 2.44 mmol) and the mixture stirred at room temperature for 24 hours. The mixture was concentrated in vacuo and the residue dissolved in water. The aqueous phase was acidified with hydrochloric acid (1M) to pH 2 and extracted with ethyl acetate. The organic layer was washed with brine (3×5 mL), dried (Na$_2$SO$_4$), filtered and the solvent removed to yield 4-(phenylbuta-1,3-diyn-1-yl)benzoic acid as a yellow solid (200 mg, 66%).

Part IV—Synthesis of tert-Butyl (2S,4S)-2-(((3R,5R)-1-(Cyclopropanecarbonyl)-5-((4-(phenylbuta-1,3-diyn-1-yl)benzamido)methyl)pyrrolidin-3-yl)carbamoyl)-4-fluoropyrrolidine-1-carboxylate To a solution of tert-butyl (2S,4S)-2-(((3R,5R)-5-(aminomethyl)-1-(cyclopropanecarbonyl)pyrrolidin-3-yl)carbamoyl)-4-fluoropyrrolidine-1-carboxylate (50 mg, 0.125 mmol) and 4-(phenylbuta-1,3-diyn-1-yl)benzoic acid (37 mg, 0.151 mmol) in dichloromethane (1 mL) was added triethylamine (26 µL, 0.188 mmol) then propylphosphonic acid (50% solution in ethyl acetate, 112 µL, 0.188 mmol) and the reaction mixture stirred at room temperature for 3 hours. The mixture was partitioned between dichloromethane and water and the phases separated. The organics were collected and the solvent removed. The residue was purified by chromatography (12 g silica cartridge, 0-10% methanol/dichloromethane gradient) to yield tert-butyl (2S,4S)-2-(((3R,5R)-1-(cyclopropanecarbonyl)-5-((4-(phenylbuta-1,3-diyn-1-yl)benzamido)methyl)pyrrolidin-3-yl)carbamoyl)-4-fluoropyrrolidine-1-carboxylate (47 mg, 59%) as a yellow solid.

Part V—Synthesis of (2S,4S)—N-((3R,5R)-1-(cyclopropanecarbonyl)-5-((4-(phenylbuta-1,3-diyn-1-yl)benzamido)methyl)pyrrolidin-3-yl)-4-fluoropyrrolidine-2-carboxamide To a solution of tert-butyl (2S,4S)-2-(((3R,5R)-1-(cyclopropanecarbonyl)-5-((4-(phenylbuta-1,3-diyn-1-yl)benzamido)methyl)pyrrolidin-3-yl)carbamoyl)-4-fluoropyrrolidine-1-carboxylate (46 mg, 0.073 mmol) in dichloromethane (0.8 mL) was added TFA (0.2 mL) and the reaction mixture stirred at room temperature for 2.5 hours. The reaction mixture was concentrated in vacuo, and the remaining TFA was azeotroped with toluene. The residue was dissolved in DMSO (1.5 mL) and purified by reverse phase preparative HPLC (Sunfire C18 19×150 mm, 10 um 5-95% ACN/water (0.1% TFA), 20 ml/min, RT) and the residue lyophilised to yield the title compound (23 mg, 49%, TFA salt) as a yellow solid. LCMS (Method 5, ESI): Rt=3.95 min, [M+H]$^+$=527.3, 99.2% purity.

Example 4—Synthesis of (2S,4S)—N-((3R,5R)-1-(Cyclopropanecarbonyl)-5-((4-(cyclopropylbuta-1,3-diyn-1-yl)benzamido)methyl)pyrrolidin-3-yl)-4-fluoropyrrolidine-2-carboxamide

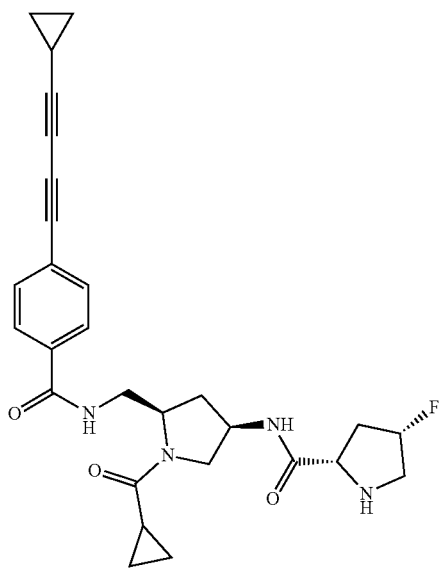 [SMILES: O=C(NC[C@H]1C[C@@H](NC(=O)[C@@H]2C[C@H](F)CN2)CN1C(=O)C1CC1)c1ccc(C#CC#CC2CC2)cc1]

Part I—Synthesis of Methyl 4-(Cyclopropylbuta-1,3-diyn-1-yl)benzoate

Methyl-4-(2,2-dibromovinyl) benzoate (500 mg 1.56 mmol), ethynylcyclopropane (185 µL 2.19 mmol), Pd$_2$(dba)$_3$ (14 mg, 0.0156 mmol) and tris(2,4,6-trimethoxyphenyl)phosphine (22 mg, 0.0625 mmol) were dissolved in DMF (6 mL). The reaction mixture was sparged with argon for 10 minutes at room temperature. Triethylamine (653 µL, 4.69 mmol) was added and the reaction mixture was stirred at 85° C. for 4 hours. The reaction mixture was cooled to room temperature, and diluted with ethyl acetate and cyclohexane (1:1). The organic phase was washed with hydrochloric acid (1M, 2×2 mL), aqueous Sodium hydroxide (2M, 3×1 mL), water (3×5 mL) and brine (3×5 mL). The organic layer was dried (Na$_2$SO$_4$), filtered and the solvent removed. The residue was purified by chromatography (25 g silica cartridge, 0-10% ethyl acetate/cyclohexane gradient) to yield methyl 4-(cyclopropylbuta-1,3-diyn-1-yl)benzoate as a yellow solid (250 mg, 71%).

Part II—Synthesis of 4-(Cyclopropylbuta-1,3-diyn-1-yl)benzoic Acid

To a solution of methyl 4-(cyclopropylbuta-1,3-diyn-1-yl)benzoate (182 mg, 0.722 mmol) in THF (3 mL) and methanol (0.8 mL) was added aqueous lithium hydroxide (2M, 722 µL, 1.44 mmol) and the mixture stirred at room temperature for 90 minutes. The mixture was concentrated in vacuo and the residue dissolved in water. The aqueous phase was acidified with hydrochloric acid (1M) to pH 2 and extracted with ethyl acetate. The organic layer was washed with brine (3×5 mL), dried (Na₂SO₄), filtered and the solvent removed to yield 4-(cyclopropylbuta-1,3-diyn-1-yl) benzoic acid as a yellow solid (152 mg, 65%).

Part III—Synthesis of tert-Butyl (2S,4S)-2-(((3R, 5R)-1-(Cyclopropanecarbonyl)-5-((4-(cyclopropylbuta-1,3-diyn-1-yl)benzamido)methyl)pyrrolidin-3-yl)carbamoyl)-4-fluoropyrrolidine-1-carboxylate To a solution of tert-butyl (2S,4S)-2-(((3R,5R)-5-(aminomethyl)-1-(cyclopropanecarbonyl)pyrrolidin-3-yl)carbamoyl)-4-fluoropyrrolidine-1-carboxylate (50 mg, 0.125 mmol) and 4-(cyclopropylbuta-1,3-diyn-1-yl)benzoic acid (32 mg, 0.151 mmol) in dichloromethane (1 mL) was added triethylamine (26 µL, 0.188 mmol) then T3P (50% solution in ethyl acetate, 112 µL, 0.188 mmol) and the reaction mixture stirred at room temperature for 3 hours. The mixture was partitioned between dichloromethane and water and the phases separated. The organics were collected and the solvent removed. The residue was used directly in the next step without further purification.

Part IV—Synthesis of (2S,4S)—N-((3R,5R)-1-(Cyclopropanecarbonyl)-5-((4-(cyclopropylbuta-1,3-diyn-1-yl)benzamido)methyl)pyrrolidin-3-yl)-4-fluoropyrrolidine-2-carboxamide To a solution of tert-butyl (2S,4S)-2-(((3R,5R)-1-(cyclopropanecarbonyl)-5-((4-(cyclopropylbuta-1,3-diyn-1-yl) benzamido)methyl)pyrrolidin-3-yl)carbamoyl)-4-fluoropyrrolidine-1-carboxylate (74 mg, 0.125 mmol) in dichloromethane (1.6 mL) was added TFA (0.4 mL) and the reaction mixture stirred at room temperature for 4 hours. The reaction mixture was concentrated in vacuo, and the remaining TFA was azeotroped with toluene. The residue was dissolved in DMSO (1.5 mL) and purified by reverse phase preparative HPLC (Sunfire C18 19×150 mm, 10 um 5-95% ACN/water (0.1% TFA), 20 ml/min, RT) and the residue lyophilised to yield the title compound (23 mg, 49%, TFA salt) as a yellow solid. LCMS (Method 5, ESI): Rt=3.58 min, [M+H]⁺=491.3, 99.0% purity. ¹H NMR (400 MHz, DMSO+ d-TFA) 7.86 (2H, d, J=8.0 Hz), 7.63 (2H, dd, J=6.7, 8.0 Hz), 5.49 (0.5H, t, J=3.5 Hz), 5.36 (0.5H, t, J=3.5 Hz), 4.44-4.20 (3H, m), 4.13-4.08 (0.5H, m), 3.98-3.93 (0.5H, m), 3.70-3.41 (5H, m), 3.22-3.20 (0.5H, m), 2.80-2.62 (1H, m), 2.50-2.39 (1H, m), 2.30-2.23 (0.5H, m), 2.10-2.03 (0.5H, m), 1.94-1.86 (0.5H, m), 1.82-1.73 (1H, m), 1.62-1.54 (1H, m), 0.97-0.90 (2H, m), 0.89-0.66 (6H, m). The compound is observed as a mixture of rotamers.

Example 5—Synthesis of (2S,4S)-4-Fluoro-N-((3R, 5R)-1-isobutyryl-5-((4-((4-(mnorpholinomethyl) phenyl)ethynyl)beiizamido)methyl)pyrrolidin-3-yl) pyrrolidine-2-carboxamide

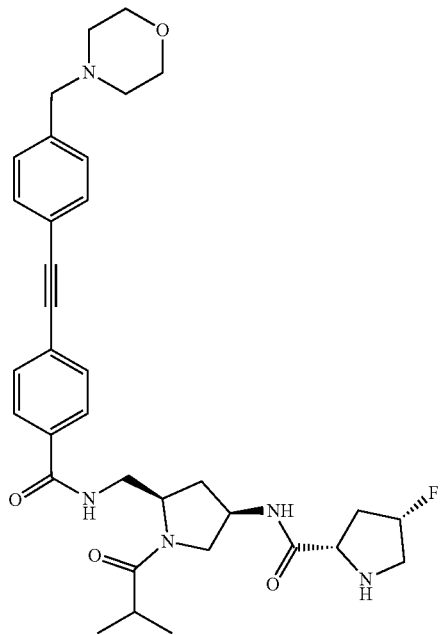 [SMILES: CC(C)C(=O)N1C[C@H](NC(=O)[C@@H]2C[C@H](F)CN2)C[C@@H]1CNC(=O)c1ccc(C#Cc2ccc(CN3CCOCC3)cc2)cc1]

Part I—Synthesis of 4-(4-Iodobenzyl)morpholine

To a solution of 4-iodobenzaldehyde (1000 mg, 4.31 mmol) in DCE (15 mL), was added morpholine (413 mg, 4.74 mmol) and glacial acetic acid (1.33 mL, 23.29 mmol). The reaction mixture stirred for 30 minutes at room temperature under argon. Sodium triacetoxyborohydride (1279 mg, 6.03 mmol) was added and reaction mixture stirred at room temperature for 28 hours. The reaction mixture was quenched with 2M NaOH (2 mL). The mixture was partitioned between ethyl acetate and water and the phases separated. The organic layer was washed with brine, dried (Na₂SO₄), filtered and the solvent removed in vacuo to yield 4-(4-iodobenzyl)morpholine as a white solid (871 mg, 67%).

Part II—Synthesis of Methyl 4-Ethynylbenzoate

Methyl 4-formylbenzoate (3560 g, 21.69 mmol) and potassium carbonate (5995 mg 43.38 mmol) were stirred in MeOH (215 mL) for 15 minutes at room temperature. Dimethyl (1-diazo-2-oxopropyl) phosphonate, 5000 mg, 26.03 mmol) was added and the reaction mixture stirred at room temperature for 150 minutes. The reaction mixture was concentrated and the residue dissolved in EtOAc. The mixture was partitioned between ethyl acetate and water and the phases separated. The organic layer was washed with brine, dried (Na₂SO₄), filtered and the solvent removed. The residue was purified by chromatography (80 g silica cartridge, 0-20% EtOAc/cyclohexane gradient) to yield methyl 4-ethynylbenzoate as a white solid (2562 mg, 74%).

Part III—Synthesis of Methyl 4-((4-(morpholinomethyl)phenyl)ethynyl)benzoate 4-(4-iodobenzylmorpholine) (1325 mg, 4.37 mmol) and methyl-4-ethynyl benzoate (840 mg, 5.24 mmol) were dissolved in acetonitrile (25.0 mL). Copper (I) Iodide (166 mg, 0.874 mmol) and bis(triphenylphosphine)palladium (II) dichloride (307 mg, 0.437 mmol) were added and reaction mixture sparged with argon for 15 minutes. Triethylamine (1.22 mL, 8.74 mmol) was added and reaction stirred at 50° C. under argon for 4 hours. The reaction mixture was cooled to room temperature and filtered through celite. The filter cake was washed EtOAc and combined organics concentrated in vacuo. The residue was purified by chromatography (80 g silica cartridge, 0-10% (2M ammonia in methanol)/dichloromethane gradient) to yield methyl 4-((4-(morpholinomethyl)phenyl)ethynyl)benzoate as a brown oil (1328 rig, 91%).

Part IV—Synthesis of 4-((4-(Morpholinomethyl)phenyl)ethynyl)benzoic Acid

To a solution of methyl 4-((4-(morpholinomethyl)phenyl) ethynyl)benzoate (1328 mg, 3.96 mmol) in THF (16 mL) and methanol (4 mL) was added 2M lithium hydroxide (3.96 mL, 7.92 mmol) and the mixture stirred at room temperature for 90 minutes. The mixture was concentrated in vacuo and the residue dissolved in water. The aqueous phase was acidified with 1M HCl to pH 2 and extracted with ethyl acetate. The organic layer was washed with brine (3×5 mL), dried (Na$_2$SO$_4$), filtered and the solvent removed to yield 4-((4-(morpholinomethyl)phenyl)ethynyl)benzoic acid as a brown solid (1108 mg, 87%).

Part V—Synthesis of tert-Butyl (2S,4S)-4-Fluoro-2-(((3R,5R)-1-isobutyryl-5-((4-((4-(morpholinomethyl)phenyl)ethynyl)benzamido)methyl)pyrrolidin-3-yl)carbamoyl)pyrrolidine-1-carboxylate To a solution of tert-butyl (2S,4S)-2-(((3R,5R)-5-(aminomethyl)-1-isobutyrylpyrrolidin-3-yl)carbamoyl)-4-fluoropyrrolidine-1-carboxylate (56 mg, 0.140 mmol) and 4-((4-(morpholinomethyl)phenyl)ethynyl)benzoic (54 mg, 0.168 mmol) in dichloromethane (1 mL) was added triethylamine (26 µL, 0.188 mmol) then HATU (64 mg, 0.168 mmol) and the reaction mixture stirred at room temperature for 3 hours. The mixture was partitioned between dichloromethane and water and the phases separated. The organics were collected and the solvent removed. The residue was used directly in the next step without further purification.

Part VI—Synthesis of (2S,4S)-4-Fluoro-N-((3R,5R)-1-isobutyryl-5-((4-((4-(morphioliiiomethyl)phenyl)ethynyl)benzamido)methyl)pyrrolidin-3-yl)pyrrolidine-2-carboxamide To a solution of tert-butyl (2S,4S)-4-fluoro-2-(((3R,5R)-1-isobutyryl-5-((4-((4-(morpholinomethyl)phenyl)ethynyl)benzamido)methyl)pyrrolidin-3-yl)carbamoyl)pyrrolidine-1-carboxylate (66 mg, 0.0938 mmol) in dichloromethane (0.8 mL) was added TFA (0.2 mL) and the reaction mixture stirred at room temperature for 1 hour. The reaction mixture was concentrated in vacuo, and the remaining TFA was azeotroped with toluene. The residue was dissolved in DMSO (1.5 mL) and purified by reverse phase preparative HPLC (Luna Phenyl-Hexyl 21.2×150 mm, 10 m 5-60% MeOH/water (0.1% TFA), 20 mL/min, RT) and the residue lyophilised to yield the title compound (15 mg, 26%, bis TFA salt) as a yellow solid.

Example 6—Synthesis of (2S,4S)—N-((3R,5R)-5-((2-Chloro-4-((4-(morpholinomethyl)phenyl)ethynyl)benzamido)methyl)-1-(cyclopropanecarbonyl)pyrrolidin-3-yl)-4-fluoropyrrolidine-2-carboxamide

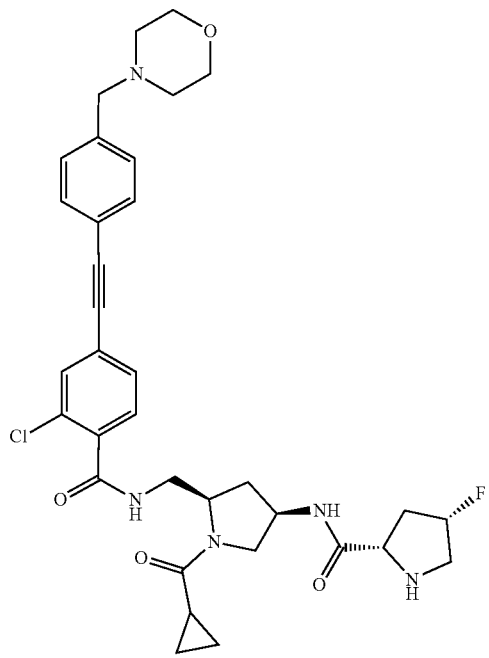 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)cc1Cl]

Part I—Synthesis of Methyl 2-Chloro-4-((trimethylsilyl)ethynyl)benzoate

A mixture of methyl 2-chloro-4-iodobenzoate (1 g, 3.37 mmol), bis(triphenylphosphine)palladium(II) dichloride (240 mg, 0.337 mmol), copper iodide (130 mg, 0.675 mmol) and ethynyltrimethylsilane (0.4 g, 4.05 mmol) in acetonitrile (18 mL) was degassed with argon for 10 mins. Triethylamine (940 µL, 6.75 mmol) was added dropwise then heated at 60° C. under argon for 4 hours. The mixture was allowed to room temperature, diluted with ethyl acetate, filtered through Celite and solvent evaporated under reduced pressure. The residue was purified by chromatography (80 g silica cartridge, 0-10% cyclohexane/ethyl acetate gradient) to yield methyl 2-chloro-4-((trimethylsilyl)ethynyl)benzoate (803 mg, 89%) as an orange oil.

Part II—Synthesis of Methyl 2-Chloro-4-ethynylbenzoate

To a solution of methyl 2-chloro-4-((trimethylsilyl)ethynyl)benzoate (803 mg, 3 mmol) in DCM (1.5 mL) and methanol (15 mL), potassium carbonate (832 mg, 6.02 mmol) was added and stirred at room temperature for 2 hours. The solvent was evaporated, partitioned between diethyl ether and water. The aqueous was extracted (×2) and the organics combined, washed with brine, dried (Na$_2$SO$_4$)

then filtered and evaporated to give methyl 2-chloro-4-ethynylbenzoate (188 mg, 32%) as a pale yellow oil.

Part III—Synthesis of Methyl 2-Chloro-4-((4-(morpholinomethyl)phenyl)ethynyl)benzoate To methyl 2-chloro-4-ethynylbenzoate (188 mg, 0.966 mmol) and 4-(4-iodobenzyl)morpholine (244 mg, 0.805 mmol) in acetonitrile (5 mL), bis(triphenylphosphine)palladium(II) dichloride (57 mg, 0.081 mmol) and copper iodide (31 mg, 0.161 mmol) were added then degassed with argon for 10 minutes. Triethylamine (220 µl, 1.6 mmol) was added then heated at 60° C. for 4 hours. The mixture was allowed to cool to room temperature, diluted with ethyl acetate, filtered through celite and solvent removed. The residue was purified by chromatography (25 g silica cartridge, 0-100% cyclohexane/ethyl acetate gradient) to yield methyl 2-chloro-4-((4-(morpholinomethyl)phenyl)ethynyl)benzoate (105 mg, 35%) as a pale yellow gum.

Part IV—Synthesis of 2-Chloro-4-((4-(morpholinomethyl)phenyl)ethynyl)benzoic Acid To methyl 2-chloro-4-((4-(morpholinomethyl)phenyl) ethynyl)benzoate (105 mg, 0.284 mmol) in THF (2.4 mL) and methanol (0.6 mL) was added 2M lithium hydroxide (0.28 mL, 0.568 mmol) and stirred at room temperature for 2 hours. The solvent was evaporated under reduced pressure. The residue was dissolved in DMSO/formic acid and purified by reverse phase chromatography (C18 column 5-98% gradient, water/CH$_3$CN/formic acid and lyophilised to yield 2-chloro-4-((4-(morpholinomethyl)phenyl)ethynyl)benzoic acid (66 mg, 65%) as a white solid.

Part V—Synthesis of tert-Butyl (2S,4S)-2-(((3R, 5R)-5-((2-Chloro-4-((4-(morpholinomethyl)phenyl) ethynyl)benzamido)methyl)-1-((2-(trimethylsilyl) ethoxy)carbonyl)pyrrolidin-3-yl)carbamoyl)-4-fluoropyrrolidine-1-carboxylate tert-Butyl (2S,4S)-2-(((3R,5R)-5-(aminomethyl)-1-((2-(trimethylsilyl)ethoxy)carbonyl)pyrrolidin-3-yl)carbamoyl)-4-fluoropyrrolidine-1-carboxylate (75 mg, 0.158 mmol) was treated with 2-chloro-4-((4-(morpholinomethyl) phenyl)ethynyl)benzoic acid (56 mg, 0.158 mmol) in DCM (2 mL) with triethylamine (66 µl, 0.474 mmol). HATU (72 mg, 0.19 mmol) was added rinsing in with DCM (2 mL). The reaction was stirred at room temperature for 2.5 hours and homogeneous solution left at room temperature for 65 h. The mixture was partitioned between DCM and brine and the phases separated. The aqueous was extracted with DCM (×3), the organics combined and solvent evaporated under reduced pressure. The residue was purified by chromatography (12 g silica cartridge, 0-5% DCM/methanol gradient) to yield tert-butyl (2S,4S)-2-(((3R,5R)-5-((2-chloro-4-((4-(morpholinomethyl)phenyl)ethynyl)benzamido)methyl)-1-((2-(trimethylsilyl)ethoxy)carbonyl)pyrrolidin-3-yl)carbamoyl)-4-fluoropyrrolidine-1-carboxylate (119 mg, 92%) as a colourless gum.

Part VI—Synthesis of tert-Butyl (2S,4S)-2-(((3R, 5R)-5-((2-Chloro-4-((4-(morpholinomethyl)phenyl) ethynyl)benzamido)methyl)pyrrolidin-3-yl)carbamoyl)-4-fluoropyrrolidine-1-carboxylate To a solution of (2S,4S)-2-(((3R,5R)-5-((2-chloro-4-((4-(morpholinomethyl)phenyl)ethynyl)benzamido)methyl)-1-((2-(trimethylsilyl)ethoxy)carbonyl)pyrrolidin-3-yl)carbamoyl)-4-fluoropyrrolidine-1-carboxylate (119 mg, 0.146 mmol) in THF (1 mL), 1M TBAF (290 µl, 0.29 mmol) was added and stirred at room temperature for 17 hours. 1M TBAF (145 ul, 0.145 mmol) was added and stirred for 3 hours. The mixture was partitioned between ethyl acetate and saturated sodium bicarbonate, extracted (×2). The organics were combined, dried (Na$_2$SO$_4$) then filtered and the solvent removed. The reside was purified by chromatography (12 g silica cartridge, 0-10% 2M NH$_3$ in Methanol/DCM) to yield tert-butyl (2S,4S)-2-(((3R,5R)-5-((2-chloro-4-((4-(morpholinomethyl)phenyl)ethynyl)benzamido) methyl)pyrrolidin-3-yl)carbamoyl)-4-fluoropyrrolidine-1-carboxylate (60 mg, 62%) as a colourless glass.

Part VII—Synthesis of tert-Butyl (2S,4S)-2-(((3R, 5R)-5-((2-Chloro-4-((4-(morpholinomethyl)phenyl) ethynyl)benzamido)methyl)-1-(cyclopropanecarbonyl)pyrrolidin-3-yl)carbamoyl)-4-fluoropyrrolidine-1-carboxylate tert-butyl (2S,4S)-2-(((3R,5R)-5-((2-chloro-4-((4-(morpholinomethyl)phenyl)ethynyl)benzamido)methyl)pyrrolidin-3-yl)carbamoyl)-4-fluoropyrrolidine-1-carboxylate (60 mg, 0.090 mmol) in DCM (1 mL) was treated with a solution of cyclopropanecarbonyl chloride (9 µl, 0.099 mmol) in DCM (1 mL) then trimethylamine (15 µl, 0.108 mmol) and stirred at room temperature for 45 minutes. The mixture was partitioned between DCM and water. The aqueous was extracted with DCM (×3), the organics combined and solvent removed to give tert-butyl (2S,4S)-2-(((3R,5R)-5-((2-chloro-4-((4-(morpholinomethyl)phenyl)ethynyl)benzamido)methyl)-1-(cyclopropanecarbonyl)pyrrolidin-3-yl) carbamoyl)-4-fluoropyrrolidine-1-carboxylate (60 mg, 91%) as a white solid.

Part VIII—Synthesis of (2S,4S)—N-((3R,5R)-5-((2-Chloro-4-((4-(morpholinomethyl)phenyl)ethynyl) benzamido)methyl)-1-(cyclopropanecarbonyl)pyrrolidin-3-yl)-4-fluoropyrrolidine-2-carboxamide (2S,4S)-2-(((3R,5R)-5-((2-chloro-4-((4-(morpholinomethyl)phenyl)ethynyl)benzamido)methyl)-1-(cyclopropanecarbonyl)pyrrolidin-3-yl)carbamoyl)-4-fluoropyrrolidine-1-carboxylate (60 mg, 0.082 mmol) was treated with DCM (1.6 mL) and TFA (0.4 mL) and stirred at room temperature for 1.5 h. The solvent was removed, toluene added and solvent removed (×2). The residue was purified by reverse phase preparative HPLC (Sunfire C18 19×150 mm, 10 um 5-95% ACN/water (0.1% TFA), 20 ml/min, RT) and the residue lyophilised to yield the title compound (43.4 mg, 62%, TFA salt) as a white solid. LCMS (Method 5, ESI): Rt=2.27 min, [M+H]$^+$=636.5, 98.6% purity.

Example 7—Synthesis of (2S,4S)—N-((3R,5R)-1-(Cyclopropanecarbonyl)-5-((2-methyl-4-((4-(morpholinomethyl)phenyl)ethynyl)benzamido)methyl)pyrrolidin-3-yl)-4-fluoropyrrolidine-2-carboxamide

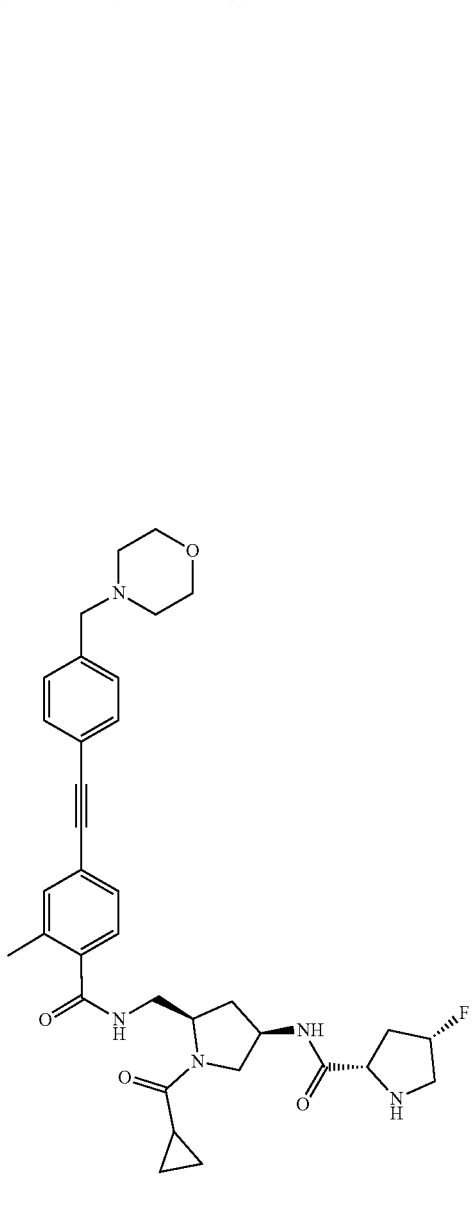 [SMILES: Cc1cc(C#Cc2ccc(CN3CCOCC3)cc2)ccc1C(=O)NC[C@H]1C[C@@H](NC(=O)[C@@H]2C[C@H](F)CN2)CN1C(=O)C1CC1]

The title compound was prepared based on procedures in Example 6. LCMS (Method 5, ESI): Rt=2.27 min, [M+H]⁺=616.4, 99.7% purity.

Example 8—Synthesis of (2S,4S)—N-((3R,5R)-1-(cyclopropanecarbonyl)-5-((3-fluoro-4-((4-(morpholinomethyl)phenyl)ethynyl)benzamido)methyl)pyrrolidin-3-yl)-4-fluoropyrrolidine-2-carboxamide

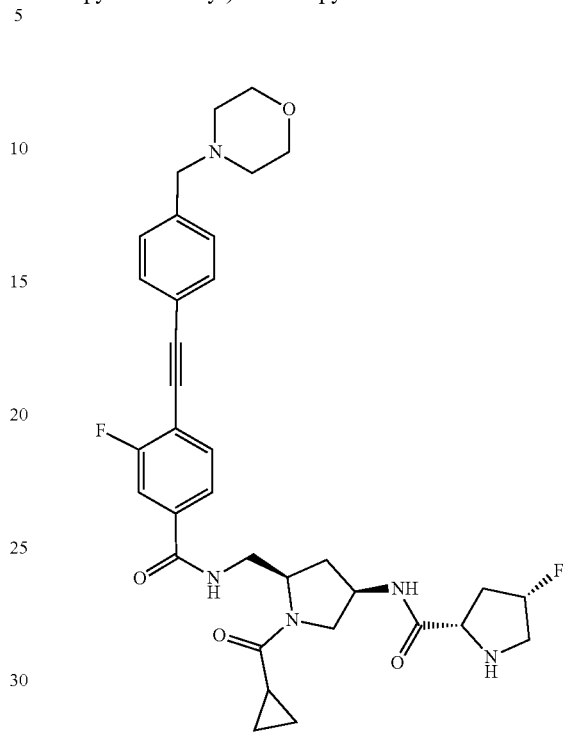

The title compound was prepared based on procedures in Example 6. LCMS (Method 5, ESI): Rt=2.30 min, [M+H]⁺ 620.5, 99.6% purity.

Example 9—Preparation of Additional Aza-heterocyclyl Carboxamide and Related Compounds Compounds in Table 2 below were prepared based on experimental procedures described in Examples 1-8 and in the Detailed Description.

TABLE 2
| Compound No. | Chemical Structure |
|---|---|
| 9A | 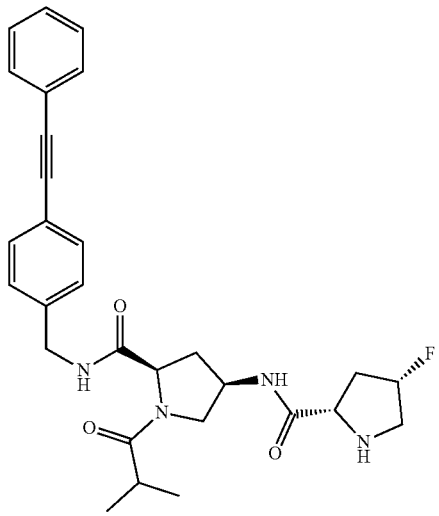 [SMILES: CC(C)C(=O)N1C[C@H](NC(=O)[C@@H]2C[C@H](F)CN2)C[C@@H]1C(=O)NCc1ccc(C#Cc2ccccc2)cc1] |
| 9B | 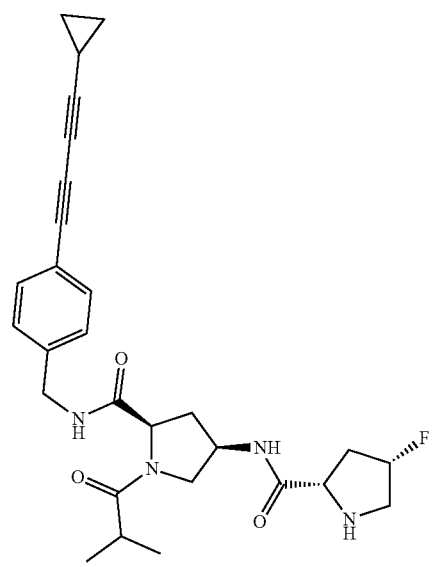 [SMILES: CC(C)C(=O)N1C[C@H](NC(=O)[C@@H]2C[C@H](F)CN2)C[C@@H]1C(=O)NCc1ccc(C#CC#CC2CC2)cc1] |
| 9C | 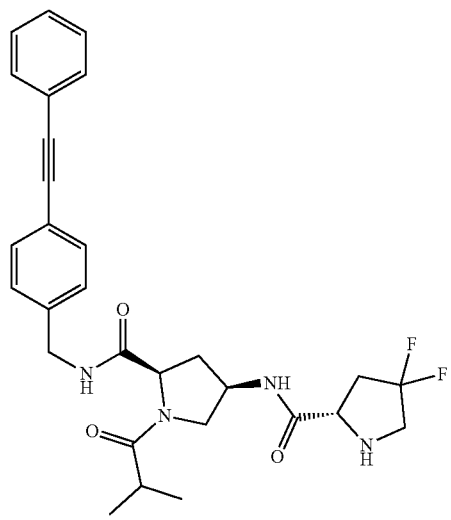 [SMILES: CC(C)C(=O)N1C[C@H](NC(=O)[C@@H]2CC(F)(F)CN2)C[C@@H]1C(=O)NCc1ccc(C#Cc2ccccc2)cc1] |

TABLE 2-continued
| Compound No. | Chemical Structure |
|---|---|
| 9D | 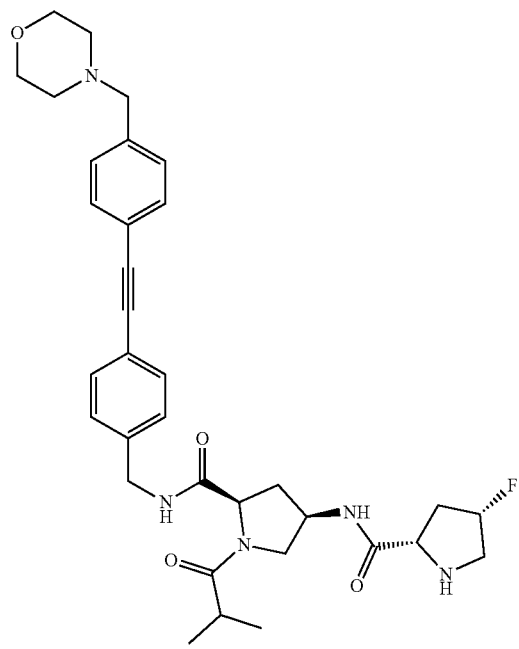 [SMILES: CC(C)C(=O)N1C[C@H](NC(=O)[C@@H]2C[C@H](F)CN2)C[C@@H]1C(=O)NCc1ccc(C#Cc2ccc(CN3CCOCC3)cc2)cc1] |
| 9E | 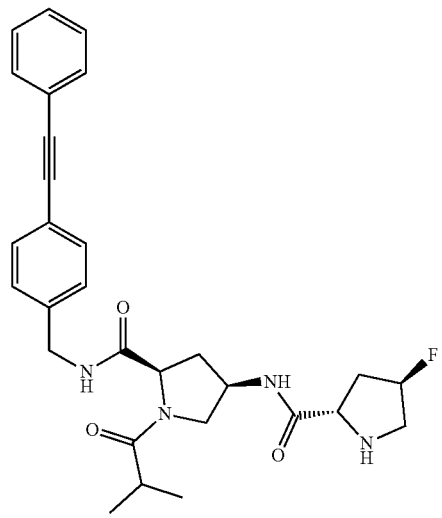 [SMILES: CC(C)C(=O)N1C[C@H](NC(=O)[C@@H]2C[C@@H](F)CN2)C[C@@H]1C(=O)NCc1ccc(C#Cc2ccccc2)cc1] |

TABLE 2-continued
| Compound No. | Chemical Structure |
|---|---|
| 9F | 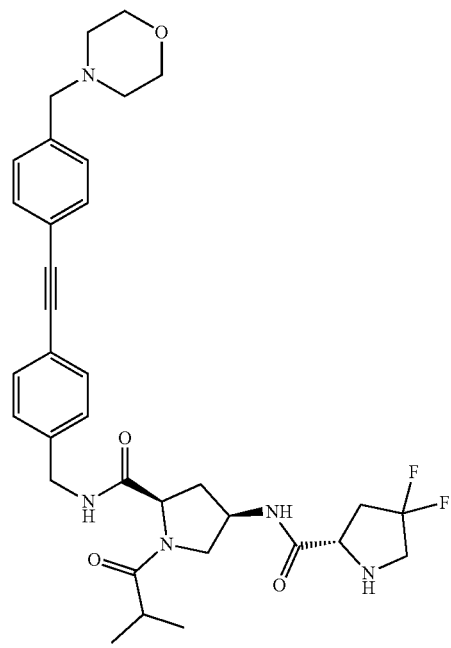 [SMILES: CC(C)C(=O)N1C[C@H](NC(=O)[C@@H]2CC(F)(F)CN2)C[C@@H]1C(=O)NCc1ccc(C#Cc2ccc(CN3CCOCC3)cc2)cc1] |
| 9G | 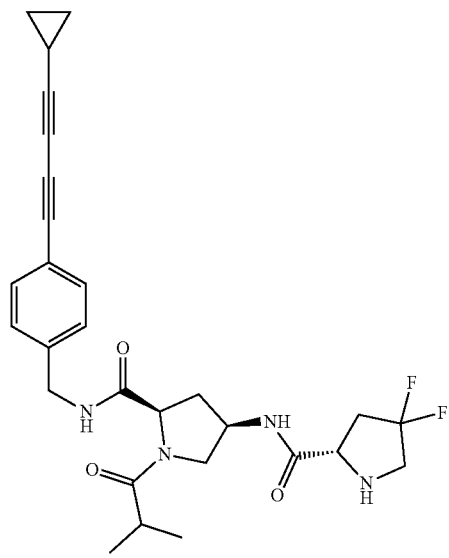 [SMILES: CC(C)C(=O)N1C[C@H](NC(=O)[C@@H]2CC(F)(F)CN2)C[C@@H]1C(=O)NCc1ccc(C#CC#CC2CC2)cc1] |

TABLE 2-continued
| Compound No. | Chemical Structure |
|---|---|
| 9H | 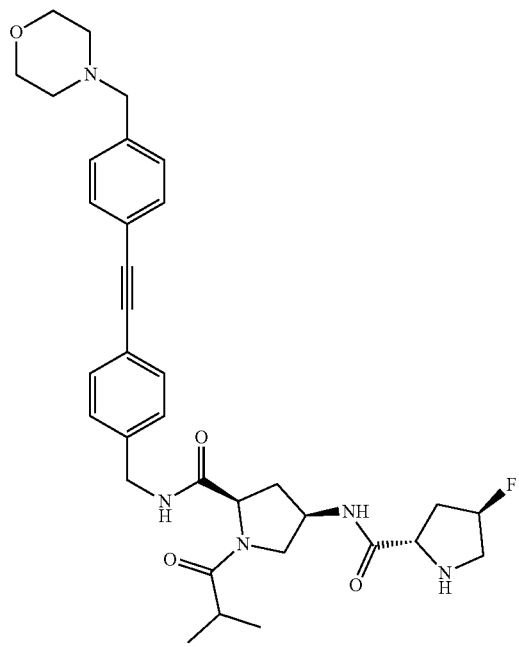 [SMILES: CC(C)C(=O)N1C[C@H](NC(=O)[C@@H]2C[C@@H](F)CN2)C[C@@H]1C(=O)NCc1ccc(C#Cc2ccc(CN3CCOCC3)cc2)cc1] |
| 9I | 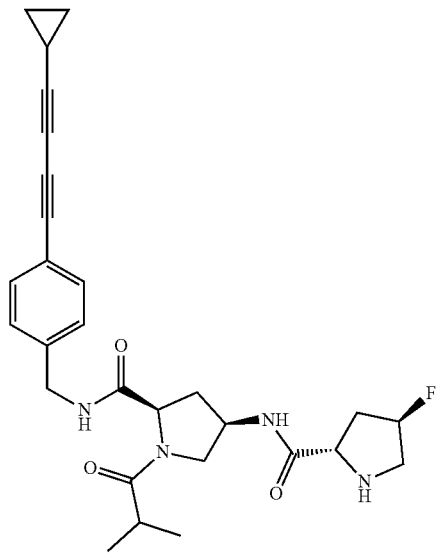 [SMILES: CC(C)C(=O)N1C[C@H](NC(=O)[C@@H]2C[C@@H](F)CN2)C[C@@H]1C(=O)NCc1ccc(C#CC#CC2CC2)cc1] |

TABLE 2-continued
| Compound No. | Chemical Structure |
|---|---|
| 9J | 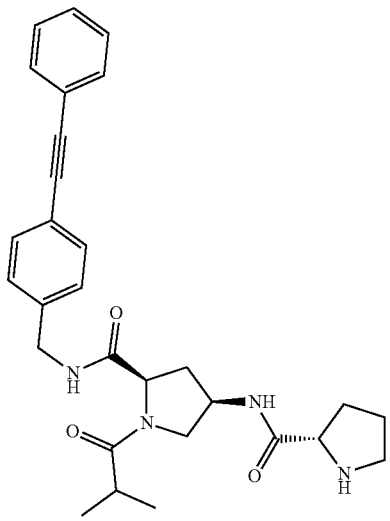 [SMILES: CC(C)C(=O)N1C[C@H](NC(=O)[C@@H]2CCCN2)C[C@@H]1C(=O)NCc1ccc(C#Cc2ccccc2)cc1] |
| 9K | 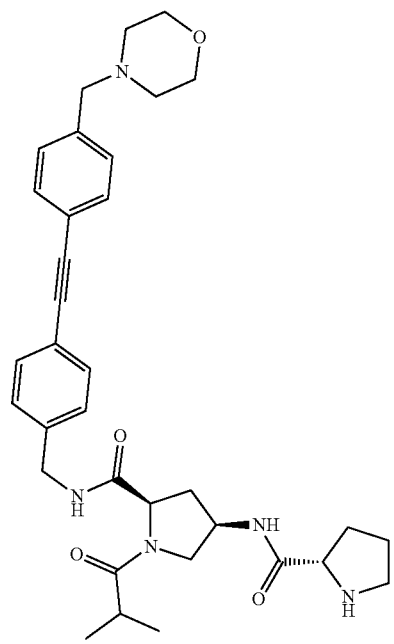 [SMILES: CC(C)C(=O)N1C[C@H](NC(=O)[C@@H]2CCCN2)C[C@@H]1C(=O)NCc1ccc(C#Cc2ccc(CN3CCOCC3)cc2)cc1] |

| Compound No. | Chemical Structure |
|---|---|
| 9L | 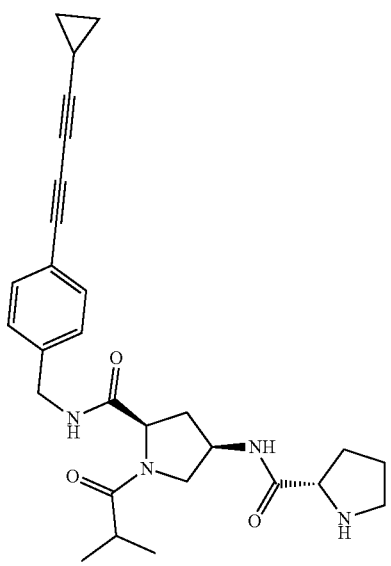 [SMILES: CC(C)C(=O)N1C[C@H](NC(=O)[C@@H]2CCCN2)C[C@@H]1C(=O)NCc1ccc(C#CC#CC2CC2)cc1] |
| 9M | 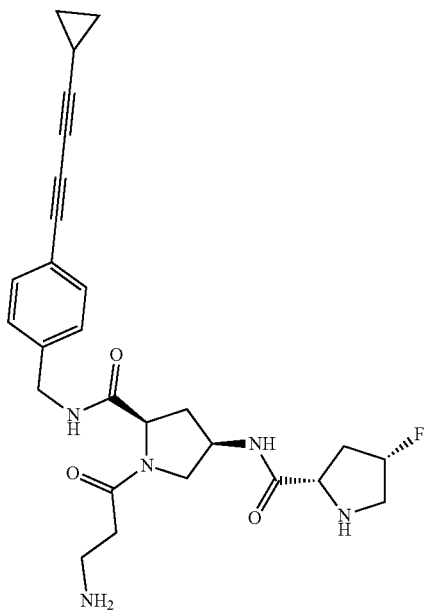 [SMILES: NCCC(=O)N1C[C@H](NC(=O)[C@@H]2C[C@H](F)CN2)C[C@@H]1C(=O)NCc1ccc(C#CC#CC2CC2)cc1] |

TABLE 2-continued

| Compound No. | Chemical Structure |
|---|---|
| 9N | 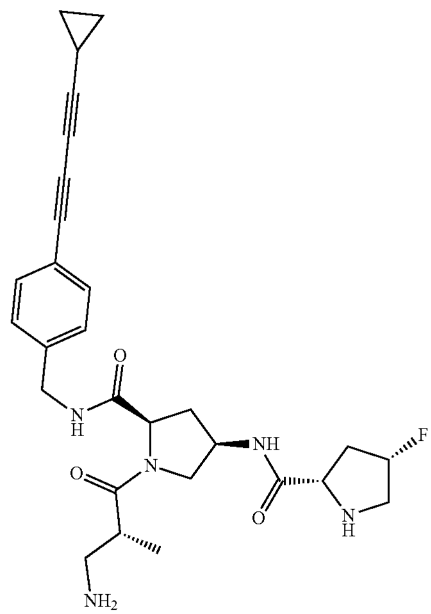 [SMILES: C[C@H](CN)C(=O)N1C[C@H](NC(=O)[C@@H]2C[C@H](F)CN2)C[C@@H]1C(=O)NCc1ccc(C#CC#CC2CC2)cc1] |
| 9O | 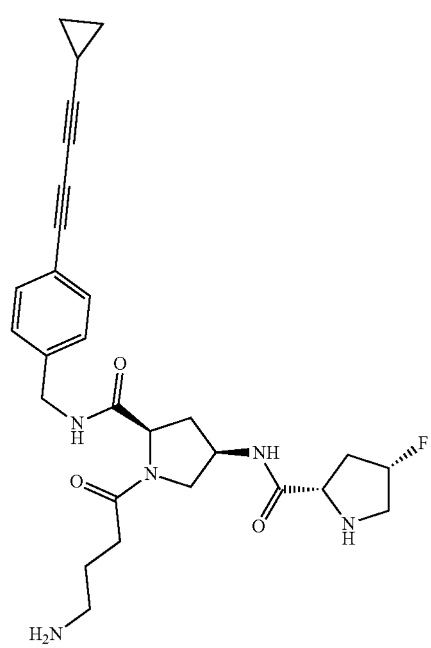 [SMILES: NCCCC(=O)N1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9P | 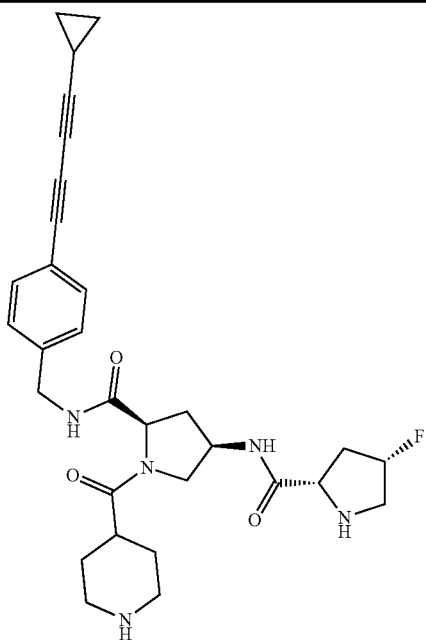 |
| 9Q | 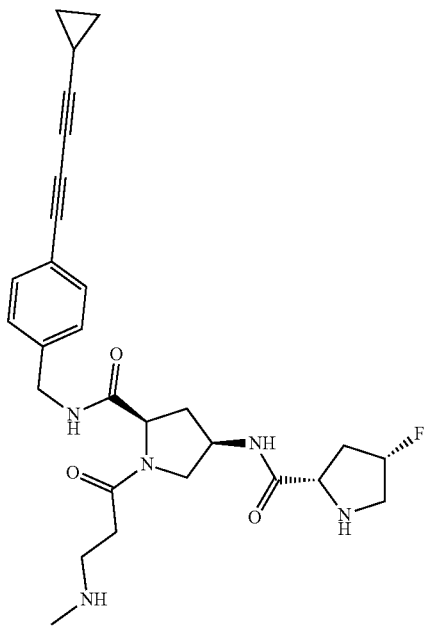 [SMILES: CNCCC(=O)N1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9R | 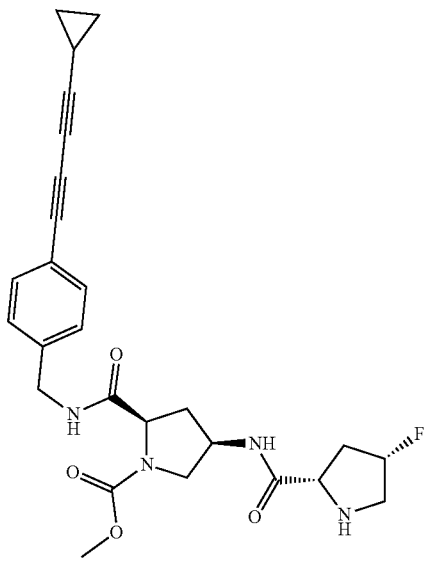 [SMILES: COC(=O)N1C[C@H](NC(=O)[C@@H]2C[C@H](F)CN2)C[C@@H]1C(=O)NCc1ccc(C#CC#CC2CC2)cc1] |
| 9S | 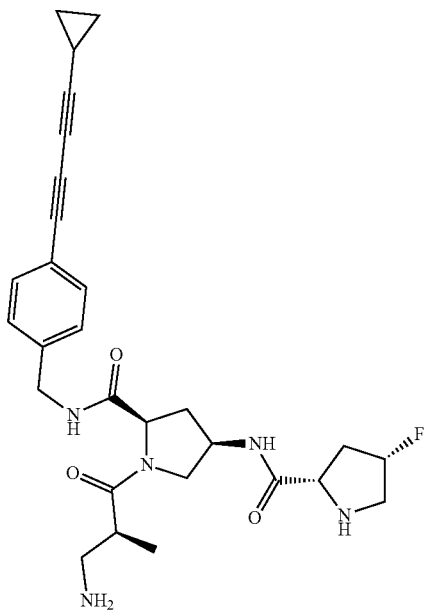 [SMILES: C[C@@H](CN)C(=O)N1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9T | 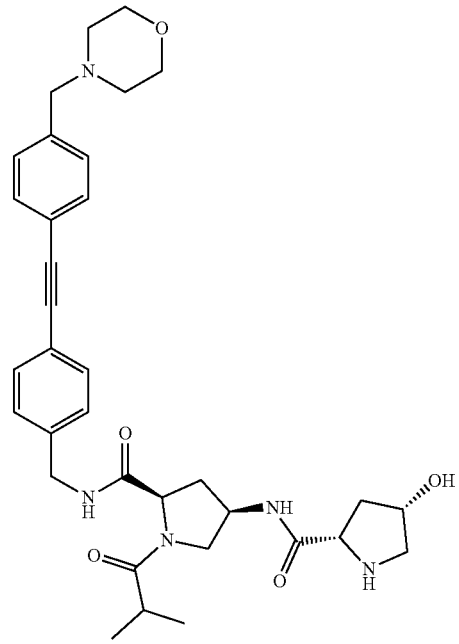 |
| 9U | 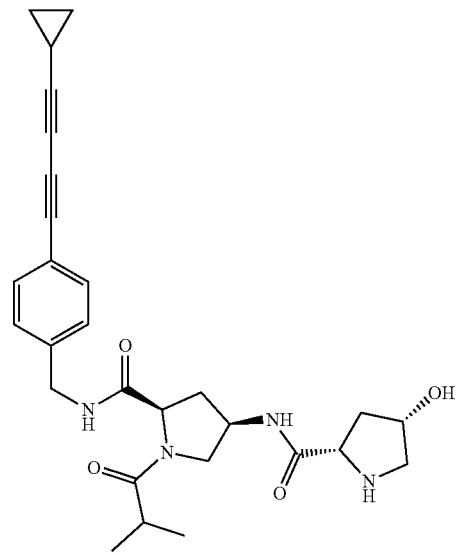 [SMILES: CC(C)C(=O)N1C[C@H](NC(=O)[C@@H]2C[C@H](O)CN2)C[C@@H]1C(=O)NCc1ccc(C#CC#CC2CC2)cc1] |

TABLE 2-continued
| Compound No. | Chemical Structure |
|---|---|
| 9V | 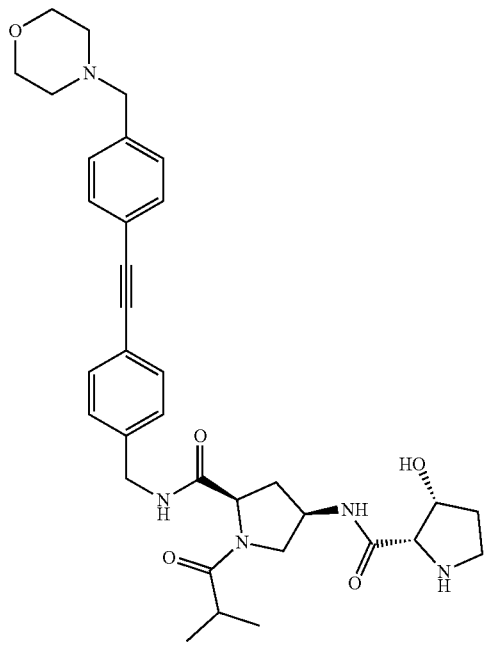 [SMILES: CC(C)C(=O)N1C[C@H](NC(=O)[C@H]2NCC[C@H]2O)C[C@@H]1C(=O)NCc1ccc(C#Cc2ccc(CN3CCOCC3)cc2)cc1] |
| 9W | 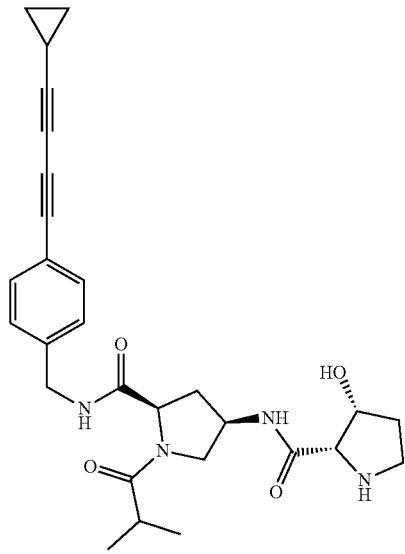 [SMILES: CC(C)C(=O)N1C[C@H](NC(=O)[C@H]2NCC[C@H]2O)C[C@@H]1C(=O)NCc1ccc(C#CC#CC2CC2)cc1] |

TABLE 2-continued
| Compound No. | Chemical Structure |
|---|---|
| 9X | 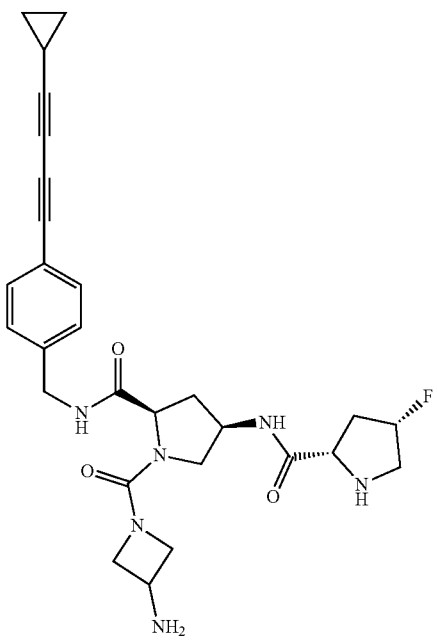 [SMILES: NC1CN(C(=O)N2C[C@H](NC(=O)[C@@H]3C[C@H](F)CN3)C[C@@H]2C(=O)NCc2ccc(C#CC#CC3CC3)cc2)C1] |
| 9Y | 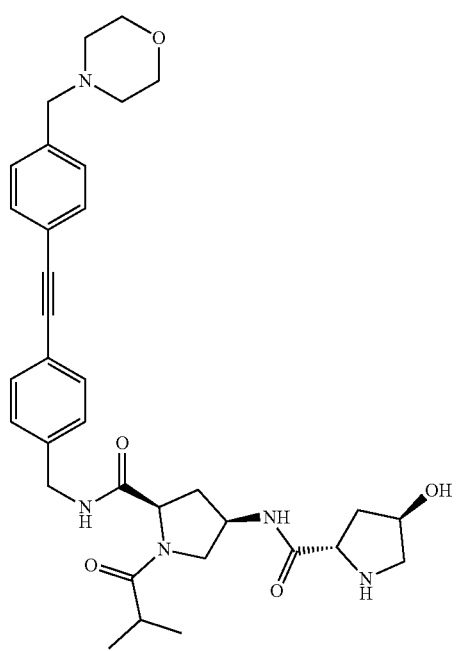 [SMILES: CC(C)C(=O)N1C[C@H](NC(=O)[C@@H]2C[C@@H](O)CN2)C[C@@H]1C(=O)NCc1ccc(C#Cc2ccc(CN3CCOCC3)cc2)cc1] |

| Compound No. | Chemical Structure |
|---|---|
| 9Z | 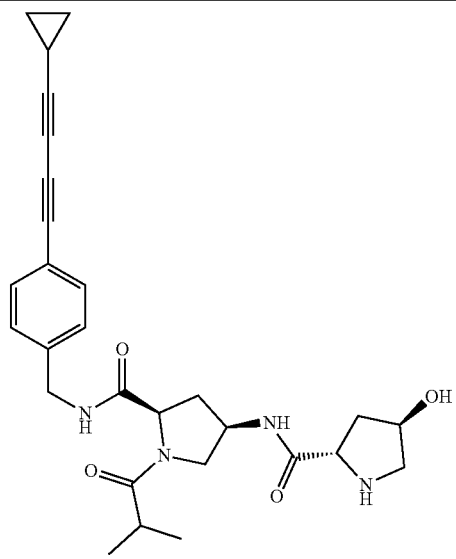 |
| 9AA | 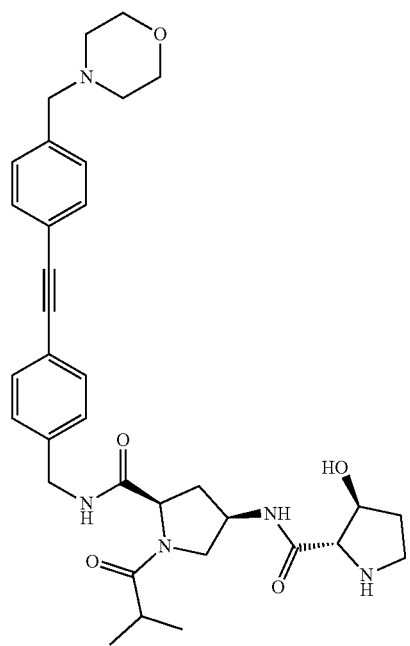 [SMILES: CC(C)C(=O)N1C[C@H](NC(=O)[C@H]2NCC[C@@H]2O)C[C@@H]1C(=O)NCc1ccc(C#Cc2ccc(CN3CCOCC3)cc2)cc1] |

TABLE 2-continued
| Compound No. | Chemical Structure |
|---|---|
| 9AB | 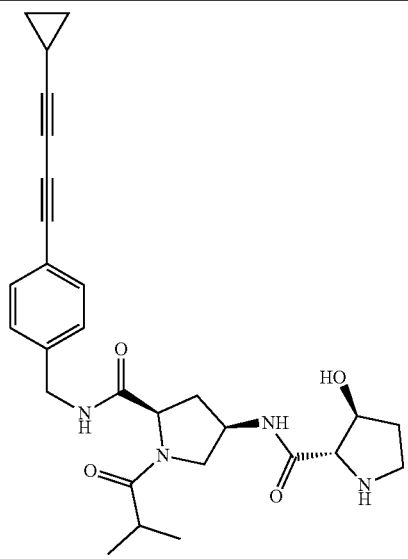 |
| 9AC | 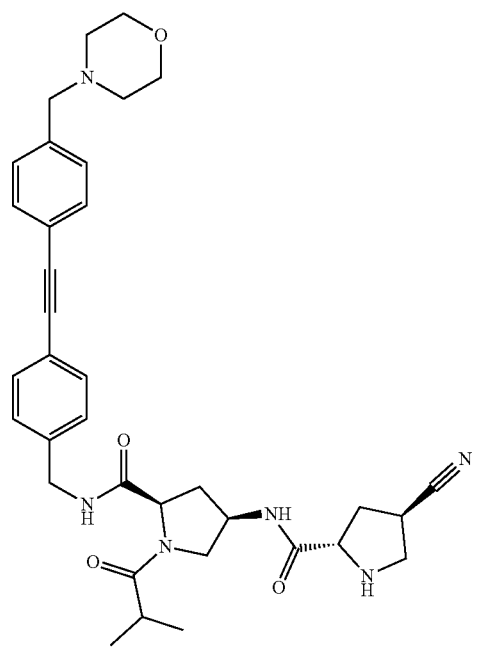 [SMILES: CC(C)C(=O)N1C[C@H](NC(=O)[C@@H]2C[C@@H](C#N)CN2)C[C@@H]1C(=O)NCc1ccc(C#Cc2ccc(CN3CCOCC3)cc2)cc1] |

| Compound No. | Chemical Structure |
|---|---|
| 9AD | 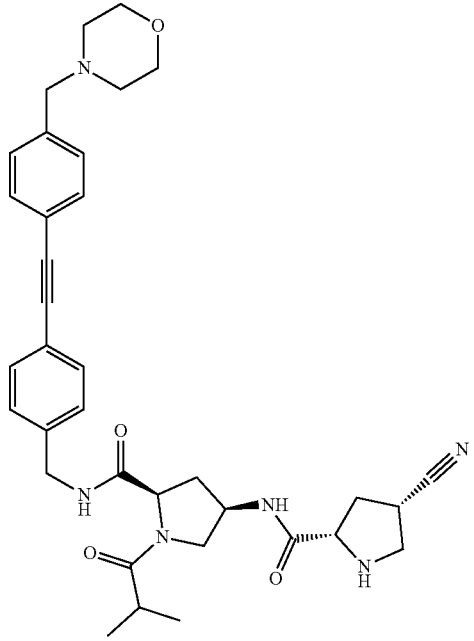 [SMILES: CC(C)C(=O)N1C[C@H](NC(=O)[C@@H]2C[C@H](C#N)CN2)C[C@@H]1C(=O)NCc1ccc(C#Cc2ccc(CN3CCOCC3)cc2)cc1] |
| 9AE | 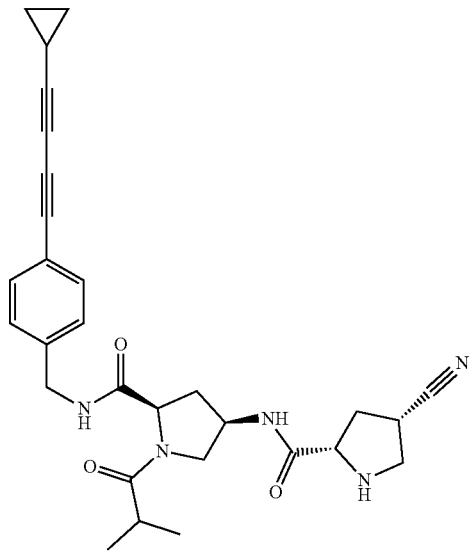 [SMILES: CC(C)C(=O)N1C[C@H](NC(=O)[C@@H]2C[C@H](C#N)CN2)C[C@@H]1C(=O)NCc1ccc(C#CC#CC2CC2)cc1] |

TABLE 2-continued
| Compound No. | Chemical Structure |
|---|---|
| 9AF | 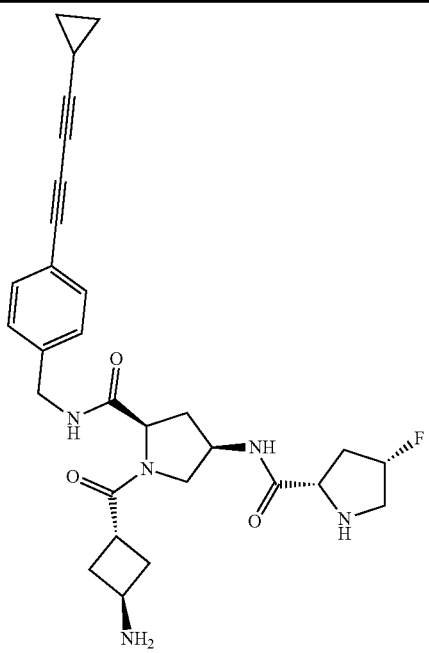 |
| 9AG | 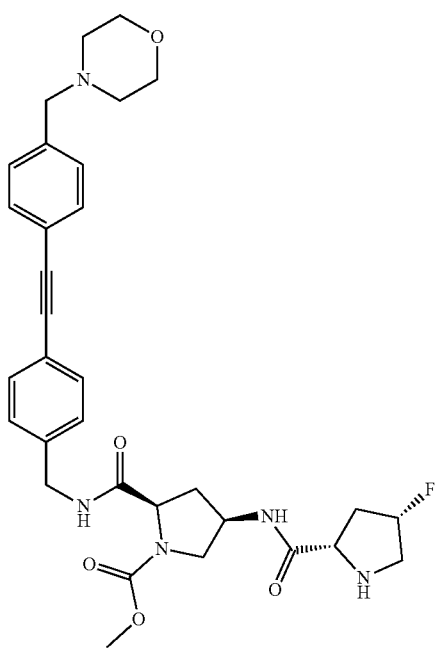 [SMILES: COC(=O)N1C[C@H](NC(=O)[C@@H]2C[C@H](F)CN2)C[C@@H]1C(=O)NCc1ccc(C#Cc2ccc(CN3CCOCC3)cc2)cc1] |

TABLE 2-continued
| Compound No. | Chemical Structure |
|---|---|
| 9AH | 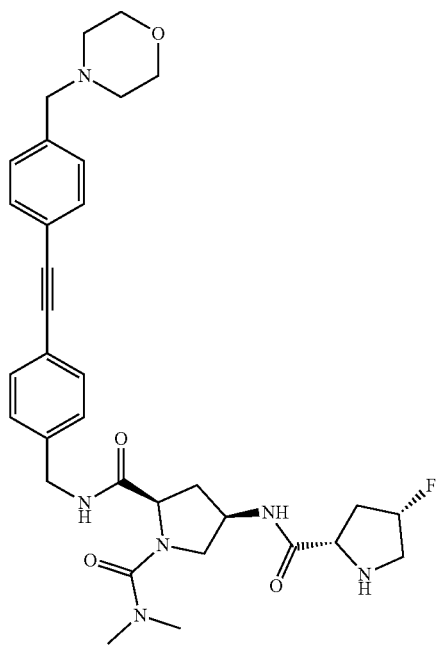 |
| 9AI | 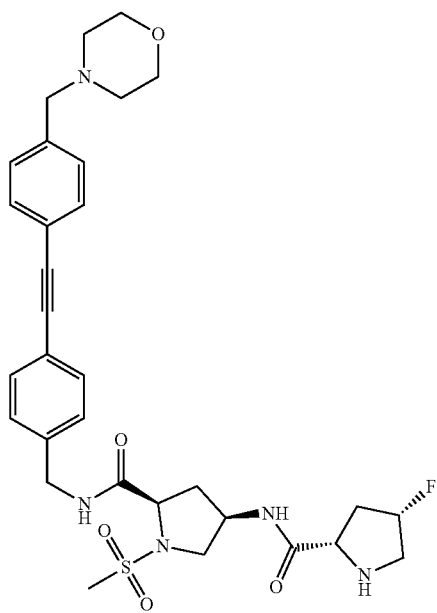 [SMILES: CS(=O)(=O)N1C[C@H](NC(=O)[C@@H]2C[C@H](F)CN2)C[C@@H]1C(=O)NCc1ccc(C#Cc2ccc(CN3CCOCC3)cc2)cc1] |

TABLE 2-continued
| Compound No. | Chemical Structure |
|---|---|
| 9AJ | 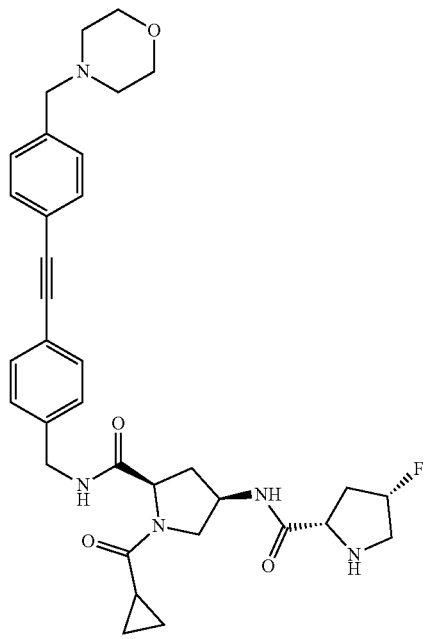 [SMILES: O=C(N[C@@H]1C[C@H](C(=O)NCc2ccc(C#Cc3ccc(CN4CCOCC4)cc3)cc2)N(C(=O)C2CC2)C1)[C@@H]1C[C@H](F)CN1] |
| 9AM | 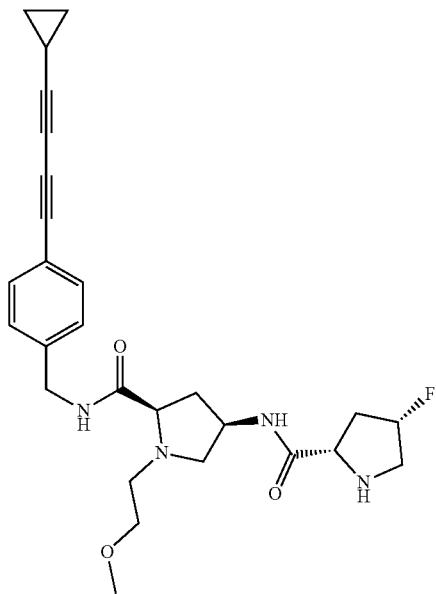 [SMILES: COCCN1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
| --- | --- |
| 9AN | 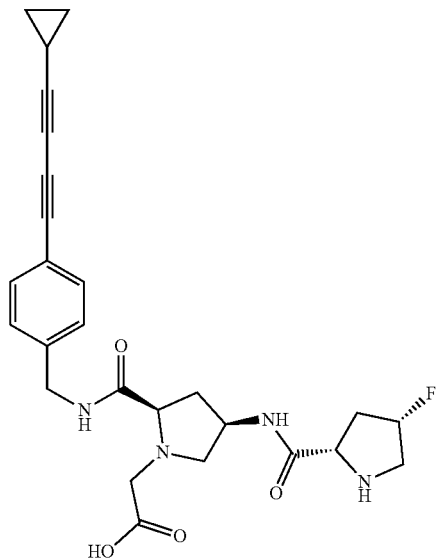 [SMILES: O=C(O)CN1C[C@H](NC(=O)[C@@H]2C[C@H](F)CN2)C[C@@H]1C(=O)NCc1ccc(C#CC#CC2CC2)cc1] |
| 9AO | 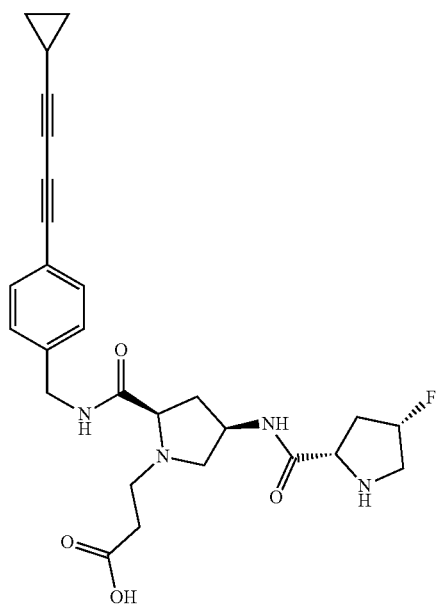 [SMILES: O=C(O)CCN1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9AP | 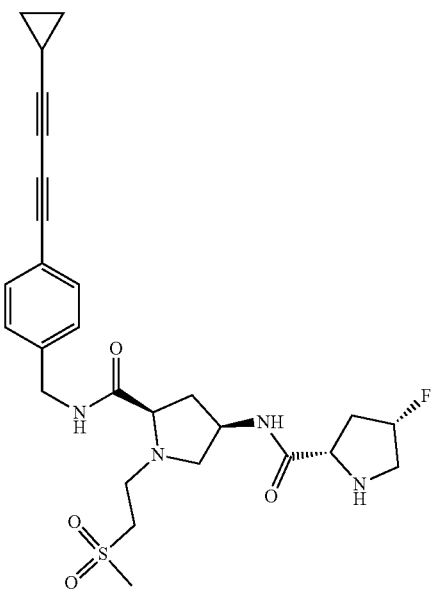 [SMILES: CS(=O)(=O)CCN1C[C@H](NC(=O)[C@@H]2C[C@H](F)CN2)C[C@@H]1C(=O)NCc1ccc(C#CC#CC2CC2)cc1] |
| 9AQ | 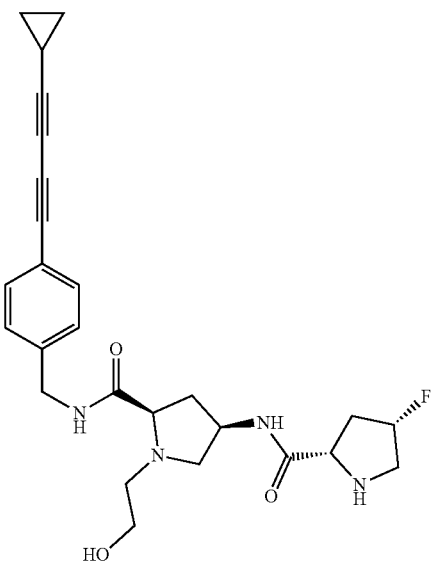 [SMILES: O=C(N[C@@H]1C[C@H](C(=O)NCc2ccc(C#CC#CC3CC3)cc2)N(CCO)C1)[C@@H]1C[C@H](F)CN1] |

TABLE 2-continued
| Compound No. | Chemical Structure |
|---|---|
| 9AR | 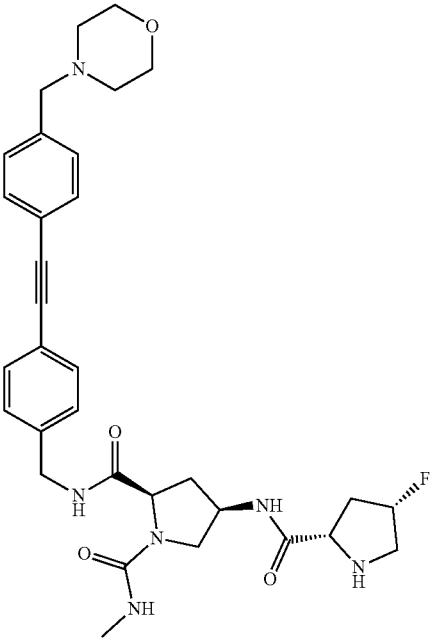 |
| 9AS | 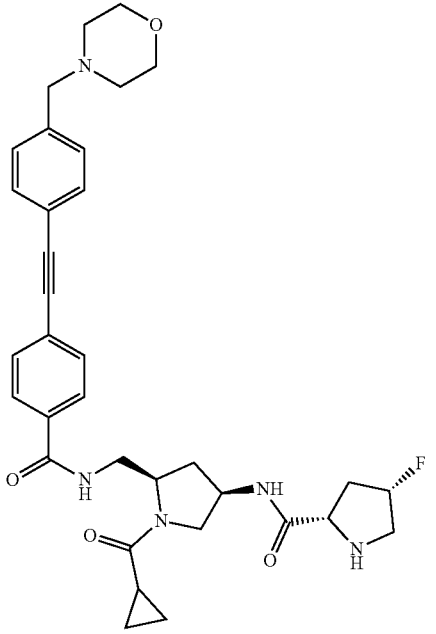 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)cc1] |
| 9AT | 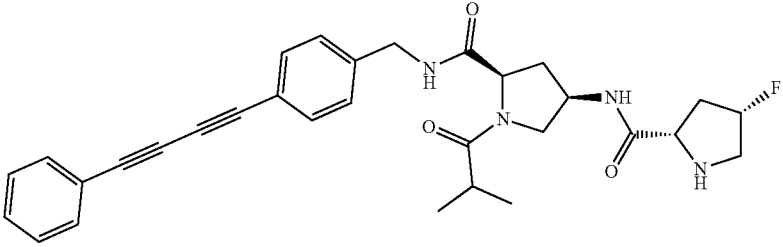 [SMILES: CC(C)C(=O)N1C[C@H](NC(=O)[C@@H]2C[C@H](F)CN2)C[C@@H]1C(=O)NCc1ccc(C#CC#Cc2ccccc2)cc1] |

TABLE 2-continued
| Compound No. | Chemical Structure |
|---|---|
| 9AV | 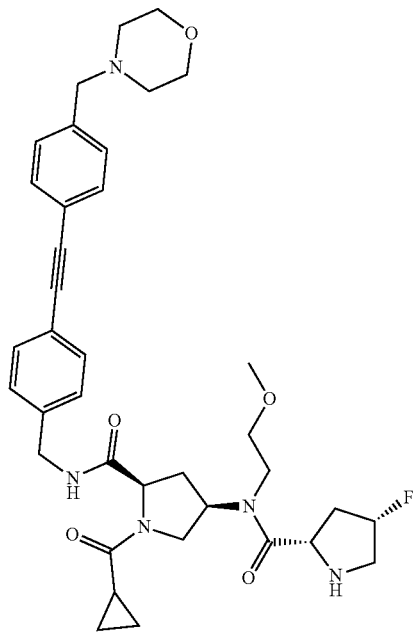 [SMILES: COCCN(C(=O)[C@@H]1C[C@H](F)CN1)[C@@H]1C[C@H](C(=O)NCc2ccc(C#Cc3ccc(CN4CCOCC4)cc3)cc2)N(C(=O)C2CC2)C1] |
| 9AW | 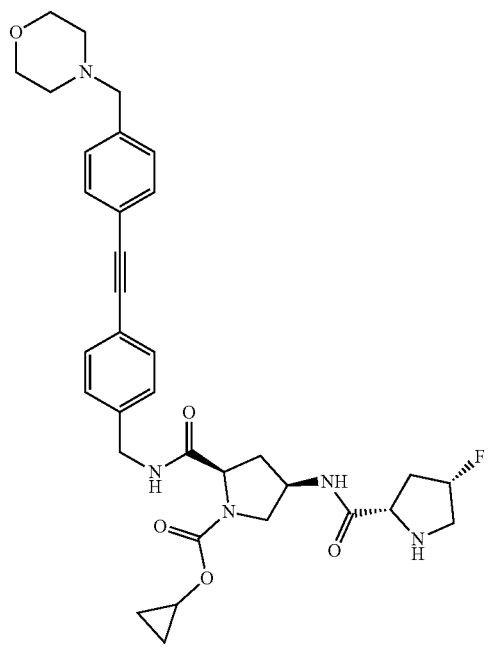 [SMILES: O=C(N[C@@H]1C[C@H](C(=O)NCc2ccc(C#Cc3ccc(CN4CCOCC4)cc3)cc2)N(C(=O)OC2CC2)C1)[C@@H]1C[C@H](F)CN1] |

TABLE 2-continued
| Compound No. | Chemical Structure |
|---|---|
| 9AX | 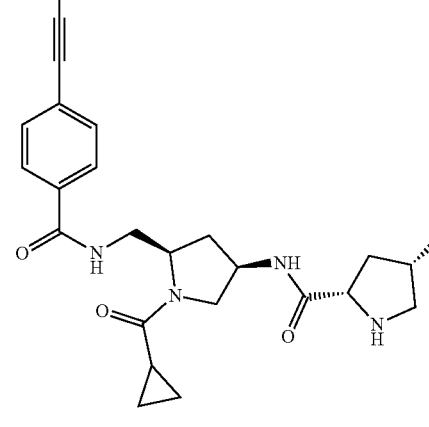 |
| 9AY | 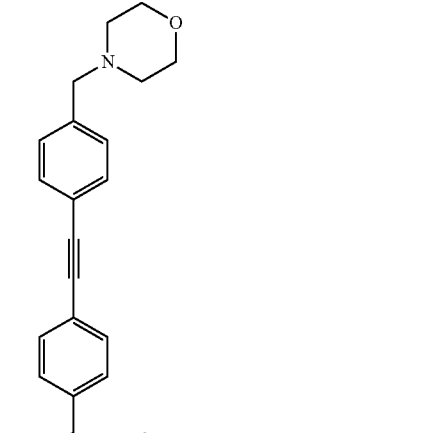 |

TABLE 2-continued
| Compound No. | Chemical Structure |
|---|---|
| 9AZ | 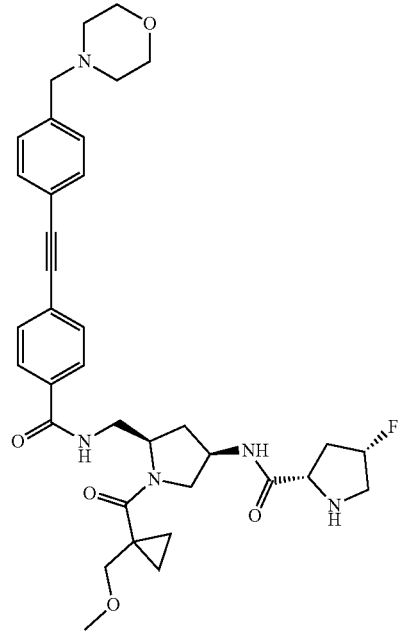 [SMILES: COCC1(C(=O)N2C[C@H](NC(=O)[C@@H]3C[C@H](F)CN3)C[C@@H]2CNC(=O)c2ccc(C#Cc3ccc(CN4CCOCC4)cc3)cc2)CC1] |
| 9BA | 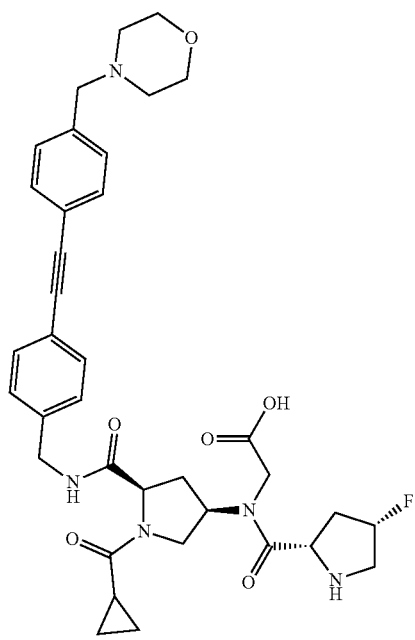 [SMILES: O=C(O)CN(C(=O)[C@@H]1C[C@H](F)CN1)[C@@H]1C[C@H](C(=O)NCc2ccc(C#Cc3ccc(CN4CCOCC4)cc3)cc2)N(C(=O)C2CC2)C1] |

TABLE 2-continued
| Compound No. | Chemical Structure |
|---|---|
| 9BB | 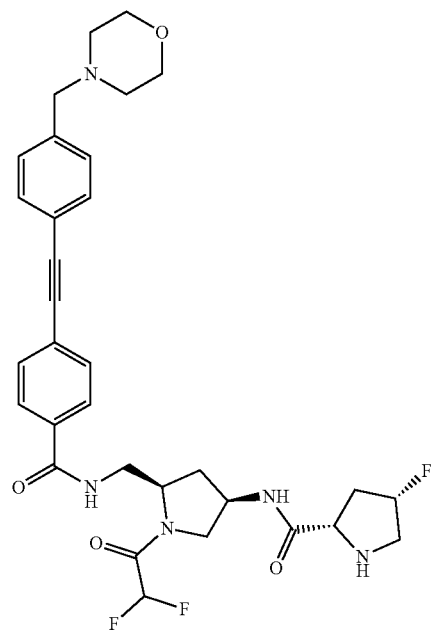 [SMILES: O=C(NC[C@H]1C[C@@H](NC(=O)[C@@H]2C[C@H](F)CN2)CN1C(=O)C(F)F)c1ccc(C#Cc2ccc(CN3CCOCC3)cc2)cc1] |
| 9BC | 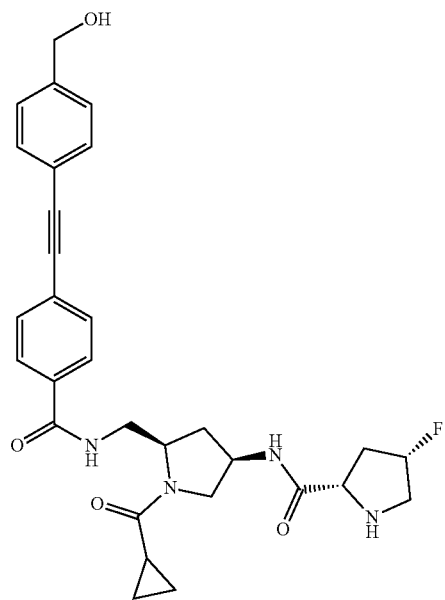 [SMILES: O=C(NC[C@H]1C[C@@H](NC(=O)[C@@H]2C[C@H](F)CN2)CN1C(=O)C1CC1)c1ccc(C#Cc2ccc(CO)cc2)cc1] |

TABLE 2-continued
| Compound No. | Chemical Structure |
|---|---|
| 9BD | 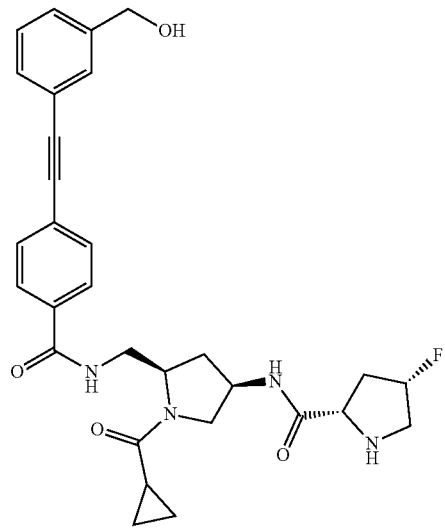 [SMILES: O=C(NC[C@H]1C[C@@H](NC(=O)[C@@H]2C[C@H](F)CN2)CN1C(=O)C1CC1)c1ccc(C#Cc2cccc(CO)c2)cc1] |
| 9BE | 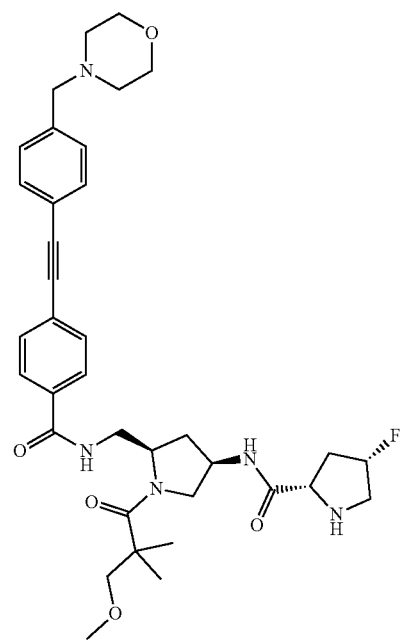 [SMILES: COCC(C)(C)C(=O)N1C[C@H](NC(=O)[C@@H]2C[C@H](F)CN2)C[C@@H]1CNC(=O)c1ccc(C#Cc2ccc(CN3CCOCC3)cc2)cc1] |

TABLE 2-continued

| Compound No. | Chemical Structure |
|---|---|
| 9BF | 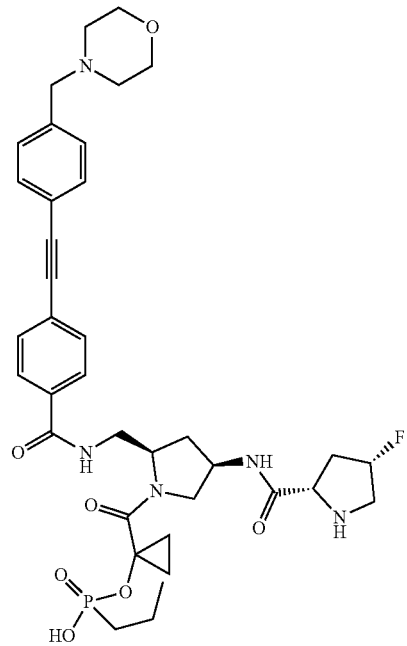 [SMILES: CCCP(=O)(O)OC1(C(=O)N2C[C@H](NC(=O)[C@@H]3C[C@H](F)CN3)C[C@@H]2CNC(=O)c2ccc(C#Cc3ccc(CN4CCOCC4)cc3)cc2)CC1] |
| 9BG | 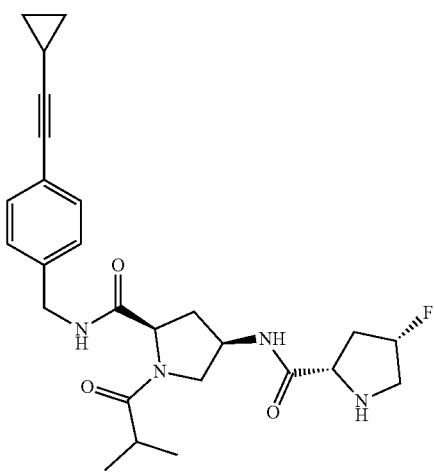 [SMILES: CC(C)C(=O)N1C[C@H](NC(=O)[C@@H]2C[C@H](F)CN2)C[C@@H]1C(=O)NCc1ccc(C#CC2CC2)cc1] |

Example 10—Synthesis of Methyl (2R,4R)-4-amino-1-isobutyrylpyrrolidine-2-carboxylate

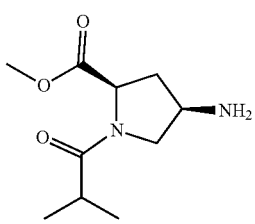

Part I—Synthesis of Methyl (2R,4R)-4-((tert-butoxycarbonyl)amino)pyrrolidine-2-carboxylate 1-Benzyl 2-methyl (2R,4R)-4-((tert-butoxycarbonyl)amino)pyrrolidine-1,2-dicarboxylate (3.00 g, 7.93 mmol) and 10% palladium on carbon (844 mg) were suspended in ethanol (20 mL) under an atmosphere of nitrogen. The nitrogen was evacuated and replaced with hydrogen gas (1 atm) and the mixture was stirred at room temperature for 18 hours. The hydrogen was evacuated, replaced with nitrogen and then the mixture was filtered through a celite pad eluting with ethyl acetate. The filtrate was collected and the solvent removed. The residue was used directly in the next step without further purification.

Part II—Synthesis of Methyl (2R,4R)-4-((tert-butoxycarbonyl)amino)-1-isobutyrylpyrrolidine-2-carboxylate To a solution of methyl (2R,4R)-4-((tert-butoxycarbonyl)amino)pyrrolidine-2-carboxylate (7.93 mmol) in dichloromethane at 0° C. under a nitrogen atmosphere was added triethylamine (1.03 mL, 10.2 mmol) and isobutyryl chloride (921 µL, 8.65 mmol). The mixture was stirred at 0° C. for 1 hour then allowed to warm to room temperature and stirred for a further 1 hour. The mixture was partitioned between dichloromethane and brine. The phases were separated and the organic layer collected, dried ($Na_2SO_4$), and the solvent removed. The residue was used directly in the next step without further purification.

Part III—Synthesis of Methyl (2R,4R)-4-amino-1-isobutyrylpyrrolidine-2-carboxylate hydrochloride Methyl (2R,4R)-4-((tert-butoxycarbonyl)amino)-1-isobutyrylpyrrolidine-2-carboxylate (7.93 mmol) was dissolved in HCl in dioxane (4M, 25 mL) and stirred at room temperature for 2 hours. The solvent was removed to yield the title compound (1.95 g, 98% yield over 3 steps, HCl salt) as a white solid. $^1$H NMR (400 MHz, DMSO) 8.55 (3H, br. s), 4.28 (1H, t, J=8.5 Hz), 4.03-3.99 (1H, m), 3.64 (3H, s), 3.53-3.49 (1H, m), 2.71-2.55 (2H, m), 1.95-1.85 (1H, m), 1.22-1.16 (1H, m), 1.03-0.98 (6H, m).

Example 11—Synthesis of tert-Butyl (4-ethynylbenzyl)carbamate

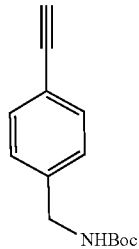 [SMILES: C#Cc1ccc(CNC(=O)OC(C)(C)C)cc1]

Part I—Synthesis of tert-Butyl (4-((trimethylsilyl)ethynyl)benzyl)carbamate tert-Butyl (4-iodobenzyl)carbamate (1.25 g, 3.75 mmol) and trimethylsilylacetylene (624 µL, 4.50 mmol) were dissolved in THF (38 mL). Copper (I) iodide (143 mg, 0.750 mmol) and bis(triphenylphosphine)palladium (II) dichloride (263 mg, 0.375 mmol) were added and the reaction mixture was sparged with argon for 5 minutes. Triethylamine (1.05 mL, 7.50 mmol) was added, and the reaction mixture was stirred at 50° C. under argon for 3 hours. The reaction mixture was cooled to room temperature and filtered through celite. The filter cake was washed with EtOAc, and the combined organics were concentrated in vacuo. The residue was purified by chromatography (80 g silica cartridge, 0-10% EtOAc/cyclohexane gradient) to yield tert-butyl (4-((trimethylsilyl)ethynyl)benzyl)carbamate (1.14 g, 100%) as a dark yellow solid.

Part II—Synthesis of tert-Butyl (4-ethynylbenzyl)carbamate

To a solution of tert-butyl (4-((trimethylsilyl)ethynyl)benzyl)carbamate (1.14 g, 3.75 mmol) in THF (20 mL) at room temperature was added TBAF (7.51 mL, 1.0M in THF, 7.51 mmol) and the reaction mixture was stirred at room temperature for 1 h. The reaction mixture was concentrated in vacuo, and the residue was purified by chromatography (80 g silica cartridge, 0-15% EtOAc/cyclohexane gradient) to yield the title compound (700 mg, 81%) as an orange solid. LCMS (Method 1, ESI) Rt=1.38 min, [M-$^t$Bu+2H]$^+$=176, 96% purity.

Example 12—Synthesis of (4-((4-(Morpholinomethyl)phenyl)ethynyl)phenyl)methanamine

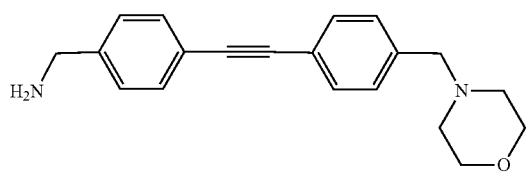 [SMILES: NCc1ccc(C#Cc2ccc(CN3CCOCC3)cc2)cc1]

Part I—Synthesis of tert-Butyl (4-((4-(morpholinomethyl)phenyl)ethynyl)benzyl)carbamate 4-(4-Iodobenzyl)morpholine (322 mg, 1.06 mmol) and tert-butyl (4-ethynylbenzyl)carbamate (295 mg, 1.28 mmol) were dissolved in acetonitrile (7.0 mL). Copper (I) iodide (40 ng, 0.213 mmol) and bis(triphenylphosphine)palladium (H) dichloride (75 mg, 0.106 mmol) were added and reaction mixture was sparged with argon for 15 minutes. Triethylamine (296 µL, 2.13 mmol) was added and the reaction mixture was stirred at 60° C. under argon for 4 hours. The reaction mixture was cooled to room temperature and filtered through celite. The filter cake was washed with EtOAc, and the combined organics were concentrated in vacuo. The residue was purified by chromatography (80 g silica cartridge, 0-10% (2M ammonia in methanol)/dichloromethane gradient) to yield tert-butyl (4-((4-(morpholinomethyl)phenyl)ethynyl)benzyl)carbamate (350 mg, 81%) as a brown solid.

Part II—Synthesis of (4-((4-(Morpholinomethyl)phenyl)ethynyl)phenyl)methanamine tert-Butyl (4-((4-(morpholinomethyl)phenyl)ethynyl)benzyl)carbamate (300 mg, 0.738 mmol) was dissolved in HCl in dioxane (4M, 3.5 mL) and stirred at room temperature for 1.5 hours. The solvent was removed to yield the title compound (270 mg, 97%, bis HCl salt) as an orange solid. LCMS (Method 3, ESI): Rt=1.37 min, [M+H]$^+$=307, 93% purity.

Example 13—Synthesis of (4-(Cyclopropylbuta-1,3-diyn-1-yl)phenyl)methanamine

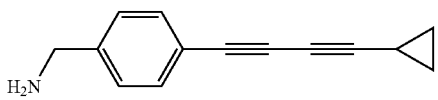

Part I—Synthesis of tert-Butyl (4-(cyclopropylbuta-1,3-diyn-1-yl)benzyl)carbamate To a solution of tert-butyl (4-ethynylbenzyl)carbamate (1.42 g, 6.14 mmol) in a mixture of methanol (30 mL) and pyridine (30 mL) was added ethynylcyclopropane (2.60 mL, 30.7 mmol) followed by copper (II) acetate (2.23 g, 12.3 mmol). The reaction mixture was stirred at room temperature for 2 days. The reaction mixture was concentrated, and the residue was partitioned between EtOAc and water. The organic layer was washed with brine, dried ($Na_2SO_4$), and concentrated. The residue was purified by chromatography (120 g silica cartridge, 0-25% EtOAc/cyclohexane gradient) to yield tert-butyl (4-(cyclopropylbuta-1,3-diyn-1-yl)benzyl)carbamate (951 mg, 53%) as a white solid.

Part II—Synthesis of (4-(Cyclopropylbuta-1,3-diyn-1-yl)phenyl)methanamine tert-Butyl (4-(cyclopropylbuta-1,3-diyn-1-yl)benzyl)carbamate (951 mg, 3.22 mmol) was dissolved in HCl in dioxane (4M, 16 mL) and stirred at room temperature for 1.5 hours. The solvent was removed to yield the title compound (727 mg, 97%, HCl salt) as a white solid.

Example 14—Synthesis of (2R,4R)-4-((2S,4S)-4-Hydroxypyrrolidine-2-carboxamido)-1-isobutyryl-N-(4-((4-(morpholinomethyl)phenyl)ethynyl)benzyl) pyrrolidine-2-carboxamide (Compound 9T

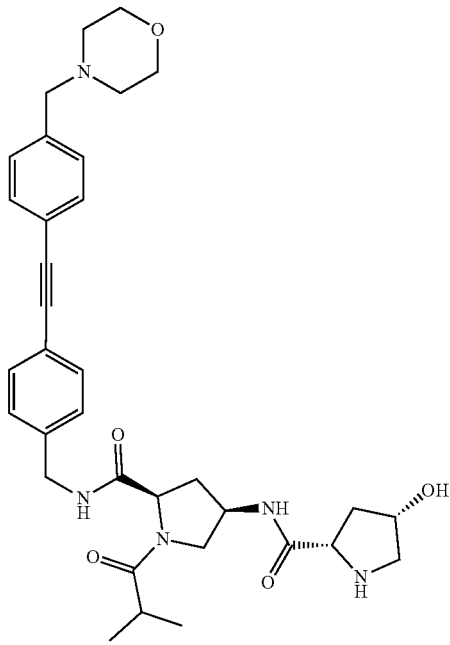 [SMILES: CC(C)C(=O)N1C[C@H](NC(=O)[C@@H]2C[C@H](O)CN2)C[C@@H]1C(=O)NCc1ccc(C#Cc2ccc(CN3CCOCC3)cc2)cc1]

Part I—Synthesis of tert-Butyl (2S,4S)-4-hydroxy-2-(((3R,5R)-1-isobutyryl-5-(methoxycarbonyl)pyrrolidin-3-yl)carbamoyl)pyrrolidine-1-carboxylate To a suspension of methyl (2R,4R)-4-amino-1-isobutyrylpyrrolidine-2-carboxylate hydrochloride (200 mg, 0.798 mmol) and (2S,4S)-1-tert-butoxycarbonyl-4-hydroxypyrrolidine-2-carboxylic acid (203 mg, 0.877 mmol) in dichloromethane (3.0 mL) at room temperature was added triethylamine (334 µL, 2.39 mmol) and HATU (364 mg, 0.957 mmol). The reaction mixture was stirred at room temperature for 1 hour then partitioned between dichloromethane and brine. The phases were separated. The organic layer was collected, dried ($Na_2SO_4$) and the solvent was removed. The residue was used directly in the next step without further purification.

Part II—Synthesis of (2R,4R)-4-((2S,4S)-1-(tert-Butoxycarbonyl)-4-hydroxypyrrolidine-2-carboxamido)-1-isobutyrylpyrrolidine-2-carboxylic acid To a solution of tert-butyl (2S,4S)-4-hydroxy-2-(((3R,5R)-1-isobutyryl-5-(methoxycarbonyl)pyrrolidin-3-yl)carbamoyl)pyrrolidine-1-carboxylate (341 mg, 0.798 mmol) in THF (3.0 mL) and methanol (1.0 mL) at room temperature was added 1M lithium hydroxide (1.00 mL, 1.00 mmol) and the mixture was stirred at room temperature for 1 hour. The solvent was removed under reduced pressure, and the residue was dissolved in water and washed twice with dichloromethane. The aqueous layer was acidified with 1M HCl, solid $Na_2SO_4$ was added, and the mixture was extracted three times with 10% methanol/dichloromethane. The combined organics were washed with brine, dried ($Na_2SO_4$) and concentrated to yield (2R,4R)-4-((2S,4S)-1-(tert-butoxycarbonyl)-4-hydroxypyrrolidine-2-carboxamido)-1-isobutyrylpyrrolidine-2-carboxylic acid (264 mg, 80%) as a white solid.

Part III—Synthesis of tert-Butyl (2S,4S)-4-hydroxy-2-(((3R,5R)-1-isobutyryl-5-((4-((4-(morpholinomethyl)phenyl)ethynyl)benzyl)carbamoyl)pyrrolidin-3-yl)carbamoyl)pyrrolidine-1-carboxylate To a solution of (2R,4R)-4-((2S,4S)-1-(tert-butoxycarbonyl)-4-hydroxypyrrolidine-2-carboxamido)-1-isobutyrylpyrrolidine-2-carboxylic acid (72 mg, 0.173 mmol) and (4-((4-(morpholinomethyl)phenyl)ethynyl)phenyl)methanamine dihydrochloride (65 mg, 0.172 mmol) in dichloromethane (2.0 mL) at room temperature was added triethylamine (72 µL, 0.519 mmol) followed by HATU (79 mg, 0.208 mmol). The mixture was stirred at room temperature for 3 hours then partitioned between dichloromethane and brine. The phases were separated and the organic layer was collected, dried ($Na_2SO_4$) and the solvent removed. The residue was purified by chromatography (12 g silica cartridge, 0-10% methanol/dichloromethane) to yield tert-butyl (2S,4S)-4-hydroxy-2-(((3R,5R)-1-isobutyryl-5-((4-((4-(morpholinomethyl)phenyl)ethynyl) benzyl)carbamoyl)pyrrolidin-3-yl)carbamoyl)pyrrolidine-1-carboxylate (75 mg, 62%) as a colorless glass.

Part IV—Synthesis of (2R,4R)-4-((2S,4S)-4-Hydroxypyrrolidine-2-carboxamido)-1-isobutyryl-N-(4-((4-(morpholinomethyl)phenyl)ethynyl)benzyl)pyrrolidine-2-carboxamide To a solution of tert-butyl (2S,4S)-4-hydroxy-2-(((3R,5R)-1-isobutyryl-5-((4-((4-(morpholinomethyl)phenyl)ethynyl)benzyl)carbamoyl)pyrrolidin-3-yl)carbamoyl)pyrrolidine-1-carboxylate (72 mg, 0.103 mmol) in dichloromethane (2.0 mL) at room temperature was added TFA (0.4 mL), and the mixture was stirred at room temperature for 3 hours. The mixture was concentrated in vacuo, and the remaining TFA was azeotroped with toluene. The residue was dissolved in DMSO (1.5 mL) and purified by reverse phase preparative HPLC (Luna Phenyl Hexyl 21.2× 150 mm, 10 μm, 5-95% MeOH/water (0.1% TFA), 20 mL/min, RT), and the residue was lyophilised to yield the title compound (48 mg, 56%, bis TFA salt) as a white solid. LCMS (Method 5, ESI): Rt=2.09 min, [M+H]⁺=602.1, 94.2% purity.

Example 15—Synthesis of (2R,4R)—N-(4-(cyclopropylbuta-1,3-diyn-1-yl)benzyl)-4-((2S,3R)-3-hydroxypyrrolidine-2-carboxamido)-1-isobutyrylpyrrolidine-2-carboxamide (Compound 9W

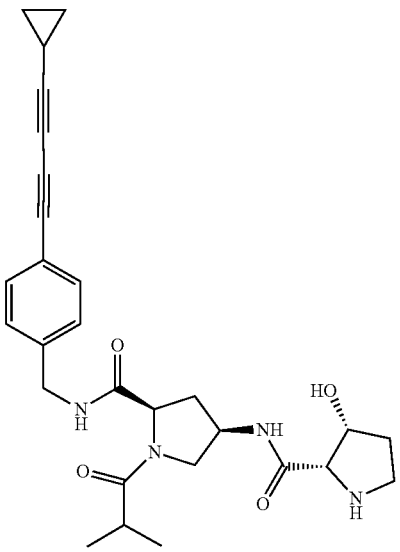 [SMILES: CC(C)C(=O)N1C[C@H](NC(=O)[C@H]2NCC[C@H]2O)C[C@@H]1C(=O)NCc1ccc(C#CC#CC2CC2)cc1]

Part I—Synthesis of tert-Butyl (2S,3R)-3-hydroxy-2-(((3R,5R)-1-isobutyryl-5-(methoxycarbonyl)pyrrolidin-3-yl)carbamoyl)pyrrolidine-1-carboxylate To a solution of methyl (2R,4R)-4-amino-1-isobutyrylpyrrolidine-2-carboxylate hydrochloride (200 mg, 0.798 mmol) and (2S,3R)-1-tert-butoxycarbonyl-3-hydroxy-pyrrolidine-2-carboxylic acid (203 mg, 0.877 mmol) in dichloromethane (3.0 mL) at room temperature was added triethylamine (334 μL, 2.39 mmol) and HATU (364 mg, 0.957 mmol). The reaction mixture was stirred at room temperature for 3 hours then partitioned between dichloromethane and brine. The phases were separated and the organic layer was collected, dried (Na₂SO₄) and the solvent was removed. The residue was used directly in the next step without further purification.

Part II—Synthesis of (2R,4R)-4-((2S,3R)-1-(tert-Butoxycarbonyl)-3-hydroxypyrrolidine-2-carboxamido)-1-isobutyrylpyrrolidine-2-carboxylic acid To a solution of tert-butyl (2S,3R)-3-hydroxy-2-(((3R,5R)-1-isobutyryl-5-(methoxycarbonyl)pyrrolidin-3-yl)carbamoyl)pyrrolidine-1-carboxylate (676 mg, 1.58 mmol) in THF (6.4 mL) and methanol (1.6 mL) was added 2M lithium hydroxide (949 μL, 1.90 mmol), and the mixture was stirred at room temperature for 1 hour. The solvent was removed under reduced pressure. The residue was dissolved in water and washed with dichloromethane (×2). The aqueous layer was acidified with 1M HCl, solid Na₂SO₄ was added, and the mixture was extracted with 10% methanol/dichloromethane (×3). The combined organics were washed with brine, dried (Na₂SO₄), and concentrated to yield (2R,4R)-4-((2S,3R)-1-(tert-butoxycarbonyl)-3-hydroxypyrrolidine-2-carboxamido)-1-isobutyrylpyrrolidine-2-carboxylic acid (420 mg, 64%) as a colorless oil.

Part III—Synthesis of tert-Butyl (2S,3R)-2-(((3R,5R)-5-((4-(cyclopropylbuta-1,3-diyn-1-yl)benzyl)carbamoyl)-1-isobutyrylpyrrolidin-3-yl)carbamoyl)-3-hydroxypyrrolidine-1-carboxylate To a suspension of (2R,4R)-4-((2S,3R)-1-(tert-butoxycarbonyl)-3-hydroxypyrrolidine-2-carboxamido)-1-isobutyrylpyrrolidine-2-carboxylic acid (100 mg, 0.242 mmol) and (4-(cyclopropylbuta-1,3-diyn-1-yl)phenyl)methanamine hydrochloride (62 mg, 0.266 mmol) in dichloromethane (2.0 mL) was added triethylamine (101 μL, 0.726 mmol) and T3P (50% solution in ethyl acetate, 216 μL, 0.363 mmol). The mixture was stirred at room temperature for 2 hours then partitioned between dichloromethane and water. The aqueous layer was re-extracted with dichloromethane, and the combined organics were dried (Biotage Isolute® Phase Separator) and concentrated. The residue was purified by chromatography (12 g silica cartridge, 0-15% methanol/dichloromethane) to yield tert-butyl (2S,3R)-2-(((3R,5R)-5-((4-(cyclopropylbuta-1,3-diyn-1-yl)benzyl)carbamoyl)-1-isobutyrylpyrrolidin-3-yl)carbamoyl)-3-hydroxypyrrolidine-1-carboxylate (110 mg, 77%) as a colorless oil.

Part IV—Synthesis of (2R,4R)—N-(4-(Cyclopropylbuta-1,3-diyn-1-yl)benzyl)-4-((2S,3R)-3-hydroxypyrrolidine-2-carboxamido)-1-isobutyrylpyrrolidine-2-carboxamide To a solution of tert-butyl (2S,3R)-2-(((3R,5R)-5-((4-(cyclopropylbuta-1,3-diyn-1-yl)benzyl)carbamoyl)-1-isobutyrylpyrrolidin-3-yl)carbamoyl)-3-hydroxypyrrolidine-1-carboxylate (110 mg, 0.186 mmol) in dichloromethane (1.5 mL) at room temperature was added TFA (0.3 mL) and the mixture was stirred at room temperature for 1.5 hours. The mixture was concentrated in vacuo, and the remaining TFA was azeotroped with toluene. The residue was dissolved in DMSO (1.5 mL) and purified by reverse phase preparative HPLC (Luna Phenyl Hexyl 21.2× 150 mm, 10 μm, 20-80% MeOH/water (0.1% TFA), 20 mL/min, RT) and the residue was lyophilised to yield the title compound (41 mg, 31%, TFA salt) as a white solid. LCMS (Method 5, ESI): Rt=3.42 min, [M+H]⁺=491.0, 98.7% purity.

Example 16—Synthesis of (2R,4R)-4-((2S,4R)-4-Cyanopyrrolidine-2-carboxamido)-1-isobutyryl-N-(4-((4-(morpholinomethyl)phenyl)ethynyl)benzyl)pyrrolidine-2-carboxamide (Compound 9AC)

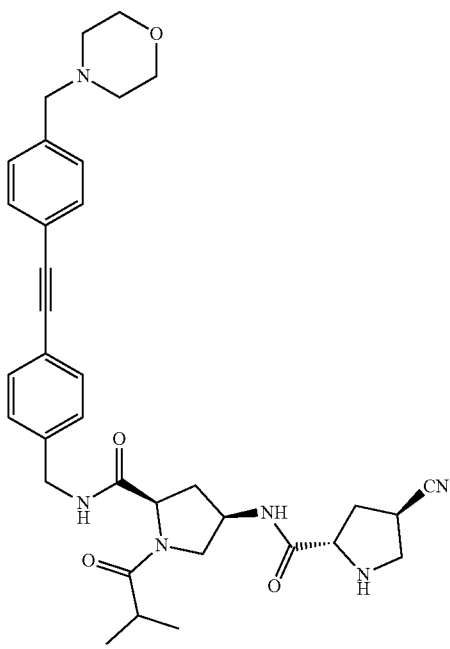

Part I—Synthesis of tert-Butyl (2S,4R)-4-cyano-2-(((3R,5R)-1-isobutyryl-5-(methoxycarbonyl)pyrrolidin-3-yl)carbamoyl)pyrrolidine-1-carboxylate To a solution of methyl (2R,4R)-4-amino-1-isobutyrylpyrrolidine-2-carboxylate hydrochloride (200 mg, 0.798 mmol) and (2S,4R)-1-(tert-Butoxycarbonyl)-4-cyanopyrrolidine-2-carboxylic acid (211 mg, 0.877 mmol) in dichloromethane (3.0 mL) at room temperature was added triethylamine (334 μL, 2.39 mmol) and HATU (364 mg, 0.957 mmol). The reaction mixture was stirred at room temperature for 2 hours then partitioned between dichloromethane and brine. The phases were separated, and the organic layer was collected, dried (Na$_2$SO$_4$) and the solvent was removed. The residue was used directly in the next step without further purification.

Part II—Synthesis of (2R,4R)-4-((2S,4R)-1-(tert-Butoxycarbonyl)-4-cyanopyrrolidine-2-carboxamido)-1-isobutyrylpyrrolidine-2-carboxylic acid To a solution of tert-butyl (2S,4R)-4-cyano-2-(((3R,5R)-1-isobutyryl-5-(methoxycarbonyl)pyrrolidin-3-yl)carbamoyl)pyrrolidine-1-carboxylate (348 mg, 0.798 mmol) in THF (3.0 mL) and methanol (1.0 mL) was added 1M lithium hydroxide (1.60 mL, 1.60 mmol) and the mixture was stirred at room temperature for 3 hours. The solvent was removed under reduced pressure, and the residue was dissolved in water and washed with dichloromethane (×2). The aqueous layer was acidified with 1M HCl, solid Na$_2$SO$_4$ was added, and the mixture was extracted with 10% methanol/dichloromethane (×3). The combined organics were washed with brine, dried (Na$_2$SO$_4$), and concentrated to yield (2R,4R)-4-((2S,4R)-1-(tert-butoxycarbonyl)-4-cyanopyrrolidine-2-carboxamido)-1-isobutyrylpyrrolidine-2-carboxylic acid (339 mg, 100%) as a white solid.

Part III—Synthesis of tert-Butyl (2S,4R)-4-cyano-2-(((3R,5R)-1-isobutyryl-5-((4-((4-(morpholinomethyl)phenyl)ethynyl)benzyl)carbamoyl)pyrrolidin-3-yl)carbamoyl) pyrrolidine-1-carboxylate To a solution of (2R,4R)-4-((2S,4R)-1-(tert-butoxycarbonyl)-4-cyanopyrrolidine-2-carboxamido)-1-isobutyrylpyrrolidine-2-carboxylic acid (84 mg, 0.200 mmol) and (4-((4-(morpholinomethyl)phenyl)ethynyl)phenyl)methanamine dihydrochloride (75 mg, 0.198 mmol) in dichloromethane (2.0 mL) at room temperature was added triethylamine (84 μL, 0.600 mmol) followed by HATU (91 mg, 0.240 mmol). The mixture was stirred at room temperature for 3 hours then partitioned between dichloromethane and brine. The phases were separated. The organic layer was collected, dried (Na$_2$SO$_4$), and the solvent was removed. The residue was purified by chromatography (12 g silica cartridge, 0-10% methanol/dichloromethane) to yield tert-butyl (2S,4R)-4-cyano-2-(((3R,5R)-1-isobutyryl-5-((4-((4-(morpholinomethyl)phenyl) ethynyl)benzyl)carbamoyl)pyrrolidin-3-yl)carbamoyl)pyrrolidine-1-carboxylate (98 mg, 69%) as a colorless glass.

Part IV—Synthesis of (2R,4R)-4-((2S,4R)-4-Cyanopyrrolidine-2-carboxamido)-1-isobutyryl-N-(4-((4-(morpholinomethyl)phenyl)ethynyl)benzyl)pyrrolidine-2-carboxamide To a solution of tert-butyl (2S,4R)-4-cyano-2-(((3R,5R)-1-isobutyryl-5-((4-((4-(morpholinomethyl)phenyl)ethynyl)benzyl)carbamoyl)pyrrolidin-3-yl)carbamoyl)pyrrolidine-1-carboxylate (98 mg, 0.138 mmol) in dichloromethane (2.0 mL) at room temperature was added TFA (0.4 mL) and the mixture was stirred at room temperature for 3 hours. The mixture was concentrated in vacuo, and the remaining TFA was azeotroped with toluene. The residue was dissolved in DMSO (1.5 mL) and purified by reverse phase preparative HPLC (Luna Phenyl Hexyl 21.2×150 mm, 10 μm, 5-60% MeOH/water (0.1% TFA), 20 mL/min, RT), and the residue was lyophilised to yield the title compound (55 mg, 48%, bis TFA salt) as a white solid. LCMS (Method 5, ESI): Rt=2.18 min, [M+H]$^+$=611.4, 99.9% purity.

Example 17—Synthesis of (2R,4R)-4-((2S,4S)-4-Cyanopyrrolidine-2-carboxamido)-1-isobutyryl-N-(4-((4-(morpholinomethyl)phenyl)ethynyl)benzyl)pyrrolidine-2-carboxamide (Compound 9AD)

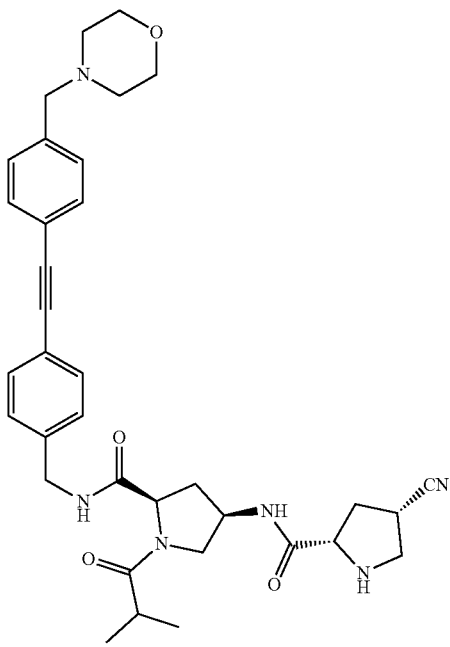

Part I—Synthesis of tert-Butyl (2S,4S)-4-cyano-2-(((3R,5R)-1-isobutyryl-5-(methoxycarbonyl)pyrrolidin-3-yl)carbamoyl)pyrrolidine-1-carboxylate To a solution of methyl (2R,4R)-4-amino-1-isobutyrylpyrrolidine-2-carboxylate hydrochloride (200 mg, 0.798 mmol) and (2S,4S)-1-(tert-Butoxycarbonyl)-4-cyanopyrrolidine-2-carboxylic acid (211 mg, 0.877 mmol) in dichloromethane (3.0 mL) at room temperature was added triethylamine (334 µL, 2.39 mmol) and HATU (364 mg, 0.957 mmol). The reaction mixture was stirred at room temperature for 2 hours then partitioned between dichloromethane and brine. The phases were separated. The organic layer was collected, dried ($Na_2SO_4$), and the solvent removed. The residue was used directly in the next step without further purification.

Part II—Synthesis of (2R,4R)-4-((2S,4S)-1-(tert-Butoxycarbonyl)-4-cyanopyrrolidine-2-carboxamido)-1-isobutyrylpyrrolidine-2-carboxylic acid To a solution of tert-butyl (2S,4S)-4-cyano-2-(((3R,5R)-1-isobutyryl-5-(methoxycarbonyl)pyrrolidin-3-yl)carbamoyl)pyrrolidine-1-carboxylate (348 mg, 0.798 mmol) in THF (3.0 mL) and methanol (1.0 mL) was added 1M lithium hydroxide (1.60 mL, 1.60 mmol), and the mixture was stirred at room temperature for 3 hours. The solvent was removed under reduced pressure, and the residue was dissolved in water and washed with dichloromethane (×2). The aqueous layer was acidified with 1M HCl, solid $Na_2SO_4$ was added, and the mixture was extracted with 10% methanol/dichloromethane (×3). The combined organics were washed with brine, dried ($Na_2SO_4$), and concentrated to yield (2R,4R)-4-((2S,4S)-1-(tert-butoxycarbonyl)-4-cyanopyrrolidine-2-carboxamido)-1-isobutyrylpyrrolidine-2-carboxylic acid (328 mg, 97%) as a white solid.

Part III—Synthesis of tert-Butyl (2S,4S)-4-cyano-2-(((3R,5R)-1-isobutyryl-5-((4-((4-(morpholinomethyl)phenyl)ethynyl)benzyl)carbamoyl)pyrrolidin-3-yl)carbamoyl) pyrrolidine-1-carboxylate To a solution of (2R,4R)-4-((2S,4S)-1-(tert-butoxycarbonyl)-4-cyanopyrrolidine-2-carboxamido)-1-isobutyrylpyrrolidine-2-carboxylic acid (84 mg, 0.200 mmol) and (4-((4-(morpholinomethyl)phenyl)ethynyl)phenyl)methanamine dihydrochloride (75 mg, 0.198 mmol) in dichloromethane (2.0 mL) at room temperature was added triethylamine (84 µL, 0.600 mmol) followed by HATU (91 mg, 0.240 mmol). The mixture was stirred at room temperature for 3 hours then partitioned between dichloromethane and brine. The phases were separated. The organic layer was collected, dried ($Na_2SO_4$), and the solvent was removed. The residue was purified by chromatography (12 g silica cartridge, 0-10% methanol/dichloromethane) to yield tert-butyl (2S,4S)-4-cyano-2-(((3R,5R)-1-isobutyryl-5-((4-((4-(morpholinomethyl)phenyl) ethynyl)benzyl)carbamoyl)pyrrolidin-3-yl)carbamoyl)pyrrolidine-1-carboxylate (96 mg, 68%) as a colorless glass.

Part IV—Synthesis of (2R,4R)-4-((2S,4S)-4-Cyanopyrrolidine-2-carboxamido)-1-isobutyryl-N-(4-((4-(morpholinomethyl)phenyl)ethynyl)benzyl)pyrrolidine-2-carboxamide To a solution of tert-butyl (2S,4S)-4-cyano-2-(((3R,5R)-1-isobutyryl-5-((4-((4-(morpholinomethyl)phenyl)ethynyl)benzyl)carbamoyl)pyrrolidin-3-yl)carbamoyl)pyrrolidine-1-carboxylate (96 mg, 0.135 mmol) in dichloromethane (2.0 mL) at room temperature was added TFA (0.4 mL), and the mixture was stirred at room temperature for 3 hours. The mixture was concentrated in vacuo, and the remaining TFA was azeotroped with toluene. The residue was dissolved in DMSO (1.5 mL) and purified by reverse phase preparative HPLC (Luna Phenyl Hexyl 21.2×150 mm, 10 µm, 5-60% MeOH/water (0.1% TFA), 20 mL/min, RT) and the residue was lyophilised to yield the title compound (62 mg, 55%, bis TFA salt) as a white solid. LCMS (Method 5, ESI): Rt=2.18 min, $[M+H]^+$=610.6, 98.8% purity.

Example 18—Synthesis of (2R,4R)-4-((2S,4S)-4-Fluoropyrrolidine-2-carboxamido)-1-(methylsulfonyl)-N-(4-((4-(morpholinomethyl)phenyl)ethynyl)benzyl)pyrrolidine-2-carboxamide (Compound 9AI)

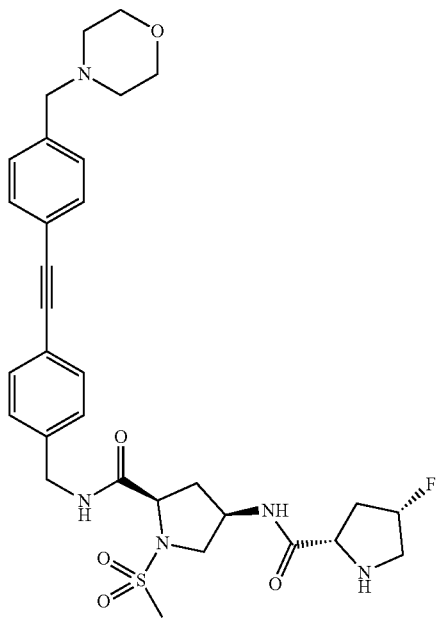 [SMILES: CS(=O)(=O)N1C[C@H](NC(=O)[C@@H]2C[C@H](F)CN2)C[C@@H]1C(=O)NCc1ccc(C#Cc2ccc(CN3CCOCC3)cc2)cc1]

Part I—Synthesis of (2R,4R)-4-((2S,4S)-1-(tert-Butoxycarbonyl)-4-fluoropyrrolidine-2-carboxamido)-1-((2-(trimethylsilyl)ethoxy)carbonyl)pyrrolidine-2-carboxylic acid To a solution of 2-methyl 1-(2-(trimethylsilyl)ethyl) (2R,4R)-4-((2S,4S)-1-(tert-butoxycarbonyl)-4-fluoropyrrolidine-2-carboxamido)pyrrolidine-1,2-dicarboxylate (4.21 g, 8.36 mmol) in a mixture of THF (32 mL) and MeOH (8.0 mL) at room temperature was added 2M lithium hydroxide (5.02 mL, 10.03 mmol), and the mixture was stirred at room temperature for 1 hour. The solvent was removed under reduced pressure, and the residue was dissolved in water and washed with dichloromethane. The aqueous layer was acidified with 1M HCl and extracted with 10% methanol/dichloromethane (×3). The combined organics were washed with brine, dried (Na$_2$SO$_4$), and concentrated. The residue was triturated with diethyl ether to yield (2R,4R)-4-((2S,4S)-1-(tert-butoxycarbonyl)-4-fluoropyrrolidine-2-carboxamido)-1-((2-(trimethylsilyl)ethoxy)carbonyl)pyrrolidine-2-carboxylic acid (3.45 g, 84%) as a white solid.

Part II—Synthesis of tert-Butyl (2S,4S)-4-fluoro-2-(((3R,5R)-5-((4-((4-(morpholinomethyl)phenyl)ethynyl)benzyl)carbamoyl)-1-((2-(trimethylsilyl)ethoxy)carbonyl)pyrrolidin-3-yl)carbamoyl)pyrrolidine-1-carboxylate To a suspension of (2R,4R)-4-((2S,4S)-1-(tert-butoxycarbonyl)-4-fluoropyrrolidine-2-carboxamido)-1-((2-(trimethylsilyl)ethoxy)carbonyl)pyrrolidine-2-carboxylic acid (500 mg, 1.02 mmol) and (4-((4-(morpholinomethyl)phenyl)ethynyl)phenyl)methanamine dihydrochloride (465 mg, 1.23 mmol) in dichloromethane (7.0 mL) was added triethylamine (427 μL, 3.06 mmol) and T3P (50% solution in ethyl acetate, 912 μL, 1.53 mmol). The mixture was stirred at room temperature for 2 hours then partitioned between dichloromethane and water. The aqueous layer was re-extracted with 10% methanol/dichloromethane, and the combined organics were dried (Na$_2$SO$_4$) and concentrated. The residue was purified by chromatography (40 g silica cartridge, 0-10% methanol/dichloromethane) to yield tert-butyl (2S,4S)-4-fluoro-2-(((3R,5R)-5-((4-((4-(morpholinomethyl)phenyl)ethynyl)benzyl)carbamoyl)-1-((2-(trimethylsilyl)ethoxy)carbonyl) pyrrolidin-3-yl)carbamoyl) pyrrolidine-1-carboxylate (600 mg, 75%) as a brown oil.

Part III—Synthesis of tert-Butyl (2S,4S)-4-fluoro-2-(((3R,5R)-5-((4-((4-(morpholinomethyl) phenyl)ethynyl)benzyl)carbamoyl)pyrrolidin-3-yl)carbamoyl)pyrrolidine-1-carboxylate To a solution of tert-butyl (2S,4S)-4-fluoro-2-(((3R,5R)-5-((4-((4-(morpholinomethyl) phenyl)ethynyl)benzyl)carbamoyl)-1-((2-(trimethylsilyl)ethoxy)carbonyl)pyrrolidin-3-yl)carbamoyl)pyrrolidine-1-carboxylate (600 mg, 0.771 mmol) in THF (4.0 mL) at room temperature was added TBAF (1.54 mL, 1.0M in THF, 1.54 mmol), and the reaction mixture was stirred at room temperature for 6 hours. A further portion of TBAF was then added (1.54 mL, 1.0M in THF, 1.54 mmol), and stirring was continued at room temperature for a further 18 hours. The reaction mixture was concentrated, and the residue was partitioned between EtOAc and water. The organic layer was washed with brine, dried (Na$_2$SO$_4$), and concentrated. The residue was purified by chromatography (25 g silica cartridge, 0-7.5% 2M ammonia in methanol/dichloromethane) to yield tert-butyl (2S,4S)-4-fluoro-2-(((3R,5R)-5-((4-((4-(morpholinomethyl) phenyl)ethynyl)benzyl)carbamoyl)pyrrolidin-3-yl)carbamoyl)pyrrolidine-1-carboxylate (433 mg, 89%) as a yellow solid.

Part IV—Synthesis of tert-Butyl (2S,4S)-4-fluoro-2-(((3R,5R)-1-(methylsulfonyl)-5-((4-((4-(morpholinomethyl)phenyl)ethynyl)benzyl)carbamoyl)pyrrolidin-3-yl)carbamoyl) pyrrolidine-1-carboxylate To a solution of tert-butyl (2S,4S)-4-fluoro-2-(((3R,5R)-5-((4-((4-(morpholinomethyl) phenyl)ethynyl)benzyl)carbamoyl)pyrrolidin-3-yl)carbamoyl)pyrrolidine-1-carboxylate (75 mg, 0.118 mmol) in dichloromethane (1.5 mL) at room temperature was added triethylamine (33 μL, 0.237 mmol) followed by methanesulfonyl chloride (10 μL, 0.130 mmol). The reaction mixture was stirred at room temperature for 1.5 hours then partitioned between dichloromethane and water. The organic layer was dried (Biotage Isolute® Phase Separator) and concentrated to yield tert-butyl (2S,4S)-4-fluoro-2-(((3R,5R)-1-(methylsulfonyl)-5-((4-((4-(morpholinomethyl)phenyl) ethynyl)benzyl)carbamoyl)pyrrolidin-3-yl)carbamoyl)pyrrolidine-1-carboxylate (42 mg, 50%) which was used directly in the next step without purification.

Part V—Synthesis of (2R,4R)-4-((2S,4S)-4-Fluoropyrrolidine-2-carboxamido)-1-(methylsulfonyl)-N-(4-((4-(morpholinomethyl)phenyl)ethynyl)benzyl) pyrrolidine-2-carboxamide To a solution of tert-butyl (2S,4S)-4-fluoro-2-(((3R,5R)-1-(methylsulfonyl)-5-((4-((4-(morpholinomethyl)phenyl) ethynyl)benzyl)carbamoyl)pyrrolidin-3-yl)carbamoyl)pyrrolidine-1-carboxylate (42 mg, 0.059 mmol) in dichloromethane (0.6 mL) at room temperature was added TFA (0.15 mL), and the mixture was stirred at room temperature for 1.5 hours. The mixture was concentrated in vacuo, and the remaining TFA was azeotroped with toluene. The residue was dissolved in DMSO (1.5 mL) and purified by reverse phase preparative HPLC (Sunfire C18 19×150 mm, 10 m, 5-60% MeCN/H$_2$O (0.1% TFA), 20 mL/min, RT), and the residue was lyophilised to yield the title compound (18 mg, 36%, bis TFA salt) as a white solid. LCMS (Method 5, ESI): Rt=2.10 min, [M+H]$^+$=612.0, 98.6% purity.

Example 19—Synthesis of (2R,4R)—N-(4-(Cyclopropylbuta-1,3-diyn-1-yl)benzyl)-4-((2S,4S)-4-fluoropyrrolidine-2-carboxamido)-1-(2-methoxyethyl)pyrrolidine-2-carboxamide (Compound 9AM)

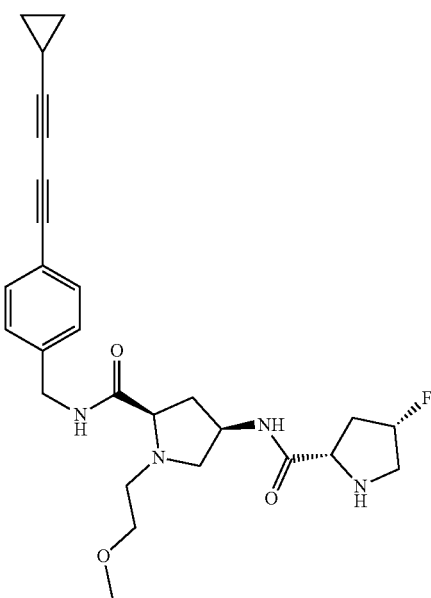 [SMILES: COCCN1C[C@H](NC(=O)[C@@H]2C[C@H](F)CN2)C[C@@H]1C(=O)NCc1ccc(C#CC#CC2CC2)cc1]

Part I—Synthesis of tert-Butyl (2S,4S)-2-(((3R,5R)-5-((4-(cyclopropylbuta-1,3-diyn-1-yl)benzyl)carbamoyl)-1-((2-(trimethylsilyl)ethoxy)carbonyl)pyrrolidin-3-yl)carbamoyl)-4-fluoropyrrolidine-1-carboxylate To a solution of (2R,4R)-4-((2S,4S)-1-(tert-butoxycarbonyl)-4-fluoropyrrolidine-2-carboxamido)-1-((2-(trimethylsilyl)ethoxy)carbonyl)pyrrolidine-2-carboxylic acid (599 mg, 1.22 mmol) and (4-(cyclopropylbuta-1,3-diyn-1-yl)phenyl)methanamine hydrochloride (340 mg, 1.47 mmol) in dichloromethane (8.5 mL) at room temperature was added triethylamine (511 μL, 3.67 mmol) and T3P (50% solution in ethyl acetate, 1.09 mL, 1.83 mmol). The mixture was stirred at room temperature for 1.5 hours then partitioned between dichloromethane and water. The aqueous layer was re-extracted with dichloromethane, and the combined organics were dried (Biotage Isolute® Phase Separator), and the solvent was removed. The residue was purified by chromatography (40 g silica cartridge, 0-10% methanol/dichloromethane gradient) to yield tert-butyl (2S,4S)-2-(((3R,5R)-5-((4-(cyclopropylbuta-1,3-diyn-1-yl)benzyl)carbamoyl)-1-((2-(trimethylsilyl)ethoxy)carbonyl)pyrrolidin-3-yl)carbamoyl)-4-fluoropyrrolidine-1-carboxylate (685 mg, 84%) as a yellow gum.

Part II—Synthesis of tert-Butyl (2S,4S)-2-(((3R,5R)-5-((4-(cyclopropylbuta-1,3-diyn-1-yl)benzyl)carbamoyl)pyrrolidin-3-yl)carbamoyl)-4-fluoropyrrolidine-1-carboxylate To a solution of tert-butyl (2S,4S)-2-(((3R,5R)-5-((4-(cyclopropylbuta-1,3-diyn-1-yl)benzyl)carbamoyl)-1-((2-(trimethylsilyl)ethoxy)carbonyl)pyrrolidin-3-yl)carbamoyl)-4-fluoropyrrolidine-1-carboxylate (685 mg, 1.03 mmol) in THF (5.0 mL) at room temperature was added TBAF (2.05 mL, 1.0M in THF, 2.05 mmol), and the reaction mixture was stirred at room temperature for 18 hours. The reaction mixture was concentrated, and the residue was partitioned between EtOAc and water. The organic layer was washed with brine, dried (Na$_2$SO$_4$), and concentrated to yield tert-butyl (2S,4S)-2-(((3R,5R)-5-((4-(cyclopropylbuta-1,3-diyn-1-yl)benzyl)carbamoyl)pyrrolidin-3-yl)carbamoyl)-4-fluoropyrrolidine-1-carboxylate (472 mg, 88%) as an off-white solid.

Part III—Synthesis of tert-Butyl (2S,4S)-2-(((3R,5R)-5-((4-(cyclopropylbuta-1,3-diyn-1-yl)benzyl)carbamoyl)-1-(2-methoxyethyl)pyrrolidin-3-yl)carbamoyl)-4-fluoropyrrolidine-1-carboxylate To a solution of tert-butyl (2S,4S)-2-(((3R,5R)-5-((4-(cyclopropylbuta-1,3-diyn-1-yl)benzyl)carbamoyl)pyrrolidin-3-yl)carbamoyl)-4-fluoropyrrolidine-1-carboxylate (80 mg, 0.153 mmol) in acetonitrile (0.7 mL) at room temperature was added cesium carbonate (75 mg, 0.230 mmol) and 2-bromoethyl methyl ether (16 μL, 0.168 mmol). The reaction mixture was stirred at room temperature for 3 hours, then at 50° C. for 17 hours, and then at 75° C. for 4 hours. A further portion of 2-bromoethyl methyl ether (16 μL, 0.168 mmol) was added, and stirring was continued at 75° C. for 18 hours. The reaction mixture was diluted with water and extracted with EtOAc, then the organic layer was dried (Na$_2$SO$_4$) and concentrated. The residue was purified by chromatography (4 g silica cartridge, 0-10% methanol/dichloromethane gradient) to yield tert-butyl (2S,4S)-2-(((3R,5R)-5-((4-(cyclopropylbuta-1,3-diyn-1-yl)benzyl)carbamoyl)-1-(2-methoxyethyl)pyrrolidin-3-yl)carbamoyl)-4-fluoropyrrolidine-1-carboxylate (65 mg, 73%) as a colourless gum.

Part IV—Synthesis of (2R,4R)—N-(4-(Cyclopropylbuta-1,3-diyn-1-yl)benzyl)-4-((2S,4S)-4-fluoropyrrolidine-2-carboxamido)-1-(2-methoxyethyl)pyrrolidine-2-carboxamide To a solution of tert-butyl (2S,4S)-2-(((3R,5R)-5-((4-(cyclopropylbuta-1,3-diyn-1-yl)benzyl)carbamoyl)-1-(2-methoxyethyl)pyrrolidin-3-yl)carbamoyl)-4-fluoropyrrolidine-1-carboxylate (65 mg, 0.112 mmol) in dichloromethane (1.0 mL) at room temperature was added TFA (0.25 mL), and the mixture was stirred at room temperature for 1.5 hours. The mixture was concentrated in vacuo, and the remaining TFA was azeotroped with toluene. The residue was dissolved in DMSO (1.5 mL) and purified by reverse phase preparative HPLC (Sunfire C18 19×150 mm, 10 m, 5-95% MeCN/H$_2$O (0.1% TFA), 20 mL/min, RT), and the residue was lyophilised to yield the title compound (12 mg, 15%, bis TFA salt) as a white solid. LCMS (Method 5, ESI): Rt=2.97 min, [M+H]⁺=481.4, 96.8% purity.

Example 20—Synthesis of 2-((2R,4R)-2-((4-(Cyclopropylbuta-1,3-diyn-1-yl)benzyl)carbamoyl)-4-((2S,4S)-4-fluoropyrrolidine-2-carboxamido)pyrrolidin-1-yl)acetic acid (Compound 9AN)

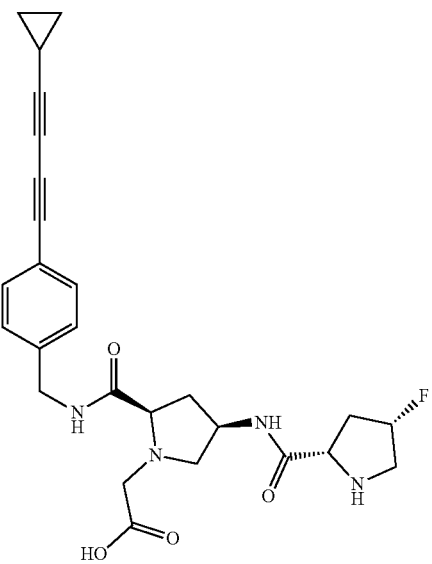 [SMILES: O=C(O)CN1C[C@H](NC(=O)[C@@H]2C[C@H](F)CN2)C[C@@H]1C(=O)NCc1ccc(C#CC#CC2CC2)cc1]

Part I—Synthesis of tert-Butyl (2S,4S)-2-(((3R,5R)-1-(2-(tert-butoxy)-2-oxoethyl)-5-((4-(cyclopropylbuta-1,3-diyn-1-yl)benzyl)carbamoyl)pyrrolidin-3-yl)carbamoyl)-4-fluoropyrrolidine-1-carboxylate To a solution of tert-butyl (2S,4S)-2-(((3R,5R)-5-((4-(cyclopropylbuta-1,3-diyn-1-yl)benzyl)carbamoyl)pyrrolidin-3-yl)carbamoyl)-4-fluoropyrrolidine-1-carboxylate (80 mg, 0.153 mmol) in acetonitrile (0.7 mL) at room temperature was added cesium carbonate (75 mg, 0.230 mmol) and tert-butyl bromoacetate (25 µL, 0.168 mmol). The reaction mixture was stirred at room temperature for 3 hours then warmed to 50° C. and stirred for a further 18 hours. The reaction mixture was diluted with water and extracted with EtOAc, then the organic layer was dried (Na₂SO₄) and concentrated. The residue was purified by chromatography (4 g silica cartridge, 0-10% methanol/dichloromethane gradient) to yield tert-butyl (2S,4S)-2-(((3R,5R)-1-(2-(tert-butoxy)-2-oxoethyl)-5-((4-(cyclopropylbuta-1,3-diyn-1-yl)benzyl)carbamoyl)pyrrolidin-3-yl)carbamoyl)-4-fluoropyrrolidine-1-carboxylate (55 mg, 57%) as a colourless glass.

Part II—Synthesis of 2-((2R,4R)-2-((4-(Cyclopropylbuta-1,3-diyn-1-yl)benzyl)carbamoyl)-4-((2S,4S)-4-fluoropyrrolidine-2-carboxamido)pyrrolidin-1-yl)acetic acid To a solution of tert-butyl (2S,4S)-2-(((3R,5R)-1-(2-(tert-butoxy)-2-oxoethyl)-5-((4-(cyclopropylbuta-1,3-diyn-1-yl)benzyl)carbamoyl)pyrrolidin-3-yl)carbamoyl)-4-fluoropyrrolidine-1-carboxylate (54 mg, 0.085 mmol) in dichloromethane (0.8 mL) at room temperature was added TFA (0.2 mL), and the mixture was stirred at room temperature for 1.5 hours. An additional portion of TFA (0.2 mL) was added, and stirring was continued at room temperature for a further 3 hours. The mixture was concentrated in vacuo, and the remaining TFA was azeotroped with toluene. The residue was dissolved in DMSO (1.5 mL) and purified by reverse phase preparative HPLC (Sunfire C18 19×150 mm, 10 m, 5-60% MeCN/H₂O (0.1% TFA), 20 mL/min, RT), and the residue was lyophilised to yield the title compound (12 mg, 20%, bis TFA salt) as a white solid. LCMS (Method 5, ESI): Rt=3.09 min, [M+H]⁺=481.3, 96.0% purity.

Example 21—Synthesis of (2R,4R)-1-(Cyclopropanecarbonyl)-4-((2S,4S)-4-fluoro-N-(2-methoxyethyl)pyrrolidine-2-carboxamido)-N-(4-((4-(morpholinomethyl)phenyl)ethynyl) benzyl)pyrrolidine-2-carboxamide (Compound 9AV)

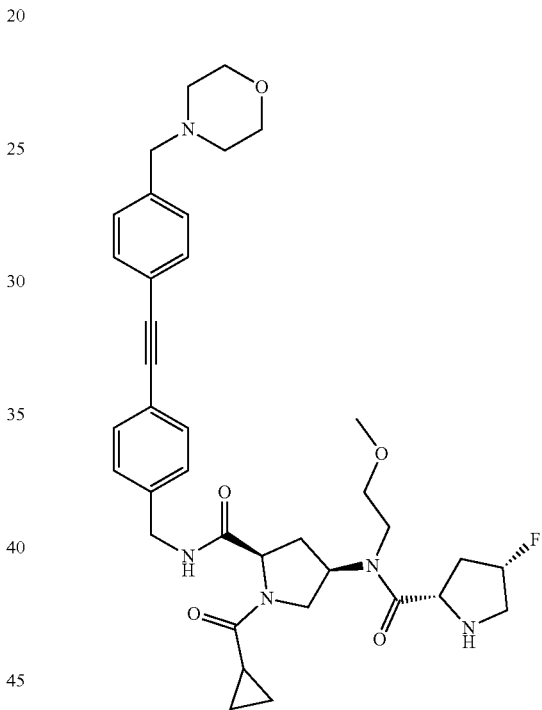

Part I—Synthesis of 1-Benzyl 2-methyl (2R,4R)-4-((2-methoxyethyl)amino)pyrrolidine-1,2-dicarboxylate To a solution of 1-benzyl 2-methyl (2R,4R)-4-aminopyrrolidine-1,2-dicarboxylate hydrochloride (408 mg, 1.30 mmol) in DMF (6.5 mL) at room temperature was added 2-bromoethyl methyl ether (268 µL, 2.85 mmol) and potassium carbonate (573 mg, 4.15 mmol). The reaction mixture was stirred at 60° C. for 18 hours then cooled to room temperature and diluted with water. The mixture was extracted with EtOAc (×3), and the combined organics were washed with brine, dried (Na₂SO₄), and concentrated. The residue was purified by chromatography (40 g silica cartridge, 0-5% 2M ammonia in methanol/dichloromethane gradient) to yield 1-benzyl 2-methyl (2R,4R)-4-((2-methoxyethyl)amino)pyrrolidine-1,2-dicarboxylate (297 mg, 68%) as a colourless oil.

Part II—Synthesis of 1-Benzyl 2-methyl (2R,4R)-4-((2S,4S)-1-(tert-butoxycarbonyl)-4-fluoro-N-(2-methoxyethyl)pyrrolidine-2-carboxamido)pyrrolidine-1,2-dicarboxylate To a solution of 1-benzyl 2-methyl (2R,4R)-4-((2-methoxyethyl)amino)pyrrolidine-1,2-dicarboxylate (297 mg, 0.883 mmol) and N-Boc-cis-4-fluoro-L-proline (412 mg, 1.77 mmol) in 2-methyltetrahydrofuran (4.0 mL) at room temperature was added triethylamine (492 µL, 3.53 mmol) and T3P (50% solution in ethyl acetate, 1.58 mL, 2.65 mmol). The reaction mixture was stirred at 70° C. for 4 hours. The mixture was then cooled to room temperature, diluted with EtOAc, and washed with saturated NaHCO$_3$ (aq). The organic layer was dried (Na$_2$SO$_4$) and concentrated. The residue was purified by chromatography (25 g silica cartridge, 0-5% 2M ammonia in methanol/dichloromethane gradient) to yield 1-benzyl 2-methyl (2R,4R)-4-((2S,4S)-1-(tert-butoxycarbonyl)-4-fluoro-N-(2-methoxyethyl)pyrrolidine-2-carboxamido)pyrrolidine-1,2-dicarboxylate (430 mg, 88%) as a yellow gum.

Part III—Synthesis of tert-Butyl (2S,4S)-4-fluoro-2-(((3R,5R)-5-(methoxycarbonyl) pyrrolidin-3-yl)(2-methoxyethyl)carbamoyl)pyrrolidine-1-carboxylate 1-Benzyl 2-methyl (2R,4R)-4-((2S,4S)-1-(tert-butoxycarbonyl)-4-fluoro-N-(2-methoxyethyl)pyrrolidine-2-carboxamido)pyrrolidine-1,2-dicarboxylate (430 mg, 0.780 mmol) and 10% palladium on carbon (43 mg) were suspended in ethanol (8.0 mL) under an atmosphere of nitrogen. The nitrogen was evacuated and replaced with hydrogen gas (1 atm), and the mixture was stirred at room temperature for 4.5 hours. The hydrogen was evacuated, replaced with nitrogen, and then the mixture was filtered through a celite pad eluting with ethyl acetate. The filtrate was concentrated. The residue was purified by chromatography (25 g silica cartridge, 0-10% 2M ammonia in methanol/dichloromethane gradient) to yield tert-butyl (2S,4S)-4-fluoro-2-(((3R,5R)-5-(methoxycarbonyl)pyrrolidin-3-yl)(2-methoxyethyl)carbamoyl)pyrrolidine-1-carboxylate (180 mg, 55%) as a colorless oil.

Part IV—Synthesis of tert-Butyl (2S,4S)-2-(((3R,5R)-1-(cyclopropanecarbonyl)-5-(methoxycarbonyl)pyrrolidin-3-yl)(2-methoxyethyl)carbamoyl)-4-fluoropyrrolidine-1-carboxylate To a solution of tert-butyl (2S,4S)-4-fluoro-2-(((3R,5R)-5-(methoxycarbonyl) pyrrolidin-3-yl)(2-methoxyethyl)carbamoyl)pyrrolidine-1-carboxylate (180 mg, 0.431 mmol) in dichloromethane (2.0 mL) at room temperature was added cyclopropanecarbonyl chloride (43 µL, 0.474 mmol) and triethylamine (72 µL, 0.517 mmol), and the reaction mixture was stirred at room temperature for 1.5 hours. The mixture was then partitioned between DCM and water. The organic layer was dried (Biotage Isolute® Phase Separator) and concentrated to yield tert-butyl (2S,4S)-2-(((3R,5R)-1-(cyclopropanecarbonyl)-5-(methoxycarbonyl)pyrrolidin-3-yl)(2-methoxyethyl)carbamoyl)-4-fluoropyrrolidine-1-carboxylate (164 mg, 78%) as a white foam, which was used directly in the next step without further purification.

Part V—Synthesis of (2R,4R)-4-((2S,4S)-1-(tert-Butoxycarbonyl)-4-fluoro-N-(2-methoxyethyl)pyrrolidine-2-carboxamido)-1-(cyclopropanecarbonyl)pyrrolidine-2-carboxylic acid To a solution of tert-butyl (2S,4S)-2-(((3R,5R)-1-(cyclopropanecarbonyl)-5-(methoxycarbonyl)pyrrolidin-3-yl)(2-methoxyethyl)carbamoyl)-4-fluoropyrrolidine-1-carboxylate (164 mg, 0.338 mmol) in a mixture of THF (2.0 mL) and methanol (1.0 mL) at room temperature was added 2M lithium hydroxide (186 µL, 0.372 mmol), and the mixture was stirred at room temperature for 6 hours. An additional portion of 2M lithium hydroxide (186 µL, 0.372 mmol) was then added, and stirring was continued at room temperature for a further 1 hour. The reaction mixture was diluted with water and washed with EtOAc. The aqueous layer was acidified with 1M HCl and extracted with 10% methanol/dichloromethane (×3). The combined organics were dried (Na$_2$SO$_4$) and concentrated to yield (2R,4R)-4-((2S,4S)-1-(tert-butoxycarbonyl)-4-fluoro-N-(2-methoxyethyl)pyrrolidine-2-carboxamido)-1-(cyclopropanecarbonyl)pyrrolidine-2-carboxylic acid (140 mg, 88%) as a white solid.

Part VI—Synthesis of tert-Butyl (2S,4S)-2-(((3R,5R)-1-(cyclopropanecarbonyl)-5-((4-((4-(morpholinomethyl)phenyl)ethynyl)benzyl)carbamoyl)pyrrolidin-3-yl)(2-methoxyethyl) carbamoyl)-4-fluoropyrrolidine-1-carboxylate To a suspension of (2R,4R)-4-((2S,4S)-1-(tert-butoxycarbonyl)-4-fluoro-N-(2-methoxyethyl)pyrrolidine-2-carboxamido)-1-(cyclopropanecarbonyl)pyrrolidine-2-carboxylic acid (140 mg, 0.297 mmol) and (4-((4-(morpholinomethyl)phenyl)ethynyl)phenyl)methanamine dihydrochloride (118 mg, 0.312 mmol) in dichloromethane (3.0 mL) was added triethylamine (145 µL, 1.04 mmol) and T3P (50% solution in ethyl acetate, 265 µL, 0.445 mmol). The mixture was stirred at room temperature for 5 hours then partitioned between dichloromethane and water. The organic layer was dried (Biotage Isolute® Phase Separator) and concentrated to give tert-butyl (2S,4S)-2-(((3R,5R)-1-(cyclopropanecarbonyl)-5-((4-((4-(morpholinomethyl)phenyl) ethynyl)benzyl)carbamoyl)pyrrolidin-3-yl)(2-methoxyethyl)carbamoyl)-4-fluoropyrrolidine-1-carboxylate (143 mg, 63%) which was used directly in the next step without further purification.

Part VII—Synthesis of (2R,4R)-1-(Cyclopropanecarbonyl)-4-((2S,4S)-4-fluoro-N-(2-methoxyethyl)pyrrolidine-2-carboxamido)-N-(4-((4-(morpholinomethyl)phenyl)ethynyl) benzyl)pyrrolidine-2-carboxamide To a solution of tert-butyl (2S,4S)-2-(((3R,5R)-1-(cyclopropanecarbonyl)-5-((4-((4-(morpholinomethyl)phenyl) ethynyl)benzyl)carbamoyl)pyrrolidin-3-yl)(2-methoxyethyl) carbamoyl)-4-fluoropyrrolidine-1-carboxylate (143 mg, 0.188 mmol) in dichloromethane (1.6 mL) at room temperature was added TFA (0.4 mL). The reaction mixture was stirred at room temperature for 2 hours. The mixture was concentrated in vacuo. The residue was dissolved in DMSO (3.0 mL) and purified by reverse phase preparative HPLC (Xselect Phenyl-Hexyl 21.2×150 mm, 10 m, 5-95% MeOH/H$_2$O (0.1% TFA), 20 mL/min, RT), and the residue was lyophilised to yield the title compound (66 mg, 40%, bis TFA salt) as a white solid. LCMS (Method 5, ESI): Rt=2.31 min, [M+H]$^+$=660.5, 98.3% purity.

Example 22—Synthesis of 1-((2R,4R)-4-((2S,4S)-4-fluoropyrrolidine-2-carboxamido)-2-((4-((4-(morpholinomethyl)phenyl)ethynyl)benzamido)methyl)pyrrolidine-1-carbonyl)cyclopropyl hydrogen propylphosphonate

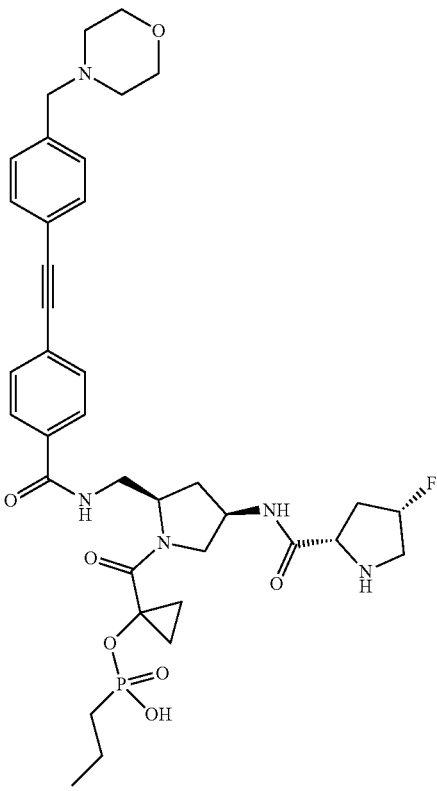 [SMILES: CCCP(=O)(O)OC1(C(=O)N2C[C@H](NC(=O)[C@@H]3C[C@H](F)CN3)C[C@@H]2CNC(=O)c2ccc(C#Cc3ccc(CN4CCOCC4)cc3)cc2)CC1]

Part I—Synthesis of tert-butyl (2S,4S)-4-fluoro-2-(((3R,5R)-1-(1-((hydroxy(propyl)phosphoryl)oxy)cyclopropane-1-carbonyl)-5-((4-((4-(morpholinomethyl)phenyl)ethynyl)benzamido)methyl)pyrrolidin-3-yl)carbamoyl)pyrrolidine-1-carboxylate To a solution of tert-butyl (2S,4S)-4-fluoro-2-(((3R,5R)-5-((4-((4-(morpholinomethyl) phenyl)ethynyl)benzyl)carbamoyl)pyrrolidin-3-yl)carbamoyl)pyrrolidine-1-carboxylate (50 mg, 0.0789 mmol) in dichloromethane (1.0 mL) was added 1-hydroxy-1-cyclopropanecarboxylic acid (9 mg, 0.0868 mmol), triethylamine (16 μL, 0.118 mmol), and T3P (50% solution in ethyl acetate, 70 μL, 0.118 mmol). The mixture was stirred at room temperature for 3 hours then warmed to 35° C. and stirred for a further 18 hours. The mixture was then partitioned between dichloromethane and water, and then the organic layer was collected, dried (Biotage Isolute® Phase Separator), and the solvent removed. The residue was used directly in the next step without further purification.

Part II—Synthesis of 1-((2R,4R)-4-((2S,4S)-4-fluoropyrrolidine-2-carboxamido)-2-((4-((4-(morpholinomethyl)phenyl)ethynyl)benzamido)methyl)pyrrolidine-1-carbonyl)cyclopropyl hydrogen propylphosphonate To a solution of tert-butyl (2S,4S)-4-fluoro-2-(((3R,5R)-1-(1-((hydroxy(propyl)phosphoryl)oxy)cyclopropane-1-carbonyl)-5-((4-((4-(morpholinomethyl)phenyl)ethynyl)benzamido)methyl)pyrrolidin-3-yl)carbamoyl)pyrrolidine-1-carboxylate (0.0789 mmol) in dichloromethane (1.0 mL) at room temperature was added TFA (0.2 mL). The reaction mixture was stirred at room temperature for 2 hours. The mixture was concentrated in vacuo, and the remaining TFA was azeotroped with toluene. The residue was dissolved in DMSO (1.5 mL) and purified by reverse phase preparative HPLC (Sunfire C18 19×150 mm, 10 μm, 5-60% MeCN/H$_2$O (0.1% TFA), 20 mL/min, RT), and the residue was lyophilised to yield the title compound (35 mg, 55%, bis TFA salt) as a white solid. LCMS (Method 5, ESI): Rt=2.25 min, [M+H]$^+$=724, 97.4% purity.

Example 23—Biochemical Assay for Inhibition of LpxC

Exemplary compounds from the above Examples were tested for ability to inhibit LpxC activity using an in vitro substrate deacetylation assay with ADDA™ analysis. Assay procedures and results are described below.

Part I—Procedures for In Vitro Substrate Deacetylation Assay

Dilutions of test compound were pre-incubated with 5 nM *P. aeruginosa* or *E. coli* LpxC for 10 minutes at room temperature in 50 mM NaH$_2$PO$_4$, 500 mM sucrose, 0.2 mg/mL BSA, pH 7.2 and <1% DMSO. Reactions were initiated by the addition of 2× substrate (UDP-3-O—(R-3-hydroxydecanoyl)-N-acetylglucosamine, Carbosynth Ltd, UK, for *P. aeruginosa* LpxC and UDP-3-O—(R-3-hydroxymyristoyl)-N-acetylglucosamine, BOC Sciences, USA, for *E. coli* LpxC), in 50 mM NaH$_2$PO$_4$, 0.5 mg/mL BSA, pH 7.2, to a final concentration of 2.5 μM. Reactions proceeded for 1 hour at room temperature prior to quenching with and equal volume of 2% acetic acid.

For ADDA™ analysis, an aliquot of assay sample was withdrawn from each well of the 384-well plate and applied to a Hypercarb cartridge (Optimize Technologies, USA) under conditions designed to retain analytes of interest. Analytes were eluted using 1:1:2 acetone:acetonitrile:water containing 5 mM ammonium acetate then analysed by triple-quadrupole mass spectrometry. Mass spectrometry was carried out using electrospray ionization in negative ion mode. Daughter ion peaks representing detected substrate (*P. aeruginosa*: parent Q1 mass=775.8 amu, daughter Q3 mass=384.7 amu *E. coli*: parent Q1 mass=833.0 amu, daughter Q3 mass=385.0 amu, collision energy=analyte specific, dwell time=50 ms) were identified using a multiple-reaction monitoring protocol.

Total activity (0% inhibition) was obtained from reactions containing no compound, and 100% inhibition is defined as reactions in the presence of 1 μM CHIR-090 (N-[(1S,2R)-2-hydroxy-1-[(hydroxyamino)carbonyl]propyl]-4-[2-[4-(4-morpholinylmethyl)phenyl]ethynyl]-benzamide). For IC$_{50}$ determinations, peak areas of the substrate and product were compared to compute the proportion of substrate reacted by the LpxC enzyme at each compound concentration. The fractional activity was converted to percentage inhibition and plotted against compound concentration in Activity-Base™ and fit using a four-parameter logistic using non-linear regression to yield the IC$_{50}$ value.

Part II—Results

Experimental results are provided in Table 3 below. For *E. coli*, the symbol "++++" indicates an IC$_{50}$ less than 0.5 μM.

The symbol "+++" indicates an $IC_{50}$ in the range of 0.5 µM to 2.5 µM. The symbol "++" indicates an $IC_{50}$ in the range of greater than 2.5 µM to 10 µM. The symbol "+" indicates an $IC_{50}$ greater than 10 µM.

For *P. aeruginosa*, the symbol "**" indicates an $IC_{50}$ less than 0.05 µM. The symbol "*" indicates an $IC_{50}$ in the range of 0.05 µM to 0.1 µM. The symbol "**" indicates an $IC_{50}$ in the range of greater than 0.1 µM to 1.0 µM. The symbol "*" indicates an $IC_{50}$ greater than 1.0 µM.

TABLE 3

| Title Compound from Example No. | *E. coli* $IC_{50}$ | *P. aeruginosa* $IC_{50}$ |
|---|---|---|
| 5 | ++++ | **** |
| 6 | ++++ | *** |
| 7 | ++++ | *** |
| 8 | ++++ | **** |
| 9A | +++ | *** |
| 9B | +++ | **** |
| 9C | +++ | ** |
| 9D | ++++ | **** |
| 9E | + | ** |
| 9F | +++ | *** |
| 9G | +++ | *** |
| 9H | ++ | ** |
| 9I | ++ | ** |
| 9J | ++ | ** |
| 9K | +++ | *** |
| 9L | +++ | ** |
| 9M | ++ | *** |
| 9N | +++ | *** |
| 9O | ++ | *** |
| 9P | ++ | ** |
| 9Q | ++ | *** |
| 9R | +++ | **** |
| 9S | +++ | *** |
| 9T | ++ | ** |
| 9U | ++ | ** |
| 9V | ++ | ** |
| 9W | + | ** |
| 9X | +++ | **** |
| 9Y | ++++ | *** |
| 9Z | ++++ | **** |
| 9AA | +++ | **** |
| 9AB | +++ | **** |
| 9AC | +++ | **** |
| 9AD | ++++ | **** |
| 9AE | +++ | **** |
| 9AF | +++ | *** |
| 9AG | ++++ | **** |
| 9AH | +++ | **** |
| 9AI | ++++ | **** |
| 9AJ | ++++ | **** |
| 9AM | ++ | ** |
| 9AN | ++++ | *** |
| 9AO | ++ | ** |
| 9AP | +++ | ** |
| 9AQ | ++ | ** |
| 9AR | ++++ | **** |
| 9AS | ++++ | **** |
| 9AT | +++ | **** |
| 9AV | + | * |
| 9AW | ++++ | **** |
| 9AX | ++++ | **** |
| 9BG | + | ** |

Example 24—Broth Microdilution Minimum Inhibition Concentration Assay

Exemplary compounds from the above Examples were tested to determine their minimum inhibitory concentration (MIC) for exemplary strains of *Escherichia* and *Pseudomonas* bacteria using broth microdilution methods. Assay procedures and results are described below.

Part I—Procedures for Broth Microdilution Minimum Inhibition Concentration Assay Broth microdilution assays were conducted according to Clinical and Laboratory Standards Institute guidelines (CLSI, M07-A11: Clinical and Laboratory Standards Institute. Methods for Dilution Antimicrobial Susceptibility Tests for Bacteria that Grow Aerobically; Approved Standard-11th Edition. Wayne, PA: CLSI, 2018). Briefly, a 0.5 McFarland standard suspension was made from bacterial isolates on non-selective, solid media. The inocula were adjusted to give a bacterial concentration of $1 \times 10^6$ CFU/mL. Serial doubling-dilutions of each compound were prepared in cation-adjusted Mueller-Hinton broth (Sigma-Aldrich) in 96-well microdilution plates. A 50 µL aliquot of the inoculum was added to each microdilution plate and, within 15 minutes, incubated at 37° C. in air for 16-20 h. Following incubation, the lowest concentration to completely inhibit all visible growth to the unaided eye was determined as the MIC. The test was controlled by the determination of piperacillin MIC against both *E. coli* ATCC 25922 and *P. aeruginosa* ATCC 27853 and ensuring accordance with the ranges published in CLSI supplementary document M100 (CLSI, M100Ed29: Clinical and Laboratory Standards Institute. Performance Standards for Antimicrobial Susceptibility Testing, 29th Edition. Wayne, PA: CLSI, 2018).

Multiple enterobacteriaceae strains were tested, including *E. coli* ATCC 25922 and *K. pneumoniae* ATCC 43816. WT *E. coli* BW25113 was tested with an isogenic mutant deficient in acrA mediated efflux by clean deletion. WT *P. aeruginosa* PAO1 was tested with an isogenic mutant deficient in MexA mediated efflux by clean deletion.

Part II—Results

Experimental results are provided in Table 4, which provides MIC values for wild-type *E. coli* BW25113 ("*E. coli* WT MIC"), an isogenic mutant deficient in acrA mediated efflux by clean deletion ("*E. coli* KO MIC"), wild-type *P. aeruginosa* PAO1 ("*P. aeruginosa* WT MIC"), and an isogenic mutant deficient in MexA mediated efflux by clean deletion ("*P. aeruginosa* KG MIC").

The symbol "+++" indicates an MIC less than 20 µM. The symbol "++" indicates an MIC in the range of 20 µM to 100 µM. The symbol "+" indicates an MIC greater than 100 µM.

TABLE 4

| Title Compound from Example No. | *E. coli* WT MIC | *E. coli* KO MIC | *P. aeruginosa* WT MIC | *P. aeruginosa* KO MIC |
|---|---|---|---|---|
| 5 | +++ | +++ | + | +++ |
| 6 | +++ | +++ | + | +++ |
| 7 | +++ | +++ | + | +++ |
| 8 | +++ | +++ | ++ | +++ |
| 9A | + | ++ | + | ++ |
| 9B | + | ++ | + | +++ |
| 9C | + | ++ | + | + |
| 9D | ++ | +++ | + | +++ |
| 9E | + | + | + | + |
| 9F | + | ++ | + | ++ |
| 9G | + | ++ | + | ++ |
| 9H | + | + | + | + |
| 9I | + | + | + | + |
| 9J | + | ++ | + | + |
| 9K | + | ++ | + | ++ |
| 9L | + | ++ | + | ++ |
| 9M | + | + | + | + |
| 9N | + | + | + | + |

TABLE 4-continued

| Title Compound from Example No. | E. coli WT MIC | E. coli KO MIC | P. aeruginosa WT MIC | P. aeruginosa KO MIC |
|---|---|---|---|---|
| 9O | + | + | + | + |
| 9P | + | + | + | + |
| 9Q | + | + | + | + |
| 9R | + | +++ | + | +++ |
| 9S | + | + | + | + |
| 9T | + | + | + | + |
| 9U | + | + | + | ++ |
| 9V | + | + | + | + |
| 9W | + | + | + | + |
| 9X | + | ++ | + | +++ |
| 9Y | + | ++ | + | ++ |
| 9Z | + | ++ | + | ++ |
| 9AA | + | + | + | ++ |
| 9AB | + | ++ | + | ++ |
| 9AC | + | + | + | + |
| 9AD | + | ++ | + | +++ |
| 9AE | + | + | + | ++ |
| 9AF | + | + | + | + |
| 9AG | ++ | +++ | + | +++ |
| 9AH | + | ++ | + | +++ |
| 9AI | + | ++ | + | +++ |
| 9AJ | ++ | +++ | + | +++ |
| 9AM | + | + | + | + |
| 9AN | + | + | + | ++ |
| 9AO | + | + | + | + |
| 9AP | + | + | + | + |
| 9AQ | + | + | + | + |
| 9AR | + | ++ | + | +++ |
| 9AS | +++ | +++ | + | +++ |
| 9AT | + | +++ | + | +++ |
| 9AV | + | + | + | + |
| 9AW | + | +++ | + | +++ |
| 9AX | +++ | +++ | + | +++ |
| 9BG | + | + | + | + |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A compound represented by Formula I:

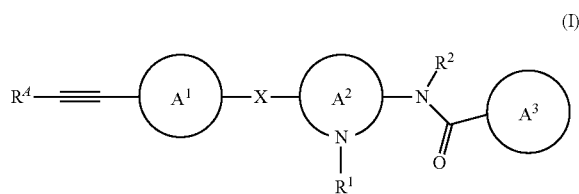

(I)

or a pharmaceutically acceptable salt thereof, wherein:
$A^1$ is 6-10 membered arylene or 5-10 membered heterocyclylene;

$A^2$ is a 4-10 membered aza heterocyelylene 4-6 membered saturated aza-heterocyclylene;

$A^3$ is one of the following:
a 4-10 membered aza-heterocyclyl optionally substituted with 1, 2, or 3 occurrences of $R^7$; or
a 3-10 membered cycloalkyl substituted by (i) —N($R^3$)($R^4$) and (ii) 0, 1, 2, or 3 occurrences of $R^7$;

X is —C(O)N($R^3$)—($C_{0-6}$ alkylene)-ψ or —($C_{0-6}$ alkylene)-N($R^3$)C(O)-ψ; wherein ψ is a bond to $A^2$;

$R^4$ is one of the following:
3-6 membered carbocyclyl substituted with (i) 0, 1, or 2 occurrences of $R^6$ and (ii) 1 occurrence of $Y_1$; 3-6 membered heterocyclyl substituted with (i) 0, 1, or 2 occurrences of $R^6$ and (ii) 1 occurrence of $Y^1$; or

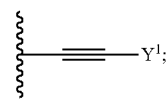

$Y^1$ is —($C_{0-6}$ alkylene)-(3-10 membered heterocyclyl), —($C_{0-6}$ alkylene)-(3-10 membered carbocyclyl), —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, —($C_{1-6}$ alkylene)-N($R^3$)($R^4$), 3-7 membered heteroalkyl, —O—($C_{1-6}$ alkylene)-$CO_2R^3$, or hydrogen;

$R^1$ is —C(O)—$R^5$, —$CO_2$—$R^5$, —S(O)$_2$—$R^5$, —C(O)N($R^3$)($R^4$), $R^5$, or hydrogen;

$R^2$ is hydrogen, $C_{1-6}$ alkyl, —($C_{0-6}$ alkylene)-($C_{3-6}$ cycloalkyl), —($C_{1-6}$ alkylene)-($C_{1-6}$ alkoxyl), or —($C_{1-6}$ alkylene)-$CO_2R^3$;

$R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl); or an occurrence of $R^3$ and $R^4$ attached to the same nitrogen atom are taken together with the nitrogen atom to which they are attached to form a heterocyclic ring;

$R^5$ is —$C_{1-6}$ alkyl, —$C_{1-6}$ haloalkyl, —$C_{1-6}$ hydroxyalkyl, —($C_{0-6}$ alkylene)-(3-7 membered heterocyclyl), —($C_{0-6}$ alkylene)-(3-7 membered saturated carbocyclyl), —($C_{1-6}$ alkylene)-N($R^3$)($R^4$), —($C_{1-6}$ alkylene)-($C_{1-6}$ alkoxyl), —($C_{1-6}$ alkylene)-$CO_2R^3$, —($C_{1-6}$ alkylene)-$SO_2R^3$, or —($C_{1-6}$ alkylene)-O—P(O)(OH)($R^3$);

$R^6$ represents independently for each occurrence halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or cyano; and $R^7$ represents independently for each occurrence halogen, hydroxyl, cyano, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), —($C_{0-6}$ alkylene)-N($R^3$)($R^4$), —($C_{0-6}$ alkylene)-($C_{3-7}$ cycloalkyl), or —($C_{0-6}$ alkylene)-(4-10 membered heterocycloalkyl).

2. The compound of claim 1, wherein $A^1$ is phenylene.

3. The compound of claim 1, wherein $A^2$ is pyrrolidinylene.

4. The compound of claim 1, wherein $A^3$ is a 4-6 membered saturated aza-heterocyclyl optionally substituted with 1, 2, or 3 occurrences of $R^7$.

5. The compound of claim 1, wherein the compound is represented by Formula I-A:

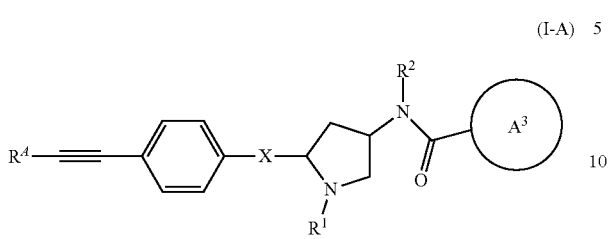

(I-A)

or a pharmaceutically acceptable salt thereof, wherein:
$A^3$ is 4-7 membered aza-heterocyclyl optionally substituted with 1, 2, or 3 occurrences of $R^7$;
X is —C(O)N($R^3$)—($C_{1-3}$ alkylene)-ψ or —($C_{1-3}$ alkylene)-N($R^3$)C(O)-ψ; wherein ψ is a bond to the pyrrolidinyl group;
$R^4$ is one of the following:
phenyl or 5-6 membered heteroaryl substituted with (i) 0, 1, or 2 occurrences of $R^6$ and (ii) 1 occurrence of $Y^1$; or

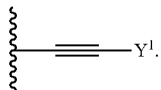

$Y^1$ is —($C_{0-6}$ alkylene)-(3-10 membered heterocyclyl), —($C_{0-6}$ alkylene)-(3-10 membered carbocyclyl), —($C_{0-6}$ alkylene)-$CO_2R^3$, —($C_{0-6}$ alkylene)-C(O)N($R^3$)($R^4$), —($C_{0-6}$ alkylene)-N($R^3$)C(O)$R^4$, —($C_{0-6}$ alkylene)-N($R^3$)C(O)N($R^3$)($R^4$), —($C_{0-6}$ alkylene)-N($R^3$)S(O)$_2R^4$, —($C_{0-6}$ alkylene)-S(O)$_2$N($R^3$)$R^4$, $C_{1-6}$ hydroxyalkyl, or —($C_{1-6}$ alkylene)-N($R^3$)($R^4$);
$R^1$ is —C(O)—$R^5$, —$CO_2$—$R^5$, or —S(O)$_2$—$R^5$;
$R^2$ is hydrogen, $C_{1-6}$ alkyl, or —($C_{0-6}$ alkylene)-($C_{3-6}$ cycloalkyl);
$R^3$ and $R^4$ each represent independently for each occurrence hydrogen, $C_{1-6}$ alkyl, $C_{1-6}$ haloalkyl, or —($C_{0-6}$ alkylene)-($C_{3-6}$ cycloalkyl); or an occurrence of $R^3$ and $R^4$ attached to the same nitrogen atom are taken together with the nitrogen atom to which they are attached to form a heterocyclic ring;
$R^5$ is —$C_{1-6}$ alkyl, —$C_{1-6}$ haloalkyl, —($C_{0-6}$ alkylene)-(3-7 membered heterocyclyl), —($C_{0-6}$ alkylene)-(3-7 membered saturated carbocyclyl), or —($C_{1-6}$ alkylene)-N($R^3$)($R^4$);
$R^6$ represents independently for each occurrence halogen, hydroxyl, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or cyano; and
$R^7$ represents independently for each occurrence halogen, hydroxyl, cyano, $C_{1-6}$ alkyl, $C_{1-6}$ haloalkyl, $C_{1-6}$ hydroxyalkyl, $C_{1-6}$ alkoxyl, —($C_{1-6}$ alkylene)-($C_{1-6}$ alkoxyl), or —($C_{0-6}$ alkylene)-N($R^3$)($R^4$).

6. The compound of claim 5, wherein the compound is represented by Formula I-A.

7. The compound of claim 5, wherein $A^3$ is pyrrolidinyl optionally substituted with 1, 2, or 3 occurrences of $R^7$.

8. The compound of claim 5, wherein $A^3$ is

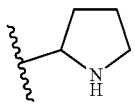

optionally substituted with 1, 2, or 3 occurrences of $R^7$.

9. The compound of claim 5, wherein X is —C(O)N($R^3$)—($C_{1-3}$ alkylene)-ψ.

10. The compound of claim 5, wherein $R^1$ is —C(O)—$R^5$.

11. The compound of claim 5, wherein $R^4$ is phenyl substituted with 1 occurrence of $Y^1$.

12. The compound of claim 5, wherein $R^4$ is

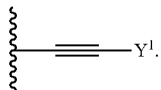

13. The compound of claim 5, wherein $Y^1$ is —($C_{1-3}$ alkylene)-(morpholinyl optionally substituted with 1 or 2 substituents independently selected from the group consisting of halogen, hydroxyl, $C_{1-6}$ alkyl, $C_{1-6}$ haloalkyl, $C_{1-6}$ hydroxyalkyl, and $C_{1-6}$ alkoxyl).

14. The compound of claim 5, wherein $Y^1$ is —($C_{0-6}$ alkylene)-(3-6 membered saturated carbocyclyl).

15. The compound of claim 5, wherein $Y^1$ is cyclopropyl.

16. A pharmaceutical composition comprising a compound of claim 1 and a pharmaceutically acceptable carrier.

17. A method of treating a bacterial infection in a patient, comprising administering to a patient in need thereof a therapeutically effective amount of a compound of claim 1 to treat the bacterial infection.

18. The method of claim 17, wherein the bacterial infection is an infection by a *Staphylococcus, Streptococcus, Enterococcus, Pseudomonas, Escherichia, Fusobacterium, Klebsiella, Haemophilus, Bordetella, Serratia, Proteus, Enterobacter, Campylobacter, Citrobacter, Vibrio, Morganella, Salmonella, Shigella, Acinetobacter, Legionella, Bacteroides, Neisseria, Moraxella, Chlamydia, Helicobacter, Prevotella, Porphyromonas, Veillonella, Bilophila, Centipeda, Leptotrichia, Selenomonas,* or *Sutterella* bacterium, or a combination thereof.

19. A method of inducing death of a bacterial cell, comprising exposing a bacterial cell to an effective amount of a compound of claim 1 to induce death of the bacterial cell.

20. A method of inhibiting the activity of LpxC, comprising exposing an LpxC to an effective amount of a compound of claim 1 to inhibit the activity of the LpxC.

21. A compound in any one of Tables 1, 2, or 3-A, or a pharmaceutically acceptable salt thereof:
TABLE 1
Compound No.  Chemical Structure
I-1
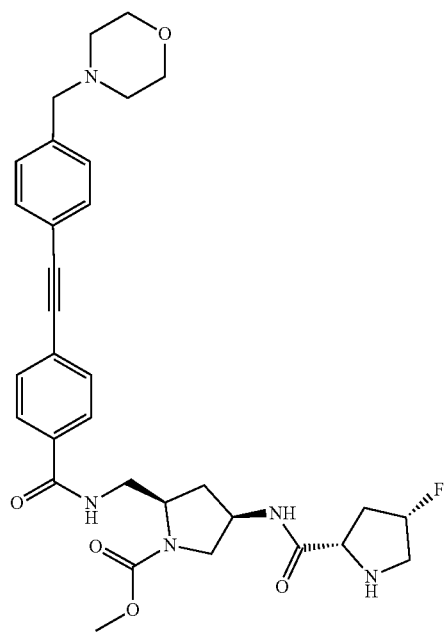 [SMILES: COC(=O)N1C[C@H](NC(=O)[C@@H]2C[C@H](F)CN2)C[C@@H]1CNC(=O)c1ccc(C#Cc2ccc(CN3CCOCC3)cc2)cc1]
I-2
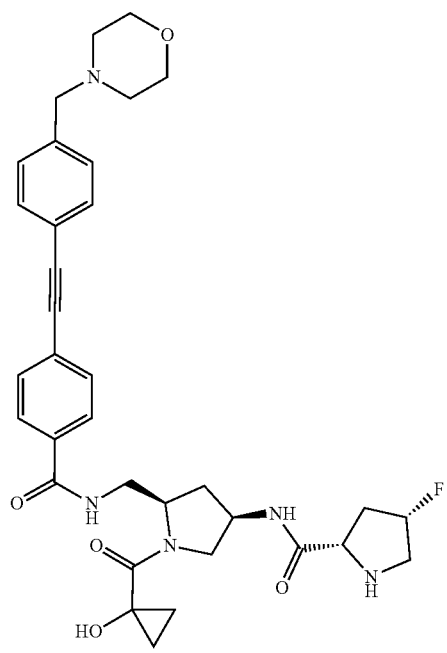 [SMILES: O=C(NC[C@H]1C[C@@H](NC(=O)[C@@H]2C[C@H](F)CN2)CN1C(=O)C1(O)CC1)c1ccc(C#Cc2ccc(CN3CCOCC3)cc2)cc1]

TABLE 1-continued
| Compound No. | Chemical Structure |
| --- | --- |
| I-3 | 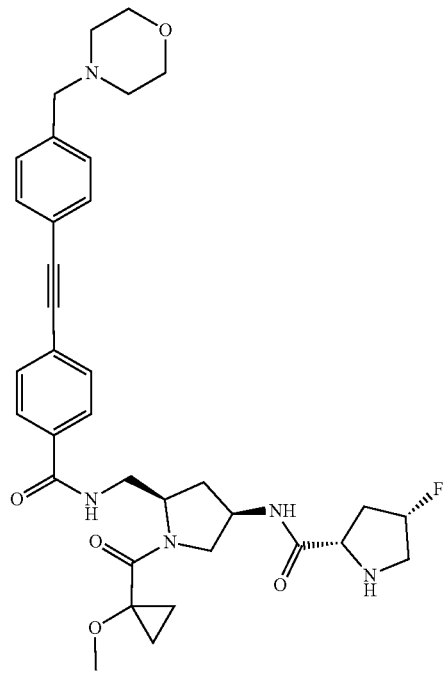 [SMILES: COC1(C(=O)N2C[C@H](NC(=O)[C@@H]3C[C@H](F)CN3)C[C@@H]2CNC(=O)c2ccc(C#Cc3ccc(CN4CCOCC4)cc3)cc2)CC1] |
| I-4 | 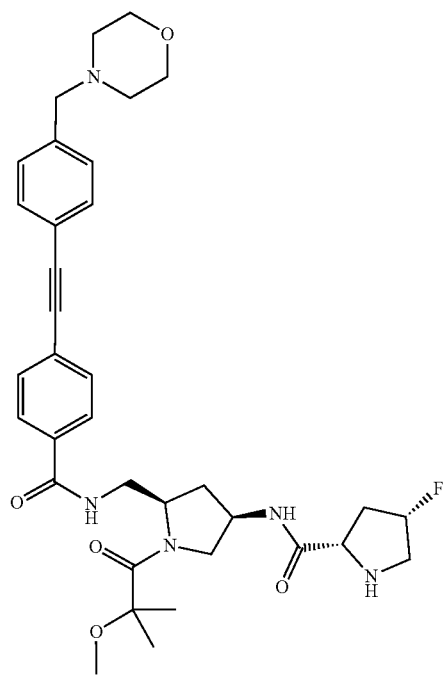 [SMILES: COC(C)(C)C(=O)N1C[C@H](NC(=O)[C@@H]2C[C@H](F)CN2)C[C@@H]1CNC(=O)c1ccc(C#Cc2ccc(CN3CCOCC3)cc2)cc1] |

TABLE 1-continued
| Compound No. | Chemical Structure |
|---|---|
| I-5 | 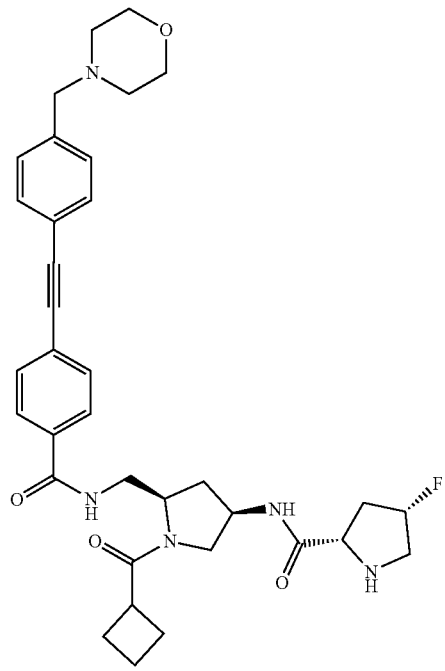 [SMILES: O=C(NC[C@H]1C[C@@H](NC(=O)[C@@H]2C[C@H](F)CN2)CN1C(=O)C1CCC1)c1ccc(C#Cc2ccc(CN3CCOCC3)cc2)cc1] |
| I-6 | 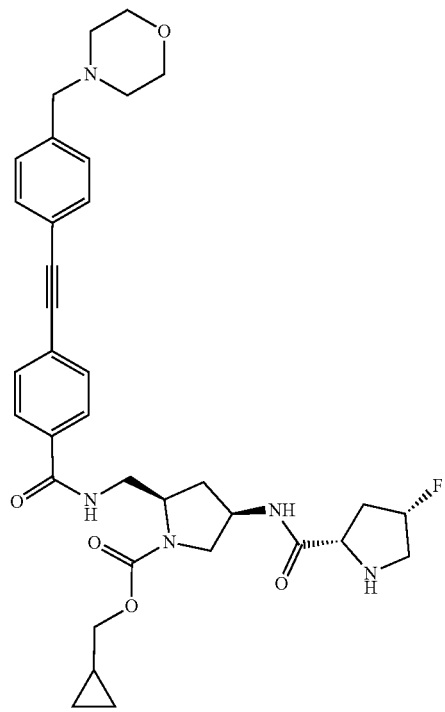 [SMILES: O=C(NC[C@H]1C[C@@H](NC(=O)[C@@H]2C[C@H](F)CN2)CN1C(=O)OCC1CC1)c1ccc(C#Cc2ccc(CN3CCOCC3)cc2)cc1] |

TABLE 1-continued
| Compound No. | Chemical Structure |
|---|---|
| I-7 | 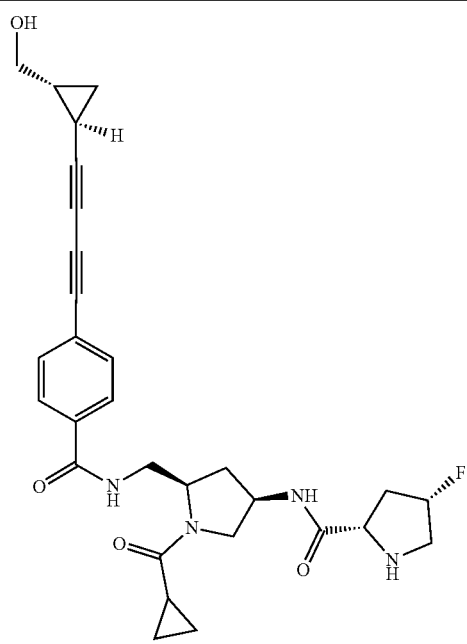 |
| I-8 | 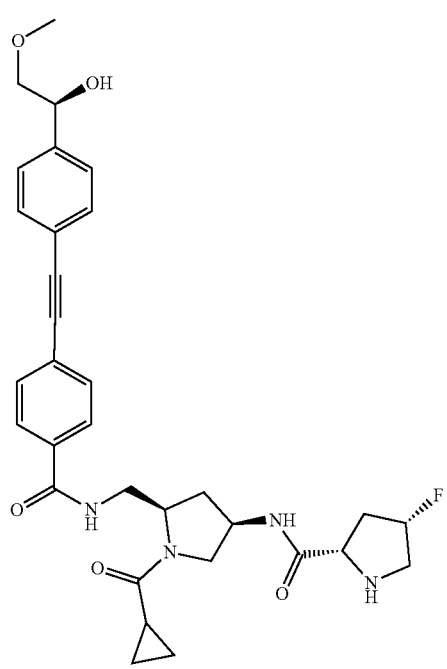 [SMILES: COC[C@@H](O)c1ccc(C#Cc2ccc(C(=O)NC[C@H]3C[C@@H](NC(=O)[C@@H]4C[C@H](F)CN4)CN3C(=O)C3CC3)cc2)cc1] |

TABLE 1-continued
| Compound No. | Chemical Structure |
|---|---|
| I-9 | 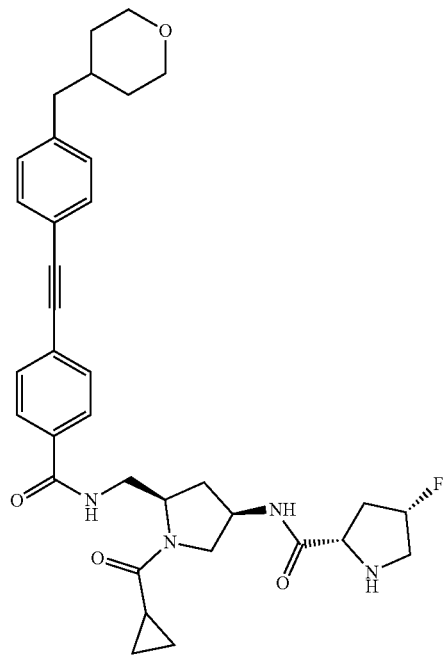 [SMILES: O=C(NC[C@H]1C[C@@H](NC(=O)[C@@H]2C[C@H](F)CN2)CN1C(=O)C1CC1)c1ccc(C#Cc2ccc(CC3CCOCC3)cc2)cc1] |
| I-10 | 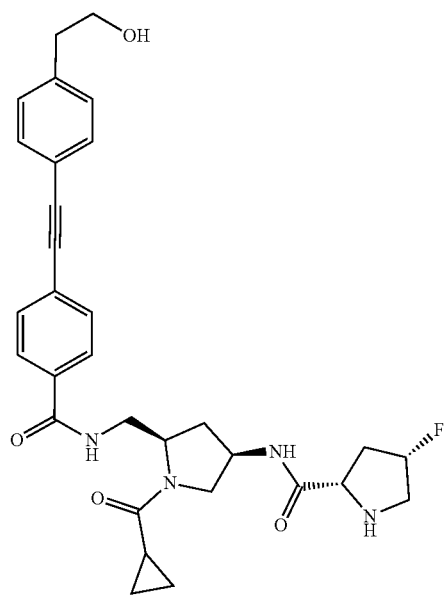 [SMILES: O=C(NC[C@H]1C[C@@H](NC(=O)[C@@H]2C[C@H](F)CN2)CN1C(=O)C1CC1)c1ccc(C#Cc2ccc(CCO)cc2)cc1] |

213
214
TABLE 1-continued
Compound No. Chemical Structure
I-11
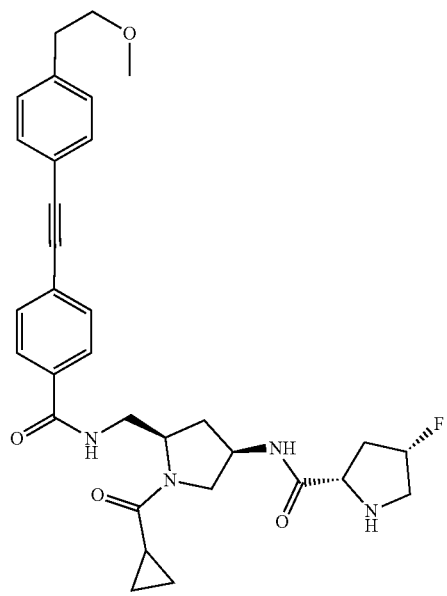 [SMILES: COCCc1ccc(C#Cc2ccc(C(=O)NC[C@H]3C[C@@H](NC(=O)[C@@H]4C[C@H](F)CN4)CN3C(=O)C3CC3)cc2)cc1]
I-12
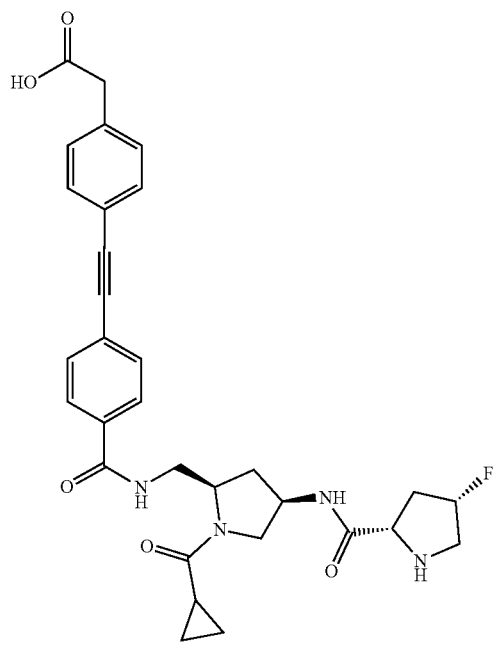 [SMILES: O=C(O)Cc1ccc(C#Cc2ccc(C(=O)NC[C@H]3C[C@@H](NC(=O)[C@@H]4C[C@H](F)CN4)CN3C(=O)C3CC3)cc2)cc1]

TABLE 1-continued
| Compound No. | Chemical Structure |
| --- | --- |
| I-13 | 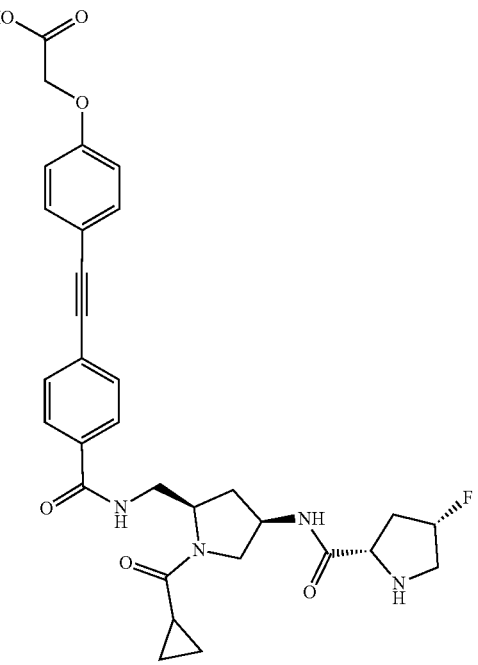 |
| I-14 | 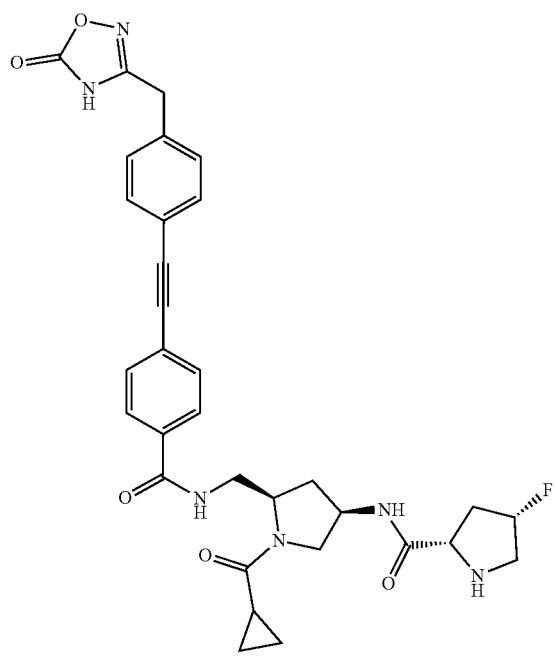 [SMILES: O=C(NC[C@H]1C[C@@H](NC(=O)[C@@H]2C[C@H](F)CN2)CN1C(=O)C1CC1)c1ccc(C#Cc2ccc(Cc3noc(=O)[nH]3)cc2)cc1] |

TABLE 1-continued
| Compound No. | Chemical Structure |
|---|---|
| I-15 | 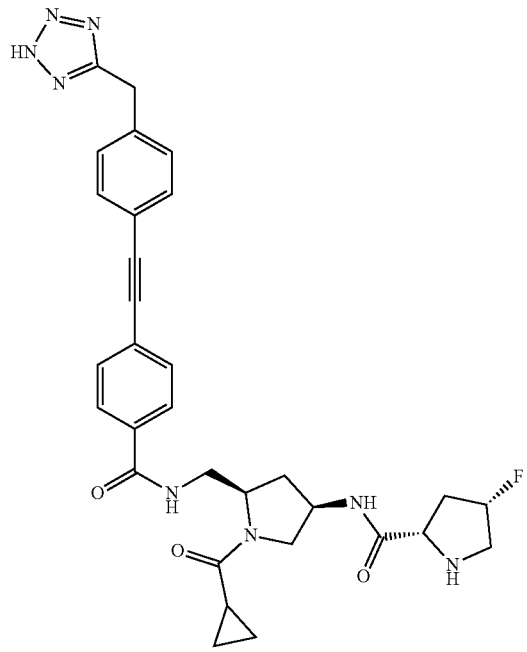 [SMILES: O=C(NC[C@H]1C[C@@H](NC(=O)[C@@H]2C[C@H](F)CN2)CN1C(=O)C1CC1)c1ccc(C#Cc2ccc(Cc3nn[nH]n3)cc2)cc1] |
| I-16 | 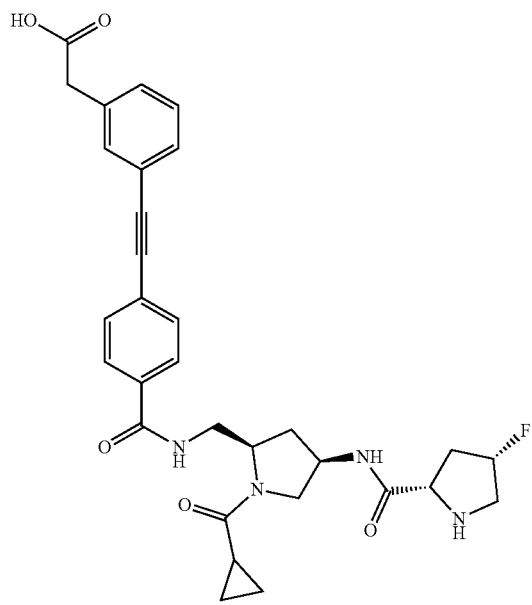 [SMILES: O=C(O)Cc1cccc(C#Cc2ccc(C(=O)NC[C@H]3C[C@@H](NC(=O)[C@@H]4C[C@H](F)CN4)CN3C(=O)C3CC3)cc2)c1] |

TABLE 1-continued
| Compound No. | Chemical Structure |
|---|---|
| I-17 | 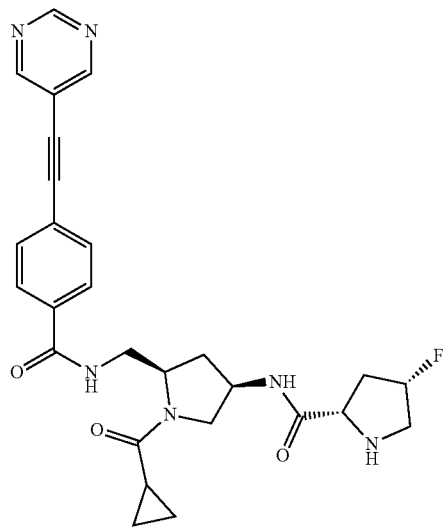 [SMILES: O=C(NC[C@H]1C[C@@H](NC(=O)[C@@H]2C[C@H](F)CN2)CN1C(=O)C1CC1)c1ccc(C#Cc2cncnc2)cc1] |
| I-18 | 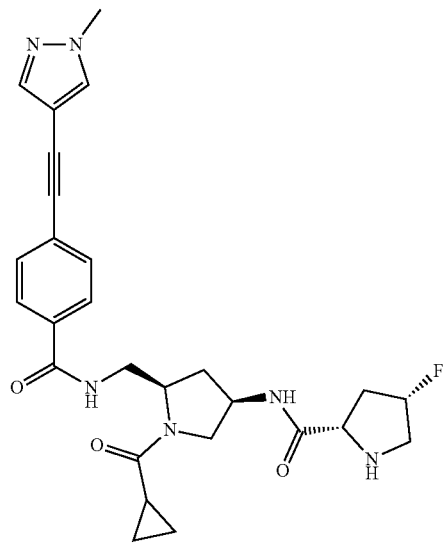 [SMILES: Cn1cc(C#Cc2ccc(C(=O)NC[C@H]3C[C@@H](NC(=O)[C@@H]4C[C@H](F)CN4)CN3C(=O)C3CC3)cc2)cn1] |

TABLE 1-continued
| Compound No. | Chemical Structure |
|---|---|
| I-19 | 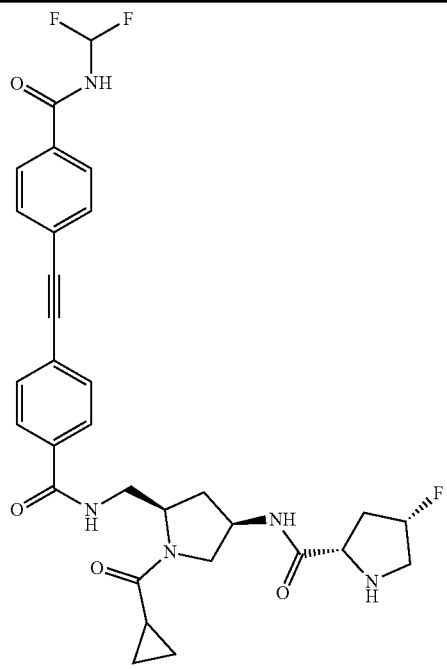 |
| I-20 | 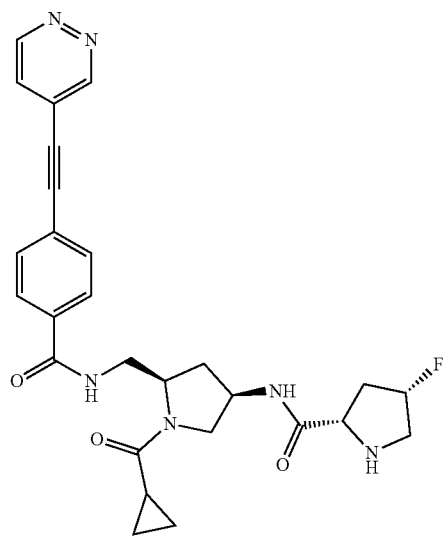 [SMILES: O=C(NC[C@H]1C[C@@H](NC(=O)[C@@H]2C[C@H](F)CN2)CN1C(=O)C1CC1)c1ccc(C#Cc2ccnnc2)cc1] |

TABLE 1-continued
| Compound No. | Chemical Structure |
|---|---|
| I-21 | 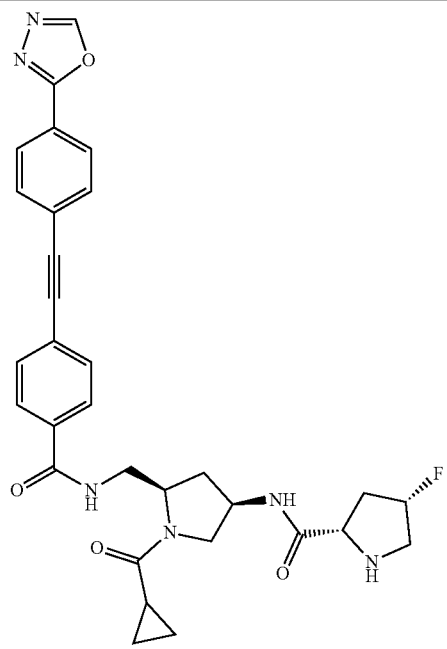 [SMILES: O=C(NC[C@H]1C[C@@H](NC(=O)[C@@H]2C[C@H](F)CN2)CN1C(=O)C1CC1)c1ccc(C#Cc2ccc(-c3nnco3)cc2)cc1] |
| I-22 | 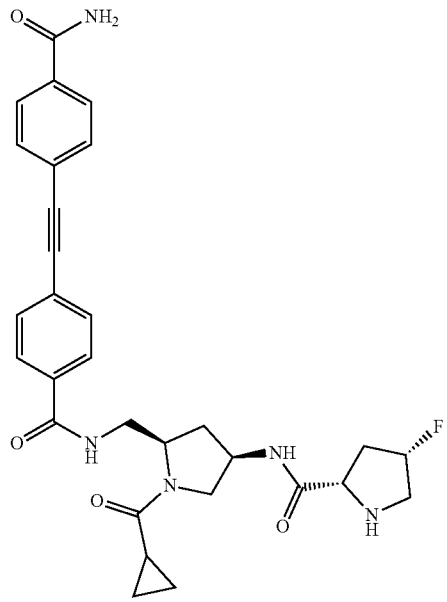 [SMILES: NC(=O)c1ccc(C#Cc2ccc(C(=O)NC[C@H]3C[C@@H](NC(=O)[C@@H]4C[C@H](F)CN4)CN3C(=O)C3CC3)cc2)cc1] |

TABLE 1-continued
| Compound No. | Chemical Structure |
|---|---|
| I-23 | 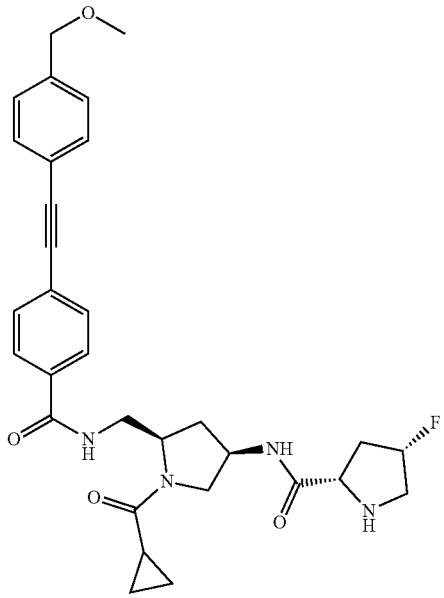 [SMILES: COCc1ccc(C#Cc2ccc(C(=O)NC[C@H]3C[C@@H](NC(=O)[C@@H]4C[C@H](F)CN4)CN3C(=O)C3CC3)cc2)cc1] |
| I-24 | 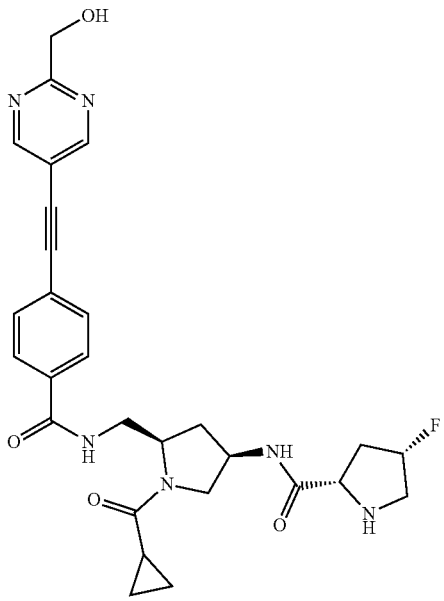 [SMILES: O=C(NC[C@H]1C[C@@H](NC(=O)[C@@H]2C[C@H](F)CN2)CN1C(=O)C1CC1)c1ccc(C#Cc2cnc(CO)nc2)cc1] |

TABLE 1-continued
| Compound No. | Chemical Structure |
|---|---|
| I-25 | 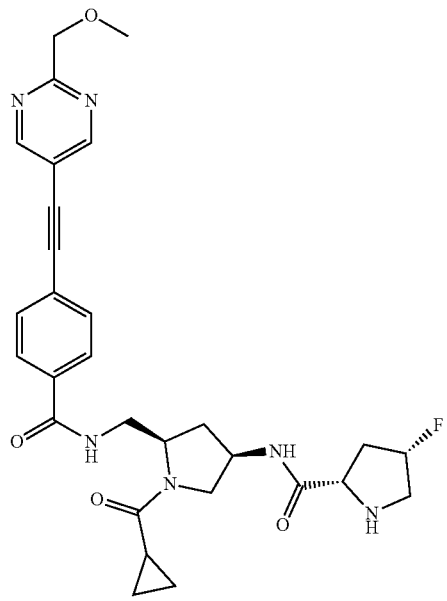 [SMILES: COCc1ncc(C#Cc2ccc(C(=O)NC[C@H]3C[C@@H](NC(=O)[C@@H]4C[C@H](F)CN4)CN3C(=O)C3CC3)cc2)cn1] |
| I-26 | 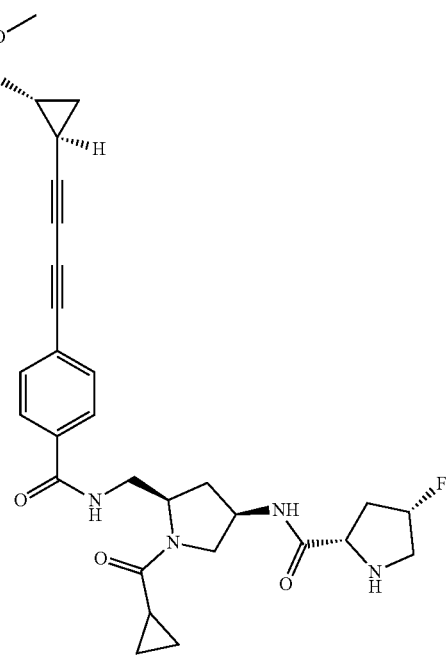 |

TABLE 1-continued
| Compound No. | Chemical Structure |
|---|---|
| I-27 | 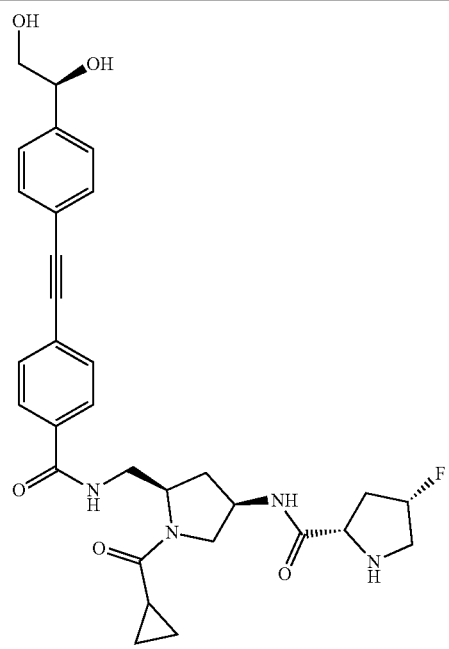 [SMILES: O=C(NC[C@H]1C[C@@H](NC(=O)[C@@H]2C[C@H](F)CN2)CN1C(=O)C1CC1)c1ccc(C#Cc2ccc([C@H](O)CO)cc2)cc1] |
| I-28 | 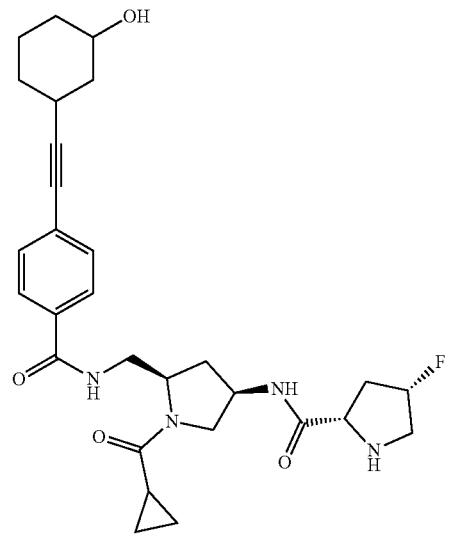 [SMILES: O=C(NC[C@H]1C[C@@H](NC(=O)[C@@H]2C[C@H](F)CN2)CN1C(=O)C1CC1)c1ccc(C#CC2CCCC(O)C2)cc1] |

TABLE 1-continued
| Compound No. | Chemical Structure |
|---|---|
| I-29 | 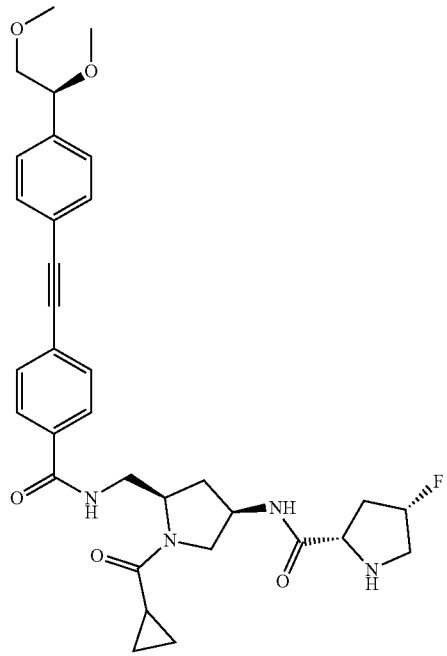 [SMILES: COC[C@@H](OC)c1ccc(C#Cc2ccc(C(=O)NC[C@H]3C[C@@H](NC(=O)[C@@H]4C[C@H](F)CN4)CN3C(=O)C3CC3)cc2)cc1] |
| I-30 | 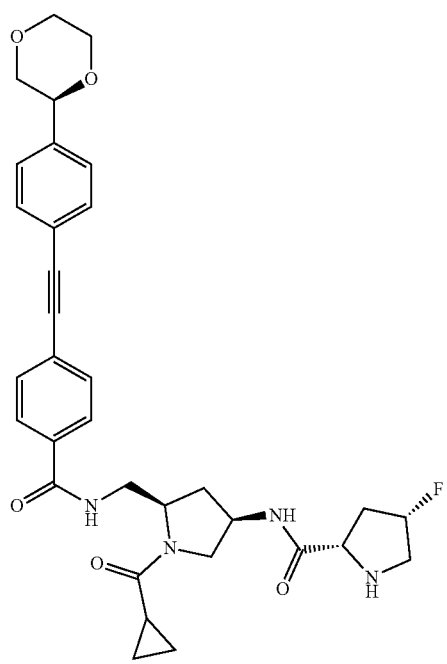 |

TABLE 1-continued
| Compound No. | Chemical Structure |
|---|---|
| I-31 | 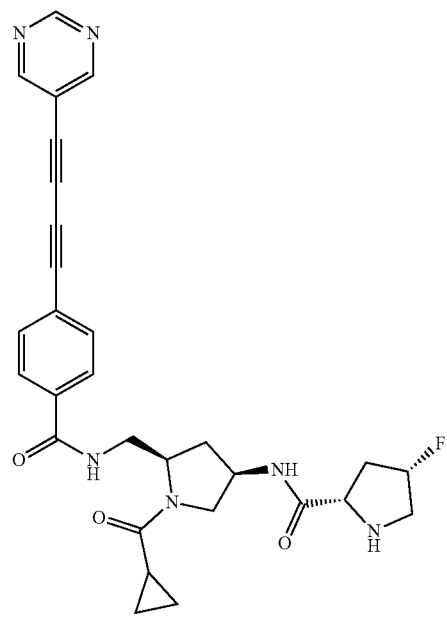 [SMILES: O=C(NC[C@H]1C[C@@H](NC(=O)[C@@H]2C[C@H](F)CN2)CN1C(=O)C1CC1)c1ccc(C#CC#Cc2cncnc2)cc1] |
| I-32 | 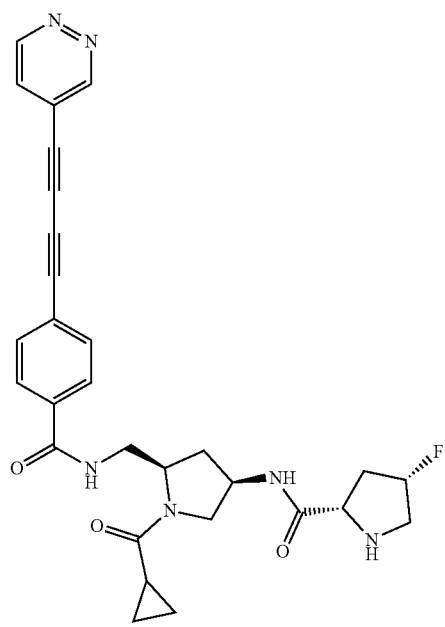 [SMILES: O=C(NC[C@H]1C[C@@H](NC(=O)[C@@H]2C[C@H](F)CN2)CN1C(=O)C1CC1)c1ccc(C#CC#Cc2ccnnc2)cc1] |

TABLE 1-continued
| Compound No. | Chemical Structure |
| --- | --- |
| I-33 | 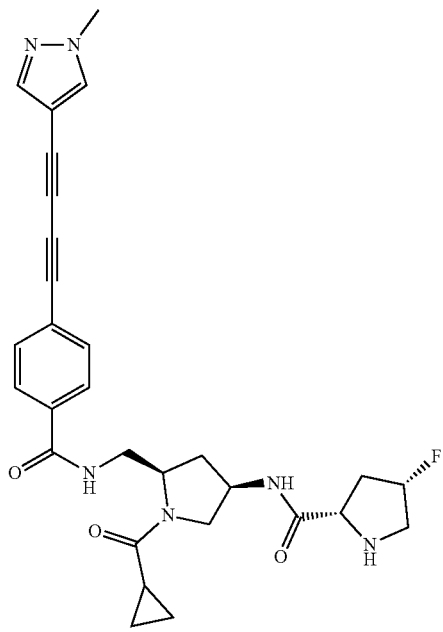 [SMILES: Cn1cc(C#CC#Cc2ccc(C(=O)NC[C@H]3C[C@@H](NC(=O)[C@@H]4C[C@H](F)CN4)CN3C(=O)C3CC3)cc2)cn1] |
| I-34 | 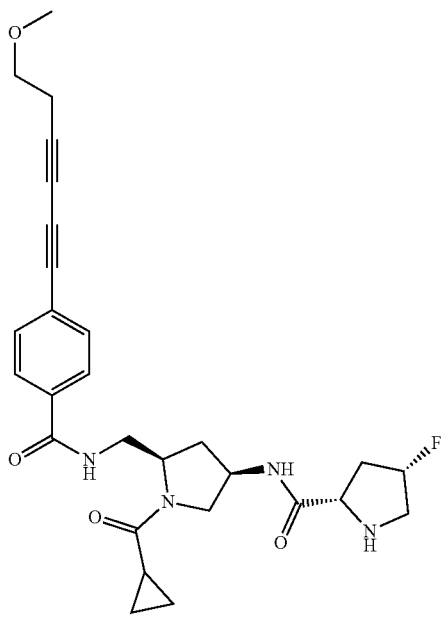 [SMILES: COCCC#CC#Cc1ccc(C(=O)NC[C@H]2C[C@@H](NC(=O)[C@@H]3C[C@H](F)CN3)CN2C(=O)C2CC2)cc1] |

TABLE 1-continued
| Compound No. | Chemical Structure |
| --- | --- |
| I-35 | 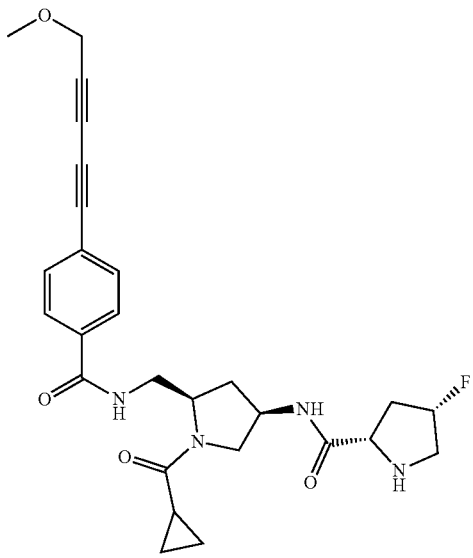 [SMILES: COCC#CC#Cc1ccc(C(=O)NC[C@H]2C[C@@H](NC(=O)[C@@H]3C[C@H](F)CN3)CN2C(=O)C2CC2)cc1] |
| I-36 | 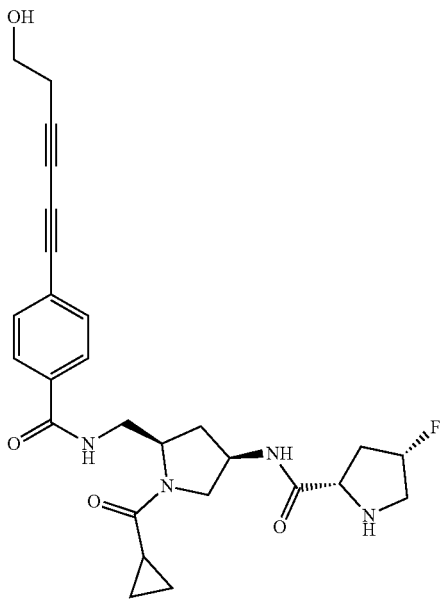 [SMILES: O=C(NC[C@H]1C[C@@H](NC(=O)[C@@H]2C[C@H](F)CN2)CN1C(=O)C1CC1)c1ccc(C#CC#CCCO)cc1] |

TABLE 1-continued
| Compound No. | Chemical Structure |
| --- | --- |
| I-37 | 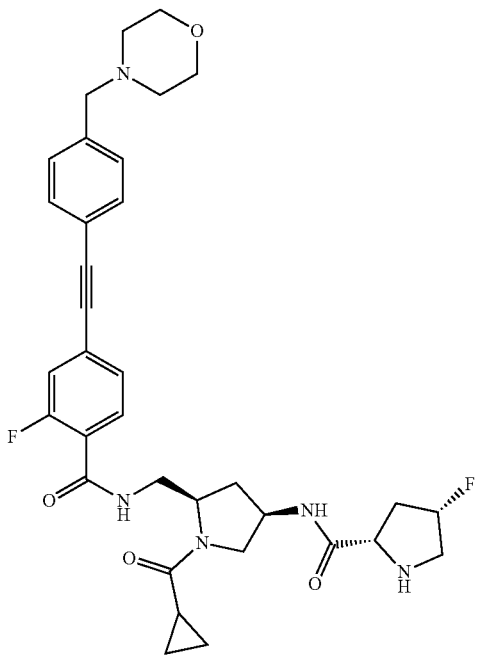 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)cc1F] |
| I-38 | 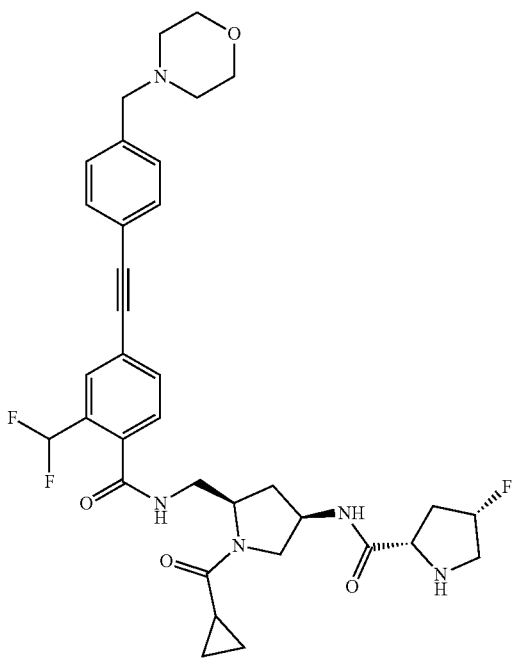 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)cc1C(F)F] |

TABLE 1-continued
Compound No. Chemical Structure
I-39
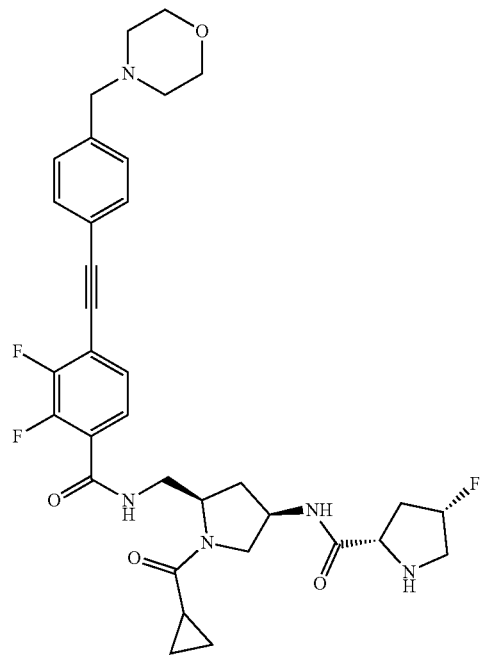 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)c(F)c1F]
I-40
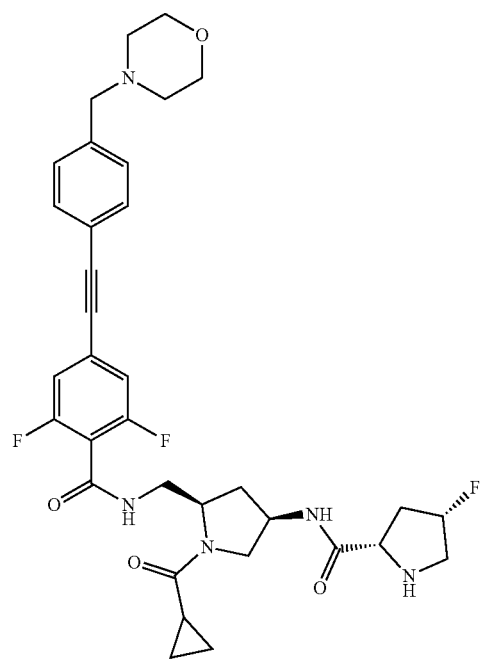 [SMILES: O=C(NC[C@H]1C[C@@H](NC(=O)[C@@H]2C[C@H](F)CN2)CN1C(=O)C1CC1)c1c(F)cc(C#Cc2ccc(CN3CCOCC3)cc2)cc1F]

TABLE 1-continued
| Compound No. | Chemical Structure |
| --- | --- |
| I-41 | 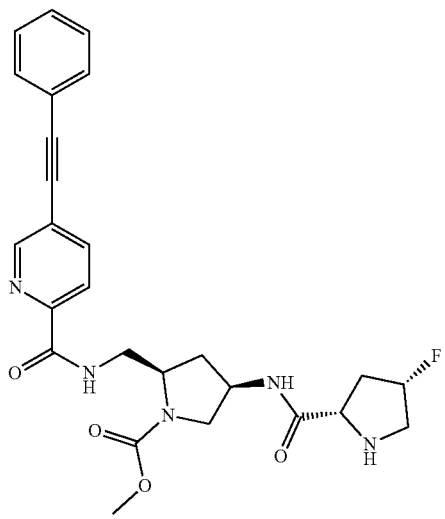 [SMILES: COC(=O)N1C[C@H](NC(=O)[C@@H]2C[C@H](F)CN2)C[C@@H]1CNC(=O)c1ccc(C#Cc2ccccc2)cn1] |
| I-42 | 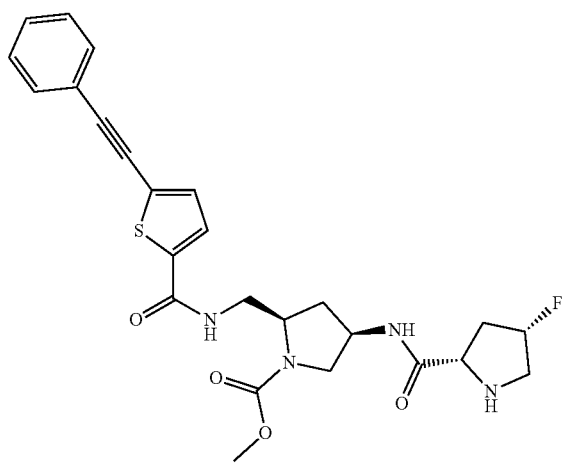 [SMILES: COC(=O)N1C[C@H](NC(=O)[C@@H]2C[C@H](F)CN2)C[C@@H]1CNC(=O)c1ccc(C#Cc2ccccc2)s1] |
| I-43 | 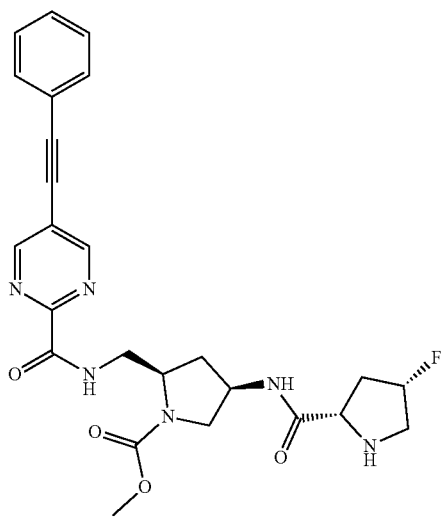 [SMILES: COC(=O)N1C[C@H](NC(=O)[C@@H]2C[C@H](F)CN2)C[C@@H]1CNC(=O)c1ncc(C#Cc2ccccc2)cn1] |

TABLE 1-continued
| Compound No. | Chemical Structure |
|---|---|
| I-44 | 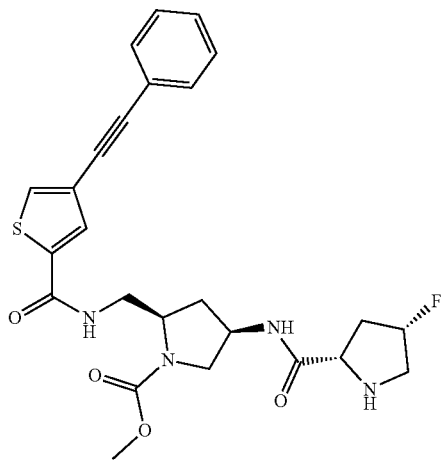 |
| I-45 | 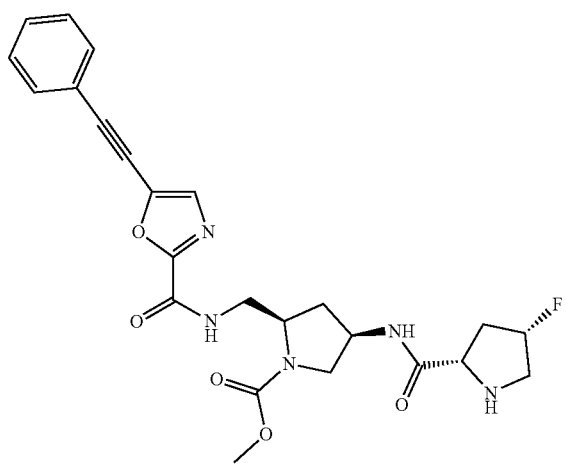 [SMILES: COC(=O)N1C[C@H](NC(=O)[C@@H]2C[C@H](F)CN2)C[C@@H]1CNC(=O)c1ncc(C#Cc2ccccc2)o1] |
| I-46 | 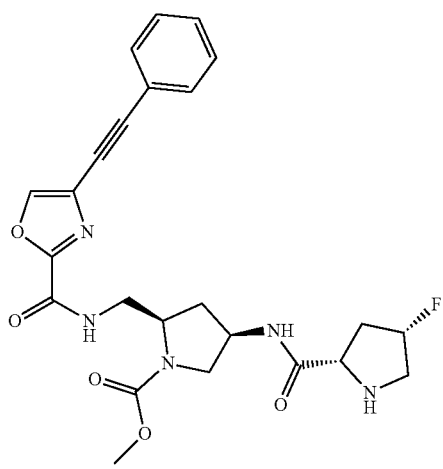 [SMILES: COC(=O)N1C[C@H](NC(=O)[C@@H]2C[C@H](F)CN2)C[C@@H]1CNC(=O)c1nc(C#Cc2ccccc2)co1] |

TABLE 1-continued
| Compound No. | Chemical Structure |
|---|---|
| I-47 | 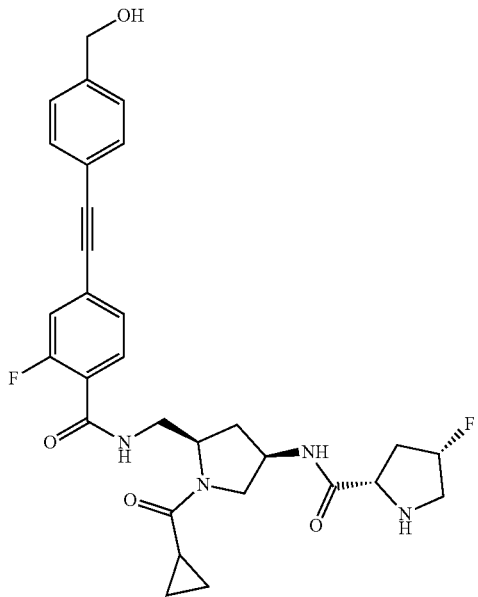 [SMILES: O=C(NC[C@H]1C[C@@H](NC(=O)[C@@H]2C[C@H](F)CN2)CN1C(=O)C1CC1)c1ccc(C#Cc2ccc(CO)cc2)cc1F] |
| I-48 | 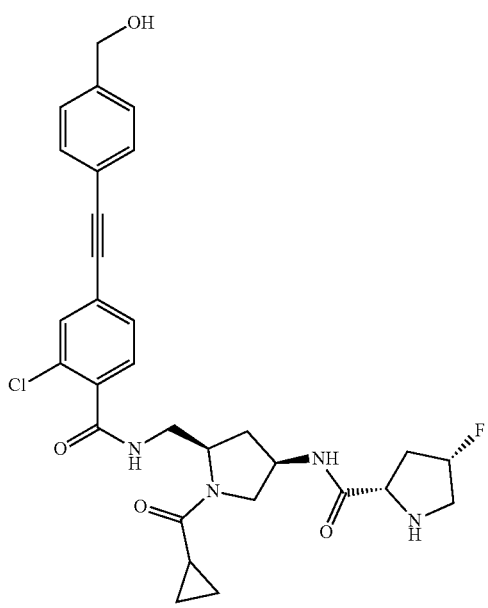 [SMILES: O=C(NC[C@H]1C[C@@H](NC(=O)[C@@H]2C[C@H](F)CN2)CN1C(=O)C1CC1)c1ccc(C#Cc2ccc(CO)cc2)cc1Cl] |

TABLE 1-continued
| Compound No. | Chemical Structure |
|---|---|
| I-49 | 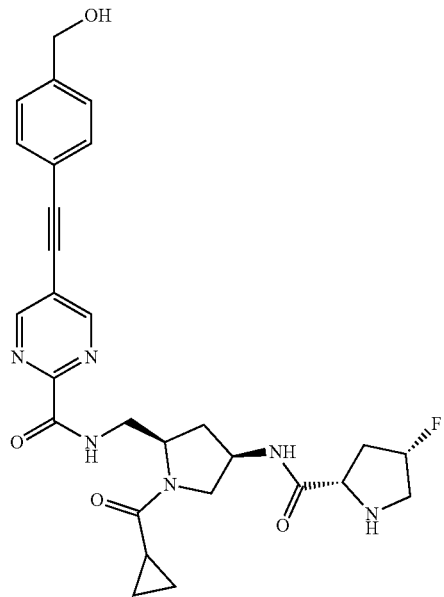 [SMILES: O=C(NC[C@H]1C[C@@H](NC(=O)[C@@H]2C[C@H](F)CN2)CN1C(=O)C1CC1)c1ncc(C#Cc2ccc(CO)cc2)cn1] |
| I-50 | 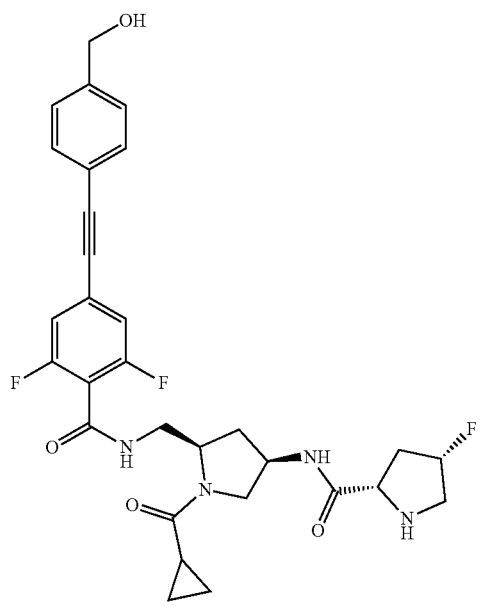 [SMILES: O=C(NC[C@H]1C[C@@H](NC(=O)[C@@H]2C[C@H](F)CN2)CN1C(=O)C1CC1)c1c(F)cc(C#Cc2ccc(CO)cc2)cc1F] |

TABLE 1-continued
| Compound No. | Chemical Structure |
|---|---|
| I-51 | 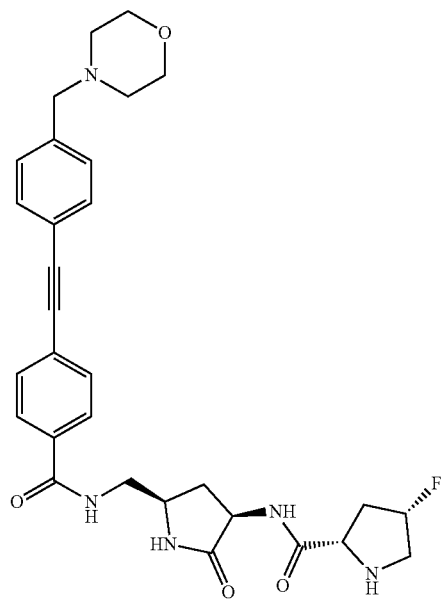 [SMILES: O=C(NC[C@H]1C[C@@H](NC(=O)[C@@H]2C[C@H](F)CN2)C(=O)N1)c1ccc(C#Cc2ccc(CN3CCOCC3)cc2)cc1] |
| I-52 | 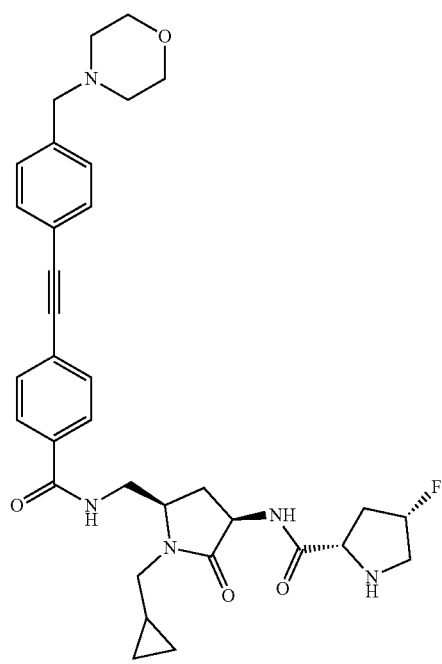 [SMILES: O=C(NC[C@H]1C[C@@H](NC(=O)[C@@H]2C[C@H](F)CN2)C(=O)N1CC1CC1)c1ccc(C#Cc2ccc(CN3CCOCC3)cc2)cc1] |

TABLE 1-continued
Compound No. Chemical Structure
I-53
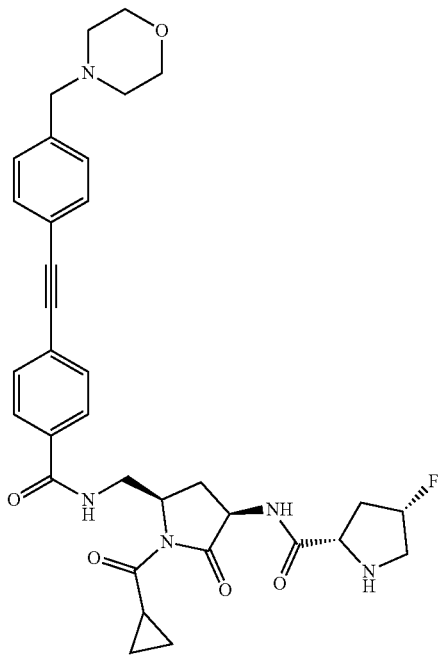 [SMILES: O=C(NC[C@H]1C[C@@H](NC(=O)[C@@H]2C[C@H](F)CN2)C(=O)N1C(=O)C1CC1)c1ccc(C#Cc2ccc(CN3CCOCC3)cc2)cc1]
I-54
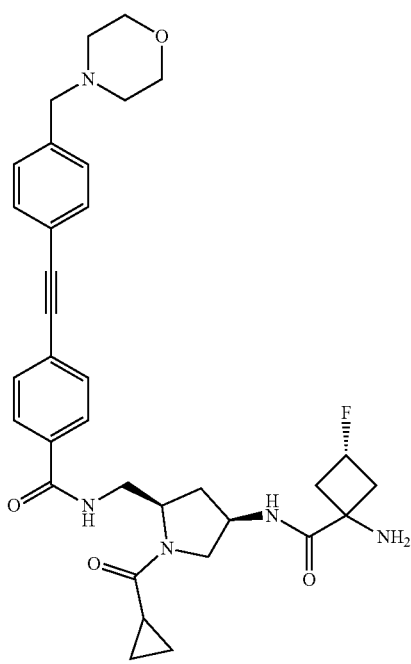

TABLE 1-continued
| Compound No. | Chemical Structure |
|---|---|
| I-55 | 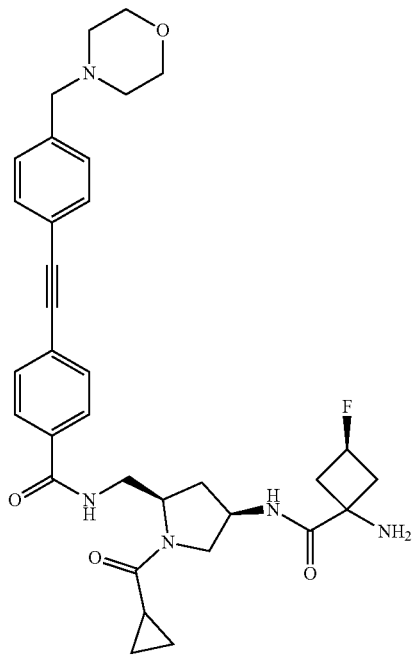 |
| I-56 | 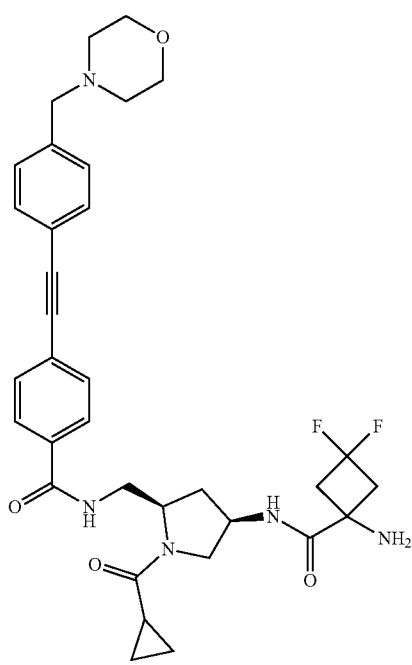 [SMILES: NC1(C(=O)N[C@@H]2C[C@H](CNC(=O)c3ccc(C#Cc4ccc(CN5CCOCC5)cc4)cc3)N(C(=O)C3CC3)C2)CC(F)(F)C1] |

TABLE 1-continued
| Compound No. | Chemical Structure |
|---|---|
| I-57 | 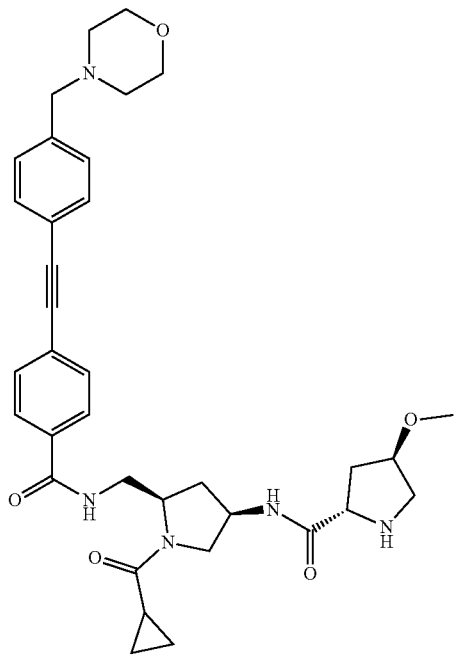 [SMILES: CO[C@H]1CN[C@H](C(=O)N[C@@H]2C[C@H](CNC(=O)c3ccc(C#Cc4ccc(CN5CCOCC5)cc4)cc3)N(C(=O)C3CC3)C2)C1] |
| I-58 | 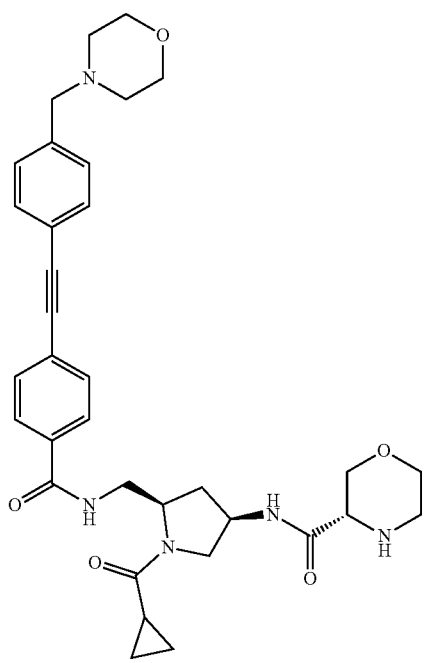 [SMILES: O=C(NC[C@H]1C[C@@H](NC(=O)[C@@H]2COCCN2)CN1C(=O)C1CC1)c1ccc(C#Cc2ccc(CN3CCOCC3)cc2)cc1] |

TABLE 1-continued
| Compound No. | Chemical Structure |
|---|---|
| I-59 | 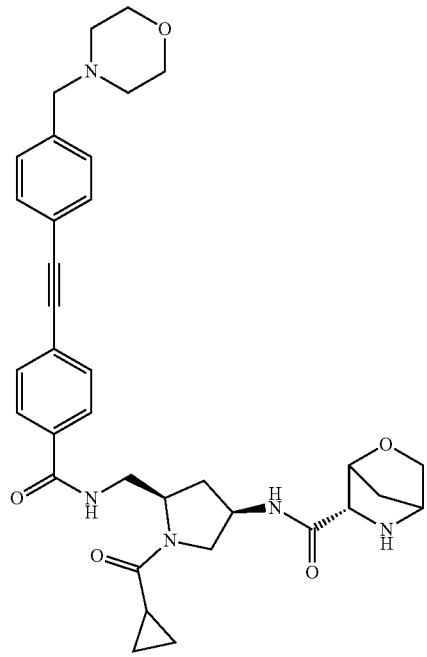 [SMILES: O=C(NC[C@H]1C[C@@H](NC(=O)[C@H]2NC3COC2C3)CN1C(=O)C1CC1)c1ccc(C#Cc2ccc(CN3CCOCC3)cc2)cc1] |
TABLE 2
| Compound No. | Chemical Structure |
|---|---|
| 9A | 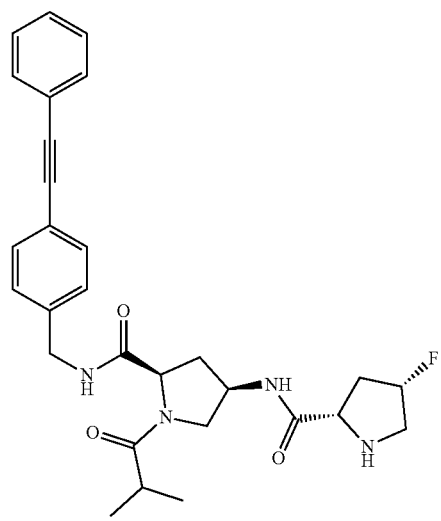 [SMILES: CC(C)C(=O)N1C[C@H](NC(=O)[C@@H]2C[C@H](F)CN2)C[C@@H]1C(=O)NCc1ccc(C#Cc2ccccc2)cc1] |

TABLE 2-continued
| Compound No. | Chemical Structure |
|---|---|
| 9B | 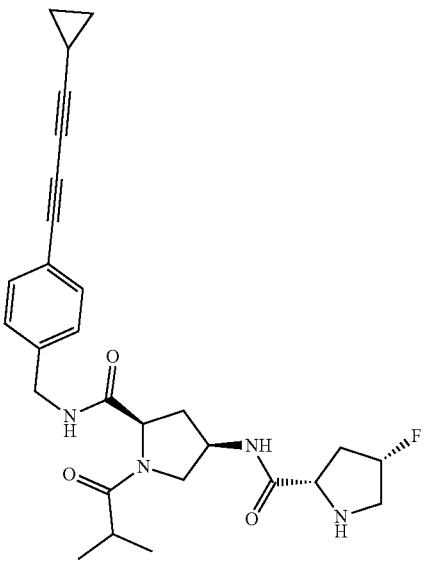 [SMILES: CC(C)C(=O)N1C[C@H](NC(=O)[C@@H]2C[C@H](F)CN2)C[C@@H]1C(=O)NCc1ccc(C#CC#CC2CC2)cc1] |
| 9C | 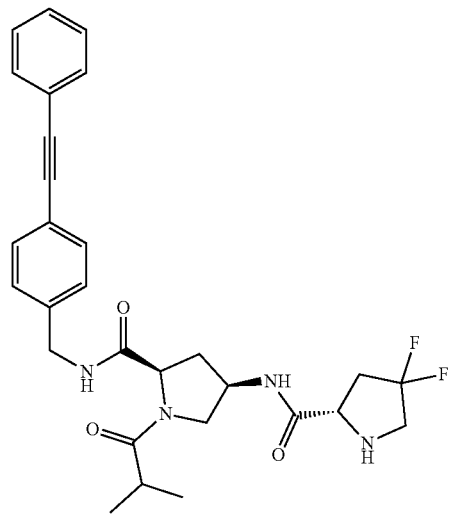 [SMILES: CC(C)C(=O)N1C[C@H](NC(=O)[C@@H]2CC(F)(F)CN2)C[C@@H]1C(=O)NCc1ccc(C#Cc2ccccc2)cc1] |

TABLE 2-continued
| Compound No. | Chemical Structure |
|---|---|
| 9D | 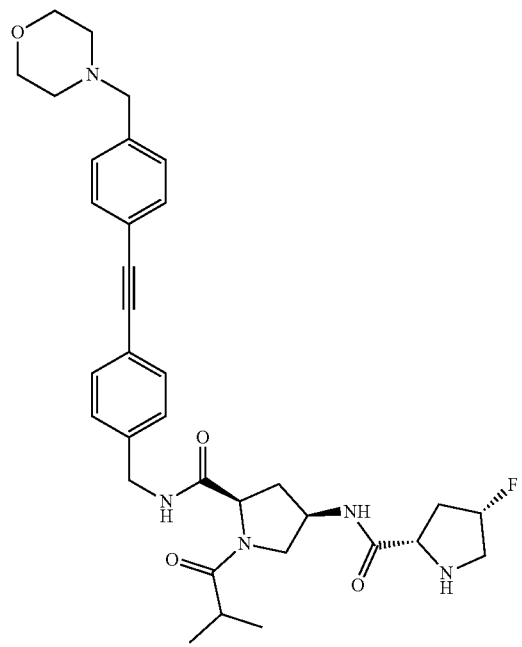 [SMILES: CC(C)C(=O)N1C[C@H](NC(=O)[C@@H]2C[C@H](F)CN2)C[C@@H]1C(=O)NCc1ccc(C#Cc2ccc(CN3CCOCC3)cc2)cc1] |
| 9E | 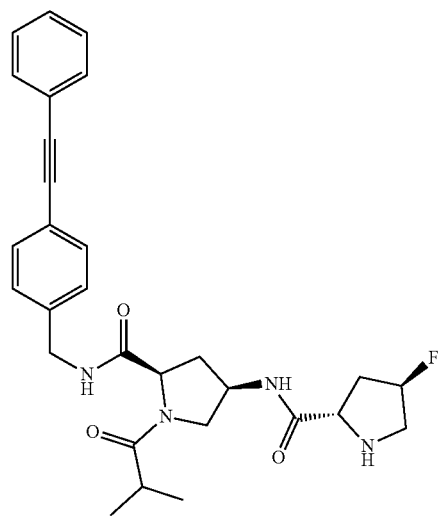 [SMILES: CC(C)C(=O)N1C[C@H](NC(=O)[C@@H]2C[C@@H](F)CN2)C[C@@H]1C(=O)NCc1ccc(C#Cc2ccccc2)cc1] |

TABLE 2-continued
| Compound No. | Chemical Structure |
|---|---|
| 9F | 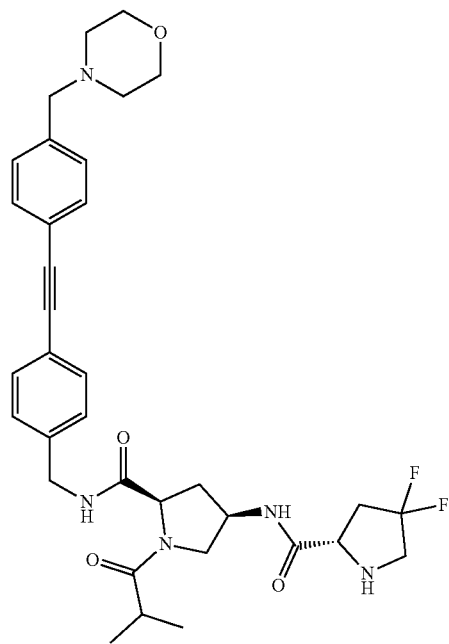 [SMILES: CC(C)C(=O)N1C[C@H](NC(=O)[C@@H]2CC(F)(F)CN2)C[C@@H]1C(=O)NCc1ccc(C#Cc2ccc(CN3CCOCC3)cc2)cc1] |
| 9G | 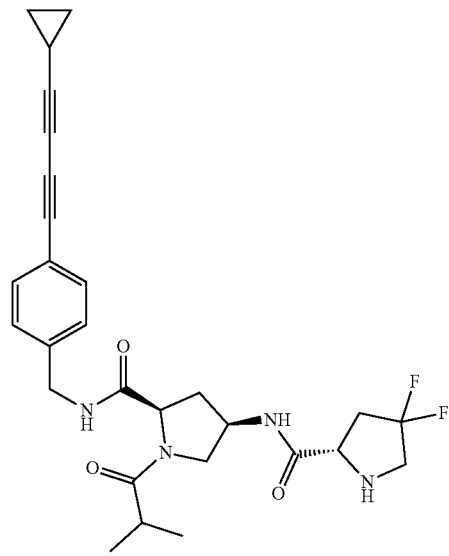 [SMILES: CC(C)C(=O)N1C[C@H](NC(=O)[C@@H]2CC(F)(F)CN2)C[C@@H]1C(=O)NCc1ccc(C#CC#CC2CC2)cc1] |

TABLE 2-continued
| Compound No. | Chemical Structure |
|---|---|
| 9H | 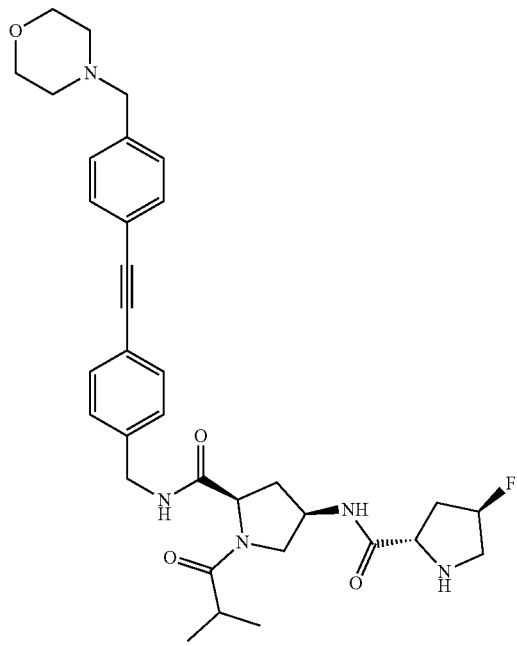 [SMILES: CC(C)C(=O)N1C[C@H](NC(=O)[C@@H]2C[C@@H](F)CN2)C[C@@H]1C(=O)NCc1ccc(C#Cc2ccc(CN3CCOCC3)cc2)cc1] |
| 9I | 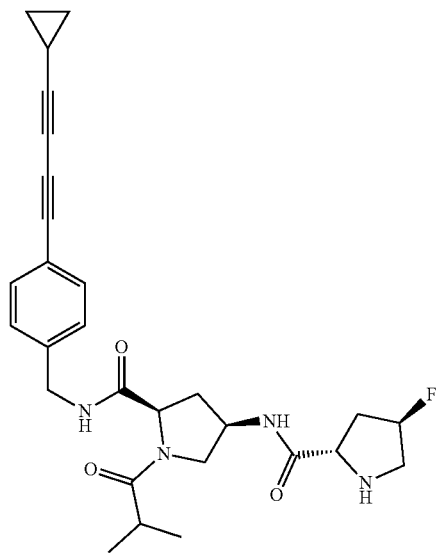 [SMILES: CC(C)C(=O)N1C[C@H](NC(=O)[C@@H]2C[C@@H](F)CN2)C[C@@H]1C(=O)NCc1ccc(C#CC#CC2CC2)cc1] |

TABLE 2-continued
| Compound No. | Chemical Structure |
|---|---|
| 9J | 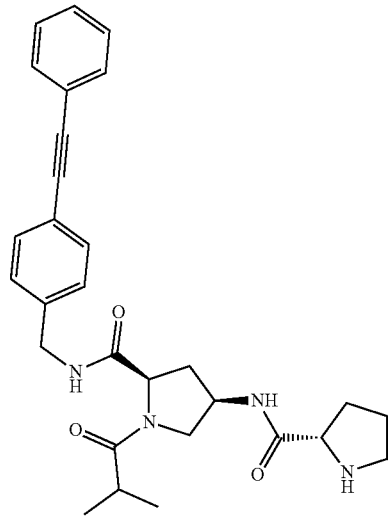 [SMILES: CC(C)C(=O)N1C[C@H](NC(=O)[C@@H]2CCCN2)C[C@@H]1C(=O)NCc1ccc(C#Cc2ccccc2)cc1] |
| 9K | 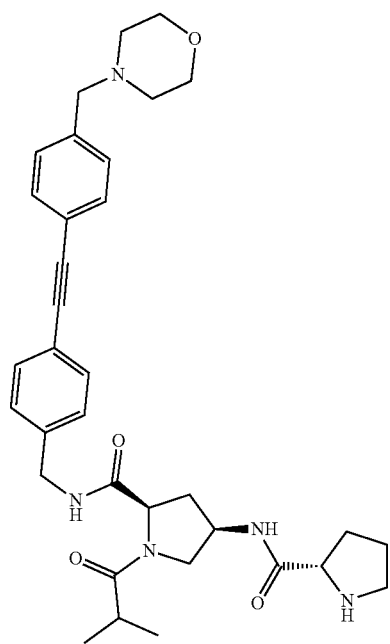 [SMILES: CC(C)C(=O)N1C[C@H](NC(=O)[C@@H]2CCCN2)C[C@@H]1C(=O)NCc1ccc(C#Cc2ccc(CN3CCOCC3)cc2)cc1] |

TABLE 2-continued
| Compound No. | Chemical Structure |
|---|---|
| 9L | 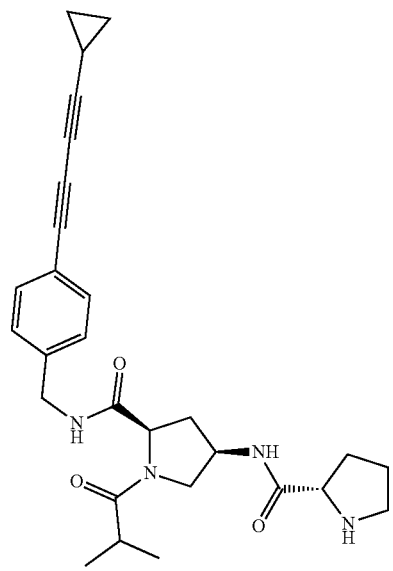 [SMILES: CC(C)C(=O)N1C[C@H](NC(=O)[C@@H]2CCCN2)C[C@@H]1C(=O)NCc1ccc(C#CC#CC2CC2)cc1] |
| 9M | 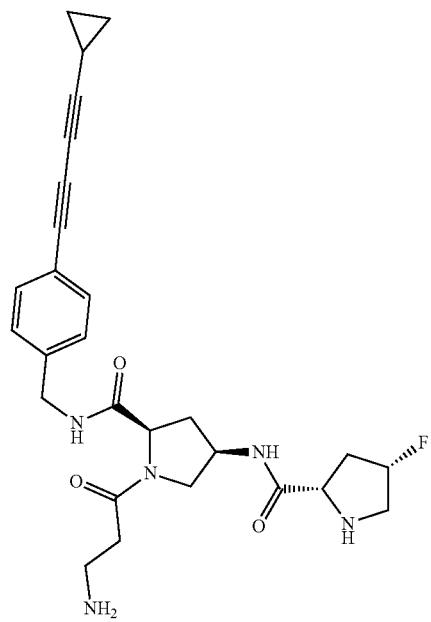 [SMILES: NCCC(=O)N1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9N | 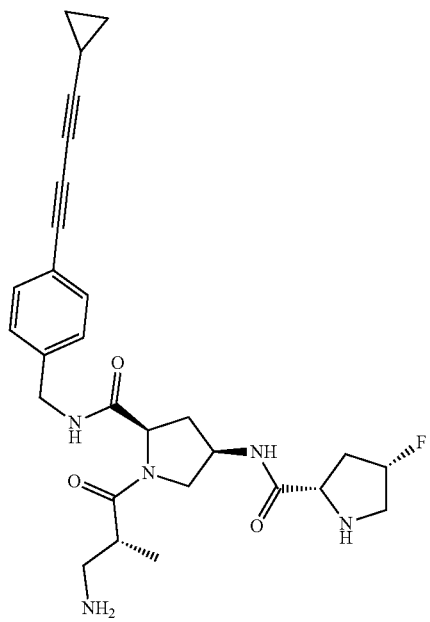 [SMILES: C[C@H](CN)C(=O)N1C[C@H](NC(=O)[C@@H]2C[C@H](F)CN2)C[C@@H]1C(=O)NCc1ccc(C#CC#CC2CC2)cc1] |
| 9O | 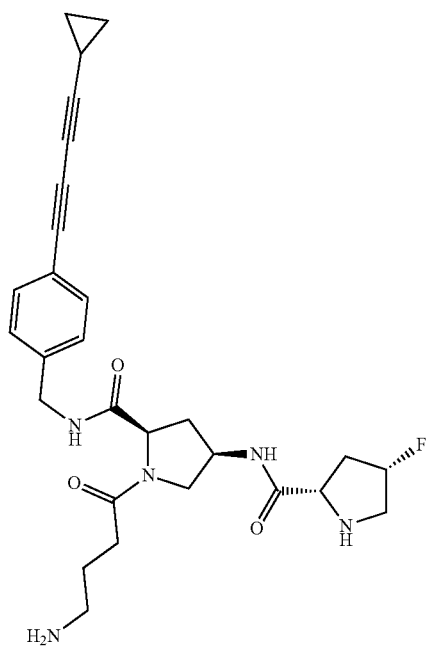 [SMILES: NCCCC(=O)N1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9P | 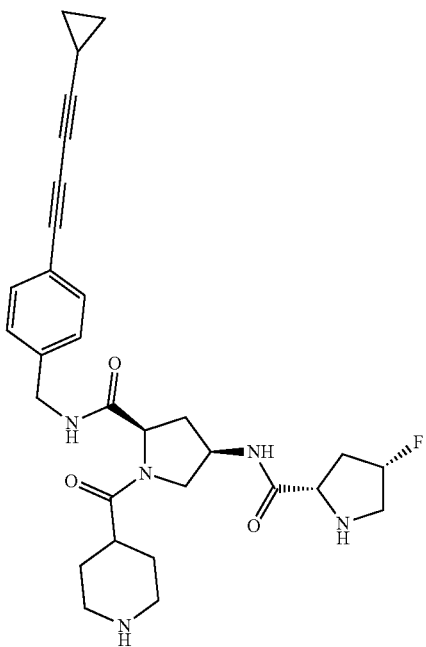 [SMILES: O=C(N[C@@H]1C[C@H](C(=O)NCc2ccc(C#CC#CC3CC3)cc2)N(C(=O)C2CCNCC2)C1)[C@@H]1C[C@H](F)CN1] |
| 9Q | 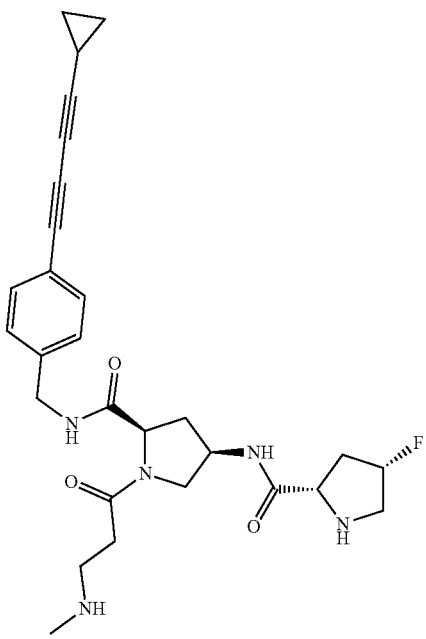 [SMILES: CNCCC(=O)N1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9R | 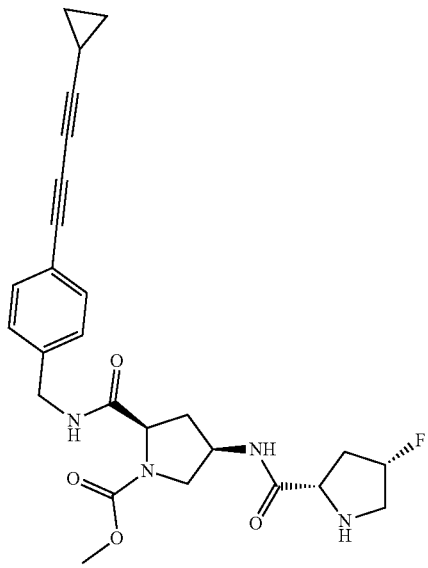 [SMILES: COC(=O)N1C[C@H](NC(=O)[C@@H]2C[C@H](F)CN2)C[C@@H]1C(=O)NCc1ccc(C#CC#CC2CC2)cc1] |
| 9S | 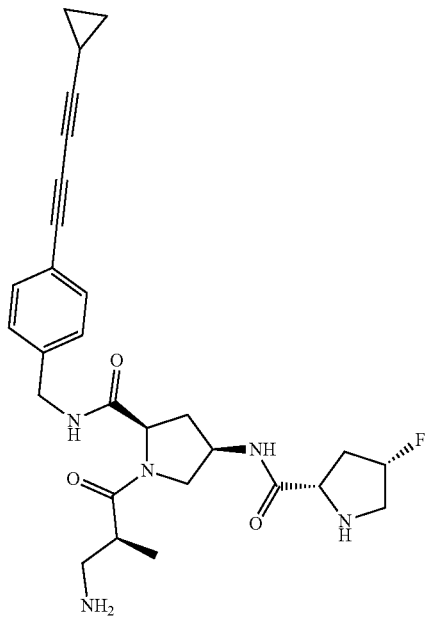 [SMILES: C[C@@H](CN)C(=O)N1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9T | 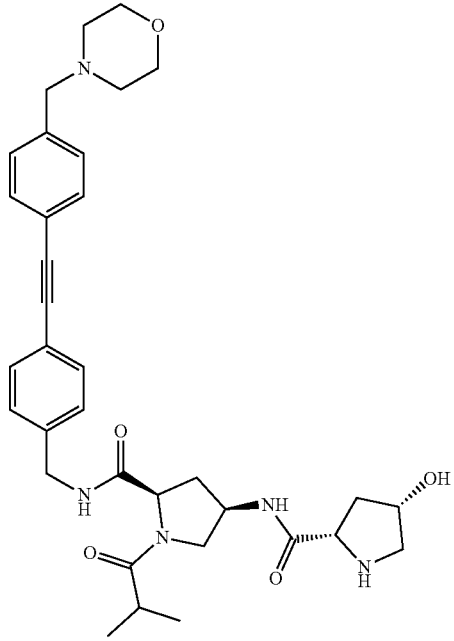 [SMILES: CC(C)C(=O)N1C[C@H](NC(=O)[C@@H]2C[C@H](O)CN2)C[C@@H]1C(=O)NCc1ccc(C#Cc2ccc(CN3CCOCC3)cc2)cc1] |
| 9U | 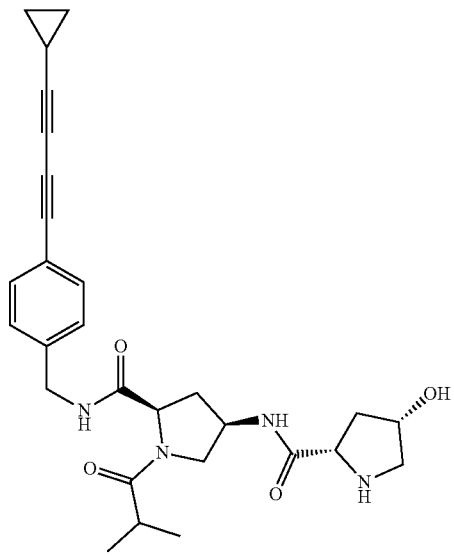 [SMILES: CC(C)C(=O)N1C[C@H](NC(=O)[C@@H]2C[C@H](O)CN2)C[C@@H]1C(=O)NCc1ccc(C#CC#CC2CC2)cc1] |

TABLE 2-continued
| Compound No. | Chemical Structure |
|---|---|
| 9V | 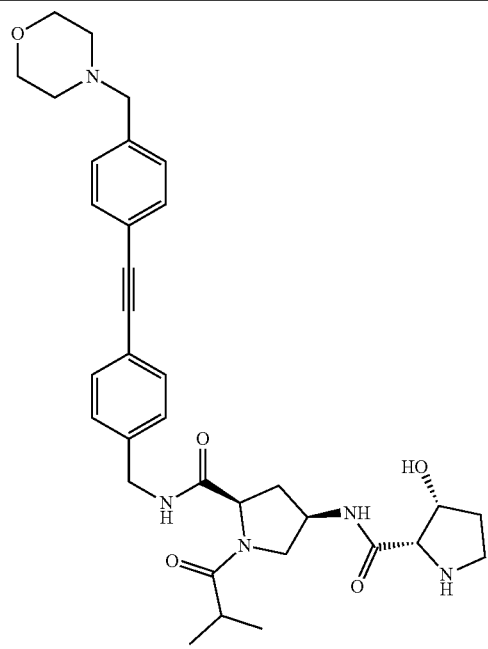 |
| 9W | 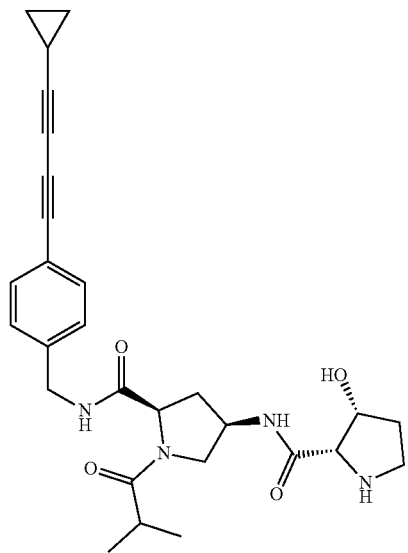 |

| Compound No. | Chemical Structure |
|---|---|
| 9X | 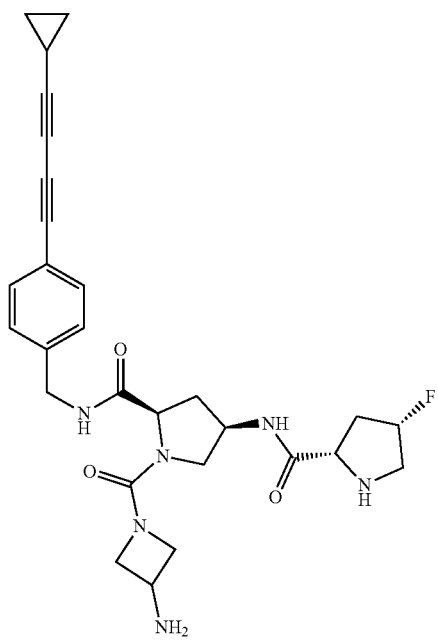 [SMILES: NC1CN(C(=O)N2C[C@H](NC(=O)[C@@H]3C[C@H](F)CN3)C[C@@H]2C(=O)NCc2ccc(C#CC#CC3CC3)cc2)C1] |
| 9Y | 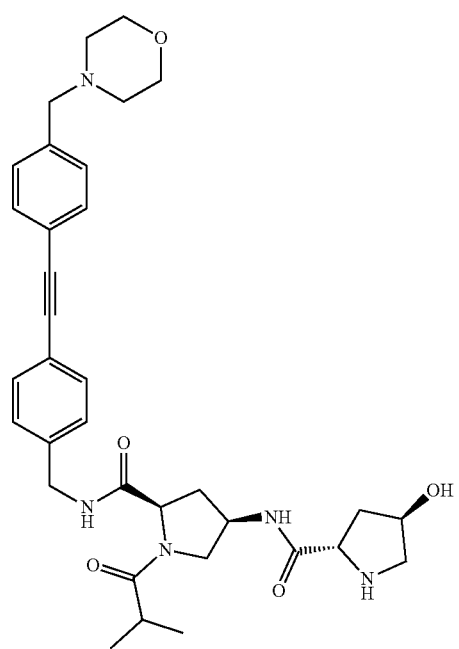 [SMILES: CC(C)C(=O)N1C[C@H](NC(=O)[C@@H]2C[C@@H](O)CN2)C[C@@H]1C(=O)NCc1ccc(C#Cc2ccc(CN3CCOCC3)cc2)cc1] |

TABLE 2-continued
| Compound No. | Chemical Structure |
|---|---|
| 9Z | 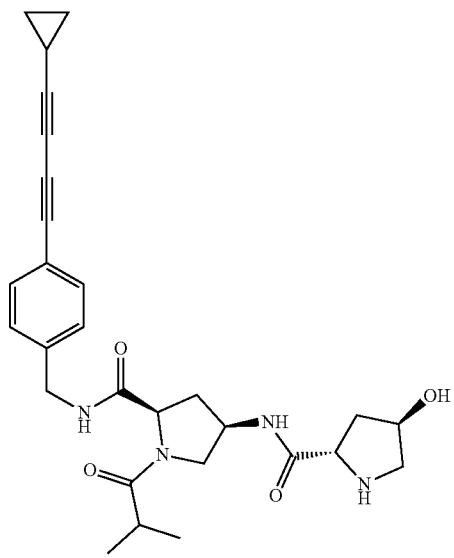 [SMILES: CC(C)C(=O)N1C[C@H](NC(=O)[C@@H]2C[C@@H](O)CN2)C[C@@H]1C(=O)NCc1ccc(C#CC#CC2CC2)cc1] |
| 9AA | 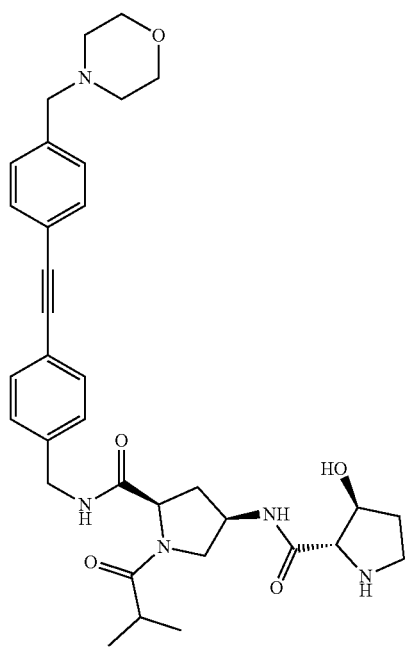 [SMILES: CC(C)C(=O)N1C[C@H](NC(=O)[C@H]2NCC[C@@H]2O)C[C@@H]1C(=O)NCc1ccc(C#Cc2ccc(CN3CCOCC3)cc2)cc1] |

TABLE 2-continued
| Compound No. | Chemical Structure |
|---|---|
| 9AB | 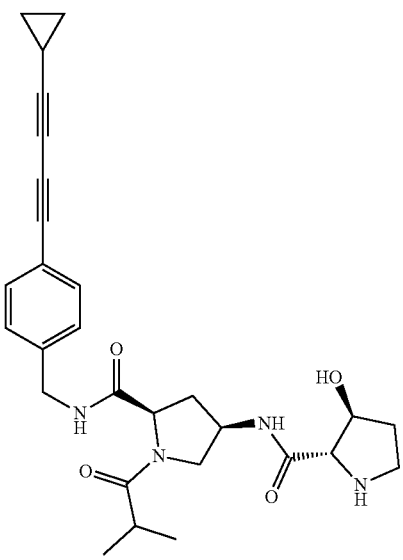 [SMILES: CC(C)C(=O)N1C[C@H](NC(=O)[C@H]2NCC[C@@H]2O)C[C@@H]1C(=O)NCc1ccc(C#CC#CC2CC2)cc1] |
| 9AC | 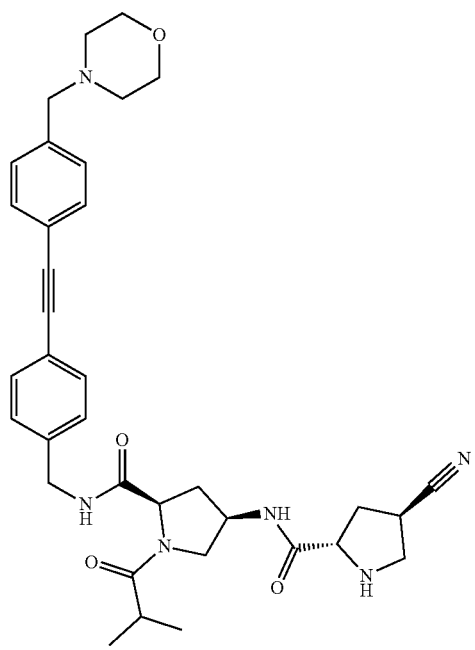 [SMILES: CC(C)C(=O)N1C[C@H](NC(=O)[C@@H]2C[C@@H](C#N)CN2)C[C@@H]1C(=O)NCc1ccc(C#Cc2ccc(CN3CCOCC3)cc2)cc1] |

| Compound No. | Chemical Structure |
|---|---|
| 9AD | 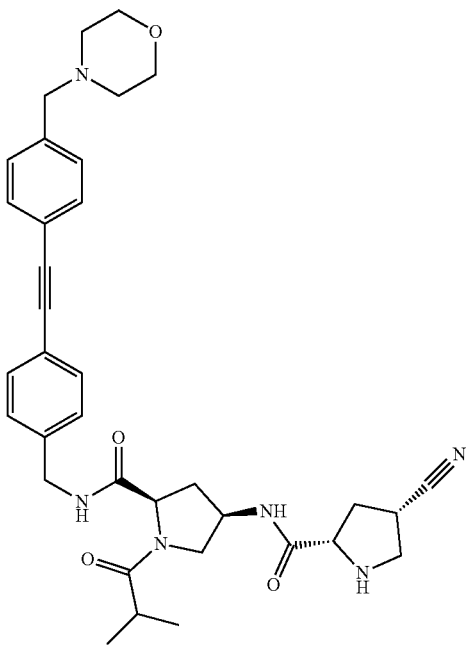 [SMILES: CC(C)C(=O)N1C[C@H](NC(=O)[C@@H]2C[C@H](C#N)CN2)C[C@@H]1C(=O)NCc1ccc(C#Cc2ccc(CN3CCOCC3)cc2)cc1] |
| 9AE | 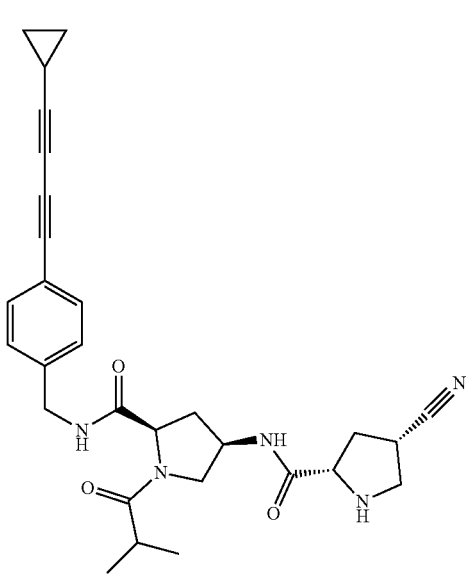 [SMILES: CC(C)C(=O)N1C[C@H](NC(=O)[C@@H]2C[C@H](C#N)CN2)C[C@@H]1C(=O)NCc1ccc(C#CC#CC2CC2)cc1] |

TABLE 2-continued
| Compound No. | Chemical Structure |
|---|---|
| 9AF | 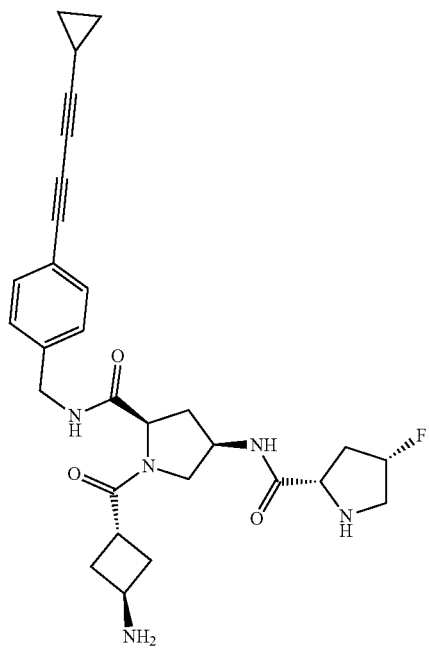 [SMILES: N[C@H]1C[C@H](C(=O)N2C[C@H](NC(=O)[C@@H]3C[C@H](F)CN3)C[C@@H]2C(=O)NCc2ccc(C#CC#CC3CC3)cc2)C1] |
| 9AG | 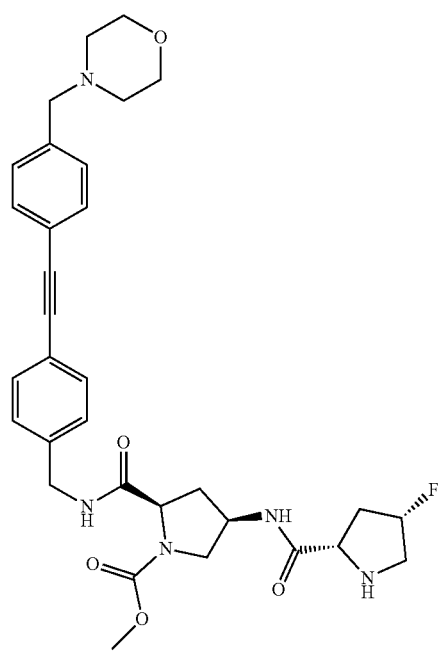 [SMILES: COC(=O)N1C[C@H](NC(=O)[C@@H]2C[C@H](F)CN2)C[C@@H]1C(=O)NCc1ccc(C#Cc2ccc(CN3CCOCC3)cc2)cc1] |

TABLE 2-continued
| Compound No. | Chemical Structure |
|---|---|
| 9AH | 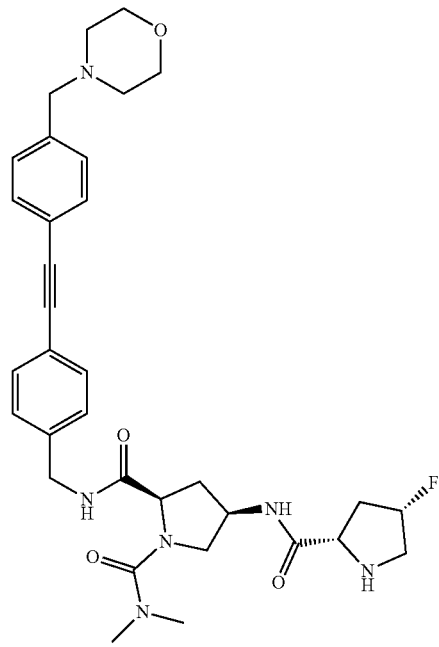 [SMILES: CN(C)C(=O)N1C[C@H](NC(=O)[C@@H]2C[C@H](F)CN2)C[C@@H]1C(=O)NCc1ccc(C#Cc2ccc(CN3CCOCC3)cc2)cc1] |
| 9AI | 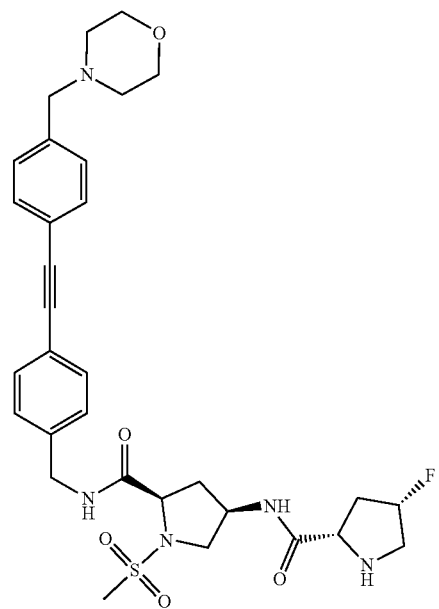 [SMILES: CS(=O)(=O)N1C[C@H](NC(=O)[C@@H]2C[C@H](F)CN2)C[C@@H]1C(=O)NCc1ccc(C#Cc2ccc(CN3CCOCC3)cc2)cc1] |

TABLE 2-continued
| Compound No. | Chemical Structure |
|---|---|
| 9AJ | 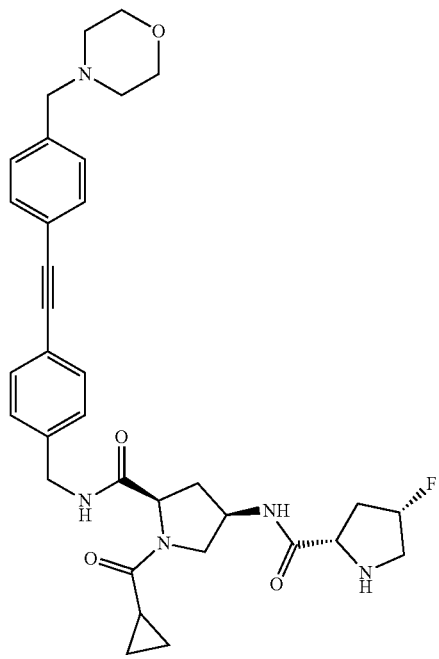 [SMILES: O=C(N[C@@H]1C[C@H](C(=O)NCc2ccc(C#Cc3ccc(CN4CCOCC4)cc3)cc2)N(C(=O)C2CC2)C1)[C@@H]1C[C@H](F)CN1] |
| 9AM | 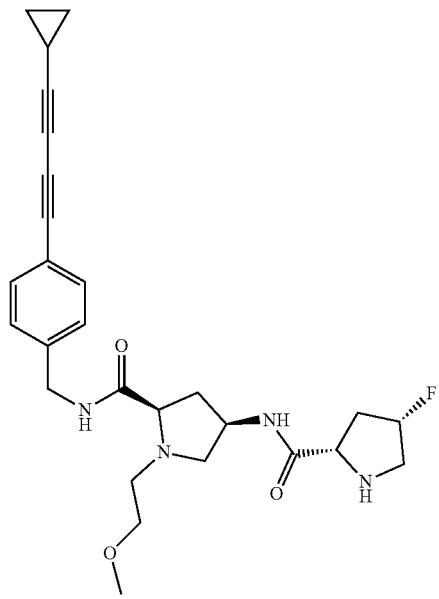 [SMILES: COCCN1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9AN | 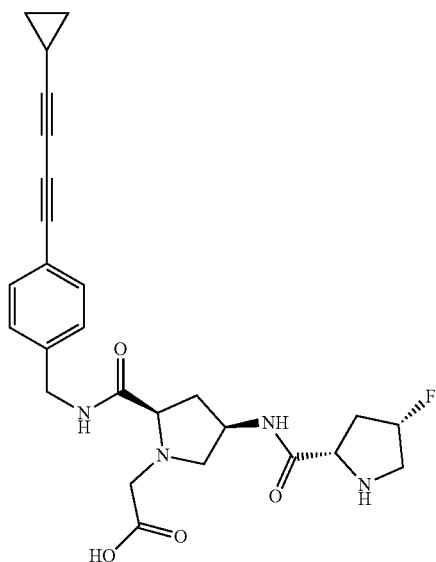 [SMILES: O=C(O)CN1C[C@H](NC(=O)[C@@H]2C[C@H](F)CN2)C[C@@H]1C(=O)NCc1ccc(C#CC#CC2CC2)cc1] |
| 9AO | 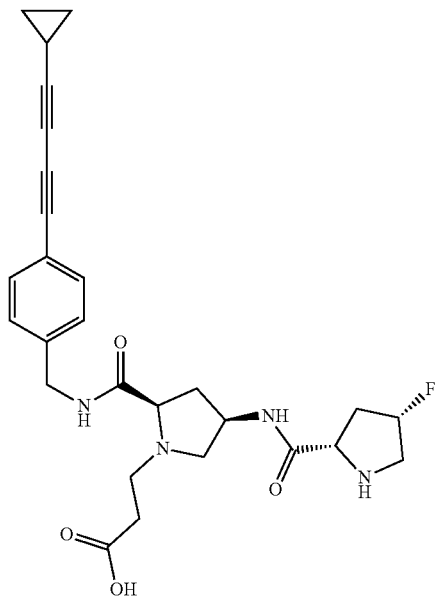 [SMILES: O=C(O)CCN1C[C@H](NC(=O)[C@@H]2C[C@H](F)CN2)C[C@@H]1C(=O)NCc1ccc(C#CC#CC2CC2)cc1] |

TABLE 2-continued
| Compound No. | Chemical Structure |
|---|---|
| 9AP | 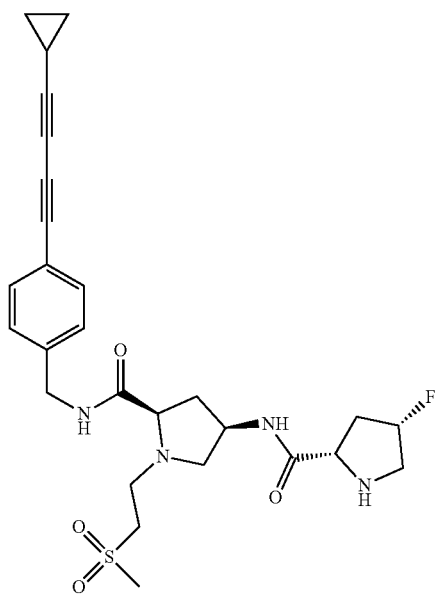 [SMILES: CS(=O)(=O)CCN1C[C@H](NC(=O)[C@@H]2C[C@H](F)CN2)C[C@@H]1C(=O)NCc1ccc(C#CC#CC2CC2)cc1] |
| 9AQ | 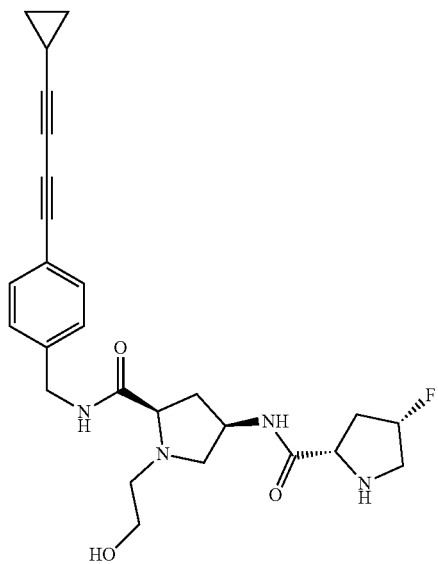 [SMILES: O=C(N[C@@H]1C[C@H](C(=O)NCc2ccc(C#CC#CC3CC3)cc2)N(CCO)C1)[C@@H]1C[C@H](F)CN1] |

TABLE 2-continued
| Compound No. | Chemical Structure |
|---|---|
| 9AR | 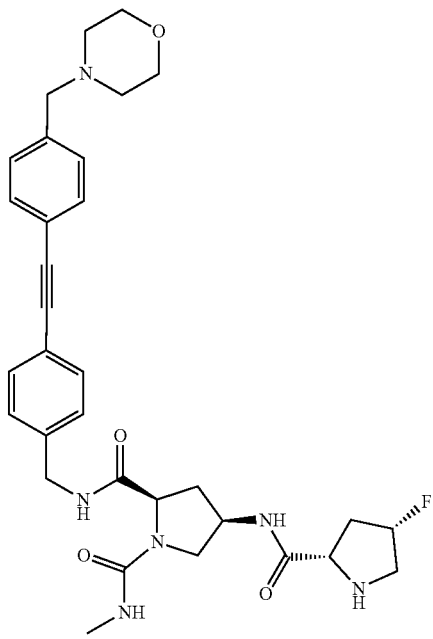 [SMILES: CNC(=O)N1C[C@H](NC(=O)[C@@H]2C[C@H](F)CN2)C[C@@H]1C(=O)NCc1ccc(C#Cc2ccc(CN3CCOCC3)cc2)cc1] |
| 9AS | 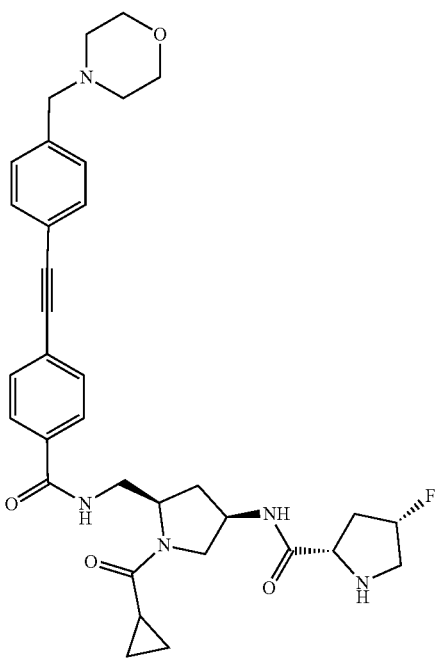 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)cc1] |
| 9AT | 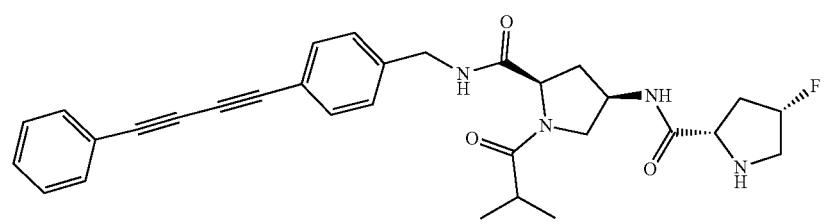 [SMILES: CC(C)C(=O)N1C[C@H](NC(=O)[C@@H]2C[C@H](F)CN2)C[C@@H]1C(=O)NCc1ccc(C#CC#Cc2ccccc2)cc1] |

TABLE 2-continued
| Compound No. | Chemical Structure |
|---|---|
| 9AV | 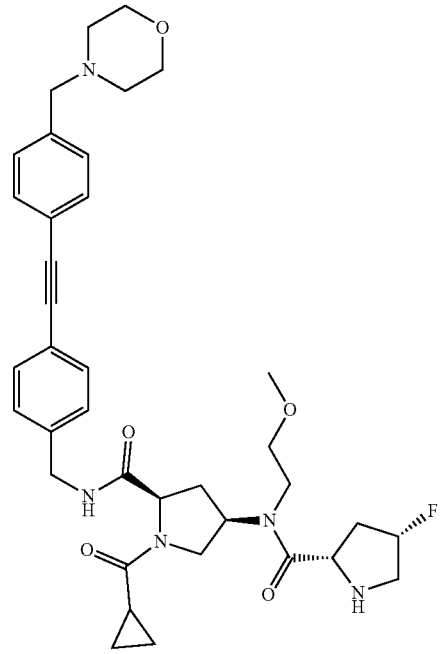 [SMILES: COCCN(C(=O)[C@@H]1C[C@H](F)CN1)[C@@H]1C[C@H](C(=O)NCc2ccc(C#Cc3ccc(CN4CCOCC4)cc3)cc2)N(C(=O)C2CC2)C1] |
| 9AW | 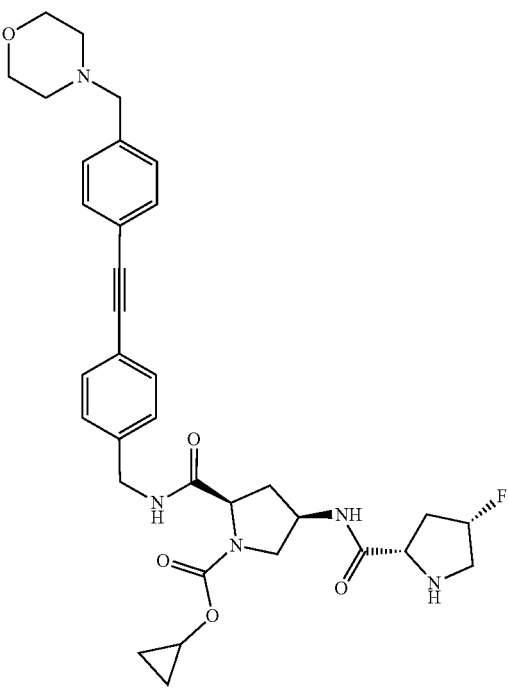 [SMILES: O=C(N[C@@H]1C[C@H](C(=O)NCc2ccc(C#Cc3ccc(CN4CCOCC4)cc3)cc2)N(C(=O)OC2CC2)C1)[C@@H]1C[C@H](F)CN1] |

| Compound No. | Chemical Structure |
|---|---|
| 9AX | 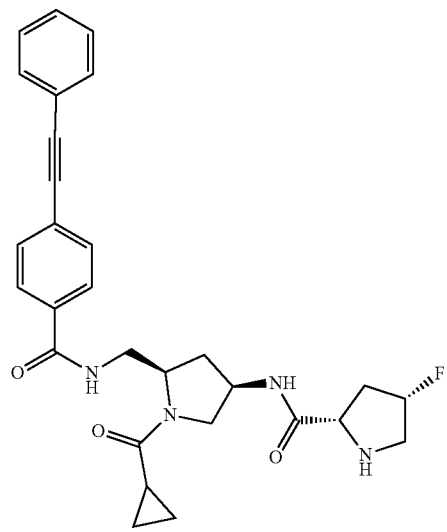 [SMILES: O=C(NC[C@H]1C[C@@H](NC(=O)[C@@H]2C[C@H](F)CN2)CN1C(=O)C1CC1)c1ccc(C#Cc2ccccc2)cc1] |
| 9AY | 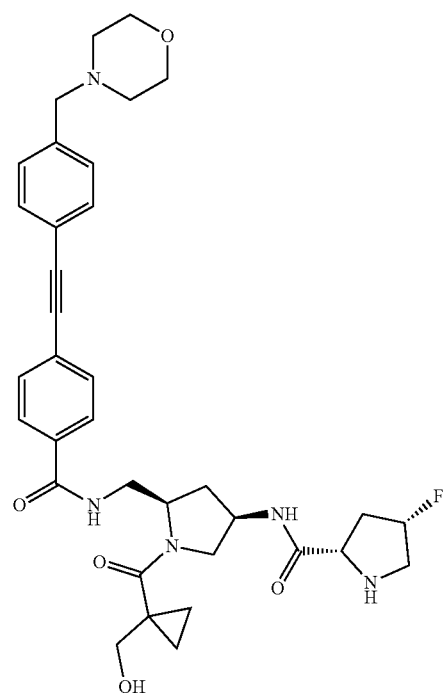 [SMILES: O=C(NC[C@H]1C[C@@H](NC(=O)[C@@H]2C[C@H](F)CN2)CN1C(=O)C1(CO)CC1)c1ccc(C#Cc2ccc(CN3CCOCC3)cc2)cc1] |

TABLE 2-continued
| Compound No. | Chemical Structure |
|---|---|
| 9AZ | 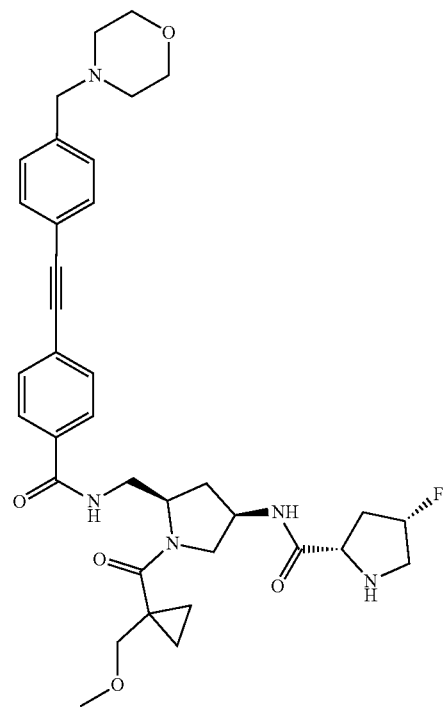 [SMILES: COCC1(C(=O)N2C[C@H](NC(=O)[C@@H]3C[C@H](F)CN3)C[C@@H]2CNC(=O)c2ccc(C#Cc3ccc(CN4CCOCC4)cc3)cc2)CC1] |
| 9BA | 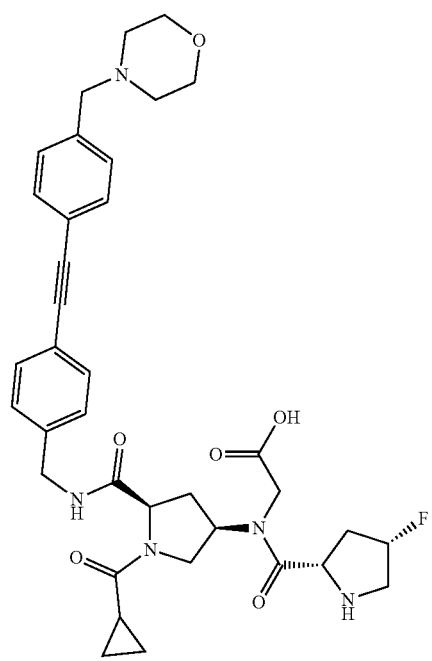 [SMILES: O=C(O)CN(C(=O)[C@@H]1C[C@H](F)CN1)[C@@H]1C[C@H](C(=O)NCc2ccc(C#Cc3ccc(CN4CCOCC4)cc3)cc2)N(C(=O)C2CC2)C1] |

TABLE 2-continued
| Compound No. | Chemical Structure |
|---|---|
| 9BB | 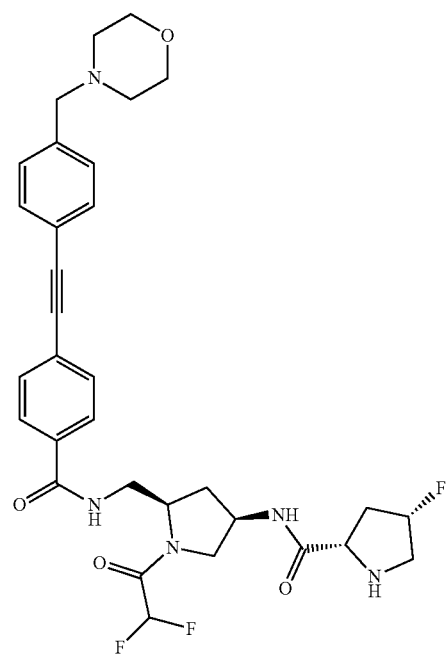 [SMILES: O=C(NC[C@H]1C[C@@H](NC(=O)[C@@H]2C[C@H](F)CN2)CN1C(=O)C(F)F)c1ccc(C#Cc2ccc(CN3CCOCC3)cc2)cc1] |
| 9BC | 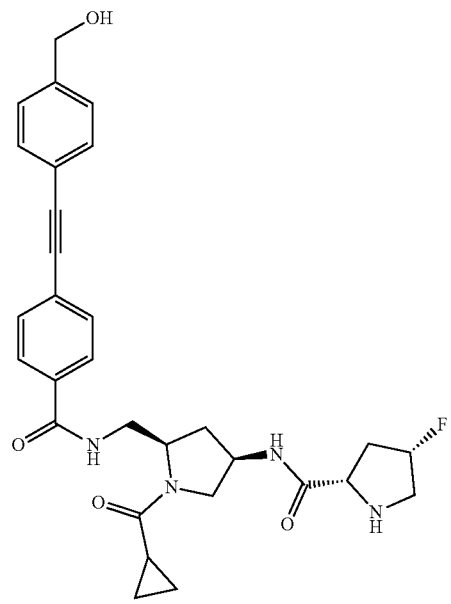 [SMILES: O=C(NC[C@H]1C[C@@H](NC(=O)[C@@H]2C[C@H](F)CN2)CN1C(=O)C1CC1)c1ccc(C#Cc2ccc(CO)cc2)cc1] |

TABLE 2-continued
| Compound No. | Chemical Structure |
|---|---|
| 9BD | 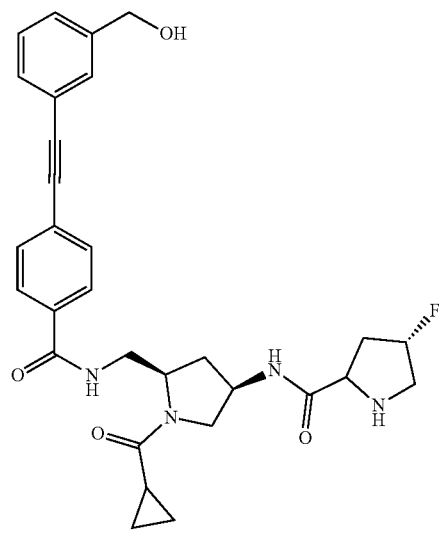 [SMILES: O=C(NC[C@H]1C[C@@H](NC(=O)C2C[C@H](F)CN2)CN1C(=O)C1CC1)c1ccc(C#Cc2cccc(CO)c2)cc1] |
| 9BE | 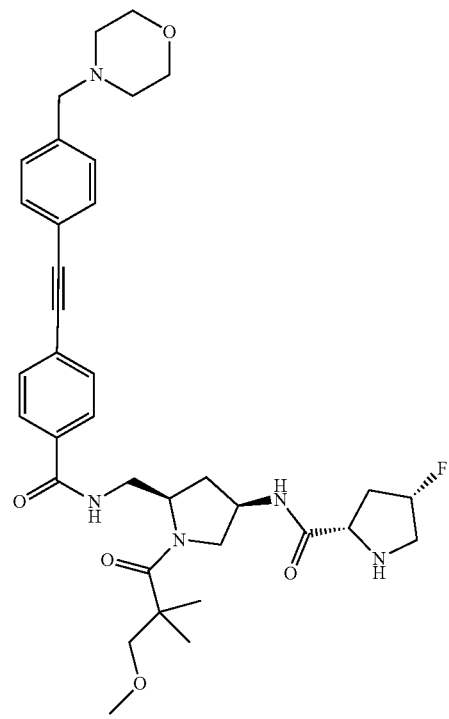 [SMILES: COCC(C)(C)C(=O)N1C[C@H](NC(=O)[C@@H]2C[C@H](F)CN2)C[C@@H]1CNC(=O)c1ccc(C#Cc2ccc(CN3CCOCC3)cc2)cc1] |

TABLE 2-continued
| Compound No. | Chemical Structure |
|---|---|
| 9BF | 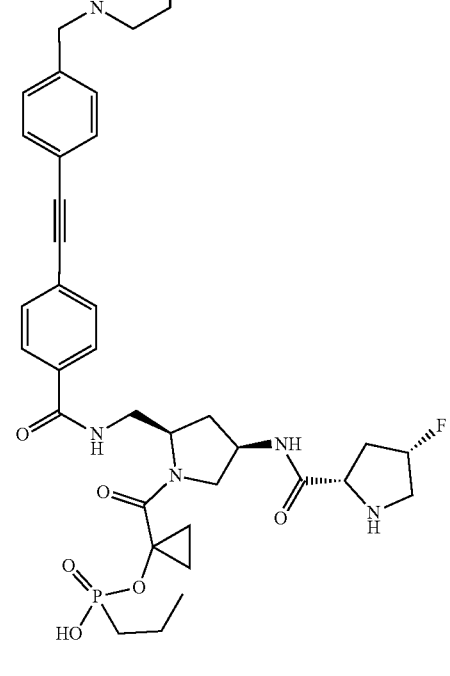 |
| 9BG | 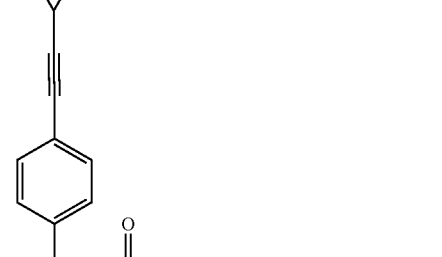 |

TABLE 3-A
| Title Compound from Example No. | Chemical Structure |
|---|---|
| 5 | 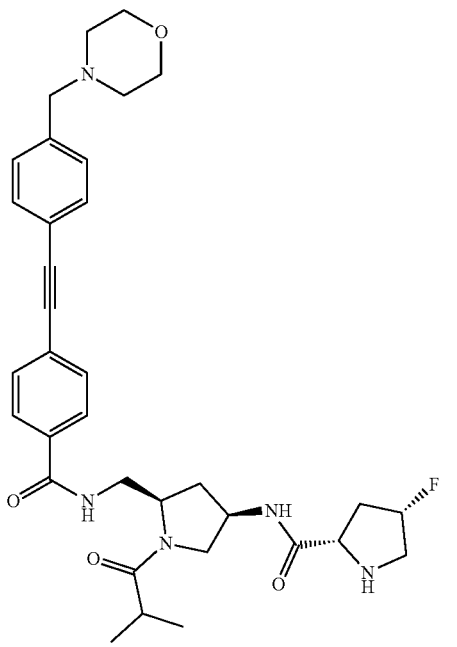 [SMILES: CC(C)C(=O)N1C[C@H](NC(=O)[C@@H]2C[C@H](F)CN2)C[C@@H]1CNC(=O)c1ccc(C#Cc2ccc(CN3CCOCC3)cc2)cc1] |
| 6 | 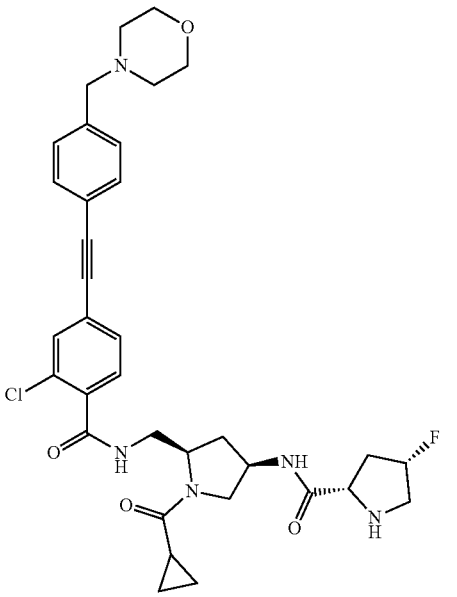 [SMILES: O=C(NC[C@H]1C[C@@H](NC(=O)[C@@H]2C[C@H](F)CN2)CN1C(=O)C1CC1)c1ccc(C#Cc2ccc(CN3CCOCC3)cc2)cc1Cl] |
| 7 | 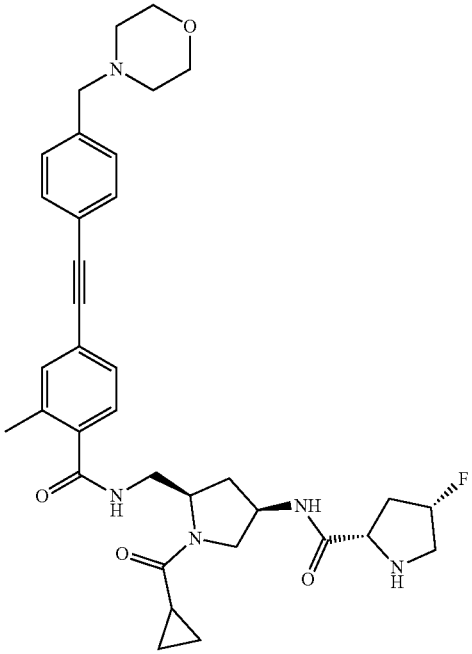 [SMILES: Cc1cc(C#Cc2ccc(CN3CCOCC3)cc2)ccc1C(=O)NC[C@H]1C[C@@H](NC(=O)[C@@H]2C[C@H](F)CN2)CN1C(=O)C1CC1] |
| 8 | 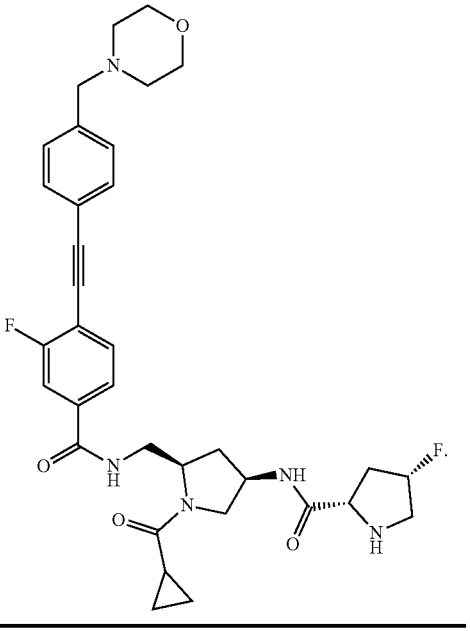 |
* * * * *